United States Patent
Urgaonkar et al.

(10) Patent No.: US 11,739,089 B2
(45) Date of Patent: Aug. 29, 2023

(54) ACETAMIDO-PHENYLTETRAZOLE DERIVATIVES AND METHODS OF USING THE SAME

(71) Applicant: Athenex, Inc., Buffalo, NY (US)

(72) Inventors: Sameer Urgaonkar, Williamsville, NY (US); Ahmed M. Said, Williamsville, NY (US); Nader N. Nasief Abdel Sayed, Amherst, NY (US); Laura Beth Pitzonka, Blasdell, NY (US); Murray John Cutler, Markham (CA); Michael P. Smolinski, Amherst, NY (US); Johnson Yiu-Nam Lau, Houston, TX (US)

(73) Assignee: Athenex, Inc., Buffalo, NY (US)

( * ) Notice: Subject to any disclaimer, the term of this patent is extended or adjusted under 35 U.S.C. 154(b) by 15 days.

(21) Appl. No.: 17/495,935

(22) Filed: Oct. 7, 2021

(65) Prior Publication Data

US 2022/0106312 A1   Apr. 7, 2022

Related U.S. Application Data

(60) Provisional application No. 63/088,788, filed on Oct. 7, 2020.

(51) Int. Cl.
| | |
|---|---|
| *C07D 471/04* | (2006.01) |
| *C07D 401/14* | (2006.01) |
| *C07D 405/14* | (2006.01) |
| *C07D 487/06* | (2006.01) |
| *A61P 35/00* | (2006.01) |

(52) U.S. Cl.
CPC ............ *C07D 471/04* (2013.01); *A61P 35/00* (2018.01); *C07D 401/14* (2013.01); *C07D 405/14* (2013.01); *C07D 487/06* (2013.01)

(58) Field of Classification Search
CPC .. C07D 471/04; C07D 401/14; C07D 405/14; C07D 487/06; C07D 487/04; A61P 35/00
See application file for complete search history.

(56) References Cited

U.S. PATENT DOCUMENTS

| | | | |
|---|---|---|---|
| 7,625,926 B2 | 12/2009 | Bang et al. | |
| 8,680,277 B2 | 3/2014 | Bang et al. | |
| 8,940,908 B2 | 1/2015 | Bang et al. | |
| 9,283,218 B2 | 3/2016 | Kim et al. | |
| 9,867,801 B2 | 1/2018 | Srinivasan et al. | |
| 10,835,511 B2 | 11/2020 | Chan et al. | |
| 2018/0153878 A1 | 6/2018 | Park et al. | |
| 2019/0105397 A1 | 4/2019 | Yoon et al. | |
| 2021/0023042 A1 | 1/2021 | Chan et al. | |

FOREIGN PATENT DOCUMENTS

| | | |
|---|---|---|
| WO | WO 94/01408 A1 | 1/1994 |
| WO | WO 98/17648 A1 | 4/1998 |
| WO | WO 2005/033097 A1 | 4/2005 |
| WO | WO-2022076663 A1 | 4/2022 |

OTHER PUBLICATIONS

Verweij, M., Preventive Medicine Between Obligation and Aspiration 2013, Springer Science and Business Media Ch. 3; excerpt p. 1-31.*
Paek, I. B., "Metabolism of a new P-glycoprotein inhibitor HM-30181 in rats using liquid chromatography/electrospray mass spectrometry." Rapid Communications in Mass Spectrometry: An International Journal Devoted to the Rapid Dissemination of Up-to-the-Minute Research in Mass Spectrometry 20.9 (2006): 1457-1462.*
Köhler, S. C., "HM30181 derivatives as novel potent and selective inhibitors of the breast cancer resistance protein (BCRP/ABCG2)." Journal of Medicinal Chemistry 58.9 (2015): 3910-3921.*
Dodic et al. "Synthesis and Activity against Multidrug Resistance in Chinese Hamster Ovary Cells of New Acridone-4-carboxamides", J. Med. Chem. 1995,38, 2418-2426.
Labrie et al. "In vitro activity of novel dual action MDR anthranilamide modulators with inhibitory activity at CYP-450", Bioorganic and Medicinal Chemistry, 2006, vol. 14, p. 7972-7987.
Labrie et al. "In vitro activity of novel dual action MDR anthranilamide modulators with inhibitory activity at CYP-450 (Part 2)", Bioorganic and Medicinal Chemistry, 2007, vol. 15, p. 3854-3868.

* cited by examiner

*Primary Examiner* — John M Mauro
(74) *Attorney, Agent, or Firm* — Cooley LLP; Heidi A. Erlacher; Chen Chen

(57) ABSTRACT

The present disclosure relates to compounds of Formula (IA)

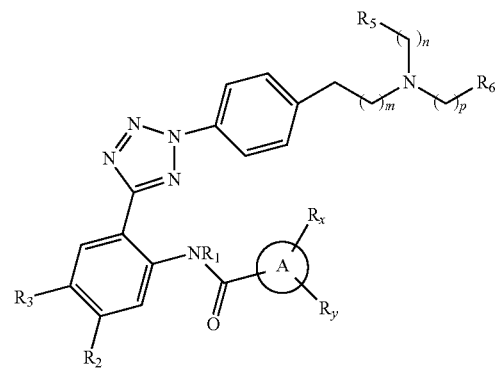

and to their prodrugs, pharmaceutically acceptable salts, pharmaceutical compositions, methods of use, and methods for their preparation. The compounds disclosed herein are useful for the treatment of disorders in which P-glycoprotein and/or cytochrome P450 (e.g. CYP3A4) is modulated (e.g., cancers which have developed multi-drug resistance).

23 Claims, No Drawings

ACETAMIDO-PHENYLTETRAZOLE DERIVATIVES AND METHODS OF USING THE SAME

RELATED APPLICATION

This application claims priority to, and the benefit of, U.S. Provisional Application No. 63/088,788, filed on Oct. 7, 2020, the contents of which is incorporated herein in their entirety.

FIELD OF THE DISCLOSURE

The present disclosure relates to acetamido-phenyltetrazole derivatives which possess P-glycoprotein modulation activity and/or modulation activity against drug metabolizing enzyme cytochrome P450 (e.g., CYP3A4 and/or CYP3A5 isoforms) and are useful the treatment of the human or animal body. The present disclosure also relates to processes for the preparation of these compounds, to pharmaceutical compositions comprising them, and to their uses in the treatment of disorders in which the expression of P-glycoprotein and/or cytochrome P450 isoforms (e.g., CYP3A4 or CYP3A5) is modulated (e.g., in a cancer which has developed multi-drug resistance). The present disclosure also relates to the use of the compounds of the instant disclosure for improving oral bioavailability of therapeutics which are substrates of P-glycoprotein and/or cytochrome P450. The present disclosure also relates to the use of the compounds of the instant disclosure for increasing brain distribution of therapeutics which are substrates of P-glycoprotein and/or cytochrome P450.

BACKGROUND

Many anticancer agents (e.g., vinca alkaloid, anthracycline, epipodophilotoxin, paclitaxel, and docetaxel) become ineffective when administered to a patient having multi-drug resistance (MDR) which has been caused by the presence of overexpressed P-glycoprotein. P-glycoprotein modulates intracellular accumulation of the administered anticancer agent by pumping the agent out of the tumor cell. Expression of the drug metabolizing CYP3A4 protein in breast, colorectal, esophageal tumors, and Ewing's sarcoma may curb the intracellular concentration of anticancer agents by forming metabolites with reduced antitumor activity. This action of CYP3A4 limits the efficacy of anticancer agents or contributes to the development of resistance to these agents. Modulation of P-glycoprotein and/or cytochrome P450 enzymes (e.g., CYP3A4) in the tumor cells may increase the sensitivity of these cells to anticancer agents.

P-glycoprotein is also expressed in normal healthy tissues, e.g. the small intestine. Intestinal P-glycoprotein does not allow its substrates to cross the epithelial cells lining the intestinal wall resulting in poor oral bioavailability of these substrates. Additionally, the anticancer agent may also suffer from first pass metabolism by cytochrome P450 enzymes (e.g., CYP3A4 and/or CYP3A5 isoforms) present in the small intestine as well as in the liver causing further reduction in their oral bioavailability. Accordingly, there is a need to enhance the bioavailability of anticancer agents by dual targeting modulation of P-glycoprotein and cytochrome P450 (e.g., CYP3A4 and/or CYP3A5 isoforms) enzymes.

The localization of P-glycoprotein in the endothelial cells of the blood-brain barrier also significantly limits the transport of P-glycoprotein substrates from the blood to the brain. Modulating P-glycoprotein at the blood-brain barrier may be beneficial in the treatment of a number of central nervous system (CNS) disorders, e.g., a brain tumor such as glioblastoma.

The conventional P-glycoprotein modulators, such as verapamil and cyclosporin A, cause serious adverse effects (e.g., blood pressure decline and immunity suppression). Thus, several new P-glycoprotein modulators such as piperidine-2-carboxylate, acridine, piperazine-2,5-dione, anthranilic acid and methanodibenzosuberan derivatives have been developed. However, the newly introduced P-glycoprotein modulators have been reported to have toxicity and other adverse effects. This disclosure arises from a need to provide further compounds for the modulation of P-glycoprotein and cytochrome P450 (e.g., CYP3A4 and CYP3A5 isoforms) enzymes that reduce serious adverse effects, while a) markedly enhancing the bioavailability of the substrates of these enzymes, including anticancer agents, b) overcoming the multi-drug resistance of tumors, and c) improving the delivery of the P-glycoprotein substrates to the brain.

SUMMARY

In one aspect, the present disclosure provides a compound of Formula (IA):

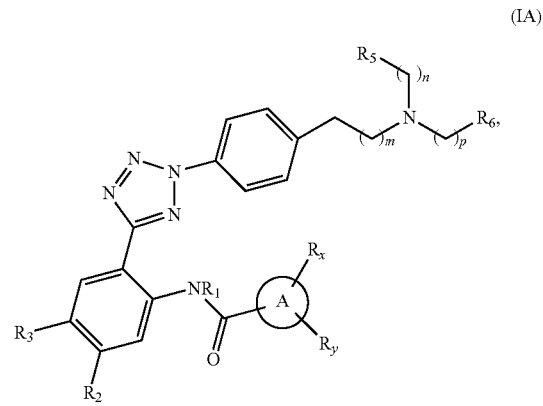

(IA)

or a pharmaceutically acceptable prodrug, solvate, enantiomer, stereoisomer, tautomer, or salt thereof, wherein:

A is $C_{3-10}$ cycloalkyl, 3- to 14-membered heterocyclyl comprising 1-4 heteroatoms selected from N, O, and S, $C_{6-10}$ aryl, or 5- to 14-membered heteroaryl comprising 1-4 heteroatoms selected from N, O, and S, wherein the cycloalkyl or heterocyclyl is optionally substituted with oxo;

each $R_x$ and $R_y$ is independently H, $C_{1-6}$ alkyl, $C_{2-6}$ alkenyl, $C_{2-6}$ alkynyl, $C_{1-6}$ alkoxy, halogen, —CN, —OH, —$NH_2$, 3- to 10-membered heterocyclyl comprising 1-4 heteroatoms selected from N, O, and S, or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, —C(O)N$R_{11}$—S(O)$_2$—N($R_{11}$)$_2$, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently oxo, halogen, —OH, —NH$_2$, —CN, —C(O)$R_{10}$, —C(O)O$R_{10}$, —C(O)N($R_{10}$)$_2$, $C_{1-3}$ alkyl, $C_{2-6}$ alkenyl, $C_{2-6}$ alkynyl, $C_{1-6}$ alkoxy, —NH($C_{1-6}$ alkyl), —N($C_{1-6}$ alkyl)$_2$, —O—(CH$_2$)$_t$—$R_8$, —NH—(CH$_2$)$_t$—$R_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$;

$R_8$ is —OH, $C_{1-6}$ alkoxy, $C_{1-6}$ alkoxy-OH, —NH$_2$, —NH($C_{1-6}$ alkyl), —N($C_{1-6}$ alkyl)$_2$, —SH, —S($C_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl, or heteroaryl is optionally substituted by one or more $R_9$;

each $R_9$ is independently —(CH$_2$)$_u$-(5- to 10-membered heteroaryl comprising 1-4 heteroatoms selected from N, O, and S) or —(CH$_2$)$_u$—($C_{6-10}$ aryl), wherein the heteroaryl or aryl is optionally substituted with one or more halogen, —CN, —OH, or —NH$_2$;

each $R_{10}$ is independently halogen, —OH, —NH$_2$, —CN, $C_{1-6}$ alkyl, $C_2$-6 alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$;

each n, m, and p is independently 0 or 1;

t is 1, 2, or 3; and u is 0, 1, 2, or 3, wherein when $R_5$ and $R_6$ together with the atoms to which they are attached form a heterocyclyl or heteroaryl substituted with two $R_7$ and both $R_7$ are —O-methyl, then either (a) one of $R_2$ and $R_3$ is not —O-methyl; or (b) $R_x$ or $R_y$ is 5- to 10-membered heteroaryl comprising 1-4 heteroatoms selected from N, O, and S.

In one aspect, the present disclosure provides a compound of Formula (I):

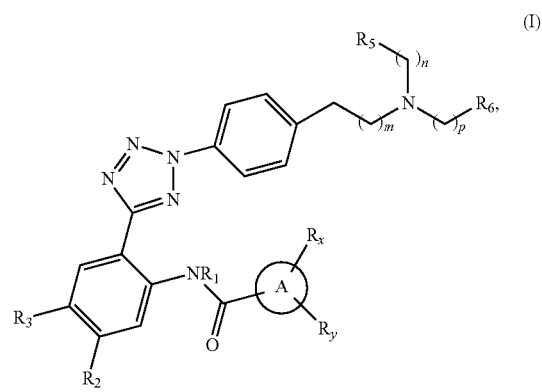

or a pharmaceutically acceptable prodrug, solvate, enantiomer, stereoisomer, tautomer, or salt thereof, wherein:

A is $C_{3-10}$ cycloalkyl, 3- to 14-membered heterocyclyl comprising 1-4 heteroatoms selected from N, O, and S, $C_{6-10}$ aryl, or 5- to 14-membered heteroaryl comprising 1-4 heteroatoms selected from N, O, and S, wherein the cycloalkyl or heterocyclyl is optionally substituted with oxo;

each $R_x$ and $R_y$ is independently H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)NR$_{11}$—S(O)$_2$$R_{11}$, —C(O)NR$_{11}$—S(O)$_2$—O$R_{11}$, —C(O)NR$_{11}$—S(O)$_2$—N($R_{11}$)$_2$, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each R₇ is independently oxo, halogen, —OH, —NH₂, —CN, —C(O)R₁₀, —C(O)OR₁₀, —C(O)N(R₁₀)₂, $C_{1-3}$ alkyl, $C_{2-6}$ alkenyl, $C_{2-6}$ alkynyl, $C_{1-6}$ alkoxy, —NH($C_{1-6}$ alkyl), —N($C_{1-6}$ alkyl)₂, —O—(CH₂)ₜ—R₈, —NH—(CH₂)ₜ—R₈, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more R₁₀;

R₈ is —OH, $C_{1-6}$ alkoxy, $C_{1-6}$ alkoxy-OH, —NH₂, —NH($C_{1-6}$ alkyl), —N($C_{1-6}$ alkyl)₂, —SH, —S($C_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl, or heteroaryl is optionally substituted by one or more R₉;

each R₉ is independently —(CH₂)ᵤ-(5- to 10-membered heteroaryl comprising 1-4 heteroatoms selected from N, O, and S) or —(CH₂)ᵤ—($C_{6-10}$ aryl), wherein the heteroaryl or aryl is optionally substituted with one or more halogen, —CN, —OH, or —NH₂;

each R₁₀ is independently halogen, —OH, —NH₂, —CN, $C_{1-6}$ alkyl, $C_{2-6}$ alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each R₁₁ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH₂, or two R₁₁ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH₂;

each n, m, and p is independently 0 or 1;

t is 1, 2, or 3; and u is 0, 1, 2, or 3, wherein when R₅ and R₆ together with the atoms to which they are attached form a heterocyclyl or heteroaryl substituted with two R₇, then one R₇ is not —O-methyl.

In one aspect, the present disclosure provides a compound of Formula (I'):

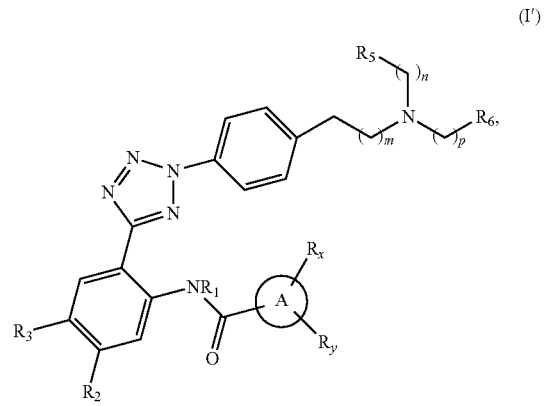

(I')

or a pharmaceutically acceptable prodrug, solvate, enantiomer, stereoisomer, tautomer, or salt thereof, wherein:

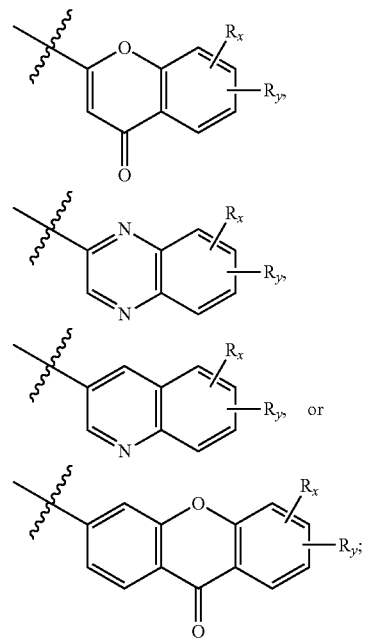

each Rₓ and Rᵧ is independently H, $C_{1-6}$ alkyl, $C_{2-6}$ alkenyl, $C_{2-6}$ alkynyl, $C_{1-6}$ alkoxy, halogen, —CN, —OH, —NH₂, 3- to 10-membered heterocyclyl comprising 1-4 heteroatoms selected from N, O, and S, or 5- to 10-membered heteroaryl comprising 1-4 heteroatoms selected from N, O, and S;

R₁ is H, $C_{1-6}$ alkyl, $C_{2-6}$ alkenyl, or $C_{2-6}$ alkynyl;

each R₂ and R₃ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)R₁₁, —C(O)OR₁₁, —C(O)N(R₁₁)₂, —C(O)NR₁₁—S(O)₂R₁₁, —C(O)NR₁₁—S(O)₂—OR₁₁, —C(O)NR₁₁—S(O)₂—N(R₁₁)₂, or —O-(5- to 10-membered heteroaryl comprising 1-4 heteroatoms selected from N, O, and S), wherein either R₂ or R₃ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each R₅ and R₆ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently oxo, halogen, —OH, —NH$_2$, —CN, —C(O)$R_{10}$, —C(O)O$R_{10}$, —C(O)N($R_{10}$)$_2$, $C_{1-3}$ alkyl, $C_{2-6}$ alkenyl, $C_{2-6}$ alkynyl, $C_{1-6}$ alkoxy, —NH($C_{1-6}$ alkyl), —N($C_{1-6}$ alkyl)$_2$, —O—(CH$_2$)$_t$—$R_8$, —NH—(CH$_2$)$_t$—$R_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$;

$R_8$ is —OH, $C_{1-6}$ alkoxy, $C_{1-6}$ alkoxy-OH, —NH$_2$, —NH($C_{1-6}$ alkyl), —N($C_{1-6}$ alkyl)$_2$, —SH, —S($C_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl, or heteroaryl is optionally substituted by one or more $R_9$;

each $R_9$ is independently —(CH$_2$)$_u$-(5- to 10-membered heteroaryl comprising 1-4 heteroatoms selected from N, O, and S) or —(CH$_2$)$_u$—($C_{6-10}$ aryl), wherein the heteroaryl or aryl is optionally substituted with one or more halogen, —CN, —OH, or —NH$_2$;

each $R_{10}$ is independently halogen, —OH, —NH$_2$, —CN, $C_{1-6}$ alkyl, $C_{2-6}$ alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$;

each n, m, and p is independently 0 or 1;

t is 1, 2, or 3; and u is 0, 1, 2, or 3, wherein when $R_5$ and $R_6$ together with the atoms to which they are attached form a heterocyclyl or heteroaryl substituted with two $R_7$, then one $R_7$ is not —O-methyl.

In one aspect, the present disclosure provides a compound of Formula (II):

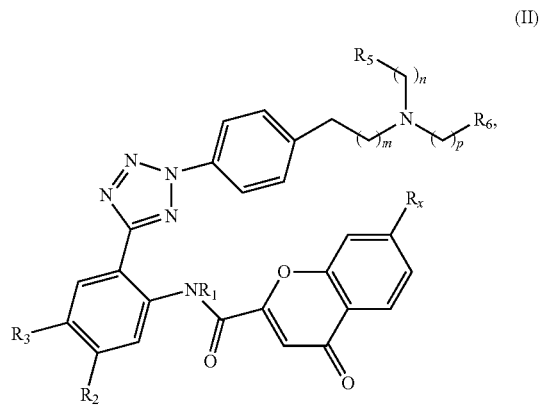

(II)

or a pharmaceutically acceptable prodrug, solvate, enantiomer, stereoisomer, tautomer, or salt thereof, wherein:

$R_x$ is H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)NR$_{11}$—S(O)$_2$$R_{11}$, —C(O)NR$_{11}$—S(O)$_2$—O$R_{11}$, —C(O)NR$_{11}$—S(O)$_2$—N($R_{11}$)$_2$, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently oxo, halogen, —OH, —NH$_2$, —CN, —C(O)$R_{10}$, —C(O)O$R_{10}$, —C(O)N($R_{10}$)$_2$, $C_{1-3}$ alkyl, $C_{2-6}$ alkenyl, $C_{2-6}$ alkynyl, $C_{1-6}$ alkoxy, —NH($C_{1-6}$ alkyl), —N($C_{1-6}$ alkyl)$_2$, —O—(CH$_2$)$_t$—$R_8$, —NH—(CH$_2$)$_t$—$R_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$;

$R_8$ is —OH, $C_{1-6}$ alkoxy, $C_{1-6}$ alkoxy-OH, —NH$_2$, —NH($C_{1-6}$ alkyl), —N($C_{1-6}$ alkyl)$_2$, —SH, —S($C_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl or heteroaryl is optionally substituted by one or more $R_9$;

each $R_9$ is independently —$(CH_2)_u$-(5- to 10-membered heteroaryl comprising 1-4 heteroatoms selected from N, O, and S) or —$(CH_2)_u$—($C_{6-10}$ aryl), wherein the heteroaryl or aryl is optionally substituted with one or more halogen, —CN, —OH, or —$NH_2$;

each $R_{10}$ is independently halogen, —OH, —$NH_2$, —CN, $C_{1-6}$ alkyl, $C_{2-6}$ alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —$NH_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —$NH_2$;

each n, m, and p is independently 0 or 1;

t is 1, 2, or 3; and u is 0, 1, 2, or 3, wherein when $R_5$ and $R_6$ together with the atoms to which they are attached form a heterocyclyl or heteroaryl substituted with two $R_7$, then one $R_7$ is not —O-methyl.

In one aspect, the present disclosure provides a compound of Formula (IA'):

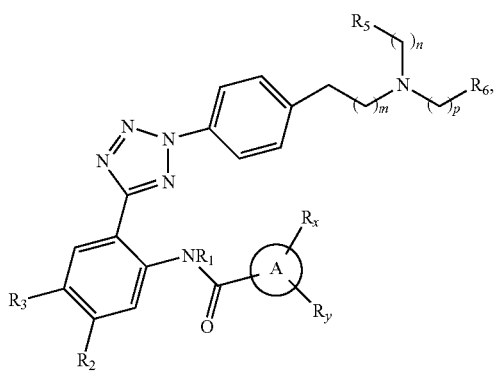

(IA')

or a pharmaceutically acceptable prodrug, solvate, enantiomer, stereoisomer, tautomer, or salt thereof, wherein:

A is $C_{3-10}$ cycloalkyl, 3- to 14-membered heterocyclyl comprising 1-4 heteroatoms selected from N, O, and S, $C_{6-10}$ aryl, or 5- to 14-membered heteroaryl comprising 1-4 heteroatoms selected from N, O, and S, wherein the cycloalkyl or heterocyclyl is optionally substituted with oxo;

each $R_x$ and $R_y$ is independently H or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, —O—$C_{1-6}$ alkyl, —O—$C_{2-6}$ alkenyl, —O—$C_{2-6}$ alkynyl, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

$R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently $C_{1-6}$ alkoxy; and each n, m, and p is independently 0 or 1, wherein (a) one of $R_2$ and $R_3$ is not —O-methyl; or (b) $R_x$ or $R_y$ is 5- to 10-membered heteroaryl comprising 1-4 heteroatoms selected from N, O, and S.

In one aspect, the present disclosure provides a compound obtainable by, or obtained by, a method for preparing a compound as described herein (e.g., a method comprising one or more steps described in Schemes 1-6).

In one aspect, the present disclosure provides a pharmaceutical composition comprising a compound of the present disclosure, or a pharmaceutically acceptable prodrug, solvate, enantiomer, stereoisomer, tautomer, or salt thereof, and a pharmaceutically acceptable diluent or carrier.

In one aspect, the present disclosure provides an intermediate as described herein, being suitable for use in a method for preparing a compound as described herein (e.g., the intermediate is selected from the intermediates described in Examples 1-16).

In one aspect, the present disclosure provides a method of modulating P-glycoprotein activity (e.g., in vitro or in vivo) and/or cytochrome P450 activity (e.g., in vitro or in vivo), comprising contacting a cell with an effective amount of a compound of the present disclosure or a pharmaceutically acceptable prodrug, solvate, enantiomer, stereoisomer, tautomer, or salt thereof.

In one aspect, the present disclosure provides a method of treating or preventing a disease or disorder disclosed herein in a subject in need thereof, comprising administering to the subject a therapeutically effective amount of a compound of the present disclosure or a pharmaceutically acceptable prodrug, solvate, enantiomer, stereoisomer, tautomer, or salt thereof, or a pharmaceutical composition of the present disclosure.

In one aspect, the present disclosure provides a compound of the present disclosure or a pharmaceutically acceptable prodrug, solvate, enantiomer, stereoisomer, tautomer, or salt thereof for use in modulating P-glycoprotein activity (e.g., in vitro or in vivo) and/or cytochrome P450 activity (e.g., in vitro or in vivo).

In one aspect, the present disclosure provides a compound of the present disclosure or a pharmaceutically acceptable prodrug, solvate, enantiomer, stereoisomer, tautomer, or salt thereof for use in treating or preventing a disease or disorder disclosed herein.

In one aspect, the present disclosure provides use of a compound of the present disclosure or a pharmaceutically acceptable prodrug, solvate, enantiomer, stereoisomer, tautomer, or salt thereof in the manufacture of a medicament for modulating P-glycoprotein activity (e.g., in vitro or in vivo) and/or cytochrome P450 activity (e.g., in vitro or in vivo).

In one aspect, the present disclosure provides use of a compound of the present disclosure or a pharmaceutically acceptable prodrug, solvate, enantiomer, stereoisomer, tautomer, or salt thereof in the manufacture of a medicament for treating or preventing a disease or disorder disclosed herein.

In one aspect, the present disclosure provides a method of preparing a compound of the present disclosure.

In one aspect, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the present disclosure. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Compounds of the Present Disclosure

In one aspect, the present disclosure provides a compound of Formula (IA):

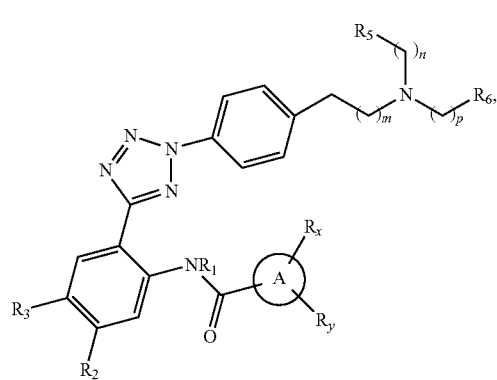

(IA)

or a pharmaceutically acceptable prodrug, solvate, enantiomer, stereoisomer, tautomer, or salt thereof, wherein:

A is $C_{3-10}$ cycloalkyl, 3- to 14-membered heterocyclyl comprising 1-4 heteroatoms selected from N, O, and S, $C_{6-10}$ aryl, or 5- to 14-membered heteroaryl comprising 1-4 heteroatoms selected from N, O, and S, wherein the cycloalkyl or heterocyclyl is optionally substituted with oxo;

each $R_x$ and $R_y$ is independently H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)R$_{11}$, —C(O)OR$_{11}$, —C(O)N(R$_{11}$)$_2$, —C(O)NR$_{11}$—S(O)$_2$R$_{11}$, —C(O)NR$_{11}$—S(O)$_2$—OR$_{11}$, —C(O)NR$_{11}$—S(O)$_2$—N(R$_{11}$)$_2$, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)R$_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently oxo, halogen, —OH, —NH$_2$, —CN, —C(O)R$_{10}$, —C(O)OR$_{10}$, —C(O)N(R$_{10}$)$_2$, $C_{1-3}$ alkyl, $C_{2-6}$ alkenyl, $C_{2-6}$ alkynyl, $C_{1-6}$ alkoxy, —NH($C_{1-6}$ alkyl), —N($C_{1-6}$ alkyl)$_2$, —O—(CH$_2$)$_t$—R$_8$, —NH—(CH$_2$)$_t$—R$_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$;

$R_8$ is —OH, $C_{1-6}$ alkoxy, $C_{1-6}$ alkoxy-OH, —NH$_2$, —NH($C_{1-6}$ alkyl), —N($C_{1-6}$ alkyl)$_2$, —SH, —S($C_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl, or heteroaryl is optionally substituted by one or more $R_9$;

each $R_9$ is independently —(CH$_2$)$_u$-(5- to 10-membered heteroaryl comprising 1-4 heteroatoms selected from N, O, and S) or —(CH$_2$)$_u$—($C_{6-10}$ aryl), wherein the heteroaryl or aryl is optionally substituted with one or more halogen, —CN, —OH, or —NH$_2$;

each $R_{10}$ is independently halogen, —OH, —NH$_2$, —CN, $C_{1-6}$ alkyl, $C_{2-6}$ alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$;

each n, m, and p is independently 0 or 1;

t is 1, 2, or 3; and u is 0, 1, 2, or 3, wherein when $R_5$ and $R_6$ together with the atoms to which they are attached form a heterocyclyl or heteroaryl substituted with two $R_7$ and both $R_7$ are —O-methyl, then either (a) one of $R_2$ and $R_3$ is not —O-methyl; or (b) $R_x$ or $R_y$ is 5- to 10-membered heteroaryl comprising 1-4 heteroatoms selected from N, O, and S.

In one aspect, the present disclosure provides a compound of Formula (I):

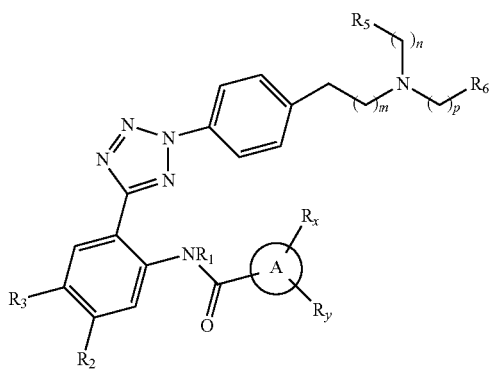

(I)

or a pharmaceutically acceptable prodrug, solvate, enantiomer, stereoisomer, tautomer, or salt thereof, wherein:

A is $C_{3-10}$ cycloalkyl, 3- to 14-membered heterocyclyl comprising 1-4 heteroatoms selected from N, O, and S, $C_{6-10}$ aryl, or 5- to 14-membered heteroaryl comprising 1-4 heteroatoms selected from N, O, and S, wherein the cycloalkyl or heterocyclyl is optionally substituted with oxo;

each $R_x$ and $R_y$ is independently H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)R$_{11}$, —C(O)OR$_{11}$, —C(O)N(R$_{11}$)$_2$, —C(O)NR$_{11}$—S(O)$_2$R$_{11}$, —C(O)NR$_{11}$—S(O)$_2$—OR$_{11}$, —C(O)NR$_{11}$—S(O)$_2$—N(R$_{11}$)$_2$, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)R$_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently oxo, halogen, —OH, —NH$_2$, —CN, —C(O)R$_{10}$, —C(O)OR$_{10}$, —C(O)N(R$_{10}$)$_2$, $C_{1-3}$ alkyl, $C_{2-6}$ alkenyl, $C_{2-6}$ alkynyl, $C_{1-6}$ alkoxy, —NH(C$_{1-6}$ alkyl), —N(C$_{1-6}$ alkyl)$_2$, —O—(CH$_2$)$_t$—R$_8$, —NH—(CH$_2$)$_t$—R$_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$;

$R_8$ is —OH, $C_{1-6}$ alkoxy, $C_{1-6}$ alkoxy-OH, —NH$_2$, —NH(C$_{1-6}$ alkyl), —N(C$_{1-6}$ alkyl)$_2$, —SH, —S(C$_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl, or heteroaryl is optionally substituted by one or more $R_9$;

each $R_9$ is independently —(CH$_2$)$_u$-(5- to 10-membered heteroaryl comprising 1-4 heteroatoms selected from N, O, and S) or —(CH$_2$)$_u$—(C$_{6-10}$ aryl), wherein the heteroaryl or aryl is optionally substituted with one or more halogen, —CN, —OH, or —NH$_2$;

each $R_{10}$ is independently halogen, —OH, —NH$_2$, —CN, $C_{1-6}$ alkyl, $C_{2-6}$ alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$;

each n, m, and p is independently 0 or 1;
t is 1, 2, or 3; and
u is 0, 1, 2, or 3,
wherein when $R_5$ and $R_6$ together with the atoms to which they are attached form a heterocyclyl or heteroaryl substituted with two $R_7$, then one $R_7$ is not —O-methyl.

In one aspect, the present disclosure provides a compound of Formula (I'):

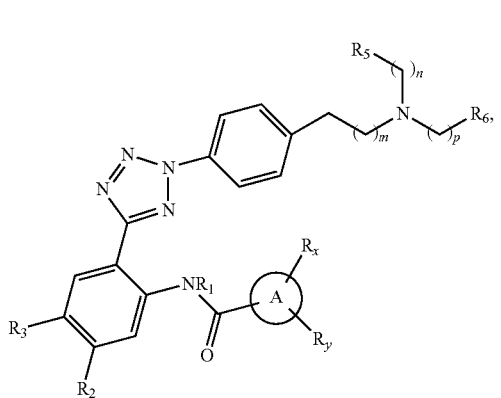

(I')

or a pharmaceutically acceptable prodrug, solvate, enantiomer, stereoisomer, tautomer, or salt thereof, wherein:
A is

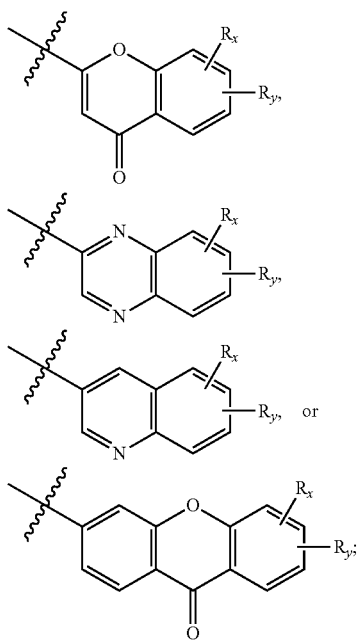

each $R_x$ and $R_y$ is independently H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S;
$R_1$ is H, $C_{1-6}$ alkyl, $C_{2-6}$ alkenyl, or $C_{2-6}$ alkynyl;
each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)R$_{11}$, —C(O)OR$_{11}$, —C(O)N(R$_{11}$)$_2$, —C(O)NR$_{11}$—S(O)$_2$R$_{11}$, —C(O)NR$_{11}$—S(O)$_2$—OR$_{11}$, —C(O)NR$_{11}$—S(O)$_2$—N(R$_{11}$)$_2$, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)R$_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently oxo, halogen, —OH, —NH$_2$, —CN, —C(O)R$_{10}$, —C(O)OR$_{10}$, —C(O)N(R$_{10}$)$_2$, $C_{1-3}$ alkyl, $C_{2-6}$ alkenyl, $C_{2-6}$ alkynyl, $C_{1-6}$ alkoxy, —NH($C_{1-6}$ alkyl), —N($C_{1-6}$ alkyl)$_2$, —O—(CH$_2$)$_t$—R$_8$, —NH—(CH$_2$)$_t$—R$_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$;

$R_8$ is —OH, $C_{1-6}$ alkoxy, $C_{1-6}$ alkoxy-OH, —NH$_2$, —NH($C_{1-6}$ alkyl), —N($C_{1-6}$ alkyl)$_2$, —SH, —S($C_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl, or heteroaryl is optionally substituted by one or more $R_9$;

each $R_9$ is independently —(CH$_2$)$_u$-(5- to 10-membered heteroaryl comprising 1-4 heteroatoms selected from N, O, and S) or —(CH$_2$)$_u$—($C_{6-10}$ aryl), wherein the heteroaryl or aryl is optionally substituted with one or more halogen, —CN, —OH, or —NH$_2$;

each $R_{10}$ is independently halogen, —OH, —NH$_2$, —CN, $C_{1-6}$ alkyl, $C_{2-6}$ alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$;

each n, m, and p is independently 0 or 1;

t is 1, 2, or 3; and u is 0, 1, 2, or 3, wherein when $R_5$ and $R_6$ together with the atoms to which they are attached form a heterocyclyl or heteroaryl substituted with two $R_7$, then one $R_7$ is not —O-methyl.

In one aspect, the present disclosure provides a compound of Formula (II):

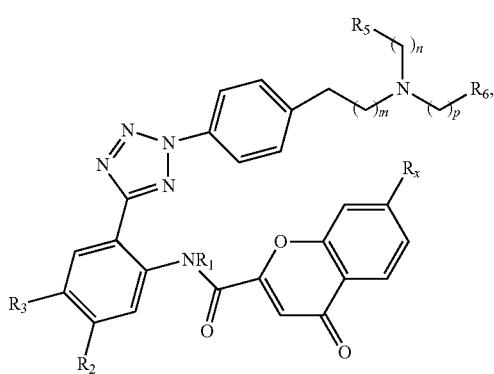

(II)

or a pharmaceutically acceptable prodrug, solvate, enantiomer, stereoisomer, tautomer, or salt thereof, wherein:

$R_x$ is H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2$$R_{11}$, —C(O)N$R_{11}$—S(O)$_2$—O$R_{11}$, —C(O)N$R_{11}$—S(O)$_2$—N($R_{11}$)$_2$, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently oxo, halogen, —OH, —NH$_2$, —CN, —C(O)$R_{10}$, —C(O)O$R_{10}$, —C(O)N($R_{10}$)$_2$, $C_{1-3}$ alkyl, $C_{2-6}$ alkenyl, $C_{2-6}$ alkynyl, $C_{1-6}$ alkoxy, —NH($C_{1-6}$ alkyl), —N($C_{1-6}$ alkyl)$_2$, —O—(CH$_2$)$_t$—$R_8$, —NH—(CH$_2$)$_t$—$R_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$;

$R_8$ is —OH, $C_{1-6}$ alkoxy, $C_{1-6}$ alkoxy-OH, —NH$_2$, —NH($C_{1-6}$ alkyl), —N($C_{1-6}$ alkyl)$_2$, —SH, —S($C_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl or heteroaryl is optionally substituted by one or more $R_9$;

each $R_9$ is independently —(CH$_2$)$_u$-(5- to 10-membered heteroaryl comprising 1-4 heteroatoms selected from N, O, and S) or —(CH$_2$)$_u$—(C$_{6-10}$ aryl), wherein the heteroaryl or aryl is optionally substituted with one or more halogen, —CN, —OH, or —NH$_2$;

each $R_{10}$ is independently halogen, —OH, —NH$_2$, —CN, $C_{1-6}$ alkyl, $C_{2-6}$ alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$;

each n, m, and p is independently 0 or 1;

t is 1, 2, or 3; and u is 0, 1, 2, or 3, wherein when $R_5$ and $R_6$ together with the atoms to which they are attached form a heterocyclyl or heteroaryl substituted with two $R_7$, then one $R_7$ is not —O-methyl.

In one aspect, the present disclosure provides a compound of Formula (IA'):

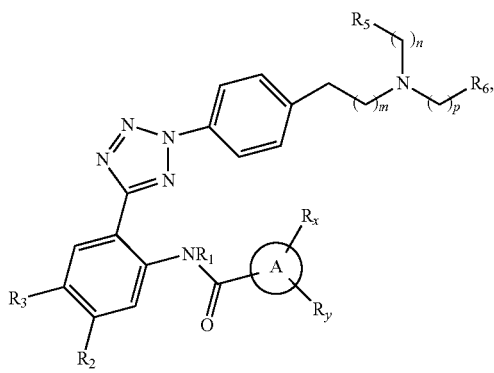

(IA')

or a pharmaceutically acceptable prodrug, solvate, enantiomer, stereoisomer, tautomer, or salt thereof, wherein:

A is $C_{3-10}$ cycloalkyl, 3- to 14-membered heterocyclyl comprising 1-4 heteroatoms selected from N, O, and S, $C_{6-10}$ aryl, or 5- to 14-membered heteroaryl comprising 1-4 heteroatoms selected from N, O, and S, wherein the cycloalkyl or heterocyclyl is optionally substituted with oxo;

each $R_x$ and $R_y$ is independently H or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, —O—$C_{1-6}$ alkyl, —O—$C_{2-6}$ alkenyl, —O—$C_{2-6}$ alkynyl, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

$R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently $C_{1-6}$ alkoxy; and each n, m, and p is independently 0 or 1, wherein (a) one of $R_2$ and $R_3$ is not —O-methyl; or (b) $R_x$ or $R_y$ is 5- to 10-membered heteroaryl comprising 1-4 heteroatoms selected from N, O, and S.

It is understood that, for a compound of Formula (IA), (I), (I'), (II), or (IA'), A, $R_x$, $R_y$, $R_1$, $R_2$, $R_3$, $R_5$, $R_6$, $R_7$, $R_8$, $R_9$, $R_{10}$, $R_{11}$, n, m, p, t, and u can each be, where applicable, selected from the groups described herein, and any group described herein for any of A, $R_x$, $R_y$, $R_1$, $R_2$, $R_3$, $R_5$, $R_6$, $R_7$, $R_8$, $R_9$, $R_{10}$, $R_{11}$, n, m, p, t, and u can be combined, where applicable, with any group described herein for one or more of the remainder of A, $R_x$, $R_y$, $R_1$, $R_2$, $R_3$, $R_5$, $R_6$, $R_7$, $R_8$, $R_9$, $R_{10}$, $R_{11}$, n, m, p, t, and u.

In some embodiments, a N atom of the compound is an N-oxide.

In some embodiments, the N-oxide has the formula

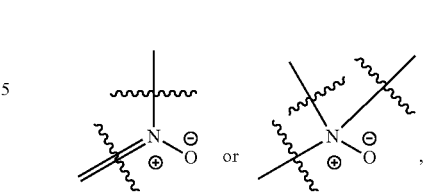

wherein $\xi$ indicates attachment to the compound of Formula (IA), (I), (I'), (II), or (IA').

In some embodiments, the N-oxide has the formula

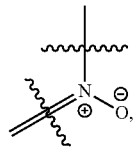

wherein $\xi$ indicates attachment to the compound of Formula (IA), (I), (I'), (II), or (IA').

In some embodiments, the N-oxide has the formula

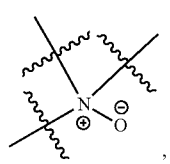

wherein $\xi$ indicates attachment to the compound of Formula (IA), (I), (I'), (II), or (IA').

In some embodiments, A is $C_{3-10}$ cycloalkyl, 3- to 14-membered heterocyclyl comprising 1-4 heteroatoms selected from N, O, and S, $C_{6-10}$ aryl, or 5- to 14-membered heteroaryl comprising 1-4 heteroatoms selected from N, O, and S, wherein the cycloalkyl or heterocyclyl is optionally substituted with oxo.

In some embodiments, A is $C_{3-10}$ cycloalkyl, 3- to 14-membered heterocyclyl comprising 1-4 heteroatoms selected from N, O, and S, $C_{6-10}$ aryl, or 5- to 14-membered heteroaryl comprising 1-4 heteroatoms selected from N, O, and S.

In some embodiments, A is $C_{3-10}$ cycloalkyl or 3- to 14-membered heterocyclyl comprising 1-4 heteroatoms selected from N, O, and S, wherein the cycloalkyl or heterocyclyl is optionally substituted with oxo.

In some embodiments, A is $C_{3-10}$ cycloalkyl or 3- to 14-membered heterocyclyl comprising 1-4 heteroatoms selected from N, O, and S.

In some embodiments, A is $C_{3-10}$ cycloalkyl optionally substituted with oxo.

In some embodiments, A is $C_3$ cycloalkyl. In some embodiments, A is $C_4$ cycloalkyl. In some embodiments, A is $C_5$ cycloalkyl. In some embodiments, A is $C_6$ cycloalkyl. In some embodiments, A is $C_7$ cycloalkyl. In some embodiments, A is $C_8$ cycloalkyl. In some embodiments, A is $C_9$ cycloalkyl. In some embodiments, A is $C_{10}$ cycloalkyl.

In some embodiments, A is $C_3$ cycloalkyl optionally substituted with oxo. In some embodiments, A is $C_4$ cycloalkyl optionally substituted with oxo. In some embodiments, A is $C_5$ cycloalkyl optionally substituted with oxo. In some embodiments, A is $C_6$ cycloalkyl optionally substituted with oxo. In some embodiments, A is $C_7$ cycloalkyl optionally substituted with oxo. In some embodiments, A is $C_8$ cycloalkyl optionally substituted with oxo. In some embodiments, A is $C_9$ cycloalkyl optionally substituted with oxo. In some embodiments, A is $C_{10}$ cycloalkyl optionally substituted with oxo.

In some embodiments, A is $C_3$-$C_7$ monocyclic cycloalkyl. In some embodiments, A is $C_3$-$C_7$ monocyclic saturated cycloalkyl. In some embodiments, A is $C_3$-$C_7$ monocyclic partially saturated cycloalkyl. In some embodiments, A is $C_9$-$C_{10}$ bicyclic cycloalkyl. In some embodiments, A is $C_9$-$C_{10}$ bicyclic saturated cycloalkyl. In some embodiments, A is $C_9$-$C_{10}$ bicyclic partially saturated cycloalkyl. In some embodiments, A is $C_5$-$C_{10}$ polycyclic cycloalkyl.

In some embodiments, A is $C_3$-$C_7$ monocyclic cycloalkyl optionally substituted with oxo. In some embodiments, A is $C_3$-$C_7$ monocyclic saturated cycloalkyl optionally substituted with oxo. In some embodiments, A is $C_3$-$C_7$ monocyclic partially saturated cycloalkyl optionally substituted with oxo. In some embodiments, A is $C_9$-$C_{10}$ bicyclic cycloalkyl optionally substituted with oxo. In some embodiments, A is $C_9$-$C_{10}$ bicyclic saturated cycloalkyl optionally substituted with oxo. In some embodiments, A is $C_9$-$C_{10}$ bicyclic partially saturated cycloalkyl optionally substituted with oxo. In some embodiments, A is $C_5$-$C_{10}$ polycyclic cycloalkyl optionally substituted with oxo.

In some embodiments, A is 3- to 14-membered heterocyclyl comprising 1-4 heteroatoms selected from N, O, and S.

In some embodiments, A is 3- to 14-membered heterocyclyl comprising 1-4 heteroatoms selected from N, O, and S, optionally substituted with oxo.

In some embodiments, A is 3- to 10-membered heterocyclyl comprising 1-4 heteroatoms selected from N, O, and S.

In some embodiments, A is 3- to 10-membered heterocyclyl comprising 1-4 heteroatoms selected from N, O, and S, optionally substituted with oxo.

In some embodiments, A is 3-membered heterocyclyl comprising 1 heteroatom selected from N, O, and S. In some embodiments, A is 4-membered heterocyclyl comprising 1-2 heteroatoms selected from N, O, and S. In some embodiments, A is 5-membered heterocyclyl comprising 1-3 heteroatoms selected from N, O, and S. In some embodiments, A is 6-membered heterocyclyl comprising 1-4 heteroatoms selected from N, O, and S. In some embodiments, A is 7-membered heterocyclyl comprising 1-4 heteroatoms selected from N, O, and S. In some embodiments, A is 8-membered heterocyclyl comprising 1-4 heteroatoms selected from N, O, and S. In some embodiments, A is 9-membered heterocyclyl comprising 1-4 heteroatoms selected from N, O, and S. In some embodiments, A is 10-membered heterocyclyl comprising 1-4 heteroatoms selected from N, O, and S. In some embodiments, A is 11-membered heterocyclyl comprising 1-4 heteroatoms selected from N, O, and S. In some embodiments, A is 12-membered heterocyclyl comprising 1-4 heteroatoms selected from N, O, and S. In some embodiments, A is 13-membered heterocyclyl comprising 1-4 heteroatoms selected from N, O, and S. In some embodiments, A is 14-membered heterocyclyl comprising 1-4 heteroatoms selected from N, O, and S.

In some embodiments, A is 3-membered heterocyclyl comprising 1 heteroatom selected from N, O, and S, optionally substituted with oxo. In some embodiments, A is 4-membered heterocyclyl comprising 1-2 heteroatoms selected from N, O, and S, optionally substituted with oxo. In some embodiments, A is 5-membered heterocyclyl comprising 1-3 heteroatoms selected from N, O, and S, optionally substituted with oxo. In some embodiments, A is 6-membered heterocyclyl comprising 1-4 heteroatoms selected from N, O, and S, optionally substituted with oxo. In some embodiments, A is 7-membered heterocyclyl comprising 1-4 heteroatoms selected from N, O, and S, optionally substituted with oxo. In some embodiments, A is 8-membered heterocyclyl comprising 1-4 heteroatoms selected from N, O, and S, optionally substituted with oxo. In some embodiments, A is 9-membered heterocyclyl comprising 1-4 heteroatoms selected from N, O, and S, optionally substituted with oxo. In some embodiments, A is 10-membered heterocyclyl comprising 1-4 heteroatoms selected from N, O, and S, optionally substituted with oxo. In some embodiments, A is 11-membered heterocyclyl comprising 1-4 heteroatoms selected from N, O, and S, optionally substituted with oxo. In some embodiments, A is 12-membered heterocyclyl comprising 1-4 heteroatoms selected from N, O, and S, optionally substituted with oxo. In some embodiments, A is 13-membered heterocyclyl comprising 1-4 heteroatoms selected from N, O, and S, optionally substituted with oxo. In some embodiments, A is 14-membered heterocyclyl comprising 1-4 heteroatoms selected from N, O, and S, optionally substituted with oxo.

In some embodiments, A is 7- to 10-membered bicyclic heterocyclyl comprising 1-4 heteroatoms selected from N, O, and S.

In some embodiments, A is 7- to 10-membered bicyclic heterocyclyl comprising 1-4 heteroatoms selected from N, O, and S, optionally substituted with oxo.

In some embodiments, A is 7-membered bicyclic heterocyclyl comprising 1-4 heteroatoms selected from N, O, and S. In some embodiments, A is 8-membered bicyclic heterocyclyl comprising 1-4 heteroatoms selected from N, O, and S. In some embodiments, A is 9-membered bicyclic heterocyclyl comprising 1-4 heteroatoms selected from N, O, and S. In some embodiments, A is 10-membered bicyclic heterocyclyl comprising 1-4 heteroatoms selected from N, O, and S.

In some embodiments, A is 7-membered bicyclic heterocyclyl comprising 1-4 heteroatoms selected from N, O, and S, optionally substituted with oxo. In some embodiments, A is 8-membered bicyclic heterocyclyl comprising 1-4 heteroatoms selected from N, O, and S, optionally substituted with oxo. In some embodiments, A is 9-membered bicyclic heterocyclyl comprising 1-4 heteroatoms selected from N, O, and S, optionally substituted with oxo. In some embodiments, A is 10-membered bicyclic heterocyclyl comprising 1-4 heteroatoms selected from N, O, and S, optionally substituted with oxo.

In some embodiments, A is 8- to 14-membered polycyclic heterocyclyl comprising 1-4 heteroatoms selected from N, O, and S.

In some embodiments, A is 8- to 14-membered polycyclic heterocyclyl comprising 1-4 heteroatoms selected from N, O, and S, optionally substituted with oxo.

In some embodiments, A is 8- to 10-membered polycyclic heterocyclyl comprising 1-4 heteroatoms selected from N, O, and S.

In some embodiments, A is 8- to 10-membered polycyclic heterocyclyl comprising 1-4 heteroatoms selected from N, O, and S, optionally substituted with oxo.

In some embodiments, A is 14-membered polycyclic heterocyclyl comprising 1-4 heteroatoms selected from N, O, and S.

In some embodiments, A is 14-membered polycyclic heterocyclyl comprising 1-4 heteroatoms selected from N, O, and S, optionally substituted with oxo.

In some embodiments, A is 14-membered polycyclic heterocyclyl comprising 1-4 heteroatoms selected from N, O, and S, substituted with oxo.

In some embodiments, A is $C_{6-10}$ aryl or 5- to 10-membered heteroaryl comprising 1-4 heteroatoms selected from N, O, and S.

In some embodiments, A is $C_{6-10}$ aryl. In some embodiments, A is $C_5$-$C_6$ aryl. In some embodiments, A is phenyl.

In some embodiments, A is 5- to 14-membered heteroaryl comprising 1-4 heteroatoms selected from N, O, and S.

In some embodiments, A is 5- to 10-membered heteroaryl comprising 1-4 heteroatoms selected from N, O, and S.

In some embodiments, A is 5-membered heteroaryl comprising 1-4 heteroatoms selected from N, O, and S. In some embodiments, A is 6-membered heteroaryl comprising 1-4 heteroatoms selected from N, O, and S. In some embodiments, A is 7-membered heteroaryl comprising 1-4 heteroatoms selected from N, O, and S. In some embodiments, A is 8-membered heteroaryl comprising 1-4 heteroatoms selected from N, O, and S. In some embodiments, A is 9-membered heteroaryl comprising 1-4 heteroatoms selected from N, O, and S. In some embodiments, A is 10-membered heteroaryl comprising 1-4 heteroatoms selected from N, O, and S. In some embodiments, A is 11-membered heteroaryl comprising 1-4 heteroatoms selected from N, O, and S. In some embodiments, A is 12-membered heteroaryl comprising 1-4 heteroatoms selected from N, O, and S. In some embodiments, A is 13-membered heteroaryl comprising 1-4 heteroatoms selected from N, O, and S. In some embodiments, A is 14-membered heteroaryl comprising 1-4 heteroatoms selected from N, O, and S.

In some embodiments, A is 9- to 10-membered bicyclic heteroaryl comprising 1-4 heteroatoms selected from N, O, and S.

In some embodiments, A is 9-membered bicyclic heteroaryl comprising 1-4 heteroatoms selected from N, O, and S. In some embodiments, A is 10-membered bicyclic heteroaryl comprising 1-4 heteroatoms selected from N, O, and S.

In some embodiments, A is 9- to 10-membered polycyclic heteroaryl comprising 1-4 heteroatoms selected from N, O, and S.

In some embodiments, A is

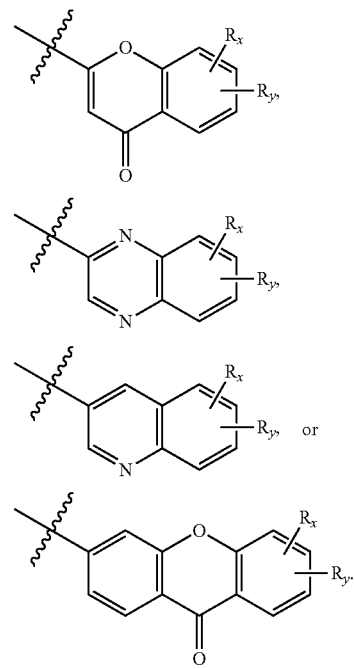

In some embodiments, A is

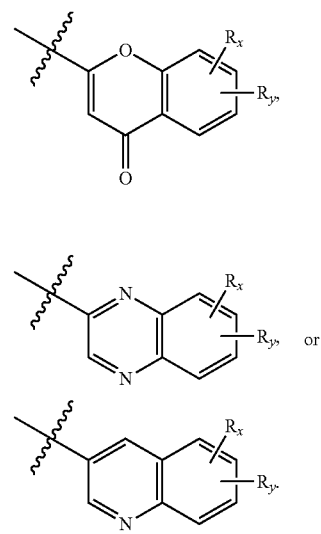

In some embodiments, A is

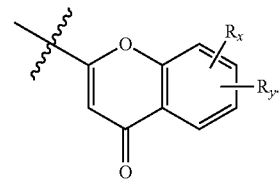

In some embodiments, A is

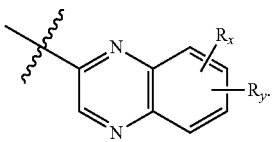

In some embodiments, A is

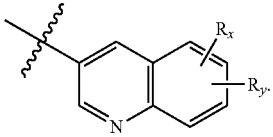

In some embodiments, A is

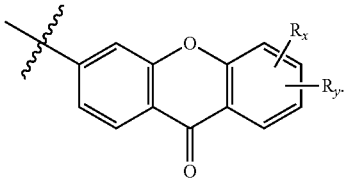

In some embodiments, each $R_x$ and $R_y$ is independently H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S.

In some embodiments, each $R_x$ and $R_y$ is independently H, $C_{1-6}$ alkyl, $C_{2-6}$ alkenyl, $C_{2-6}$ alkynyl, $C_{1-6}$ alkoxy, halogen, —CN, —OH, or —NH$_2$.

In some embodiments, each $R_x$ and $R_y$ is H.

In some embodiments, each $R_x$ and $R_y$ is independently $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S.

In some embodiments, each $R_x$ and $R_y$ is independently $C_{1-6}$ alkyl, $C_{2-6}$ alkenyl, $C_{2-6}$ alkynyl, $C_{1-6}$ alkoxy, halogen, —CN, —OH, or —NH$_2$.

In some embodiments, each $R_x$ and $R_y$ is independently 3- to 10-membered heterocyclyl comprising 1-4 heteroatoms selected from N, O, and S, or 5- to 10-membered heteroaryl comprising 1-4 heteroatoms selected from N, O, and S.

In some embodiments, each $R_x$ and $R_y$ is independently H, $C_{1-6}$ alkyl, or —OH.

In some embodiments, $R_x$ is H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S.

In some embodiments, $R_x$ is H, $C_{1-6}$ alkyl, $C_{2-6}$ alkenyl, $C_{2-6}$ alkynyl, $C_{1-6}$ alkoxy, halogen, —CN, —OH, or —NH$_2$.

In some embodiments, $R_x$ is H.

In some embodiments, $R_x$ is $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S.

In some embodiments, $R_x$ is $C_{1-6}$ alkyl, $C_{2-6}$ alkenyl, $C_{2-6}$ alkynyl, $C_{1-6}$ alkoxy, halogen, —CN, —OH, or —NH$_2$.

In some embodiments, $R_x$ is $C_{1-6}$ alkyl, $C_{2-6}$ alkenyl, $C_{2-6}$ alkynyl, or $C_{1-6}$ alkoxy.

In some embodiments, $R_x$ is $C_{1-6}$ alkyl, $C_{2-6}$ alkenyl, or $C_{2-6}$ alkynyl.

In some embodiments, $R_x$ is $C_{1-6}$ alkyl. In some embodiments, $R_x$ is methyl. In some embodiments, $R_x$ is ethyl. In some embodiments, $R_x$ is propyl. In some embodiments, $R_x$ is butyl. In some embodiments, $R_x$ is pentyl. In some embodiments, $R_x$ is hexyl. In some embodiments, $R_x$ is isopropyl. In some embodiments, $R_x$ is isobutyl. In some embodiments, $R_x$ is isopentyl. In some embodiments, $R_x$ is isohexyl. In some embodiments, $R_x$ is secbutyl. In some embodiments, $R_x$ is secpentyl. In some embodiments, $R_x$ is sechexyl. In some embodiments, $R_x$ is tertbutyl.

In some embodiments, $R_x$ is $C_{2-6}$ alkenyl. In some embodiments, $R_x$ is $C_2$ alkenyl. In some embodiments, $R_x$ is $C_3$ alkenyl. In some embodiments, $R_x$ is $C_4$ alkenyl. In some embodiments, $R_x$ is $C_5$ alkenyl. In some embodiments, $R_x$ is $C_6$ alkenyl.

In some embodiments, $R_x$ is $C_{2-6}$ alkynyl. In some embodiments, $R_x$ is $C_2$ alkynyl. In some embodiments, $R_x$ is $C_3$ alkynyl. In some embodiments, $R_x$ is $C_4$ alkynyl. In some embodiments, $R_x$ is $C_5$ alkynyl. In some embodiments, $R_x$ is $C_6$ alkynyl.

In some embodiments, $R_x$ is $C_{1-6}$ alkoxy. In some embodiments, $R_x$ is methoxy. In some embodiments, $R_x$ is ethoxy. In some embodiments, $R_x$ is propoxy. In some embodiments, $R_x$ is butoxy. In some embodiments, $R_x$ is pentoxy. In some embodiments, $R_x$ is hexoxy.

In some embodiments, $R_x$ is halogen, —CN, —OH, or —NH$_2$.

In some embodiments, $R_x$ is halogen. In some embodiments, $R_x$ is F, Cl, Br, or I. In some embodiments, $R_x$ is F, Cl, or Br. In some embodiments, $R_x$ is F. In some embodiments, $R_x$ is Cl. In some embodiments, $R_x$ is Br. In some embodiments, $R_x$ is I.

In some embodiments, $R_x$ is —CN. In some embodiments, $R_x$ is —OH. In some embodiments, $R_x$ is —NH$_2$.

In some embodiments, $R_x$ is 3- to 10-membered heterocyclyl comprising 1-4 heteroatoms selected from N, O, and S, or 5- to 10-membered heteroaryl comprising 1-4 heteroatoms selected from N, O, and S.

In some embodiments, $R_x$ is 3- to 10-membered heterocyclyl comprising 1-4 heteroatoms selected from N, O, and S.

In some embodiments, $R_x$ is 3-membered heterocyclyl comprising 1-4 heteroatoms selected from N, O, and S. In some embodiments, $R_x$ is 4-membered heterocyclyl comprising 1-4 heteroatoms selected from N, O, and S. In some embodiments, $R_x$ is 5-membered heterocyclyl comprising 1-4 heteroatoms selected from N, O, and S. In some embodiments, $R_x$ is 6-membered heterocyclyl comprising 1-4 heteroatoms selected from N, O, and S. In some embodiments, $R_x$ is 7-membered heterocyclyl comprising 1-4 heteroatoms selected from N, O, and S. In some embodiments, $R_x$ is 8-membered heterocyclyl comprising 1-4 heteroatoms selected from N, O, and S. In some embodiments, $R_x$ is 9-membered heterocyclyl comprising 1-4 heteroatoms selected from N, O, and S. In some embodiments, $R_x$ is 10-membered heterocyclyl comprising 1-4 heteroatoms selected from N, O, and S.

In some embodiments, $R_x$ is 5- to 10-membered heteroaryl comprising 1-4 heteroatoms selected from N, O, and S.

In some embodiments, $R_x$ is 5-membered heteroaryl comprising 1-4 heteroatoms selected from N, O, and S. In some embodiments, $R_x$ is 6-membered heteroaryl comprising 1-4 heteroatoms selected from N, O, and S. In some embodiments, $R_x$ is 7-membered heteroaryl comprising 1-4 heteroatoms selected from N, O, and S. In some embodiments, $R_x$ is 8-membered heteroaryl comprising 1-4 heteroatoms selected from N, O, and S. In some embodiments, $R_x$ is 9-membered heteroaryl comprising 1-4 heteroatoms selected from N, O, and S. In some embodiments, $R_x$ is 10-membered heteroaryl comprising 1-4 heteroatoms selected from N, O, and S.

In some embodiments, each $R_x$ is H, $C_{1-6}$ alkyl, or —OH.

In some embodiments, $R_y$ is H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S.

In some embodiments, $R_y$ is H, $C_{1-6}$ alkyl, $C_{2-6}$ alkenyl, $C_{2-6}$ alkynyl, $C_{1-6}$ alkoxy, halogen, —CN, —OH, or —NH$_2$.

In some embodiments, $R_y$ is H.

In some embodiments, $R_y$ is $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S.

In some embodiments, $R_y$ is $C_{1-6}$ alkyl, $C_{2-6}$ alkenyl, $C_{2-6}$ alkynyl, $C_{1-6}$ alkoxy, halogen, —CN, —OH, or —NH$_2$.

In some embodiments, $R_y$ is $C_{1-6}$ alkyl, $C_{2-6}$ alkenyl, $C_{2-6}$ alkynyl, or $C_{1-6}$ alkoxy.

In some embodiments, $R_y$ is $C_{1-6}$ alkyl, $C_{2-6}$ alkenyl, or $C_{2-6}$ alkynyl.

In some embodiments, $R_y$ is $C_{1-6}$ alkyl. In some embodiments, $R_y$ is methyl. In some embodiments, $R_y$ is ethyl. In some embodiments, $R_y$ is propyl. In some embodiments, $R_y$ is butyl. In some embodiments, $R_y$ is pentyl. In some embodiments, $R_y$ is hexyl. In some embodiments, $R_y$ is isopropyl. In some embodiments, $R_y$ is isobutyl. In some embodiments, $R_y$ is isopentyl. In some embodiments, $R_y$ is isohexyl. In some embodiments, $R_y$ is secbutyl. In some embodiments, $R_y$ is secpentyl. In some embodiments, $R_y$ is sechexyl. In some embodiments, $R_y$ is tertbutyl.

In some embodiments, $R_y$ is $C_{2-6}$ alkenyl. In some embodiments, $R_y$ is $C_2$ alkenyl. In some embodiments, $R_y$ is $C_3$ alkenyl. In some embodiments, $R_y$ is $C_4$ alkenyl. In some embodiments, $R_y$ is $C_5$ alkenyl. In some embodiments, $R_y$ is $C_6$ alkenyl.

In some embodiments, $R_y$ is $C_{2-6}$ alkynyl. In some embodiments, $R_y$ is $C_2$ alkynyl. In some embodiments, $R_y$ is $C_3$ alkynyl. In some embodiments, $R_y$ is $C_4$ alkynyl. In some embodiments, $R_y$ is $C_5$ alkynyl. In some embodiments, $R_y$ is $C_6$ alkynyl.

In some embodiments, $R_y$ is $C_{1-6}$ alkoxy. In some embodiments, $R_y$ is methoxy. In some embodiments, $R_y$ is ethoxy. In some embodiments, $R_y$ is propoxy. In some embodiments, $R_y$ is butoxy. In some embodiments, $R_y$ is pentoxy. In some embodiments, $R_y$ is hexoxy.

In some embodiments, $R_y$ is halogen, —CN, —OH, or —NH$_2$.

In some embodiments, $R_y$ is halogen. In some embodiments, $R_y$ is F, Cl, Br, or I. In some embodiments, $R_y$ is F, Cl, or Br. In some embodiments, $R_y$ is F. In some embodiments, $R_y$ is Cl. In some embodiments, $R_y$ is Br. In some embodiments, $R_y$ is I.

In some embodiments, $R_y$ is —CN. In some embodiments, $R_y$ is —OH. In some embodiments, $R_y$ is —NH$_2$.

In some embodiments, $R_y$ is 3- to 10-membered heterocyclyl comprising 1-4 heteroatoms selected from N, O, and S, or 5- to 10-membered heteroaryl comprising 1-4 heteroatoms selected from N, O, and S.

In some embodiments, $R_y$ is 3- to 10-membered heterocyclyl comprising 1-4 heteroatoms selected from N, O, and S.

In some embodiments, $R_y$ is 3-membered heterocyclyl comprising 1-4 heteroatoms selected from N, O, and S. In some embodiments, $R_y$ is 4-membered heterocyclyl comprising 1-4 heteroatoms selected from N, O, and S. In some embodiments, $R_y$ is 5-membered heterocyclyl comprising 1-4 heteroatoms selected from N, O, and S. In some embodiments, $R_y$ is 6-membered heterocyclyl comprising 1-4 heteroatoms selected from N, O, and S. In some embodiments, $R_y$ is 7-membered heterocyclyl comprising 1-4 heteroatoms selected from N, O, and S. In some embodiments, $R_y$ is 8-membered heterocyclyl comprising 1-4 heteroatoms selected from N, O, and S. In some embodiments, $R_y$ is 9-membered heterocyclyl comprising 1-4 heteroatoms selected from N, O, and S. In some embodiments, $R_y$ is 10-membered heterocyclyl comprising 1-4 heteroatoms selected from N, O, and S.

In some embodiments, $R_y$ is 5- to 10-membered heteroaryl comprising 1-4 heteroatoms selected from N, O, and S.

In some embodiments, $R_y$ is 5-membered heteroaryl comprising 1-4 heteroatoms selected from N, O, and S. In some embodiments, $R_y$ is 6-membered heteroaryl comprising 1-4 heteroatoms selected from N, O, and S. In some embodiments, $R_y$ is 7-membered heteroaryl comprising 1-4 heteroatoms selected from N, O, and S. In some embodiments, $R_y$ is 8-membered heteroaryl comprising 1-4 heteroatoms selected from N, O, and S. In some embodiments, $R_y$ is 9-membered heteroaryl comprising 1-4 heteroatoms selected from N, O, and S. In some embodiments, $R_y$ is 10-membered heteroaryl comprising 1-4 heteroatoms selected from N, O, and S.

In some embodiments, each $R_y$ is H, $C_{1-6}$ alkyl, or —OH.

In some embodiments, $R_1$ is H, $C_{1-6}$ alkyl, $C_{2-6}$ alkenyl, or $C_{2-6}$ alkynyl.

In some embodiments, $R_1$ is H.

In some embodiments, $R_1$ is $C_{1-6}$ alkyl, $C_{2-6}$ alkenyl, or $C_{2-6}$ alkynyl.

In some embodiments, $R_1$ is $C_{1-6}$ alkyl. In some embodiments, $R_1$ is methyl. In some embodiments, $R_1$ is ethyl. In some embodiments, $R_1$ is propyl. In some embodiments, $R_1$ is butyl. In some embodiments, $R_1$ is pentyl. In some embodiments, $R_1$ is hexyl. In some embodiments, $R_1$ is isopropyl. In some embodiments, $R_1$ is isobutyl. In some embodiments, $R_1$ is isopentyl. In some embodiments, $R_1$ is isohexyl. In some embodiments, $R_1$ is secbutyl. In some embodiments, $R_1$ is secpentyl. In some embodiments, $R_1$ is sechexyl. In some embodiments, $R_1$ is tertbutyl.

In some embodiments, $R_1$ is $C_{2-6}$ alkenyl. In some embodiments, $R_1$ is $C_2$ alkenyl. In some embodiments, $R_1$ is $C_3$ alkenyl. In some embodiments, $R_1$ is $C_4$ alkenyl. In some embodiments, $R_1$ is $C_5$ alkenyl. In some embodiments, $R_1$ is $C_6$ alkenyl.

In some embodiments, $R_1$ is $C_{2-6}$ alkynyl. In some embodiments, $R_1$ is $C_2$ alkynyl. In some embodiments, $R_1$ is $C_3$ alkynyl. In some embodiments, $R_1$ is $C_4$ alkynyl. In some embodiments, $R_1$ is $C_5$ alkynyl. In some embodiments, $R_1$ is $C_6$ alkynyl.

In some embodiments, each $R_1$ is H or $C_{1-6}$ alkyl.

In some embodiments, each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, —C(O)N$R_{11}$—S(O)$_2$—N($R_{11}$)$_2$, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S.

In some embodiments, each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, or —C(O)N$R_{11}$—S(O)$_2$—N($R_{11}$)$_2$, wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S.

In some embodiments, each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, —C(O)N$R_{11}$—S(O)$_2$—N($R_{11}$)$_2$, or —O-(5- to 10-membered heteroaryl comprising 1-4 heteroatoms selected from N, O, and S).

In some embodiments, each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, or —C(O)N$R_{11}$—S(O)$_2$—N($R_{11}$)$_2$, wherein either $R_2$ or $R_3$ is not H.

In some embodiments, each $R_2$ and $R_3$ is independently $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, —C(O)N$R_{11}$—S(O)$_2$—N($R_{11}$)$_2$, or —O-(5- to 10-membered heteroaryl comprising 1-4 heteroatoms selected from N, O, and S).

In some embodiments, each $R_2$ and $R_3$ is independently $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, or —C(O)N$R_{11}$—S(O)$_2$—N($R_{11}$)$_2$.

In some embodiments, each $R_2$ and $R_3$ is independently —O—$C_{1-6}$ alkyl, —C(O)$R_{11}$, —C(O)O$R_{11}$, —C(O)N($R_{11}$)$_2$, or —C(O)N$R_{11}$—S(O)$_2R_{11}$.

In some embodiments, either $R_2$ or $R_3$ is not H.

In some embodiments, $R_2$ is not H.

In some embodiments, $R_3$ is not H.

In some embodiments, $R_2$ is H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, —C(O)N$R_{11}$—S(O)$_2$—N($R_{11}$)$_2$, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S.

In some embodiments, $R_2$ is H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, —C(O)N$R_{11}$—S(O)$_2$—N($R_{11}$)$_2$, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S.

In some embodiments, $R_2$ is H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, —C(O)N$R_{11}$—S(O)$_2$—N($R_{11}$)$_2$, or —O-(5- to 10-membered heteroaryl comprising 1-4 heteroatoms selected from N, O, and S).

In some embodiments, $R_2$ is H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, —C(O)N$R_{11}$—S(O)$_2$—N($R_{11}$)$_2$.

In some embodiments, $R_2$ is H.

In some embodiments, $R_2$ is $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, —C(O)N$R_{11}$—S(O)$_2$—N($R_{11}$)$_2$, or —O-(5- to 10-membered heteroaryl comprising 1-4 heteroatoms selected from N, O, and S).

In some embodiments, $R_2$ is $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, or —C(O)N$R_{11}$—S(O)$_2$—N($R_{11}$)$_2$.

In some embodiments, $R_2$ is $C_{2-6}$ alkenyl or $C_{2-6}$ alkynyl.

In some embodiments, $R_2$ is $C_{2-6}$ alkenyl. In some embodiments, $R_2$ is $C_2$ alkenyl. In some embodiments, $R_2$ is $C_3$ alkenyl. In some embodiments, $R_2$ is $C_4$ alkenyl. In some embodiments, $R_2$ is $C_5$ alkenyl. In some embodiments, $R_2$ is $C_6$ alkenyl.

In some embodiments, $R_2$ is $C_{2-6}$ alkynyl. In some embodiments, $R_2$ is $C_2$ alkynyl. In some embodiments, $R_2$ is $C_3$ alkynyl. In some embodiments, $R_2$ is $C_4$ alkynyl. In some embodiments, $R_2$ is $C_5$ alkynyl. In some embodiments, $R_2$ is $C_6$ alkynyl.

In some embodiments, $R_2$ is —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, or —C(O)N$R_{11}$—S(O)$_2$—N($R_{11}$)$_2$.

In some embodiments, $R_2$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S.

In some embodiments, $R_2$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is optionally substituted with $C_{6-10}$ aryl.

In some embodiments, $R_2$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is optionally substituted with 5- to 13-membered heteroaryl comprising 1-4 heteroatoms selected from N, O, and S.

In some embodiments, $R_2$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is substituted with $C_{6-10}$ aryl or 5- to 13-membered heteroaryl comprising 1-4 heteroatoms selected from N, O, and S.

In some embodiments, $R_2$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is substituted with $C_{6-10}$ aryl.

In some embodiments, $R_2$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is substituted with 5- to 13-membered heteroaryl comprising 1-4 heteroatoms selected from N, O, and S.

In some embodiments, $R_2$ is —O—$C_{1-6}$ alkyl, —O—$C_{2-6}$ alkenyl, or —O—$C_{2-6}$ alkynyl.

In some embodiments, $R_2$ is —O—$C_{1-6}$ alkyl optionally substituted with $C_{6-10}$ aryl or 5- to 13-membered heteroaryl comprising 1-4 heteroatoms selected from N, O, and S.

In some embodiments, $R_2$ is —O—$C_{1-6}$ alkyl optionally substituted with $C_{6-10}$ aryl.

In some embodiments, $R_2$ is —O—$C_{1-6}$ alkyl optionally substituted with phenyl.

In some embodiments, $R_2$ is —O-methyl optionally substituted with phenyl.

In some embodiments, $R_2$ is —O—$C_{1-6}$ alkyl substituted with phenyl.

In some embodiments, $R_2$ is —O-methyl substituted with phenyl.

In some embodiments, $R_2$ is —O—$C_{1-6}$ alkyl optionally substituted with 5- to 13-membered heteroaryl comprising 1-4 heteroatoms selected from N, O, and S.

In some embodiments, $R_2$ is —O—$C_{1-6}$ alkyl substituted with $C_{6-10}$ aryl or 5- to 13-membered heteroaryl comprising 1-4 heteroatoms selected from N, O, and S.

In some embodiments, $R_2$ is —O—$C_{1-6}$ alkyl substituted with $C_{6-10}$ aryl.

In some embodiments, $R_2$ is —O—$C_{1-6}$ alkyl substituted with 5- to 13-membered heteroaryl comprising 1-4 heteroatoms selected from N, O, and S.

In some embodiments, $R_2$ is —O—$C_{1-6}$ alkyl. In some embodiments, $R_2$ is —O-methyl. In some embodiments, $R_2$ is —O-ethyl. In some embodiments, $R_2$ is —O-propyl. In some embodiments, $R_2$ is —O-butyl. In some embodiments, $R_2$ is —O-pentyl. In some embodiments, $R_2$ is —O-hexyl. In some embodiments, $R_2$ is —O-isopropyl. In some embodiments, $R_2$ is —O-isobutyl.

In some embodiments, $R_2$ is —O-isopentyl. In some embodiments, $R_2$ is —O-isohexyl. In some embodiments, $R_2$ is —O-secbutyl. In some embodiments, $R_2$ is —O-secpentyl. In some embodiments, $R_2$ is —O-sechexyl. In some embodiments, $R_2$ is —O-tertbutyl.

In some embodiments, $R_2$ is —O—$C_{2-6}$ alkenyl optionally substituted with $C_{6-10}$ aryl or 5- to 13-membered heteroaryl comprising 1-4 heteroatoms selected from N, O, and S.

In some embodiments, $R_2$ is —O—$C_{2-6}$ alkenyl optionally substituted with $C_{6-10}$ aryl.

In some embodiments, $R_2$ is —O—$C_{2-6}$ alkenyl optionally substituted with 5- to 13-membered heteroaryl comprising 1-4 heteroatoms selected from N, O, and S.

In some embodiments, $R_2$ is —O—$C_{2-6}$ alkenyl substituted with $C_{6-10}$ aryl or 5- to 13-membered heteroaryl comprising 1-4 heteroatoms selected from N, O, and S.

In some embodiments, $R_2$ is —O—$C_{2-6}$ alkenyl substituted with $C_{6-10}$ aryl.

In some embodiments, $R_2$ is —O—$C_{2-6}$ alkenyl substituted with 5- to 13-membered heteroaryl comprising 1-4 heteroatoms selected from N, O, and S.

In some embodiments, $R_2$ is —O—$C_{2-6}$ alkenyl. In some embodiments, $R_2$ is —O—$C_2$ alkenyl. In some embodiments, $R_2$ is —O—$C_3$ alkenyl. In some embodiments, $R_2$ is —O—$C_4$ alkenyl. In some embodiments, $R_2$ is —O—$C_5$ alkenyl. In some embodiments, $R_2$ is —O—$C_6$ alkenyl.

In some embodiments, $R_2$ is —O—$C_{2-6}$ alkynyl optionally substituted with $C_{6-10}$ aryl or 5- to 13-membered heteroaryl comprising 1-4 heteroatoms selected from N, O, and S.

In some embodiments, $R_2$ is —O—$C_{2-6}$ alkynyl optionally substituted with $C_{6-10}$ aryl.

In some embodiments, $R_2$ is —O—$C_{2-6}$ alkynyl optionally substituted with 5- to 13-membered heteroaryl comprising 1-4 heteroatoms selected from N, O, and S.

In some embodiments, $R_2$ is —O—$C_{2-6}$ alkynyl substituted with $C_{6-10}$ aryl or 5- to 13-membered heteroaryl comprising 1-4 heteroatoms selected from N, O, and S.

In some embodiments, $R_2$ is —O—$C_{2-6}$ alkynyl substituted with $C_{6-10}$ aryl.

In some embodiments, $R_2$ is —O—$C_{2-6}$ alkynyl substituted with 5- to 13-membered heteroaryl comprising 1-4 heteroatoms selected from N, O, and S.

In some embodiments, $R_2$ is —O—$C_{2-6}$ alkynyl. In some embodiments, $R_2$ is —O—$C_2$ alkynyl. In some embodiments, $R_2$ is —O—$C_3$ alkynyl. In some embodiments, $R_2$ is —O—$C_4$ alkynyl. In some embodiments, $R_2$ is —O—$C_5$ alkynyl. In some embodiments, $R_2$ is —O—$C_6$ alkynyl.

In some embodiments, $R_2$ is —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, or —C(O)N$R_{11}$—S(O)$_2$—N($R_{11}$)$_2$.

In some embodiments, $R_2$ is —C(O)$R_{11}$, —C(O)O$R_{11}$, or —C(O)N($R_{11}$)$_2$.

In some embodiments, $R_2$ is —C(O)$R_{11}$. In some embodiments, $R_2$ is —C(O)O$R_{11}$. In some embodiments, $R_2$ is —C(O)N($R_{11}$)$_2$.

In some embodiments, $R_2$ is —C(O)N$R_{11}$—S(O)$_2R_{11}$, —C(O)N$R_{11}$—S(O)$_2$—O$R_{11}$, or —C(O)N$R_{11}$—S(O)$_2$—N($R_{11}$)$_2$.

In some embodiments, $R_2$ is —C(O)N$R_{11}$—S(O)$_2R_{11}$. In some embodiments, $R_2$ is —C(O)N$R_{11}$—S(O)$_2$—O$R_{11}$. In some embodiments, $R_2$ is —C(O)N$R_{11}$—S(O)$_2$—N($R_{11}$)$_2$.

In some embodiments, $R_2$ is —O—$C_{1-6}$ alkyl, —C(O)$R_{11}$, —C(O)O$R_{11}$, —C(O)N($R_{11}$)$_2$, or —C(O)N$R_{11}$—S(O)$_2R_{11}$.

In some embodiments, $R_2$ is —O-(5- to 10-membered heteroaryl comprising 1-4 heteroatoms selected from N, O, and S).

In some embodiments, $R_2$ is —O-(5-membered heteroaryl comprising 1-4 heteroatoms selected from N, O, and S). In some embodiments, $R_2$ is —O-(6-membered heteroaryl comprising 1-4 heteroatoms selected from N, O, and S). In some embodiments, $R_2$ is —O-(7-membered heteroaryl comprising 1-4 heteroatoms selected from N, O, and S). In some embodiments, $R_2$ is —O-(8-membered heteroaryl comprising 1-4 heteroatoms selected from N, O, and S). In some embodiments, $R_2$ is —O-(9-membered heteroaryl comprising 1-4 heteroatoms selected from N, O, and S). In some embodiments, $R_2$ is —O-(10-membered heteroaryl comprising 1-4 heteroatoms selected from N, O, and S).

In some embodiments, $R_2$ is —O-methyl, —O-methyl substituted by phenyl, or —C(O)$_2$CH$_3$.

In some embodiments, $R_2$ is —O-methyl or —O-methyl substituted by phenyl.

In some embodiments, $R_3$ is H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, —C(O)N$R_{11}$—S(O)$_2$—N($R_{11}$)$_2$, or —O-(5- to 10-membered heteroaryl comprising 1-4 heteroatoms selected from N, O, and S), wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S.

In some embodiments, $R_3$ is H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—

$S(O)_2R_{11}$, —$C(O)NR_{11}$—$S(O)_2$—$OR_{11}$, or —$C(O)NR_{11}$—$S(O)_2$—$N(R_{11})_2$, wherein either $R_2$ or $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S.

In some embodiments, $R_3$ is H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —$C(O)R_{11}$, —$C(O)OR_{11}$, —$C(O)N(R_{11})_2$, —$C(O)NR_{11}$—$S(O)_2R_{11}$, —$C(O)NR_{11}$—$S(O)_2$—$OR_{11}$, —$C(O)NR_{11}$—$S(O)_2$—$N(R_{11})_2$, or —O-(5- to 10-membered heteroaryl comprising 1-4 heteroatoms selected from N, O, and S).

In some embodiments, $R_3$ is H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —$C(O)R_{11}$, —$C(O)OR_{11}$, —$C(O)N(R_{11})_2$, —$C(O)NR_{11}$—$S(O)_2R_{11}$, —$C(O)NR_{11}$—$S(O)_2$—$OR_{11}$, or —$C(O)NR_{11}$—$S(O)_2$—$N(R_{11})_2$.

In some embodiments, $R_3$ is H.

In some embodiments, $R_3$ is $C_{2-6}$ alkenyl, $C_{2-6}$ alkynyl, —O—$C_{1-6}$ alkyl, —O—$C_{2-6}$ alkenyl, —O—$C_{2-6}$ alkynyl, —$C(O)R_{11}$, —$C(O)OR_{11}$, —$C(O)N(R_{11})_2$, —$C(O)NR_{11}$—$S(O)_2R_{11}$, —$C(O)NR_{11}$—$S(O)_2$—$OR_{11}$, —$C(O)NR_{11}$—$S(O)_2$—$N(R_{11})_2$, or —O-(5- to 10-membered heteroaryl comprising 1-4 heteroatoms selected from N, O, and S).

In some embodiments, $R_3$ is $C_{2-6}$ alkenyl, $C_{2-6}$ alkynyl, —O—$C_{1-6}$ alkyl, —O—$C_{2-6}$ alkenyl, —O—$C_{2-6}$ alkynyl, —$C(O)R_{11}$, —$C(O)OR_{11}$, —$C(O)N(R_{11})_2$, —$C(O)NR_{11}$—$S(O)_2R_{11}$, —$C(O)NR_{11}$—$S(O)_2$—$OR_{11}$, or —$C(O)NR_{11}$—$S(O)_2$—$N(R_{11})_2$.

In some embodiments, $R_3$ is $C_{2-6}$ alkenyl or $C_{2-6}$ alkynyl.

In some embodiments, $R_3$ is $C_{2-6}$ alkenyl. In some embodiments, $R_3$ is $C_2$ alkenyl. In some embodiments, $R_3$ is $C_3$ alkenyl. In some embodiments, $R_3$ is $C_4$ alkenyl. In some embodiments, $R_3$ is $C_5$ alkenyl. In some embodiments, $R_3$ is $C_6$ alkenyl.

In some embodiments, $R_3$ is $C_{2-6}$ alkynyl. In some embodiments, $R_3$ is $C_2$ alkynyl. In some embodiments, $R_3$ is $C_3$ alkynyl. In some embodiments, $R_3$ is $C_4$ alkynyl. In some embodiments, $R_3$ is $C_5$ alkynyl. In some embodiments, $R_3$ is $C_6$ alkynyl.

In some embodiments, $R_3$ is —O—$C_{1-6}$ alkyl, —O—$C_{2-6}$ alkenyl, —O—$C_{2-6}$ alkynyl, —$C(O)R_{11}$, —$C(O)OR_{11}$, —$C(O)N(R_{11})_2$, —$C(O)NR_{11}$—$S(O)_2R_{11}$, —$C(O)NR_{11}$—$S(O)_2$—$OR_{11}$, or —$C(O)NR_{11}$—$S(O)_2$—$N(R_{11})_2$.

In some embodiments, $R_3$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S.

In some embodiments, $R_3$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is optionally substituted with $C_{6-10}$ aryl.

In some embodiments, $R_3$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is optionally substituted with 5- to 13-membered heteroaryl comprising 1-4 heteroatoms selected from N, O, and S.

In some embodiments, $R_3$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is substituted with $C_{6-10}$ aryl or 5- to 13-membered heteroaryl comprising 1-4 heteroatoms selected from N, O, and S.

In some embodiments, $R_3$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is substituted with $C_{6-10}$ aryl.

In some embodiments, $R_3$ is —O—$C_{1-6}$ alkyl, —O—$C_{2-6}$ alkenyl, or —O—$C_{2-6}$ alkynyl, wherein the —O—$C_{1-6}$ alkyl, —O—$C_{2-6}$ alkenyl, or —O—$C_{2-6}$ alkynyl is substituted with 5- to 13-membered heteroaryl comprising 1-4 heteroatoms selected from N, O, and S.

In some embodiments, $R_3$ is —O—$C_{1-6}$ alkyl, —O—$C_{2-6}$ alkenyl, or —O—$C_{2-6}$ alkynyl.

In some embodiments, $R_3$ is —O—$C_{1-6}$ alkyl optionally substituted with $C_{6-10}$ aryl or 5- to 13-membered heteroaryl comprising 1-4 heteroatoms selected from N, O, and S.

In some embodiments, $R_3$ is —O—$C_{1-6}$ alkyl optionally substituted with $C_{6-10}$ aryl.

In some embodiments, $R_3$ is —O—$C_{1-6}$ alkyl optionally substituted with phenyl.

In some embodiments, $R_3$ is —O-methyl optionally substituted with phenyl.

In some embodiments, $R_3$ is —O—$C_{1-6}$ alkyl substituted with phenyl.

In some embodiments, $R_3$ is —O-methyl substituted with phenyl.

In some embodiments, $R_3$ is —O—$C_{1-6}$ alkyl optionally substituted with 5- to 13-membered heteroaryl comprising 1-4 heteroatoms selected from N, O, and S.

In some embodiments, $R_3$ is —O—$C_{1-6}$ alkyl substituted with $C_{6-10}$ aryl or 5- to 13-membered heteroaryl comprising 1-4 heteroatoms selected from N, O, and S.

In some embodiments, $R_3$ is —O—$C_{1-6}$ alkyl substituted with $C_{6-10}$ aryl.

In some embodiments, $R_3$ is —O—$C_{1-6}$ alkyl substituted with 5- to 13-membered heteroaryl comprising 1-4 heteroatoms selected from N, O, and S.

In some embodiments, $R_3$ is —O—$C_{1-6}$ alkyl. In some embodiments, $R_3$ is —O-methyl. In some embodiments, $R_3$ is —O-ethyl. In some embodiments, $R_3$ is —O-propyl. In some embodiments, $R_3$ is —O-butyl. In some embodiments, $R_3$ is —O-pentyl. In some embodiments, $R_3$ is —O-hexyl. In some embodiments, $R_3$ is —O-isopropyl. In some embodiments, $R_3$ is —O-isobutyl. In some embodiments, $R_3$ is —O-isopentyl. In some embodiments, $R_3$ is —O-isohexyl. In some embodiments, $R_3$ is —O-secbutyl. In some embodiments, $R_3$ is —O-secpentyl. In some embodiments, $R_3$ is —O-sechexyl. In some embodiments, $R_3$ is —O-tertbutyl.

In some embodiments, $R_3$ is —O—$C_{2-6}$ alkenyl optionally substituted with $C_{6-10}$ aryl or 5- to 13-membered heteroaryl comprising 1-4 heteroatoms selected from N, O, and S.

In some embodiments, $R_3$ is —O—$C_{2-6}$ alkenyl optionally substituted with $C_{6-10}$ aryl.

In some embodiments, $R_3$ is —O—$C_{2-6}$ alkenyl optionally substituted with 5- to 13-membered heteroaryl comprising 1-4 heteroatoms selected from N, O, and S.

In some embodiments, $R_3$ is —O—$C_{2-6}$ alkenyl substituted with $C_{6-10}$ aryl or 5- to 13-membered heteroaryl comprising 1-4 heteroatoms selected from N, O, and S.

In some embodiments, $R_3$ is —O—$C_{2-6}$ alkenyl substituted with $C_{6-10}$ aryl.

In some embodiments, $R_3$ is —O—$C_{2-6}$ alkenyl substituted with 5- to 13-membered heteroaryl comprising 1-4 heteroatoms selected from N, O, and S.

In some embodiments, $R_3$ is —O—$C_{2-6}$ alkenyl. In some embodiments, $R_3$ is —O—$C_2$ alkenyl. In some embodiments, $R_3$ is —O—$C_3$ alkenyl. In some embodiments, $R_3$ is —O—$C_4$ alkenyl. In some embodiments, $R_3$ is —O—$C_5$ alkenyl. In some embodiments, $R_3$ is —O—$C_6$ alkenyl.

In some embodiments, $R_3$ is —O—$C_{2-6}$ alkynyl optionally substituted with $C_{6-10}$ aryl or 5- to 13-membered heteroaryl comprising 1-4 heteroatoms selected from N, O, and S.

In some embodiments, $R_3$ is —O—$C_{2-6}$ alkynyl optionally substituted with $C_{6-10}$ aryl.

In some embodiments, $R_3$ is —O—$C_{2-6}$ alkynyl optionally substituted with 5- to 13-membered heteroaryl comprising 1-4 heteroatoms selected from N, O, and S.

In some embodiments, $R_3$ is —O—$C_{2-6}$ alkynyl substituted with $C_{6-10}$ aryl or 5- to 13-membered heteroaryl comprising 1-4 heteroatoms selected from N, O, and S.

In some embodiments, $R_3$ is —O—$C_{2-6}$ alkynyl substituted with $C_{6-10}$ aryl.

In some embodiments, $R_3$ is —O—$C_{2-6}$ alkynyl substituted with 5- to 13-membered heteroaryl comprising 1-4 heteroatoms selected from N, O, and S.

In some embodiments, $R_3$ is —O—$C_{2-6}$ alkynyl. In some embodiments, $R_3$ is —O—$C_2$ alkynyl. In some embodiments, $R_3$ is —O—$C_3$ alkynyl. In some embodiments, $R_3$ is —O—$C_4$ alkynyl. In some embodiments, $R_3$ is —O—$C_5$ alkynyl. In some embodiments, $R_3$ is —O—$C_6$ alkynyl.

In some embodiments, $R_3$ is —C(O)$R_{11}$, —C(O)O$R_{11}$, —C(O)N($R_{11}$)$_2$, —C(O)N$R_{11}$—S(O)$_2R_{11}$, —C(O)N$R_{11}$—S(O)$_2$—O$R_{11}$, or —C(O)N$R_{11}$—S(O)$_2$—N($R_{11}$)$_2$.

In some embodiments, $R_3$ is —C(O)$R_{11}$, —C(O)O$R_{11}$, or —C(O)N($R_{11}$)$_2$.

In some embodiments, $R_3$ is —C(O)$R_{11}$. In some embodiments, $R_3$ is —C(O)O$R_{11}$. In some embodiments, $R_3$ is —C(O)N($R_{11}$)$_2$.

In some embodiments, $R_3$ is —C(O)N$R_{11}$—S(O)$_2R_{11}$, —C(O)N$R_{11}$—S(O)$_2$—O$R_{11}$, or —C(O)N$R_{11}$—S(O)$_2$—N($R_{11}$)$_2$.

In some embodiments, $R_3$ is —C(O)N$R_{11}$—S(O)$_2R_{11}$. In some embodiments, $R_3$ is —C(O)N$R_{11}$—S(O)$_2$—O$R_{11}$. In some embodiments, $R_3$ is —C(O)N$R_{11}$—S(O)$_2$—N($R_{11}$)$_2$.

In some embodiments, $R_3$ is —O—$C_{1-6}$ alkyl, —C(O)$R_{11}$, —C(O)O$R_{11}$, —C(O)N($R_{11}$)$_2$, or —C(O)N$R_{11}$—S(O)$_2R_{11}$.

In some embodiments, $R_3$ is —O-(5- to 10-membered heteroaryl comprising 1-4 heteroatoms selected from N, O, and S).

In some embodiments, $R_3$ is —O-(5-membered heteroaryl comprising 1-4 heteroatoms selected from N, O, and S). In some embodiments, $R_3$ is —O-(6-membered heteroaryl comprising 1-4 heteroatoms selected from N, O, and S). In some embodiments, $R_3$ is —O-(7-membered heteroaryl comprising 1-4 heteroatoms selected from N, O, and S). In some embodiments, $R_3$ is —O-(8-membered heteroaryl comprising 1-4 heteroatoms selected from N, O, and S). In some embodiments, $R_3$ is —O-(9-membered heteroaryl comprising 1-4 heteroatoms selected from N, O, and S). In some embodiments, $R_3$ is —O-(10-membered heteroaryl comprising 1-4 heteroatoms selected from N, O, and S).

In some embodiments, $R_3$ is —O-methyl, —O-methyl substituted by phenyl, or —C(O)$_2$CH$_3$.

In some embodiments, $R_3$ is —O-methyl or —O-methyl substituted by phenyl.

In some embodiments, each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$.

In some embodiments, each $R_5$ and $R_6$ is independently $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$.

In some embodiments, each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, alkenyl, alkynyl, cycloalkyl, heterocyclyl, aryl, or heteroaryl is optionally substituted with one or more $R_7$.

In some embodiments, each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S.

In some embodiments, each $R_5$ and $R_6$ is independently H.

In some embodiments, each $R_5$ and $R_6$ is independently $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, alkenyl, alkynyl, cycloalkyl, heterocyclyl, aryl, or heteroaryl is optionally substituted with one or more $R_7$.

In some embodiments, each $R_5$ and $R_6$ is independently $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S.

In some embodiments, each $R_5$ and $R_6$ is independently H, $C_{1-6}$ alkyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, cycloalkyl, heterocyclyl, aryl, or heteroaryl is optionally substituted with one or more $R_7$.

In some embodiments, each $R_5$ and $R_6$ is independently H, $C_{1-6}$ alkyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, cycloalkyl, heterocyclyl, aryl, or heteroaryl is optionally substituted with one or more $R_7$.

In some embodiments, each $R_5$ and $R_6$ is independently H, $C_{1-6}$ alkyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, cycloalkyl, heterocyclyl, aryl, or heteroaryl is substituted with one or more $R_7$.

In some embodiments, $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is substituted with one or more $R_7$.

In some embodiments, $R_5$ is H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, alkenyl, alkynyl, cycloalkyl, heterocyclyl, aryl, or heteroaryl is optionally substituted with one or more $R_7$.

In some embodiments, $R_5$ is H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S.

In some embodiments, $R_5$ is H.

In some embodiments, $R_5$ is $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, alkenyl, alkynyl, cycloalkyl, heterocyclyl, aryl, or heteroaryl is optionally substituted with one or more $R_7$.

In some embodiments, $R_5$ is $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S.

In some embodiments, $R_5$ is $C_{1-6}$ alkyl, $C_{2-6}$ alkenyl, or $C_{2-6}$ alkynyl, wherein the alkyl, alkenyl, or alkynyl is optionally substituted with one or more $R_7$.

In some embodiments, $R_5$ is $C_{1-6}$ alkyl optionally substituted with one or more $R_7$. In some embodiments, $R_5$ is methyl optionally substituted with one or more $R_7$. In some embodiments, $R_5$ is ethyl optionally substituted with one or more $R_7$. In some embodiments, $R_5$ is propyl optionally substituted with one or more $R_7$. In some embodiments, $R_5$ is butyl optionally substituted with one or more $R_7$. In some embodiments, $R_5$ is pentyl optionally substituted with one or more $R_7$. In some embodiments, $R_5$ is hexyl optionally substituted with one or more $R_7$. In some embodiments, $R_5$ is isopropyl optionally substituted with one or more $R_7$. In some embodiments, $R_5$ is isobutyl optionally substituted with one or more $R_7$. In some embodiments, $R_5$ is isopentyl optionally substituted with one or more $R_7$. In some embodiments, $R_5$ is isohexyl optionally substituted with one or more $R_7$. In some embodiments, $R_5$ is secbutyl optionally substituted with one or more $R_7$. In some embodiments, $R_5$ is secpentyl optionally substituted with one or more $R_7$. In some embodiments, $R_5$ is sechexyl optionally substituted with one or more $R_7$. In some embodiments, $R_5$ is tertbutyl optionally substituted with one or more $R_7$.

In some embodiments, $R_5$ is $C_{2-6}$ alkenyl optionally substituted with one or more $R_7$. In some embodiments, $R_5$ is $C_2$ alkenyl optionally substituted with one or more $R_7$. In some embodiments, $R_5$ is $C_3$ alkenyl optionally substituted with one or more $R_7$. In some embodiments, $R_5$ is $C_4$ alkenyl optionally substituted with one or more $R_7$. In some embodiments, $R_5$ is $C_5$ alkenyl optionally substituted with one or more $R_7$. In some embodiments, $R_5$ is $C_6$ alkenyl optionally substituted with one or more $R_7$.

In some embodiments, $R_5$ is $C_{2-6}$ alkynyl optionally substituted with one or more $R_7$. In some embodiments, $R_5$ is $C_2$ alkynyl optionally substituted with one or more $R_7$. In some embodiments, $R_5$ is $C_3$ alkynyl optionally substituted with one or more $R_7$. In some embodiments, $R_5$ is $C_4$ alkynyl optionally substituted with one or more $R_7$. In some embodiments, $R_5$ is $C_5$ alkynyl optionally substituted with one or more $R_7$. In some embodiments, $R_5$ is $C_6$ alkynyl optionally substituted with one or more $R_7$.

In some embodiments, $R_5$ is $C_{1-6}$ alkyl, $C_{2-6}$ alkenyl, or $C_{2-6}$ alkynyl, wherein the alkyl, alkenyl, or alkynyl is substituted with one or more $R_7$.

In some embodiments, $R_5$ is $C_{1-6}$ alkyl substituted with one or more $R_7$. In some embodiments, $R_5$ is methyl substituted with one or more $R_7$. In some embodiments, $R_5$ is ethyl substituted with one or more $R_7$. In some embodiments, $R_5$ is propyl substituted with one or more $R_7$. In some embodiments, $R_5$ is butyl substituted with one or more $R_7$. In some embodiments, $R_5$ is pentyl substituted with one or more $R_7$. In some embodiments, $R_5$ is hexyl substituted with one or more $R_7$. In some embodiments, $R_5$ is isopropyl substituted with one or more $R_7$. In some embodiments, $R_5$ is isobutyl substituted with one or more $R_7$. In some embodiments, $R_5$ is isopentyl substituted with one or more $R_7$. In some embodiments, $R_5$ is isohexyl substituted with one or more $R_7$. In some embodiments, $R_5$ is secbutyl substituted with one or more $R_7$. In some embodiments, $R_5$ is secpentyl substituted with one or more $R_7$. In some embodiments, $R_5$ is sechexyl substituted with one or more $R_7$. In some embodiments, $R_5$ is tertbutyl substituted with one or more $R_7$.

In some embodiments, $R_5$ is $C_{2-6}$ alkenyl substituted with one or more $R_7$. In some embodiments, $R_5$ is $C_2$ alkenyl substituted with one or more $R_7$. In some embodiments, $R_5$ is $C_3$ alkenyl substituted with one or more $R_7$. In some embodiments, $R_5$ is $C_4$ alkenyl substituted with one or more $R_7$. In some embodiments, $R_5$ is $C_5$ alkenyl substituted with one or more $R_7$. In some embodiments, $R_5$ is $C_6$ alkenyl substituted with one or more $R_7$.

In some embodiments, $R_5$ is $C_{2-6}$ alkynyl substituted with one or more $R_7$. In some embodiments, $R_5$ is $C_2$ alkynyl substituted with one or more $R_7$. In some embodiments, $R_5$ is $C_3$ alkynyl substituted with one or more $R_7$. In some embodiments, $R_5$ is $C_4$ alkynyl substituted with one or more $R_7$. In some embodiments, $R_5$ is $C_5$ alkynyl substituted with one or more $R_7$. In some embodiments, $R_5$ is $C_6$ alkynyl substituted with one or more $R_7$.

In some embodiments, $R_5$ is $C_{1-6}$ alkyl, $C_{2-6}$ alkenyl, or $C_{2-6}$ alkynyl, wherein the alkyl, alkenyl, or alkynyl is substituted with one $R_7$.

In some embodiments, $R_5$ is $C_{1-6}$ alkyl substituted with one $R_7$. In some embodiments, $R_5$ is methyl substituted with one $R_7$. In some embodiments, $R_5$ is ethyl substituted with one $R_7$. In some embodiments, $R_5$ is propyl substituted with one $R_7$. In some embodiments, $R_5$ is butyl substituted with one $R_7$. In some embodiments, $R_5$ is pentyl substituted with one $R_7$. In some embodiments, $R_5$ is hexyl substituted with one $R_7$. In some embodiments, $R_5$ is isopropyl substituted with one $R_7$. In some embodiments, $R_5$ is isobutyl substituted with one $R_7$. In some embodiments, $R_5$ is isopentyl substituted with one $R_7$. In some embodiments, $R_5$ is isohexyl substituted with one $R_7$. In some embodiments, $R_5$ is secbutyl substituted with one $R_7$. In some embodiments, $R_5$ is secpentyl substituted with one $R_7$. In some embodiments, $R_5$ is sechexyl substituted with one $R_7$. In some embodiments, $R_5$ is tertbutyl substituted with one $R_7$.

In some embodiments, $R_5$ is $C_{2-6}$ alkenyl substituted with one $R_7$. In some embodiments, $R_5$ is $C_2$ alkenyl substituted with one $R_7$. In some embodiments, $R_5$ is $C_3$ alkenyl substituted with one $R_7$. In some embodiments, $R_5$ is $C_4$ alkenyl substituted with one $R_7$. In some embodiments, $R_5$ is $C_5$ alkenyl substituted with one $R_7$. In some embodiments, $R_5$ is $C_6$ alkenyl substituted with one $R_7$.

In some embodiments, $R_5$ is $C_{2-6}$ alkynyl substituted with one $R_7$. In some embodiments, $R_5$ is $C_2$ alkynyl substituted with one $R_7$. In some embodiments, $R_5$ is $C_3$ alkynyl substituted with one $R_7$. In some embodiments, $R_5$ is $C_4$ alkynyl substituted with one $R_7$. In some embodiments, $R_5$ is $C_5$ alkynyl substituted with one $R_7$. In some embodiments, $R_5$ is $C_6$ alkynyl substituted with one $R_7$.

In some embodiments, $R_5$ is $C_{1-6}$ alkyl, $C_{2-6}$ alkenyl, or $C_{2-6}$ alkynyl.

In some embodiments, $R_5$ is $C_{1-6}$ alkyl. In some embodiments, $R_5$ is methyl. In some embodiments, $R_5$ is ethyl. In some embodiments, $R_5$ is propyl. In some embodiments, $R_5$ is butyl. In some embodiments, $R_5$ is pentyl. In some embodiments, $R_5$ is hexyl. In some embodiments, $R_5$ is isopropyl. In some embodiments, $R_5$ is isobutyl. In some embodiments, $R_5$ is isopentyl. In some embodiments, $R_5$ is isohexyl. In some embodiments, $R_5$ is secbutyl. In some embodiments, $R_5$ is secpentyl. In some embodiments, $R_5$ is sechexyl. In some embodiments, $R_5$ is tertbutyl.

In some embodiments, $R_5$ is $C_{2-6}$ alkenyl. In some embodiments, $R_5$ is $C_2$ alkenyl. In some embodiments, $R_5$ is $C_3$ alkenyl. In some embodiments, $R_5$ is $C_4$ alkenyl. In some embodiments, $R_5$ is $C_5$ alkenyl. In some embodiments, $R_5$ is $C_6$ alkenyl.

In some embodiments, $R_5$ is $C_{2-6}$ alkynyl. In some embodiments, $R_5$ is $C_2$ alkynyl. In some embodiments, $R_5$ is $C_3$ alkynyl. In some embodiments, $R_5$ is $C_4$ alkynyl. In some embodiments, $R_5$ is $C_5$ alkynyl. In some embodiments, $R_5$ is $C_6$ alkynyl.

In some embodiments, $R_5$ is $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the cycloalkyl, heterocyclyl, aryl, or heteroaryl is optionally substituted with one or more $R_7$.

In some embodiments, $R_5$ is $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S.

In some embodiments, $R_5$ is $C_{3-10}$ cycloalkyl or 3- to 13-membered heterocyclyl comprising 1-4 heteroatoms selected from N, O, and S, wherein the cycloalkyl or heterocyclyl is optionally substituted with one or more $R_7$.

In some embodiments, $R_5$ is $C_{3-10}$ cycloalkyl or 3- to 13-membered heterocyclyl comprising 1-4 heteroatoms selected from N, O, and S.

In some embodiments, $R_5$ is $C_{3-10}$ cycloalkyl optionally substituted with one or more $R_7$.

In some embodiments, $R_5$ is $C_3$ cycloalkyl optionally substituted with one or more $R_7$. In some embodiments, $R_5$ is $C_4$ cycloalkyl optionally substituted with one or more $R_7$. In some embodiments, $R_5$ is $C_5$ cycloalkyl optionally substituted with one or more $R_7$. In some embodiments, $R_5$ is $C_6$ cycloalkyl optionally substituted with one or more $R_7$. In some embodiments, $R_5$ is $C_7$ cycloalkyl optionally substituted with one or more $R_7$. In some embodiments, $R_5$ is $C_8$ cycloalkyl optionally substituted with one or more $R_7$. In some embodiments, $R_5$ is $C_9$ cycloalkyl optionally substituted with one or more $R_7$. In some embodiments, $R_5$ is $C_{10}$ cycloalkyl optionally substituted with one or more $R_7$.

In some embodiments, $R_5$ is $C_3$-$C_7$ monocyclic cycloalkyl optionally substituted with one or more $R_7$. In some embodiments, $R_5$ is $C_3$-$C_7$ monocyclic saturated cycloalkyl optionally substituted with one or more $R_7$. In some embodiments, $R_5$ is $C_3$-$C_7$ monocyclic partially saturated cycloalkyl optionally substituted with one or more $R_7$. In some embodiments, $R_5$ is $C_9$-$C_{10}$ bicyclic cycloalkyl optionally substituted with one or more $R_7$. In some embodiments, $R_5$ is $C_9$-$C_{10}$ bicyclic saturated cycloalkyl optionally substituted with one or more $R_7$. In some embodiments, $R_5$ is $C_9$-$C_{10}$ bicyclic partially saturated cycloalkyl optionally substituted with one or more $R_7$. In some embodiments, $R_5$ is $C_5$-$C_{10}$ polycyclic cycloalkyl optionally substituted with one or more $R_7$.

In some embodiments, $R_5$ is $C_{3-10}$ cycloalkyl substituted with one or more $R_7$.

In some embodiments, $R_5$ is $C_3$ cycloalkyl substituted with one or more $R_7$. In some embodiments, $R_5$ is $C_4$ cycloalkyl substituted with one or more $R_7$. In some embodiments, $R_5$ is $C_5$ cycloalkyl substituted with one or more $R_7$. In some embodiments, $R_5$ is $C_6$ cycloalkyl substituted with one or more $R_7$. In some embodiments, $R_5$ is $C_7$ cycloalkyl substituted with one or more $R_7$. In some embodiments, $R_5$ is $C_8$ cycloalkyl substituted with one or more $R_7$. In some embodiments, $R_5$ is $C_9$ cycloalkyl substituted with one or more $R_7$. In some embodiments, $R_5$ is $C_{10}$ cycloalkyl substituted with one or more $R_7$.

In some embodiments, $R_5$ is $C_3$-$C_7$ monocyclic cycloalkyl substituted with one or more $R_7$. In some embodiments, $R_5$ is $C_3$-$C_7$ monocyclic saturated cycloalkyl substituted with one or more $R_7$. In some embodiments, $R_5$ is $C_3$-$C_7$ monocyclic partially saturated cycloalkyl substituted with one or more $R_7$. In some embodiments, $R_5$ is $C_9$-$C_{10}$ bicyclic cycloalkyl substituted with one or more $R_7$. In some embodiments, $R_5$ is $C_9$-$C_{10}$ bicyclic saturated cycloalkyl substituted with one or more $R_7$. In some embodiments, $R_5$ is $C_9$-$C_{10}$ bicyclic partially saturated cycloalkyl substituted with one or more $R_7$. In some embodiments, $R_5$ is $C_5$-$C_{10}$ polycyclic cycloalkyl substituted with one or more $R_7$.

In some embodiments, $R_5$ is $C_{3-10}$ cycloalkyl substituted with one $R_7$.

In some embodiments, $R_5$ is $C_3$ cycloalkyl substituted with one $R_7$. In some embodiments, $R_5$ is $C_4$ cycloalkyl substituted with one $R_7$. In some embodiments, $R_5$ is $C_5$ cycloalkyl substituted with one $R_7$. In some embodiments, $R_5$ is $C_6$ cycloalkyl substituted with one $R_7$. In some embodiments, $R_5$ is $C_7$ cycloalkyl substituted with one $R_7$. In some embodiments, $R_5$ is $C_8$ cycloalkyl substituted with one $R_7$. In some embodiments, $R_5$ is $C_9$ cycloalkyl substituted with one $R_7$. In some embodiments, $R_5$ is $C_{10}$ cycloalkyl substituted with one $R_7$.

In some embodiments, $R_5$ is $C_3$-$C_7$ monocyclic cycloalkyl substituted with one $R_7$. In some embodiments, $R_5$ is $C_3$-$C_7$ monocyclic saturated cycloalkyl substituted with one $R_7$. In some embodiments, $R_5$ is $C_3$-$C_7$ monocyclic partially saturated cycloalkyl substituted with one $R_7$. In some embodiments, $R_5$ is $C_9$-$C_{10}$ bicyclic cycloalkyl substituted with one $R_7$. In some embodiments, $R_5$ is $C_9$-$C_{10}$ bicyclic saturated cycloalkyl substituted with one $R_7$. In some embodiments, $R_5$ is $C_9$-$C_{10}$ bicyclic partially saturated cycloalkyl substituted with one $R_7$. In some embodiments, $R_5$ is $C_5$-$C_{10}$ polycyclic cycloalkyl substituted with one $R_7$.

In some embodiments, $R_5$ is $C_{3-10}$ cycloalkyl.

In some embodiments, $R_5$ is $C_3$ cycloalkyl. In some embodiments, $R_5$ is $C_4$ cycloalkyl. In some embodiments, $R_5$ is $C_5$ cycloalkyl. In some embodiments, $R_5$ is $C_6$ cycloalkyl. In some embodiments, $R_5$ is $C_7$ cycloalkyl. In some embodiments, $R_5$ is $C_8$ cycloalkyl. In some embodiments, $R_5$ is $C_9$ cycloalkyl. In some embodiments, $R_5$ is $C_{10}$ cycloalkyl.

In some embodiments, $R_5$ is $C_3$-$C_7$ monocyclic cycloalkyl. In some embodiments, $R_5$ is $C_3$-$C_7$ monocyclic saturated cycloalkyl. In some embodiments, $R_5$ is $C_3$-$C_7$ monocyclic partially saturated cycloalkyl. In some embodiments, $R_5$ is $C_9$-$C_{10}$ bicyclic cycloalkyl. In some embodiments, $R_5$ is $C_9$-$C_{10}$ bicyclic saturated cycloalkyl. In some embodiments, $R_5$ is $C_9$-$C_{10}$ bicyclic partially saturated cycloalkyl. In some embodiments, $R_5$ is $C_5$-$C_{10}$ polycyclic cycloalkyl.

In some embodiments, $R_5$ is 3- to 13-membered heterocyclyl comprising 1-4 heteroatoms selected from N, O, and S, optionally substituted with one or more $R_7$. In some embodiments, $R_5$ is 3-membered heterocyclyl comprising 1-4 heteroatoms selected from N, O, and S, optionally substituted with one or more $R_7$. In some embodiments, $R_5$ is 4-membered heterocyclyl comprising 1-4 heteroatoms selected from N, O, and S, optionally substituted with one or more $R_7$. In some embodiments, $R_5$ is 5-membered heterocyclyl comprising 1-4 heteroatoms selected from N, O, and S, optionally substituted with one or more $R_7$. In some embodiments, $R_5$ is 6-membered heterocyclyl comprising 1-4 heteroatoms selected from N, O, and S, optionally substituted with one or more $R_7$. In some embodiments, $R_5$ is 7-membered heterocyclyl comprising 1-4 heteroatoms selected from N, O, and S, optionally substituted with one or more $R_7$. In some embodiments, $R_5$ is 8-membered heterocyclyl comprising 1-4 heteroatoms selected from N, O, and S, optionally substituted with one or more $R_7$. In some embodiments, $R_5$ is 9-membered heterocyclyl comprising 1-4 heteroatoms selected from N, O, and S, optionally substituted with one or more $R_7$. In some embodiments, $R_5$ is 10-membered heterocyclyl comprising 1-4 heteroatoms selected from N, O, and S, optionally substituted with one or more $R_7$. In some embodiments, $R_5$ is 11-membered heterocyclyl comprising 1-4 heteroatoms selected from N, O, and S, optionally substituted with one or more $R_7$. In some embodiments, $R_5$ is 12-membered heterocyclyl comprising 1-4 heteroatoms selected from N, O, and S, optionally substituted with one or more $R_7$. In some embodiments, $R_5$ is 13-membered heterocyclyl comprising 1-4 heteroatoms selected from N, O, and S, optionally substituted with one or more $R_7$.

In some embodiments, $R_5$ is 3- to 13-membered heterocyclyl comprising 1-4 heteroatoms selected from N, O, and S, substituted with one or more $R_7$. In some embodiments, $R_5$ is 3-membered heterocyclyl comprising 1-4 heteroatoms selected from N, O, and S, substituted with one or more $R_7$. In some embodiments, $R_5$ is 4-membered heterocyclyl comprising 1-4 heteroatoms selected from N, O, and S, substituted with one or more $R_7$. In some embodiments, $R_5$ is 5-membered heterocyclyl comprising 1-4 heteroatoms selected from N, O, and S, substituted with one or more $R_7$. In some embodiments, $R_5$ is 6-membered heterocyclyl comprising 1-4 heteroatoms selected from N, O, and S, substituted with one or more $R_7$. In some embodiments, $R_5$ is 7-membered heterocyclyl comprising 1-4 heteroatoms selected from N, O, and S, substituted with one or more $R_7$. In some embodiments, $R_5$ is 8-membered heterocyclyl comprising 1-4 heteroatoms selected from N, O, and S, substituted with one or more $R_7$. In some embodiments, $R_5$ is 9-membered heterocyclyl comprising 1-4 heteroatoms selected from N, O, and S, substituted with one or more $R_7$. In some embodiments, $R_5$ is 10-membered heterocyclyl comprising 1-4 heteroatoms selected from N, O, and S, substituted with one or more $R_7$. In some embodiments, $R_5$ is 11-membered heterocyclyl comprising 1-4 heteroatoms selected from N, O, and S, substituted with one or more $R_7$. In some embodiments, $R_5$ is 12-membered heterocyclyl comprising 1-4 heteroatoms selected from N, O, and S, substituted with one or more $R_7$. In some embodiments, $R_5$ is 13-membered heterocyclyl comprising 1-4 heteroatoms selected from N, O, and S, substituted with one or more $R_7$.

In some embodiments, $R_5$ is 3- to 13-membered heterocyclyl comprising 1-4 heteroatoms selected from N, O, and S, substituted with one $R_7$. In some embodiments, $R_5$ is 3-membered heterocyclyl comprising 1-4 heteroatoms selected from N, O, and S, substituted with one $R_7$. In some embodiments, $R_5$ is 4-membered heterocyclyl comprising 1-4 heteroatoms selected from N, O, and S, substituted with one $R_7$. In some embodiments, $R_5$ is 5-membered heterocyclyl comprising 1-4 heteroatoms selected from N, O, and S, substituted with one $R_7$. In some embodiments, $R_5$ is 6-membered heterocyclyl comprising 1-4 heteroatoms selected from N, O, and S, substituted with one $R_7$. In some embodiments, $R_5$ is 7-membered heterocyclyl comprising 1-4 heteroatoms selected from N, O, and S, substituted with one $R_7$. In some embodiments, $R_5$ is 8-membered heterocyclyl comprising 1-4 heteroatoms selected from N, O, and S, substituted with one $R_7$. In some embodiments, $R_5$ is 9-membered heterocyclyl comprising 1-4 heteroatoms selected from N, O, and S, substituted with one $R_7$. In some embodiments, $R_5$ is 10-membered heterocyclyl comprising 1-4 heteroatoms selected from N, O, and S, substituted with one $R_7$. In some embodiments, $R_5$ is 11-membered heterocyclyl comprising 1-4 heteroatoms selected from N, O, and S, substituted with one $R_7$. In some embodiments, $R_5$ is 12-membered heterocyclyl comprising 1-4 heteroatoms selected from N, O, and S, substituted with one $R_7$. In some embodiments, $R_5$ is 13-membered heterocyclyl comprising 1-4 heteroatoms selected from N, O, and S, substituted with one $R_7$.

In some embodiments, $R_5$ is 3- to 13-membered heterocyclyl comprising 1-4 heteroatoms selected from N, O, and S. In some embodiments, $R_5$ is 3-membered heterocyclyl comprising 1-4 heteroatoms selected from N, O, and S. In some embodiments, $R_5$ is 4-membered heterocyclyl comprising 1-4 heteroatoms selected from N, O, and S. In some embodiments, $R_5$ is 5-membered heterocyclyl comprising 1-4 heteroatoms selected from N, O, and S. In some embodiments, $R_5$ is 6-membered heterocyclyl comprising 1-4 heteroatoms selected from N, O, and S. In some embodiments, $R_5$ is 7-membered heterocyclyl comprising 1-4 heteroatoms selected from N, O, and S. In some embodiments, $R_5$ is 8-membered heterocyclyl comprising 1-4 heteroatoms selected from N, O, and S. In some embodiments, $R_5$ is 9-membered heterocyclyl comprising 1-4 heteroatoms selected from N, O, and S. In some embodiments, $R_5$ is 10-membered heterocyclyl comprising 1-4 heteroatoms selected from N, O, and S. In some embodiments, $R_5$ is 11-membered heterocyclyl comprising 1-4 heteroatoms selected from N, O, and S. In some embodiments, $R_5$ is 12-membered heterocyclyl comprising 1-4 heteroatoms selected from N, O, and S. In some embodiments, $R_5$ is 13-membered heterocyclyl comprising 1-4 heteroatoms selected from N, O, and S.

In some embodiments, $R_5$ is 7- to 13-membered bicyclic heterocyclyl comprising 1-4 heteroatoms selected from N, O, and S, optionally substituted with one or more $R_7$. In some embodiments, $R_5$ is 7-membered bicyclic heterocyclyl comprising 1-4 heteroatoms selected from N, O, and S, optionally substituted with one or more $R_7$. In some embodiments, $R_5$ is 8-membered bicyclic heterocyclyl comprising 1-4 heteroatoms selected from N, O, and S, optionally substituted with one or more $R_7$. In some embodiments, $R_5$ is 9-membered bicyclic heterocyclyl comprising 1-4 heteroatoms selected from N, O, and S, optionally substituted with one or more $R_7$. In some embodiments, $R_5$ is 10-membered bicyclic heterocyclyl comprising 1-4 heteroatoms selected from N, O, and S, optionally substituted with one or more $R_7$. In some embodiments, $R_5$ is 11-membered bicyclic heterocyclyl comprising 1-4 heteroatoms selected from N, O, and S, optionally substituted with one or more $R_7$. In some embodiments, $R_5$ is 12-membered bicyclic heterocyclyl comprising 1-4 heteroatoms selected from N, O, and S, optionally substituted with one or more $R_7$. In some embodiments, $R_5$ is 13-membered bicyclic heterocyclyl comprising 1-4 heteroatoms selected from N, O, and S, optionally substituted with one or more $R_7$.

In some embodiments, $R_5$ is 7- to 13-membered bicyclic heterocyclyl comprising 1-4 heteroatoms selected from N, O, and S, substituted with one or more $R_7$. In some embodiments, $R_5$ is 7-membered bicyclic heterocyclyl comprising 1-4 heteroatoms selected from N, O, and S, substituted with one or more $R_7$. In some embodiments, $R_5$ is 8-membered bicyclic heterocyclyl comprising 1-4 heteroatoms selected from N, O, and S, substituted with one or more $R_7$. In some embodiments, $R_5$ is 9-membered bicyclic heterocyclyl comprising 1-4 heteroatoms selected from N, O, and S, substituted with one or more $R_7$. In some embodiments, $R_5$ is 10-membered bicyclic heterocyclyl comprising 1-4 heteroatoms selected from N, O, and S, substituted with one or more $R_7$. In some embodiments, $R_5$ is 11-membered bicyclic heterocyclyl comprising 1-4 heteroatoms selected from N, O, and S, substituted with one or more $R_7$. In some embodiments, $R_5$ is 12-membered bicyclic heterocyclyl comprising 1-4 heteroatoms selected from N, O, and S, substituted with one or more $R_7$. In some embodiments, $R_5$ is 13-membered bicyclic heterocyclyl comprising 1-4 heteroatoms selected from N, O, and S, substituted with one or more $R_7$.

In some embodiments, $R_5$ is 7- to 13-membered bicyclic heterocyclyl comprising 1-4 heteroatoms selected from N, O, and S, substituted with one $R_7$. In some embodiments, $R_5$ is 7-membered bicyclic heterocyclyl comprising 1-4 heteroatoms selected from N, O, and S, substituted with one $R_7$. In some embodiments, $R_5$ is 8-membered bicyclic heterocyclyl comprising 1-4 heteroatoms selected from N, O, and S, substituted with one $R_7$. In some embodiments, $R_5$ is 9-membered bicyclic heterocyclyl comprising 1-4 heteroatoms selected from N, O, and S, substituted with one $R_7$. In some embodiments, $R_5$ is 10-membered bicyclic heterocyclyl comprising 1-4 heteroatoms selected from N, O, and S, substituted with one $R_7$. In some embodiments, $R_5$ is 11-membered bicyclic heterocyclyl comprising 1-4 heteroatoms selected from N, O, and S, substituted with one $R_7$. In some embodiments, $R_5$ is 12-membered bicyclic heterocyclyl comprising 1-4 heteroatoms selected from N, O, and S, substituted with one $R_7$. In some embodiments, $R_5$ is 13-membered bicyclic heterocyclyl comprising 1-4 heteroatoms selected from N, O, and S, substituted with one $R_7$.

In some embodiments, $R_5$ is 7- to 13-membered bicyclic heterocyclyl comprising 1-4 heteroatoms selected from N, O, and S. In some embodiments, $R_5$ is 7-membered bicyclic heterocyclyl comprising 1-4 heteroatoms selected from N, O, and S. In some embodiments, $R_5$ is 8-membered bicyclic heterocyclyl comprising 1-4 heteroatoms selected from N, O, and S. In some embodiments, $R_5$ is 9-membered bicyclic heterocyclyl comprising 1-4 heteroatoms selected from N, O, and S. In some embodiments, $R_5$ is 10-membered bicyclic heterocyclyl comprising 1-4 heteroatoms selected from N, O, and S. In some embodiments, $R_5$ is 11-membered bicyclic heterocyclyl comprising 1-4 heteroatoms selected from N, O, and S. In some embodiments, $R_5$ is 12-membered bicyclic heterocyclyl comprising 1-4 heteroatoms selected from N, O, and S. In some embodiments, $R_5$ is 13-membered bicyclic heterocyclyl comprising 1-4 heteroatoms selected from N, O, and S.

In some embodiments, $R_5$ is 9- to 13-membered polycyclic heterocyclyl comprising 1-4 heteroatoms selected from N, O, and S, optionally substituted with one or more $R_7$. In some embodiments, $R_5$ is 9-membered polycyclic heterocyclyl comprising 1-4 heteroatoms selected from N, O, and S, optionally substituted with one or more $R_7$. In some embodiments, $R_5$ is 10-membered polycyclic heterocyclyl comprising 1-4 heteroatoms selected from N, O, and S, optionally substituted with one or more $R_7$. In some embodiments, $R_5$ is 11-membered polycyclic heterocyclyl comprising 1-4 heteroatoms selected from N, O, and S, optionally substituted with one or more $R_7$. In some embodiments, $R_5$ is 12-membered polycyclic heterocyclyl comprising 1-4 heteroatoms selected from N, O, and S, optionally substituted with one or more $R_7$. In some embodiments, $R_5$ is 13-membered polycyclic heterocyclyl comprising 1-4 heteroatoms selected from N, O, and S, optionally substituted with one or more $R_7$.

In some embodiments, $R_5$ is 9- to 13-membered polycyclic heterocyclyl comprising 1-4 heteroatoms selected from N, O, and S, substituted with one or more $R_7$. In some embodiments, $R_5$ is 9-membered polycyclic heterocyclyl comprising 1-4 heteroatoms selected from N, O, and S, substituted with one or more $R_7$. In some embodiments, $R_5$ is 10-membered polycyclic heterocyclyl comprising 1-4 heteroatoms selected from N, O, and S, substituted with one or more $R_7$. In some embodiments, $R_5$ is 11-membered polycyclic heterocyclyl comprising 1-4 heteroatoms selected from N, O, and S, substituted with one or more $R_7$. In some embodiments, $R_5$ is 12-membered polycyclic heterocyclyl comprising 1-4 heteroatoms selected from N, O, and S, substituted with one or more $R_7$. In some embodiments, $R_5$ is 13-membered polycyclic heterocyclyl comprising 1-4 heteroatoms selected from N, O, and S, substituted with one or more $R_7$.

In some embodiments, $R_5$ is 9- to 13-membered polycyclic heterocyclyl comprising 1-4 heteroatoms selected from N, O, and S, substituted with one $R_7$. In some embodiments, $R_5$ is 9-membered polycyclic heterocyclyl comprising 1-4 heteroatoms selected from N, O, and S, substituted with one $R_7$. In some embodiments, $R_5$ is 10-membered polycyclic heterocyclyl comprising 1-4 heteroatoms selected from N, O, and S, substituted with one $R_7$. In some embodiments, $R_5$ is 11-membered polycyclic heterocyclyl comprising 1-4 heteroatoms selected from N, O, and S, substituted with one $R_7$. In some embodiments, $R_5$ is 12-membered polycyclic heterocyclyl comprising 1-4 heteroatoms selected from N, O, and S, substituted with one $R_7$. In some embodiments, $R_5$ is 13-membered polycyclic heterocyclyl comprising 1-4 heteroatoms selected from N, O, and S, substituted with one $R_7$.

In some embodiments, $R_5$ is 9- to 13-membered polycyclic heterocyclyl comprising 1-4 heteroatoms selected from N, O, and S. In some embodiments, $R_5$ is 9-membered polycyclic heterocyclyl comprising 1-4 heteroatoms selected from N, O, and S. In some embodiments, $R_5$ is 10-membered polycyclic heterocyclyl comprising 1-4 heteroatoms selected from N, O, and S. In some embodiments, $R_5$ is 11-membered polycyclic heterocyclyl comprising 1-4 heteroatoms selected from N, O, and S. In some embodiments, $R_5$ is 12-membered polycyclic heterocyclyl comprising 1-4 heteroatoms selected from N, O, and S. In some embodiments, $R_5$ is 13-membered polycyclic heterocyclyl comprising 1-4 heteroatoms selected from N, O, and S.

In some embodiments, $R_5$ is $C_{6-10}$ aryl or 5- to 13-membered heteroaryl comprising 1-4 heteroatoms selected from N, O, and S, wherein the aryl or heteroaryl is optionally substituted with one or more $R_7$.

In some embodiments, $R_5$ is $C_{6-10}$ aryl or 5- to 13-membered heteroaryl comprising 1-4 heteroatoms selected from N, O, and S.

In some embodiments, $R_5$ is $C_{6-10}$ aryl optionally substituted with one or more $R_7$.

In some embodiments, $R_5$ is $C_{6-8}$ aryl optionally substituted with one or more $R_7$. In some embodiments, $R_5$ is phenyl optionally substituted with one or more $R_7$.

In some embodiments, $R_5$ is $C_{6-8}$ aryl substituted with one or more $R_7$. In some embodiments, $R_5$ is phenyl substituted with one or more $R_7$.

In some embodiments, $R_5$ is $C_{6-8}$ aryl substituted with one $R_7$. In some embodiments, $R_5$ is phenyl substituted with one $R_7$.

In some embodiments, $R_5$ is $C_{6-10}$ aryl.

In some embodiments, $R_5$ is $C_{6-8}$ aryl. In some embodiments, $R_5$ is phenyl.

In some embodiments, $R_5$ is 5- to 13-membered heteroaryl comprising 1-4 heteroatoms selected from N, O, and S, optionally substituted with one or more $R_7$. In some embodiments, $R_5$ is 5-membered heteroaryl comprising 1-4 heteroatoms selected from N, O, and S, optionally substituted with one or more $R_7$. In some embodiments, $R_5$ is 6-membered heteroaryl comprising 1-4 heteroatoms selected from N, O, and S, optionally substituted with one or more $R_7$. In some embodiments, $R_5$ is 7-membered heteroaryl comprising 1-4 heteroatoms selected from N, O, and S, optionally substituted with one or more $R_7$. In some embodiments, $R_5$ is 8-membered heteroaryl comprising 1-4 heteroatoms selected from N, O, and S, optionally substituted with one or more $R_7$. In some embodiments, $R_5$ is 9-membered heteroaryl comprising 1-4 heteroatoms selected from N, O, and S, optionally substituted with one or more $R_7$. In some embodiments, $R_5$ is 10-membered heteroaryl comprising 1-4 heteroatoms selected from N, O, and S, optionally substituted with one or more $R_7$. In some embodiments, $R_5$ is 11-membered heteroaryl comprising 1-4 heteroatoms selected from N, O, and S, optionally substituted with one or more $R_7$. In some embodiments, $R_5$ is 12-membered heteroaryl comprising 1-4 heteroatoms selected from N, O, and S, optionally substituted with one or more $R_7$. In some embodiments, $R_5$ is 13-membered heteroaryl comprising 1-4 heteroatoms selected from N, O, and S, optionally substituted with one or more $R_7$.

In some embodiments, $R_5$ is 5- to 13-membered heteroaryl comprising 1-4 heteroatoms selected from N, O, and S, substituted with one or more $R_7$. In some embodiments, $R_5$ is 5-membered heteroaryl comprising 1-4 heteroatoms selected from N, O, and S, substituted with one or more $R_7$. In some embodiments, $R_5$ is 6-membered heteroaryl comprising 1-4 heteroatoms selected from N, O, and S, substituted with one or more $R_7$. In some embodiments, $R_5$ is 7-membered heteroaryl comprising 1-4 heteroatoms selected from N, O, and S, substituted with one or more $R_7$. In some embodiments, $R_5$ is 8-membered heteroaryl comprising 1-4 heteroatoms selected from N, O, and S, substituted with one or more $R_7$. In some embodiments, $R_5$ is 9-membered heteroaryl comprising 1-4 heteroatoms selected from N, O, and S, substituted with one or more $R_7$. In some embodiments, $R_5$ is 10-membered heteroaryl comprising 1-4 heteroatoms selected from N, O, and S, substituted with one or more $R_7$. In some embodiments, $R_5$ is 11-membered heteroaryl comprising 1-4 heteroatoms selected from N, O, and S, substituted with one or more $R_7$. In some embodiments, $R_5$ is 12-membered heteroaryl comprising 1-4 heteroatoms selected from N, O, and S, substituted with one or more $R_7$. In some embodiments, $R_5$ is 13-membered heteroaryl comprising 1-4 heteroatoms selected from N, O, and S, substituted with one or more $R_7$.

In some embodiments, $R_5$ is 5- to 13-membered heteroaryl comprising 1-4 heteroatoms selected from N, O, and S, substituted with one $R_7$. In some embodiments, $R_5$ is 5-membered heteroaryl comprising 1-4 heteroatoms selected from N, O, and S, substituted with one $R_7$. In some embodiments, $R_5$ is 6-membered heteroaryl comprising 1-4 heteroatoms selected from N, O, and S, substituted with one $R_7$. In some embodiments, $R_5$ is 7-membered heteroaryl comprising 1-4 heteroatoms selected from N, O, and S, substituted with one $R_7$. In some embodiments, $R_5$ is 8-membered heteroaryl comprising 1-4 heteroatoms selected from N, O, and S, substituted with one $R_7$. In some embodiments, $R_5$ is 9-membered heteroaryl comprising 1-4 heteroatoms selected from N, O, and S, substituted with one $R_7$. In some embodiments, $R_5$ is 10-membered heteroaryl comprising 1-4 heteroatoms selected from N, O, and S, substituted with one $R_7$. In some embodiments, $R_5$ is 11-membered heteroaryl comprising 1-4 heteroatoms selected from N, O, and S, substituted with one $R_7$. In some embodiments, $R_5$ is 12-membered heteroaryl comprising 1-4 heteroatoms selected from N, O, and S, substituted with one $R_7$. In some embodiments, $R_5$ is 13-membered heteroaryl comprising 1-4 heteroatoms selected from N, O, and S, substituted with one $R_7$.

In some embodiments, $R_5$ is 5- to 13-membered heteroaryl comprising 1-4 heteroatoms selected from N, O, and S. In some embodiments, $R_5$ is 5-membered heteroaryl comprising 1-4 heteroatoms selected from N, O, and S. In some embodiments, $R_5$ is 6-membered heteroaryl comprising 1-4 heteroatoms selected from N, O, and S. In some embodiments, $R_5$ is 7-membered heteroaryl comprising 1-4 heteroatoms selected from N, O, and S. In some embodiments, $R_5$ is 8-membered heteroaryl comprising 1-4 heteroatoms selected from N, O, and S. In some embodiments, $R_5$ is 9-membered heteroaryl comprising 1-4 heteroatoms selected from N, O, and S. In some embodiments, $R_5$ is 10-membered heteroaryl comprising 1-4 heteroatoms selected from N, O, and S. In some embodiments, $R_5$ is 11-membered heteroaryl comprising 1-4 heteroatoms selected from N, O, and S. In some embodiments, $R_5$ is 12-membered heteroaryl comprising 1-4 heteroatoms selected from N, O, and S. In some embodiments, $R_5$ is 13-membered heteroaryl comprising 1-4 heteroatoms selected from N, O, and S.

In some embodiments, $R_5$ is 9- to 13-membered bicyclic heteroaryl comprising 1-4 heteroatoms selected from N, O, and S, optionally substituted with one or more $R_7$. In some embodiments, $R_5$ is 9-membered bicyclic heteroaryl comprising 1-4 heteroatoms selected from N, O, and S, optionally substituted with one or more $R_7$. In some embodiments, $R_5$ is 10-membered bicyclic heteroaryl comprising 1-4 heteroatoms selected from N, O, and S, optionally substituted with one or more $R_7$. In some embodiments, $R_5$ is 11-membered bicyclic heteroaryl comprising 1-4 heteroatoms selected from N, O, and S, optionally substituted with one or more $R_7$. In some embodiments, $R_5$ is 12-membered bicyclic heteroaryl comprising 1-4 heteroatoms selected from N, O, and S, optionally substituted with one or more $R_7$. In some embodiments, $R_5$ is 13-membered bicyclic heteroaryl comprising 1-4 heteroatoms selected from N, O, and S, optionally substituted with one or more $R_7$.

In some embodiments, $R_5$ is 9- to 13-membered bicyclic heteroaryl comprising 1-4 heteroatoms selected from N, O, and S, substituted with one or more $R_7$. In some embodiments, $R_5$ is 9-membered bicyclic heteroaryl comprising 1-4 heteroatoms selected from N, O, and S, substituted with one or more $R_7$. In some embodiments, $R_5$ is 10-membered bicyclic heteroaryl comprising 1-4 heteroatoms selected from N, O, and S, substituted with one or more $R_7$. In some embodiments, $R_5$ is 11-membered bicyclic heteroaryl comprising 1-4 heteroatoms selected from N, O, and S, substituted with one or more $R_7$. In some embodiments, $R_5$ is 12-membered bicyclic heteroaryl comprising 1-4 heteroatoms selected from N, O, and S, substituted with one or more $R_7$. In some embodiments, $R_5$ is 13-membered bicyclic heteroaryl comprising 1-4 heteroatoms selected from N, O, and S, substituted with one or more $R_7$.

In some embodiments, $R_5$ is 9- to 13-membered bicyclic heteroaryl comprising 1-4 heteroatoms selected from N, O, and S, substituted with one $R_7$. In some embodiments, $R_5$ is 9-membered bicyclic heteroaryl comprising 1-4 heteroatoms selected from N, O, and S, substituted with one $R_7$. In some embodiments, $R_5$ is 10-membered bicyclic heteroaryl comprising 1-4 heteroatoms selected from N, O, and S, substituted with one $R_7$. In some embodiments, $R_5$ is 11-membered bicyclic heteroaryl comprising 1-4 heteroatoms selected from N, O, and S, substituted with one $R_7$. In some embodiments, $R_5$ is 12-membered bicyclic heteroaryl comprising 1-4 heteroatoms selected from N, O, and S, substituted with one $R_7$. In some embodiments, $R_5$ is 13-membered bicyclic heteroaryl comprising 1-4 heteroatoms selected from N, O, and S, substituted with one $R_7$.

In some embodiments, $R_5$ is 9- to 13-membered bicyclic heteroaryl comprising 1-4 heteroatoms selected from N, O, and S. In some embodiments, $R_5$ is 9-membered bicyclic heteroaryl comprising 1-4 heteroatoms selected from N, O, and S. In some embodiments, $R_5$ is 10-membered bicyclic heteroaryl comprising 1-4 heteroatoms selected from N, O, and S. In some embodiments, $R_5$ is 11-membered bicyclic heteroaryl comprising 1-4 heteroatoms selected from N, O, and S. In some embodiments, $R_5$ is 12-membered bicyclic heteroaryl comprising 1-4 heteroatoms selected from N, O, and S. In some embodiments, $R_5$ is 13-membered bicyclic heteroaryl comprising 1-4 heteroatoms selected from N, O, and S.

In some embodiments, $R_5$ is 9- to 13-membered polycyclic heteroaryl comprising 1-4 heteroatoms selected from N, O, and S, optionally substituted with one or more $R_7$. In some embodiments, $R_5$ is 9-membered polycyclic heteroaryl comprising 1-4 heteroatoms selected from N, O, and S, optionally substituted with one or more $R_7$. In some embodiments, $R_5$ is 10-membered polycyclic heteroaryl comprising 1-4 heteroatoms selected from N, O, and S, optionally substituted with one or more $R_7$. In some embodiments, $R_5$ is 11-membered polycyclic heteroaryl comprising 1-4 heteroatoms selected from N, O, and S, optionally substituted with one or more $R_7$. In some embodiments, $R_5$ is 12-membered polycyclic heteroaryl comprising 1-4 heteroatoms selected from N, O, and S, optionally substituted with one or more $R_7$. In some embodiments, $R_5$ is 13-membered polycyclic heteroaryl comprising 1-4 heteroatoms selected from N, O, and S, optionally substituted with one or more $R_7$.

In some embodiments, $R_5$ is 9- to 13-membered polycyclic heteroaryl comprising 1-4 heteroatoms selected from N, O, and S, substituted with one or more $R_7$. In some embodiments, $R_5$ is 9-membered polycyclic heteroaryl comprising 1-4 heteroatoms selected from N, O, and S, substituted with one or more $R_7$. In some embodiments, $R_5$ is 10-membered polycyclic heteroaryl comprising 1-4 heteroatoms selected from N, O, and S, substituted with one or more $R_7$. In some embodiments, $R_5$ is 11-membered polycyclic heteroaryl comprising 1-4 heteroatoms selected from N, O, and S, substituted with one or more $R_7$. In some embodiments, $R_5$ is 12-membered polycyclic heteroaryl comprising 1-4 heteroatoms selected from N, O, and S, substituted with one or more $R_7$. In some embodiments, $R_5$ is 13-membered polycyclic heteroaryl comprising 1-4 heteroatoms selected from N, O, and S, substituted with one or more $R_7$.

In some embodiments, $R_5$ is 9- to 13-membered polycyclic heteroaryl comprising 1-4 heteroatoms selected from N, O, and S, substituted with one $R_7$. In some embodiments, $R_5$ is 9-membered polycyclic heteroaryl comprising 1-4 heteroatoms selected from N, O, and S, substituted with one $R_7$. In some embodiments, $R_5$ is 10-membered polycyclic heteroaryl comprising 1-4 heteroatoms selected from N, O, and S, substituted with one $R_7$. In some embodiments, $R_5$ is 11-membered polycyclic heteroaryl comprising 1-4 heteroatoms selected from N, O, and S, substituted with one $R_7$. In some embodiments, $R_5$ is 12-membered polycyclic heteroaryl comprising 1-4 heteroatoms selected from N, O, and S, substituted with one $R_7$. In some embodiments, $R_5$ is 13-membered polycyclic heteroaryl comprising 1-4 heteroatoms selected from N, O, and S, substituted with one $R_7$.

In some embodiments, $R_5$ is 9- to 13-membered polycyclic heteroaryl comprising 1-4 heteroatoms selected from N, O, and S. In some embodiments, $R_5$ is 9-membered polycyclic heteroaryl comprising 1-4 heteroatoms selected from N, O, and S. In some embodiments, $R_5$ is 10-membered polycyclic heteroaryl comprising 1-4 heteroatoms selected from N, O, and S. In some embodiments, $R_5$ is 11-membered polycyclic heteroaryl comprising 1-4 heteroatoms selected from N, O, and S. In some embodiments, $R_5$ is 12-membered polycyclic heteroaryl comprising 1-4 heteroatoms selected from N, O, and S. In some embodiments, $R_5$ is 13-membered polycyclic heteroaryl comprising 1-4 heteroatoms selected from N, O, and S.

In some embodiments, $R_5$ is H, $C_{1-6}$ alkyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, cycloalkyl, heterocyclyl, aryl, or heteroaryl is optionally substituted with one or more $R_7$.

In some embodiments, $R_5$ is H, $C_{1-6}$ alkyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, cycloalkyl, heterocyclyl, aryl, or heteroaryl is optionally substituted with one or more $R_7$.

In some embodiments, $R_5$ is H, $C_{1-6}$ alkyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, cycloalkyl, heterocyclyl, aryl, or heteroaryl is substituted with one or more $R_7$.

In some embodiments, $R_5$ is cyclopropyl, piperidine, tetrahydropyran, morpholine, phenyl, pyridine, pyrimidine, tetrazole, triazole, pyrazole, thiazole, oxazole, furan, pyrrole, isoxazole, 1,3-dihydro-2H-benzo[d]imidazol-2-one, indoline, indole, 2,3-diydrobenzofuran, 1H-benzo[d][1,2,3]triazole, 1H-indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_5$ is cyclopropyl, piperidine, tetrahydropyran, or morpholine.

In some embodiments, $R_5$ is phenyl, pyridine, pyrimidine, tetrazole, triazole, pyrazole, thiazole, oxazole, furan, pyrrole, isoxazole, 1,3-dihydro-2H-benzo[d]imidazol-2-one, indoline, indole, 2,3-diydrobenzofuran, 1H-benzo[d][1,2,3]triazole, 1H-indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_5$ is pyridine, pyrimidine, tetrazole, triazole, pyrazole, thiazole, oxazole, furan, pyrrole, isoxazole, 1,3-dihydro-2H-benzo[d]imidazol-2-one, indoline, indole, 2,3-diydrobenzofuran, 1H-benzo[d][1,2,3]triazole, indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_5$ is pyridine, pyrimidine, or indazole.

In some embodiments, $R_5$ is indazole.

In some embodiments, $R_5$ is tetrazole, triazole, pyrazole, thiazole, oxazole, furan, pyrrole, isoxazole, 1,3-dihydro-2H-benzo[d]imidazol-2-one, indoline, indole, 2,3-diydrobenzofuran, 1H-benzo[d][1,2,3]triazole, 1H-indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_5$ is tetrazole, triazole, pyrazole, thiazole, oxazole, furan, pyrrole, isoxazole, or imidazole.

In some embodiments, $R_5$ is 1,3-dihydro-2H-benzo[d]imidazol-2-one, indoline, indole, 2,3-diydrobenzofuran, 1H-benzo[d][1,2,3]triazole, 1H-indazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_5$ is 1,3-dihydro-2H-benzo[d]imidazol-2-one, indoline, indole, 2,3-diydrobenzofuran, 1H-benzo[d][1,2,3]triazole, 1H-indazole, imidazo[1,2-a]pyrazine, naphthalene, quinoline, 2,3-dihydrobenzo[b][1,4]dioxine, or benzo[d]oxazol-2(3H)-one, benzo[d]isoxazole.

In some embodiments, $R_5$ is 9H-carbazole.

In some embodiments, $R_6$ is H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, alkenyl, alkynyl, cycloalkyl, heterocyclyl, aryl, or heteroaryl is optionally substituted with one or more $R_7$.

In some embodiments, $R_6$ is H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S.

In some embodiments, $R_6$ is H.

In some embodiments, $R_6$ is $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, alkenyl, alkynyl, cycloalkyl, heterocyclyl, aryl, or heteroaryl is optionally substituted with one or more $R_7$.

In some embodiments, $R_6$ is $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S.

In some embodiments, $R_6$ is $C_{1-6}$ alkyl, $C_{2-6}$ alkenyl, or $C_{2-6}$ alkynyl, wherein the alkyl, alkenyl, or alkynyl is optionally substituted with one or more $R_7$.

In some embodiments, $R_6$ is $C_{1-6}$ alkyl optionally substituted with one or more $R_7$. In some embodiments, $R_6$ is methyl optionally substituted with one or more $R_7$. In some embodiments, $R_6$ is ethyl optionally substituted with one or more $R_7$. In some embodiments, $R_6$ is propyl optionally substituted with one or more $R_7$. In some embodiments, $R_6$ is butyl optionally substituted with one or more $R_7$. In some embodiments, $R_6$ is pentyl optionally substituted with one or more $R_7$. In some embodiments, $R_6$ is hexyl optionally substituted with one or more $R_7$. In some embodiments, $R_6$ is isopropyl optionally substituted with one or more $R_7$. In some embodiments, $R_6$ is isobutyl optionally substituted with one or more $R_7$. In some embodiments, $R_6$ is isopentyl optionally substituted with one or more $R_7$. In some embodiments, $R_6$ is isohexyl optionally substituted with one or more $R_7$. In some embodiments, $R_6$ is secbutyl optionally substituted with one or more $R_7$. In some embodiments, $R_6$ is secpentyl optionally substituted with one or more $R_7$. In some embodiments, $R_6$ is sechexyl optionally substituted with one or more $R_7$. In some embodiments, $R_6$ is tertbutyl optionally substituted with one or more $R_7$.

In some embodiments, $R_6$ is $C_{2-6}$ alkenyl optionally substituted with one or more $R_7$. In some embodiments, $R_6$ is $C_2$ alkenyl optionally substituted with one or more $R_7$. In some embodiments, $R_6$ is $C_3$ alkenyl optionally substituted with one or more $R_7$. In some embodiments, $R_6$ is $C_4$ alkenyl optionally substituted with one or more $R_7$. In some embodiments, $R_6$ is $C_5$ alkenyl optionally substituted with one or more $R_7$. In some embodiments, $R_6$ is $C_6$ alkenyl optionally substituted with one or more $R_7$.

In some embodiments, $R_6$ is $C_{2-6}$ alkynyl optionally substituted with one or more $R_7$. In some embodiments, $R_6$ is $C_2$ alkynyl optionally substituted with one or more $R_7$. In some embodiments, $R_6$ is $C_3$ alkynyl optionally substituted with one or more $R_7$. In some embodiments, $R_6$ is $C_4$ alkynyl optionally substituted with one or more $R_7$. In some embodiments, $R_6$ is $C_5$ alkynyl optionally substituted with one or more $R_7$. In some embodiments, $R_6$ is $C_6$ alkynyl optionally substituted with one or more $R_7$.

In some embodiments, $R_6$ is $C_{1-6}$ alkyl, $C_{2-6}$ alkenyl, or $C_{2-6}$ alkynyl, wherein the alkyl, alkenyl, or alkynyl is substituted with one or more $R_7$.

In some embodiments, $R_6$ is $C_{1-6}$ alkyl substituted with one or more $R_7$. In some embodiments, $R_6$ is methyl substituted with one or more $R_7$. In some embodiments, $R_6$ is ethyl substituted with one or more $R_7$. In some embodiments, $R_6$ is propyl substituted with one or more $R_7$. In some embodiments, $R_6$ is butyl substituted with one or more $R_7$. In some embodiments, $R_6$ is pentyl substituted with one or more $R_7$. In some embodiments, $R_6$ is hexyl substituted with one or more $R_7$. In some embodiments, $R_6$ is isopropyl substituted with one or more $R_7$. In some embodiments, $R_6$ is isobutyl substituted with one or more $R_7$. In some embodiments, $R_6$ is isopentyl substituted with one or more $R_7$. In some embodiments, $R_6$ is isohexyl substituted with one or more $R_7$. In some embodiments, $R_6$ is secbutyl substituted with one or more $R_7$. In some embodiments, $R_6$ is secpentyl substituted with one or more $R_7$. In some embodiments, $R_6$ is sechexyl substituted with one or more $R_7$. In some embodiments, $R_6$ is tertbutyl substituted with one or more $R_7$.

In some embodiments, $R_6$ is $C_{2-6}$ alkenyl substituted with one or more $R_7$. In some embodiments, $R_6$ is $C_2$ alkenyl substituted with one or more $R_7$. In some embodiments, $R_6$ is $C_3$ alkenyl substituted with one or more $R_7$. In some embodiments, $R_6$ is $C_4$ alkenyl substituted with one or more $R_7$. In some embodiments, $R_6$ is $C_5$ alkenyl substituted with one or more $R_7$. In some embodiments, $R_6$ is $C_6$ alkenyl substituted with one or more $R_7$.

In some embodiments, $R_6$ is $C_{2-6}$ alkynyl substituted with one or more $R_7$. In some embodiments, $R_6$ is $C_2$ alkynyl substituted with one or more $R_7$. In some embodiments, $R_6$ is $C_3$ alkynyl substituted with one or more $R_7$. In some embodiments, $R_6$ is $C_4$ alkynyl substituted with one or more $R_7$. In some embodiments, $R_6$ is $C_5$ alkynyl substituted with one or more $R_7$. In some embodiments, $R_6$ is $C_6$ alkynyl substituted with one or more $R_7$.

In some embodiments, $R_6$ is $C_{1-6}$ alkyl, $C_{2-6}$ alkenyl, or $C_{2-6}$ alkynyl, wherein the alkyl, alkenyl, or alkynyl is substituted with one $R_7$.

In some embodiments, $R_6$ is $C_{1-6}$ alkyl substituted with one $R_7$. In some embodiments, $R_6$ is methyl substituted with one $R_7$. In some embodiments, $R_6$ is ethyl substituted with one $R_7$. In some embodiments, $R_6$ is propyl substituted with one $R_7$. In some embodiments, $R_6$ is butyl substituted with one $R_7$. In some embodiments, $R_6$ is pentyl substituted with one $R_7$. In some embodiments, $R_6$ is hexyl substituted with one $R_7$. In some embodiments, $R_6$ is isopropyl substituted with one $R_7$. In some embodiments, $R_6$ is isobutyl substituted with one $R_7$. In some embodiments, $R_6$ is isopentyl substituted with one $R_7$. In some embodiments, $R_6$ is isohexyl substituted with one $R_7$. In some embodiments, $R_6$ is secbutyl substituted with one $R_7$. In some embodiments, $R_6$ is secpentyl substituted with one $R_7$. In some embodiments, $R_6$ is sechexyl substituted with one $R_7$. In some embodiments, $R_6$ is tertbutyl substituted with one $R_7$.

In some embodiments, $R_6$ is $C_{2-6}$ alkenyl substituted with one $R_7$. In some embodiments, $R_6$ is $C_2$ alkenyl substituted with one $R_7$. In some embodiments, $R_6$ is $C_3$ alkenyl substituted with one $R_7$. In some embodiments, $R_6$ is $C_4$ alkenyl substituted with one $R_7$. In some embodiments, $R_6$ is $C_5$ alkenyl substituted with one $R_7$. In some embodiments, $R_6$ is $C_6$ alkenyl substituted with one $R_7$.

In some embodiments, $R_6$ is $C_{2-6}$ alkynyl substituted with one $R_7$. In some embodiments, $R_6$ is $C_2$ alkynyl substituted with one $R_7$. In some embodiments, $R_6$ is $C_3$ alkynyl substituted with one $R_7$. In some embodiments, $R_6$ is $C_4$ alkynyl substituted with one $R_7$. In some embodiments, $R_6$ is $C_5$ alkynyl substituted with one $R_7$. In some embodiments, $R_6$ is $C_6$ alkynyl substituted with one $R_7$.

In some embodiments, $R_6$ is $C_{1-6}$ alkyl, $C_{2-6}$ alkenyl, or $C_{2-6}$ alkynyl.

In some embodiments, $R_6$ is $C_{1-6}$ alkyl. In some embodiments, $R_6$ is methyl. In some embodiments, $R_6$ is ethyl. In some embodiments, $R_6$ is propyl. In some embodiments, $R_6$ is butyl. In some embodiments, $R_6$ is pentyl. In some embodiments, $R_6$ is hexyl. In some embodiments, $R_6$ is isopropyl. In some embodiments, $R_6$ is isobutyl. In some embodiments, $R_6$ is isopentyl. In some embodiments, $R_6$ is isohexyl. In some embodiments, $R_6$ is secbutyl. In some embodiments, $R_6$ is secpentyl. In some embodiments, $R_6$ is sechexyl. In some embodiments, $R_6$ is tertbutyl.

In some embodiments, $R_6$ is $C_{2-6}$ alkenyl. In some embodiments, $R_6$ is $C_2$ alkenyl. In some embodiments, $R_6$ is $C_3$ alkenyl. In some embodiments, $R_6$ is $C_4$ alkenyl. In some embodiments, $R_6$ is $C_5$ alkenyl. In some embodiments, $R_6$ is $C_6$ alkenyl.

In some embodiments, $R_6$ is $C_{2-6}$ alkynyl. In some embodiments, $R_6$ is $C_2$ alkynyl. In some embodiments, $R_6$ is $C_3$ alkynyl. In some embodiments, $R_6$ is $C_4$ alkynyl. In some embodiments, $R_6$ is $C_5$ alkynyl. In some embodiments, $R_6$ is $C_6$ alkynyl.

In some embodiments, $R_6$ is $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the cycloalkyl, heterocyclyl, aryl, or heteroaryl is optionally substituted with one or more $R_7$.

In some embodiments, $R_6$ is $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S.

In some embodiments, $R_6$ is $C_{3-10}$ cycloalkyl or 3- to 13-membered heterocyclyl comprising 1-4 heteroatoms selected from N, O, and S, wherein the cycloalkyl or heterocyclyl is optionally substituted with one or more $R_7$.

In some embodiments, $R_6$ is $C_{3-10}$ cycloalkyl or 3- to 13-membered heterocyclyl comprising 1-4 heteroatoms selected from N, O, and S.

In some embodiments, $R_6$ is $C_{3-10}$ cycloalkyl optionally substituted with one or more $R_7$.

In some embodiments, $R_6$ is $C_3$ cycloalkyl optionally substituted with one or more $R_7$. In some embodiments, $R_6$ is $C_4$ cycloalkyl optionally substituted with one or more $R_7$. In some embodiments, $R_6$ is $C_5$ cycloalkyl optionally substituted with one or more $R_7$. In some embodiments, $R_6$ is $C_6$ cycloalkyl optionally substituted with one or more $R_7$. In some embodiments, $R_6$ is $C_7$ cycloalkyl optionally substituted with one or more $R_7$. In some embodiments, $R_6$ is $C_8$ cycloalkyl optionally substituted with one or more $R_7$. In some embodiments, $R_6$ is $C_9$ cycloalkyl optionally substituted with one or more $R_7$. In some embodiments, $R_6$ is $C_{10}$ cycloalkyl optionally substituted with one or more $R_7$.

In some embodiments, $R_6$ is $C_3$-$C_7$ monocyclic cycloalkyl optionally substituted with one or more $R_7$. In some embodiments, $R_6$ is $C_3$-$C_7$ monocyclic saturated cycloalkyl optionally substituted with one or more $R_7$. In some embodiments, $R_6$ is $C_3$-$C_7$ monocyclic partially saturated cycloalkyl optionally substituted with one or more $R_7$. In some embodiments, $R_6$ is $C_9$-$C_{10}$ bicyclic cycloalkyl optionally substituted with one or more $R_7$. In some embodiments, $R_6$ is $C_9$-$C_{10}$ bicyclic saturated cycloalkyl optionally substituted with one or more $R_7$. In some embodiments, $R_6$ is $C_9$-$C_{10}$ bicyclic partially saturated cycloalkyl optionally substituted with one or more $R_7$. In some embodiments, $R_6$ is $C_5$-$C_{10}$ polycyclic cycloalkyl optionally substituted with one or more $R_7$.

In some embodiments, $R_6$ is $C_{3-10}$ cycloalkyl substituted with one or more $R_7$.

In some embodiments, $R_6$ is $C_3$ cycloalkyl substituted with one or more $R_7$. In some embodiments, $R_6$ is $C_4$ cycloalkyl substituted with one or more $R_7$. In some embodiments, $R_6$ is $C_5$ cycloalkyl substituted with one or more $R_7$. In some embodiments, $R_6$ is $C_6$ cycloalkyl substituted with one or more $R_7$. In some embodiments, $R_6$ is $C_7$ cycloalkyl substituted with one or more $R_7$. In some embodiments, $R_6$ is $C_8$ cycloalkyl substituted with one or more $R_7$. In some embodiments, $R_6$ is $C_9$ cycloalkyl substituted with one or more $R_7$. In some embodiments, $R_6$ is $C_{10}$ cycloalkyl substituted with one or more $R_7$.

In some embodiments, $R_6$ is $C_3$-$C_7$ monocyclic cycloalkyl substituted with one or more $R_7$. In some embodiments, $R_6$ is $C_3$-$C_7$ monocyclic saturated cycloalkyl substituted with one or more $R_7$. In some embodiments, $R_6$ is $C_3$-$C_7$ monocyclic partially saturated cycloalkyl substituted with one or more $R_7$. In some embodiments, $R_6$ is $C_9$-$C_{10}$ bicyclic cycloalkyl substituted with one or more $R_7$. In some embodiments, $R_6$ is $C_9$-$C_{10}$ bicyclic saturated cycloalkyl substituted with one or more $R_7$. In some embodiments, $R_6$ is $C_9$-$C_{10}$ bicyclic partially saturated cycloalkyl substituted with one or more $R_7$. In some embodiments, $R_6$ is $C_5$-$C_{10}$ polycyclic cycloalkyl substituted with one or more $R_7$.

In some embodiments, $R_6$ is $C_{3-10}$ cycloalkyl substituted with one $R_7$.

In some embodiments, $R_6$ is $C_3$ cycloalkyl substituted with one $R_7$. In some embodiments, $R_6$ is $C_4$ cycloalkyl substituted with one $R_7$. In some embodiments, $R_6$ is $C_5$ cycloalkyl substituted with one $R_7$. In some embodiments, $R_6$ is $C_6$ cycloalkyl substituted with one $R_7$. In some embodiments, $R_6$ is $C_7$ cycloalkyl substituted with one $R_7$. In some embodiments, $R_6$ is $C_8$ cycloalkyl substituted with one $R_7$. In some embodiments, $R_6$ is $C_9$ cycloalkyl substituted with one $R_7$. In some embodiments, $R_6$ is $C_{10}$ cycloalkyl substituted with one $R_7$.

In some embodiments, $R_6$ is $C_3$-$C_7$ monocyclic cycloalkyl substituted with one $R_7$. In some embodiments, $R_6$ is $C_3$-$C_7$ monocyclic saturated cycloalkyl substituted with one $R_7$. In some embodiments, $R_6$ is $C_3$-$C_7$ monocyclic partially saturated cycloalkyl substituted with one $R_7$. In some embodiments, $R_6$ is $C_9$-$C_{10}$ bicyclic cycloalkyl substituted with one $R_7$. In some embodiments, $R_6$ is $C_9$-$C_{10}$ bicyclic saturated cycloalkyl substituted with one $R_7$. In some embodiments, $R_6$ is $C_9$-$C_{10}$ bicyclic partially saturated cycloalkyl substituted with one $R_7$. In some embodiments, $R_6$ is $C_5$-$C_{10}$ polycyclic cycloalkyl substituted with one $R_7$.

In some embodiments, $R_6$ is $C_{3-10}$ cycloalkyl.

In some embodiments, $R_6$ is $C_3$ cycloalkyl. In some embodiments, $R_6$ is $C_4$ cycloalkyl. In some embodiments, $R_6$ is $C_5$ cycloalkyl. In some embodiments, $R_6$ is $C_6$ cycloalkyl. In some embodiments, $R_6$ is $C_7$ cycloalkyl. In some embodiments, $R_6$ is $C_8$ cycloalkyl. In some embodiments, $R_6$ is $C_9$ cycloalkyl. In some embodiments, $R_6$ is $C_{10}$ cycloalkyl.

In some embodiments, $R_6$ is $C_3$-$C_7$ monocyclic cycloalkyl. In some embodiments, $R_6$ is $C_3$-$C_7$ monocyclic saturated cycloalkyl. In some embodiments, $R_6$ is $C_3$-$C_7$ monocyclic partially saturated cycloalkyl. In some embodiments, $R_6$ is $C_9$-$C_{10}$ bicyclic cycloalkyl. In some embodiments, $R_6$ is $C_9$-$C_{10}$ bicyclic saturated cycloalkyl. In some embodiments, $R_6$ is $C_9$-$C_{10}$ bicyclic partially saturated cycloalkyl. In some embodiments, $R_6$ is $C_5$-$C_{10}$ polycyclic cycloalkyl.

In some embodiments, $R_6$ is 3- to 13-membered heterocyclyl comprising 1-4 heteroatoms selected from N, O, and S, optionally substituted with one or more $R_7$. In some embodiments, $R_6$ is 3-membered heterocyclyl comprising 1-4 heteroatoms selected from N, O, and S, optionally substituted with one or more $R_7$. In some embodiments, $R_6$ is 4-membered heterocyclyl comprising 1-4 heteroatoms selected from N, O, and S, optionally substituted with one or more $R_7$. In some embodiments, $R_6$ is 5-membered heterocyclyl comprising 1-4 heteroatoms selected from N, O, and S, optionally substituted with one or more $R_7$. In some embodiments, $R_6$ is 6-membered heterocyclyl comprising 1-4 heteroatoms selected from N, O, and S, optionally substituted with one or more $R_7$. In some embodiments, $R_6$ is 7-membered heterocyclyl comprising 1-4 heteroatoms selected from N, O, and S, optionally substituted with one or more $R_7$. In some embodiments, $R_6$ is 8-membered heterocyclyl comprising 1-4 heteroatoms selected from N, O, and S, optionally substituted with one or more $R_7$. In some embodiments, $R_6$ is 9-membered heterocyclyl comprising 1-4 heteroatoms selected from N, O, and S, optionally substituted with one or more $R_7$. In some embodiments, $R_6$ is 10-membered heterocyclyl comprising 1-4 heteroatoms selected from N, O, and S, optionally substituted with one or more $R_7$. In some embodiments, $R_6$ is 11-membered heterocyclyl comprising 1-4 heteroatoms selected from N, O, and S, optionally substituted with one or more $R_7$. In some embodiments, $R_6$ is 12-membered heterocyclyl comprising 1-4 heteroatoms selected from N, O, and S, optionally substituted with one or more $R_7$. In some embodiments, $R_6$ is 13-membered heterocyclyl comprising 1-4 heteroatoms selected from N, O, and S, optionally substituted with one or more $R_7$.

In some embodiments, $R_6$ is 3- to 13-membered heterocyclyl comprising 1-4 heteroatoms selected from N, O, and S, substituted with one or more $R_7$. In some embodiments, $R_6$ is 3-membered heterocyclyl comprising 1-4 heteroatoms selected from N, O, and S, substituted with one or more $R_7$. In some embodiments, $R_6$ is 4-membered heterocyclyl comprising 1-4 heteroatoms selected from N, O, and S, substituted with one or more $R_7$. In some embodiments, $R_6$ is 5-membered heterocyclyl comprising 1-4 heteroatoms selected from N, O, and S, substituted with one or more $R_7$. In some embodiments, $R_6$ is 6-membered heterocyclyl comprising 1-4 heteroatoms selected from N, O, and S, substituted with one or more $R_7$. In some embodiments, $R_6$ is 7-membered heterocyclyl comprising 1-4 heteroatoms selected from N, O, and S, substituted with one or more $R_7$. In some embodiments, $R_6$ is 8-membered heterocyclyl comprising 1-4 heteroatoms selected from N, O, and S, substituted with one or more $R_7$. In some embodiments, $R_6$ is 9-membered heterocyclyl comprising 1-4 heteroatoms selected from N, O, and S, substituted with one or more $R_7$. In some embodiments, $R_6$ is 10-membered heterocyclyl comprising 1-4 heteroatoms selected from N, O, and S, substituted with one or more $R_7$. In some embodiments, $R_6$ is 11-membered heterocyclyl comprising 1-4 heteroatoms selected from N, O, and S, substituted with one or more $R_7$. In some embodiments, $R_6$ is 12-membered heterocyclyl comprising 1-4 heteroatoms selected from N, O, and S, substituted with one or more $R_7$. In some embodiments, $R_6$ is 13-membered heterocyclyl comprising 1-4 heteroatoms selected from N, O, and S, substituted with one or more $R_7$.

In some embodiments, $R_6$ is 3- to 13-membered heterocyclyl comprising 1-4 heteroatoms selected from N, O, and S, substituted with one $R_7$. In some embodiments, $R_6$ is 3-membered heterocyclyl comprising 1-4 heteroatoms selected from N, O, and S, substituted with one $R_7$. In some embodiments, $R_6$ is 4-membered heterocyclyl comprising 1-4 heteroatoms selected from N, O, and S, substituted with one $R_7$. In some embodiments, $R_6$ is 5-membered heterocyclyl comprising 1-4 heteroatoms selected from N, O, and S, substituted with one $R_7$. In some embodiments, $R_6$ is 6-membered heterocyclyl comprising 1-4 heteroatoms selected from N, O, and S, substituted with one $R_7$. In some embodiments, $R_6$ is 7-membered heterocyclyl comprising 1-4 heteroatoms selected from N, O, and S, substituted with one $R_7$. In some embodiments, $R_6$ is 8-membered heterocyclyl comprising 1-4 heteroatoms selected from N, O, and S, substituted with one $R_7$. In some embodiments, $R_6$ is 9-membered heterocyclyl comprising 1-4 heteroatoms selected from N, O, and S, substituted with one $R_7$. In some embodiments, $R_6$ is 10-membered heterocyclyl comprising 1-4 heteroatoms selected from N, O, and S, substituted with one $R_7$. In some embodiments, $R_6$ is 11-membered heterocyclyl comprising 1-4 heteroatoms selected from N, O, and S, substituted with one $R_7$. In some embodiments, $R_6$ is 12-membered heterocyclyl comprising 1-4 heteroatoms selected from N, O, and S, substituted with one $R_7$. In some embodiments, $R_6$ is 13-membered heterocyclyl comprising 1-4 heteroatoms selected from N, O, and S, substituted with one $R_7$.

In some embodiments, $R_6$ is 3- to 13-membered heterocyclyl comprising 1-4 heteroatoms selected from N, O, and S. In some embodiments, $R_6$ is 3-membered heterocyclyl comprising 1-4 heteroatoms selected from N, O, and S. In some embodiments, $R_6$ is 4-membered heterocyclyl comprising 1-4 heteroatoms selected from N, O, and S. In some embodiments, $R_6$ is 5-membered heterocyclyl comprising 1-4 heteroatoms selected from N, O, and S. In some embodiments, $R_6$ is 6-membered heterocyclyl comprising 1-4 heteroatoms selected from N, O, and S. In some embodiments, $R_6$ is 7-membered heterocyclyl comprising 1-4 heteroatoms selected from N, O, and S. In some embodiments, $R_6$ is 8-membered heterocyclyl comprising 1-4 heteroatoms selected from N, O, and S. In some embodiments, $R_6$ is 9-membered heterocyclyl comprising 1-4 heteroatoms selected from N, O, and S. In some embodiments, $R_6$ is 10-membered heterocyclyl comprising 1-4 heteroatoms selected from N, O, and S. In some embodiments, $R_6$ is 11-membered heterocyclyl comprising 1-4 heteroatoms selected from N, O, and S. In some embodiments, $R_6$ is 12-membered heterocyclyl comprising 1-4 heteroatoms selected from N, O, and S. In some embodiments, $R_6$ is 13-membered heterocyclyl comprising 1-4 heteroatoms selected from N, O, and S.

In some embodiments, $R_6$ is 7- to 13-membered bicyclic heterocyclyl comprising 1-4 heteroatoms selected from N, O, and S, optionally substituted with one or more $R_7$. In some embodiments, $R_6$ is 7-membered bicyclic heterocyclyl comprising 1-4 heteroatoms selected from N, O, and S, optionally substituted with one or more $R_7$. In some embodiments, $R_6$ is 8-membered bicyclic heterocyclyl comprising 1-4 heteroatoms selected from N, O, and S, optionally substituted with one or more $R_7$. In some embodiments, $R_6$ is 9-membered bicyclic heterocyclyl comprising 1-4 heteroatoms selected from N, O, and S, optionally substituted with one or more $R_7$. In some embodiments, $R_6$ is 10-membered bicyclic heterocyclyl comprising 1-4 heteroatoms selected from N, O, and S, optionally substituted with one or more $R_7$. In some embodiments, $R_6$ is 11-membered bicyclic heterocyclyl comprising 1-4 heteroatoms selected from N, O, and S, optionally substituted with one or more $R_7$. In some embodiments, $R_6$ is 12-membered bicyclic heterocyclyl comprising 1-4 heteroatoms selected from N, O, and S, optionally substituted with one or more $R_7$. In some embodiments, $R_6$ is 13-membered bicyclic heterocyclyl comprising 1-4 heteroatoms selected from N, O, and S, optionally substituted with one or more $R_7$.

In some embodiments, $R_6$ is 7- to 13-membered bicyclic heterocyclyl comprising 1-4 heteroatoms selected from N, O, and S, substituted with one or more $R_7$. In some embodiments, $R_6$ is 7-membered bicyclic heterocyclyl comprising 1-4 heteroatoms selected from N, O, and S, substituted with one or more $R_7$. In some embodiments, $R_6$ is 8-membered bicyclic heterocyclyl comprising 1-4 heteroatoms selected from N, O, and S, substituted with one or more $R_7$. In some embodiments, $R_6$ is 9-membered bicyclic heterocyclyl comprising 1-4 heteroatoms selected from N, O, and S, substituted with one or more $R_7$. In some embodiments, $R_6$ is 10-membered bicyclic heterocyclyl comprising 1-4 heteroatoms selected from N, O, and S, substituted with one or more $R_7$. In some embodiments, $R_6$ is 11-membered bicyclic heterocyclyl comprising 1-4 heteroatoms selected from N, O, and S, substituted with one or more $R_7$. In some embodiments, $R_6$ is 12-membered bicyclic heterocyclyl comprising 1-4 heteroatoms selected from N, O, and S, substituted with one or more $R_7$. In some embodiments, $R_6$ is 13-membered bicyclic heterocyclyl comprising 1-4 heteroatoms selected from N, O, and S, substituted with one or more $R_7$.

In some embodiments, $R_6$ is 7- to 13-membered bicyclic heterocyclyl comprising 1-4 heteroatoms selected from N, O, and S, substituted with one $R_7$. In some embodiments, $R_6$ is 7-membered bicyclic heterocyclyl comprising 1-4 heteroatoms selected from N, O, and S, substituted with one $R_7$. In some embodiments, $R_6$ is 8-membered bicyclic heterocyclyl comprising 1-4 heteroatoms selected from N, O, and S, substituted with one $R_7$. In some embodiments, $R_6$ is 9-membered bicyclic heterocyclyl comprising 1-4 heteroatoms selected from N, O, and S, substituted with one $R_7$. In some embodiments, $R_6$ is 10-membered bicyclic heterocyclyl comprising 1-4 heteroatoms selected from N, O, and S, substituted with one $R_7$. In some embodiments, $R_6$ is 11-membered bicyclic heterocyclyl comprising 1-4 heteroatoms selected from N, O, and S, substituted with one $R_7$. In some embodiments, $R_6$ is 12-membered bicyclic heterocyclyl comprising 1-4 heteroatoms selected from N, O, and S, substituted with one $R_7$. In some embodiments, $R_6$ is 13-membered bicyclic heterocyclyl comprising 1-4 heteroatoms selected from N, O, and S, substituted with one $R_7$.

In some embodiments, $R_6$ is 7- to 13-membered bicyclic heterocyclyl comprising 1-4 heteroatoms selected from N, O, and S. In some embodiments, $R_6$ is 7-membered bicyclic heterocyclyl comprising 1-4 heteroatoms selected from N, O, and S. In some embodiments, $R_6$ is 8-membered bicyclic heterocyclyl comprising 1-4 heteroatoms selected from N, O, and S. In some embodiments, $R_6$ is 9-membered bicyclic heterocyclyl comprising 1-4 heteroatoms selected from N, O, and S. In some embodiments, $R_6$ is 10-membered bicyclic heterocyclyl comprising 1-4 heteroatoms selected from N, O, and S. In some embodiments, $R_6$ is 11-membered bicyclic heterocyclyl comprising 1-4 heteroatoms selected from N, O, and S. In some embodiments, $R_6$ is 12-membered bicyclic heterocyclyl comprising 1-4 heteroatoms selected from N, O, and S. In some embodiments, $R_6$ is 13-membered bicyclic heterocyclyl comprising 1-4 heteroatoms selected from N, O, and S.

In some embodiments, $R_6$ is 9- to 13-membered polycyclic heterocyclyl comprising 1-4 heteroatoms selected from N, O, and S, optionally substituted with one or more $R_7$. In some embodiments, $R_6$ is 9-membered polycyclic heterocyclyl comprising 1-4 heteroatoms selected from N, O, and S, optionally substituted with one or more $R_7$. In some embodiments, $R_6$ is 10-membered polycyclic heterocyclyl comprising 1-4 heteroatoms selected from N, O, and S, optionally substituted with one or more $R_7$. In some embodiments, $R_6$ is 11-membered polycyclic heterocyclyl comprising 1-4 heteroatoms selected from N, O, and S, optionally substituted with one or more $R_7$. In some embodiments, $R_6$ is 12-membered polycyclic heterocyclyl comprising 1-4 heteroatoms selected from N, O, and S, optionally substituted with one or more $R_7$. In some embodiments, $R_6$ is 13-membered polycyclic heterocyclyl comprising 1-4 heteroatoms selected from N, O, and S, optionally substituted with one or more $R_7$.

In some embodiments, $R_6$ is 9- to 13-membered polycyclic heterocyclyl comprising 1-4 heteroatoms selected from N, O, and S, substituted with one or more $R_7$. In some embodiments, $R_6$ is 9-membered polycyclic heterocyclyl comprising 1-4 heteroatoms selected from N, O, and S, substituted with one or more $R_7$. In some embodiments, $R_6$ is 10-membered polycyclic heterocyclyl comprising 1-4 heteroatoms selected from N, O, and S, substituted with one or more $R_7$. In some embodiments, $R_6$ is 11-membered polycyclic heterocyclyl comprising 1-4 heteroatoms selected from N, O, and S, substituted with one or more $R_7$. In some embodiments, $R_6$ is 12-membered polycyclic heterocyclyl comprising 1-4 heteroatoms selected from N, O, and S, substituted with one or more $R_7$. In some embodiments, $R_6$ is 13-membered polycyclic heterocyclyl comprising 1-4 heteroatoms selected from N, O, and S, substituted with one or more $R_7$.

In some embodiments, $R_6$ is 9- to 13-membered polycyclic heterocyclyl comprising 1-4 heteroatoms selected from N, O, and S, substituted with one $R_7$. In some embodiments, $R_6$ is 9-membered polycyclic heterocyclyl comprising 1-4 heteroatoms selected from N, O, and S, substituted with one $R_7$. In some embodiments, $R_6$ is 10-membered polycyclic heterocyclyl comprising 1-4 heteroatoms selected from N, O, and S, substituted with one $R_7$. In some embodiments, $R_6$ is 11-membered polycyclic heterocyclyl comprising 1-4 heteroatoms selected from N, O, and S, substituted with one $R_7$. In some embodiments, $R_6$ is 12-membered polycyclic heterocyclyl comprising 1-4 heteroatoms selected from N, O, and S, substituted with one $R_7$. In some embodiments, $R_6$ is 13-membered polycyclic heterocyclyl comprising 1-4 heteroatoms selected from N, O, and S, substituted with one $R_7$.

In some embodiments, $R_6$ is 9- to 13-membered polycyclic heterocyclyl comprising 1-4 heteroatoms selected from N, O, and S. In some embodiments, $R_6$ is 9-membered polycyclic heterocyclyl comprising 1-4 heteroatoms selected from N, O, and S. In some embodiments, $R_6$ is 10-membered polycyclic heterocyclyl comprising 1-4 heteroatoms selected from N, O, and S. In some embodiments, $R_6$ is 11-membered polycyclic heterocyclyl comprising 1-4 heteroatoms selected from N, O, and S. In some embodiments, $R_6$ is 12-membered polycyclic heterocyclyl comprising 1-4 heteroatoms selected from N, O, and S. In some embodiments, $R_6$ is 13-membered polycyclic heterocyclyl comprising 1-4 heteroatoms selected from N, O, and S.

In some embodiments, $R_6$ is $C_{6-10}$ aryl or 5- to 13-membered heteroaryl comprising 1-4 heteroatoms selected from N, O, and S, wherein the aryl or heteroaryl is optionally substituted with one or more $R_7$.

In some embodiments, $R_6$ is $C_{6-10}$ aryl or 5- to 13-membered heteroaryl comprising 1-4 heteroatoms selected from N, O, and S.

In some embodiments, $R_6$ is $C_{6-10}$ aryl optionally substituted with one or more $R_7$.

In some embodiments, $R_6$ is $C_{6-8}$ aryl optionally substituted with one or more $R_7$. In some embodiments, $R_6$ is phenyl optionally substituted with one or more $R_7$.

In some embodiments, $R_6$ is $C_{6-8}$ aryl substituted with one or more $R_7$. In some embodiments, $R_6$ is phenyl substituted with one or more $R_7$.

In some embodiments, $R_6$ is $C_{6-8}$ aryl substituted with one $R_7$. In some embodiments, $R_6$ is phenyl substituted with one $R_7$.

In some embodiments, $R_6$ is $C_{6-10}$ aryl.

In some embodiments, $R_6$ is $C_{6-8}$ aryl. In some embodiments, $R_6$ is phenyl.

In some embodiments, $R_6$ is 5- to 13-membered heteroaryl comprising 1-4 heteroatoms selected from N, O, and S, optionally substituted with one or more $R_7$. In some embodiments, $R_6$ is 5-membered heteroaryl comprising 1-4 heteroatoms selected from N, O, and S, optionally substituted with one or more $R_7$. In some embodiments, $R_6$ is 6-membered heteroaryl comprising 1-4 heteroatoms selected from N, O, and S, optionally substituted with one or more $R_7$. In some embodiments, $R_6$ is 7-membered heteroaryl comprising 1-4 heteroatoms selected from N, O, and S, optionally substituted with one or more $R_7$. In some embodiments, $R_6$ is 8-membered heteroaryl comprising 1-4 heteroatoms selected from N, O, and S, optionally substituted with one or more $R_7$. In some embodiments, $R_6$ is 9-membered heteroaryl comprising 1-4 heteroatoms selected from N, O, and S, optionally substituted with one or more $R_7$. In some embodiments, $R_6$ is 10-membered heteroaryl comprising 1-4 heteroatoms selected from N, O, and S, optionally substituted with one or more $R_7$. In some embodiments, $R_6$ is 11-membered heteroaryl comprising 1-4 heteroatoms selected from N, O, and S, optionally substituted with one or more $R_7$. In some embodiments, $R_6$ is 12-membered heteroaryl comprising 1-4 heteroatoms selected from N, O, and S, optionally substituted with one or more $R_7$. In some embodiments, $R_6$ is 13-membered heteroaryl comprising 1-4 heteroatoms selected from N, O, and S, optionally substituted with one or more $R_7$.

In some embodiments, $R_6$ is 5- to 13-membered heteroaryl comprising 1-4 heteroatoms selected from N, O, and S, substituted with one or more $R_7$. In some embodiments, $R_6$ is 5-membered heteroaryl comprising 1-4 heteroatoms selected from N, O, and S, substituted with one or more $R_7$. In some embodiments, $R_6$ is 6-membered heteroaryl comprising 1-4 heteroatoms selected from N, O, and S, substituted with one or more $R_7$. In some embodiments, $R_6$ is 7-membered heteroaryl comprising 1-4 heteroatoms selected from N, O, and S, substituted with one or more $R_7$. In some embodiments, $R_6$ is 8-membered heteroaryl comprising 1-4 heteroatoms selected from N, O, and S, substituted with one or more $R_7$. In some embodiments, $R_6$ is 9-membered heteroaryl comprising 1-4 heteroatoms selected from N, O, and S, substituted with one or more $R_7$. In some embodiments, $R_6$ is 10-membered heteroaryl comprising 1-4 heteroatoms selected from N, O, and S, substituted with one or more $R_7$. In some embodiments, $R_6$ is 11-membered heteroaryl comprising 1-4 heteroatoms selected from N, O, and S, substituted with one or more $R_7$. In some embodiments, $R_6$ is 12-membered heteroaryl comprising 1-4 heteroatoms selected from N, O, and S, substituted with one or more $R_7$. In some embodiments, $R_6$ is 13-membered heteroaryl comprising 1-4 heteroatoms selected from N, O, and S, substituted with one or more $R_7$.

In some embodiments, $R_6$ is 5- to 13-membered heteroaryl comprising 1-4 heteroatoms selected from N, O, and S, substituted with one $R_7$. In some embodiments, $R_6$ is 5-membered heteroaryl comprising 1-4 heteroatoms selected from N, O, and S, substituted with one $R_7$. In some embodiments, $R_6$ is 6-membered heteroaryl comprising 1-4 heteroatoms selected from N, O, and S, substituted with one $R_7$. In some embodiments, $R_6$ is 7-membered heteroaryl comprising 1-4 heteroatoms selected from N, O, and S, substituted with one $R_7$. In some embodiments, $R_6$ is 8-membered heteroaryl comprising 1-4 heteroatoms selected from N, O, and S, substituted with one $R_7$. In some embodiments, $R_6$ is 9-membered heteroaryl comprising 1-4 heteroatoms selected from N, O, and S, substituted with one $R_7$. In some embodiments, $R_6$ is 10-membered heteroaryl comprising 1-4 heteroatoms selected from N, O, and S, substituted with one $R_7$. In some embodiments, $R_6$ is 11-membered heteroaryl comprising 1-4 heteroatoms selected from N, O, and S, substituted with one $R_7$. In some embodiments, $R_6$ is 12-membered heteroaryl comprising 1-4 heteroatoms selected from N, O, and S, substituted with one $R_7$. In some embodiments, $R_6$ is 13-membered heteroaryl comprising 1-4 heteroatoms selected from N, O, and S, substituted with one $R_7$.

In some embodiments, $R_6$ is 5- to 13-membered heteroaryl comprising 1-4 heteroatoms selected from N, O, and S. In some embodiments, $R_6$ is 5-membered heteroaryl comprising 1-4 heteroatoms selected from N, O, and S. In some embodiments, $R_6$ is 6-membered heteroaryl comprising 1-4 heteroatoms selected from N, O, and S. In some embodiments, $R_6$ is 7-membered heteroaryl comprising 1-4 heteroatoms selected from N, O, and S. In some embodiments, $R_6$ is 8-membered heteroaryl comprising 1-4 heteroatoms selected from N, O, and S. In some embodiments, $R_6$ is 9-membered heteroaryl comprising 1-4 heteroatoms selected from N, O, and S. In some embodiments, $R_6$ is 10-membered heteroaryl comprising 1-4 heteroatoms selected from N, O, and S. In some embodiments, $R_6$ is 11-membered heteroaryl comprising 1-4 heteroatoms selected from N, O, and S. In some embodiments, $R_6$ is 12-membered heteroaryl comprising 1-4 heteroatoms selected from N, O, and S. In some embodiments, $R_6$ is 13-membered heteroaryl comprising 1-4 heteroatoms selected from N, O, and S.

In some embodiments, $R_6$ is 9- to 13-membered bicyclic heteroaryl comprising 1-4 heteroatoms selected from N, O, and S, optionally substituted with one or more $R_7$. In some embodiments, $R_6$ is 9-membered bicyclic heteroaryl comprising 1-4 heteroatoms selected from N, O, and S, optionally substituted with one or more $R_7$. In some embodiments, $R_6$ is 10-membered bicyclic heteroaryl comprising 1-4 heteroatoms selected from N, O, and S, optionally substituted with one or more $R_7$. In some embodiments, $R_6$ is 11-membered bicyclic heteroaryl comprising 1-4 heteroatoms selected from N, O, and S, optionally substituted with one or more $R_7$. In some embodiments, $R_6$ is 12-membered bicyclic heteroaryl comprising 1-4 heteroatoms selected from N, O, and S, optionally substituted with one or more $R_7$. In some embodiments, $R_6$ is 13-membered bicyclic heteroaryl comprising 1-4 heteroatoms selected from N, O, and S, optionally substituted with one or more $R_7$.

In some embodiments, $R_6$ is 9- to 13-membered bicyclic heteroaryl comprising 1-4 heteroatoms selected from N, O, and S, substituted with one or more $R_7$. In some embodiments, $R_6$ is 9-membered bicyclic heteroaryl comprising 1-4 heteroatoms selected from N, O, and S, substituted with one or more $R_7$. In some embodiments, $R_6$ is 10-membered bicyclic heteroaryl comprising 1-4 heteroatoms selected from N, O, and S, substituted with one or more $R_7$. In some embodiments, $R_6$ is 11-membered bicyclic heteroaryl comprising 1-4 heteroatoms selected from N, O, and S, substituted with one or more $R_7$. In some embodiments, $R_6$ is 12-membered bicyclic heteroaryl comprising 1-4 heteroatoms selected from N, O, and S, substituted with one or more $R_7$. In some embodiments, $R_6$ is 13-membered bicyclic heteroaryl comprising 1-4 heteroatoms selected from N, O, and S, substituted with one or more $R_7$.

In some embodiments, $R_6$ is 9- to 13-membered bicyclic heteroaryl comprising 1-4 heteroatoms selected from N, O, and S, substituted with one $R_7$. In some embodiments, $R_6$ is 9-membered bicyclic heteroaryl comprising 1-4 heteroatoms selected from N, O, and S, substituted with one $R_7$. In some embodiments, $R_6$ is 10-membered bicyclic heteroaryl comprising 1-4 heteroatoms selected from N, O, and S, substituted with one $R_7$. In some embodiments, $R_6$ is 11-membered bicyclic heteroaryl comprising 1-4 heteroatoms selected from N, O, and S, substituted with one $R_7$. In some embodiments, $R_6$ is 12-membered bicyclic heteroaryl comprising 1-4 heteroatoms selected from N, O, and S, substituted with one $R_7$. In some embodiments, $R_6$ is 13-membered bicyclic heteroaryl comprising 1-4 heteroatoms selected from N, O, and S, substituted with one $R_7$.

In some embodiments, $R_6$ is 9- to 13-membered bicyclic heteroaryl comprising 1-4 heteroatoms selected from N, O, and S. In some embodiments, $R_6$ is 9-membered bicyclic heteroaryl comprising 1-4 heteroatoms selected from N, O, and S. In some embodiments, $R_6$ is 10-membered bicyclic heteroaryl comprising 1-4 heteroatoms selected from N, O, and S. In some embodiments, $R_6$ is 11-membered bicyclic heteroaryl comprising 1-4 heteroatoms selected from N, O, and S. In some embodiments, $R_6$ is 12-membered bicyclic heteroaryl comprising 1-4 heteroatoms selected from N, O, and S. In some embodiments, $R_6$ is 13-membered bicyclic heteroaryl comprising 1-4 heteroatoms selected from N, O, and S.

In some embodiments, $R_6$ is 9- to 13-membered polycyclic heteroaryl comprising 1-4 heteroatoms selected from N, O, and S, optionally substituted with one or more $R_7$. In some embodiments, $R_6$ is 9-membered polycyclic heteroaryl comprising 1-4 heteroatoms selected from N, O, and S, optionally substituted with one or more $R_7$. In some embodiments, $R_6$ is 10-membered polycyclic heteroaryl comprising 1-4 heteroatoms selected from N, O, and S, optionally substituted with one or more $R_7$. In some embodiments, $R_6$ is 11-membered polycyclic heteroaryl comprising 1-4 heteroatoms selected from N, O, and S, optionally substituted with one or more $R_7$. In some embodiments, $R_6$ is 12-membered polycyclic heteroaryl comprising 1-4 heteroatoms selected from N, O, and S, optionally substituted with one or more $R_7$. In some embodiments, $R_6$ is 13-membered polycyclic heteroaryl comprising 1-4 heteroatoms selected from N, O, and S, optionally substituted with one or more $R_7$.

In some embodiments, $R_6$ is 9- to 13-membered polycyclic heteroaryl comprising 1-4 heteroatoms selected from N, O, and S, substituted with one or more $R_7$. In some embodiments, $R_6$ is 9-membered polycyclic heteroaryl comprising 1-4 heteroatoms selected from N, O, and S, substituted with one or more $R_7$. In some embodiments, $R_6$ is 10-membered polycyclic heteroaryl comprising 1-4 heteroatoms selected from N, O, and S, substituted with one or more $R_7$. In some embodiments, $R_6$ is 11-membered polycyclic heteroaryl comprising 1-4 heteroatoms selected from N, O, and S, substituted with one or more $R_7$. In some embodiments, $R_6$ is 12-membered polycyclic heteroaryl comprising 1-4 heteroatoms selected from N, O, and S, substituted with one or more $R_7$. In some embodiments, $R_6$ is 13-membered polycyclic heteroaryl comprising 1-4 heteroatoms selected from N, O, and S, substituted with one or more $R_7$.

In some embodiments, $R_6$ is 9- to 13-membered polycyclic heteroaryl comprising 1-4 heteroatoms selected from N, O, and S, substituted with one $R_7$. In some embodiments, $R_6$ is 9-membered polycyclic heteroaryl comprising 1-4 heteroatoms selected from N, O, and S, substituted with one $R_7$. In some embodiments, $R_6$ is 10-membered polycyclic heteroaryl comprising 1-4 heteroatoms selected from N, O, and S, substituted with one $R_7$. In some embodiments, $R_6$ is 11-membered polycyclic heteroaryl comprising 1-4 heteroatoms selected from N, O, and S, substituted with one $R_7$. In some embodiments, $R_6$ is 12-membered polycyclic heteroaryl comprising 1-4 heteroatoms selected from N, O, and S, substituted with one $R_7$. In some embodiments, $R_6$ is 13-membered polycyclic heteroaryl comprising 1-4 heteroatoms selected from N, O, and S, substituted with one $R_7$.

In some embodiments, $R_6$ is 9- to 13-membered polycyclic heteroaryl comprising 1-4 heteroatoms selected from N, O, and S. In some embodiments, $R_6$ is 9-membered polycyclic heteroaryl comprising 1-4 heteroatoms selected from N, O, and S. In some embodiments, $R_6$ is 10-membered polycyclic heteroaryl comprising 1-4 heteroatoms selected from N, O, and S. In some embodiments, $R_6$ is 11-membered polycyclic heteroaryl comprising 1-4 heteroatoms selected from N, O, and S. In some embodiments, $R_6$ is 12-membered polycyclic heteroaryl comprising 1-4 heteroatoms selected from N, O, and S. In some embodiments, $R_6$ is 13-membered polycyclic heteroaryl comprising 1-4 heteroatoms selected from N, O, and S.

In some embodiments, $R_6$ is H, $C_{1-6}$ alkyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, cycloalkyl, heterocyclyl, aryl, or heteroaryl is optionally substituted with one or more $R_7$.

In some embodiments, $R_6$ is H, $C_{1-6}$ alkyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, cycloalkyl, heterocyclyl, aryl, or heteroaryl is optionally substituted with one or more $R_7$.

In some embodiments, $R_6$ is H, $C_{1-6}$ alkyl, $C_{3-10}$ cycloalkyl, 3- to 13-membered heterocyclyl comprising 1-4 heteroatoms selected from N, O, and S, $C_{6-10}$ aryl, or 5- to 13-membered heteroaryl comprising 1-4 heteroatoms selected from N, O, and S, wherein the alkyl, cycloalkyl, heterocyclyl, aryl, or heteroaryl is substituted with one or more $R_7$.

In some embodiments, $R_6$ is cyclopropyl, piperidine, tetrahydropyran, morpholine, phenyl, pyridine, pyrimidine, tetrazole, triazole, pyrazole, thiazole, oxazole, furan, pyrrole, isoxazole, 1,3-dihydro-2H-benzo[d]imidazol-2-one, indoline, indole, 2,3-dihydrobenzofuran, 1H-benzo[d][1,2,3]triazole, 1H-indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_6$ is cyclopropyl, piperidine, tetrahydropyran, or morpholine.

In some embodiments, $R_6$ is phenyl, pyridine, pyrimidine, tetrazole, triazole, pyrazole, thiazole, oxazole, furan, pyrrole, isoxazole, 1,3-dihydro-2H-benzo[d]imidazol-2-one, indoline, indole, 2,3-dihydrobenzofuran, 1H-benzo[d][1,2,3]triazole, 1H-indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_6$ is pyridine, pyrimidine, tetrazole, triazole, pyrazole, thiazole, oxazole, furan, pyrrole, isoxazole, 1,3-dihydro-2H-benzo[d]imidazol-2-one, indoline, indole, 2,3-dihydrobenzofuran, 1H-benzo[d][1,2,3]triazole, indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_6$ is pyridine, pyrimidine, or indazole.

In some embodiments, $R_6$ is indazole.

In some embodiments, $R_6$ is tetrazole, triazole, pyrazole, thiazole, oxazole, furan, pyrrole, isoxazole, 1,3-dihydro-2H-benzo[d]imidazol-2-one, indoline, indole, 2,3-diydrobenzofuran, 1H-benzo[d][1,2,3]triazole, 1H-indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_6$ is tetrazole, triazole, pyrazole, thiazole, oxazole, furan, pyrrole, isoxazole, or imidazole.

In some embodiments, $R_6$ is 1,3-dihydro-2H-benzo[d]imidazol-2-one, indoline, indole, 2,3-diydrobenzofuran, 1H-benzo[d][1,2,3]triazole, 1H-indazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_6$ is 1,3-dihydro-2H-benzo[d]imidazol-2-one, indoline, indole, 2,3-diydrobenzofuran, 1H-benzo[d][1,2,3]triazole, 1H-indazole, imidazo[1,2-a]pyrazine, naphthalene, quinoline, 2,3-dihydrobenzo[b][1,4]dioxine, or benzo[d]oxazol-2(3H)-one, benzo[d]isoxazole.

In some embodiments, $R_6$ is 9H-carbazole.

In some embodiments, $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$.

In some embodiments, $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S.

In some embodiments, $R_5$ and $R_6$ together with the atoms to which they are attached form a 4- to 10-membered heterocyclyl comprising 1-4 heteroatoms selected from N, O, and S, optionally substituted with one or more $R_7$.

In some embodiments, $R_5$ and $R_6$ together with the atoms to which they are attached form a 4-membered heterocyclyl comprising 1-4 heteroatoms selected from N, O, and S, optionally substituted with one or more $R_7$.

In some embodiments, $R_5$ and $R_6$ together with the atoms to which they are attached form a 5-membered heterocyclyl comprising 1-4 heteroatoms selected from N, O, and S, optionally substituted with one or more $R_7$.

In some embodiments, $R_5$ and $R_6$ together with the atoms to which they are attached form a 6-membered heterocyclyl comprising 1-4 heteroatoms selected from N, O, and S, optionally substituted with one or more $R_7$.

In some embodiments, $R_5$ and $R_6$ together with the atoms to which they are attached form a 7-membered heterocyclyl comprising 1-4 heteroatoms selected from N, O, and S, optionally substituted with one or more $R_7$.

In some embodiments, $R_5$ and $R_6$ together with the atoms to which they are attached form a 8-membered heterocyclyl comprising 1-4 heteroatoms selected from N, O, and S, optionally substituted with one or more $R_7$.

In some embodiments, $R_5$ and $R_6$ together with the atoms to which they are attached form a 9-membered heterocyclyl comprising 1-4 heteroatoms selected from N, O, and S, optionally substituted with one or more $R_7$.

In some embodiments, $R_5$ and $R_6$ together with the atoms to which they are attached form a 10-membered heterocyclyl comprising 1-4 heteroatoms selected from N, O, and S, optionally substituted with one or more $R_7$.

In some embodiments, $R_5$ and $R_6$ together with the atoms to which they are attached form a 4- to 10-membered heterocyclyl comprising 1-4 heteroatoms selected from N, O, and S, substituted with one or more $R_7$.

In some embodiments, $R_5$ and $R_6$ together with the atoms to which they are attached form a 4-membered heterocyclyl comprising 1-4 heteroatoms selected from N, O, and S, substituted with one or more $R_7$. In some embodiments, $R_5$ and $R_6$ together with the atoms to which they are attached form a 5-membered heterocyclyl comprising 1-4 heteroatoms selected from N, O, and S, substituted with one or more $R_7$. In some embodiments, $R_5$ and $R_6$ together with the atoms to which they are attached form a 6-membered heterocyclyl comprising 1-4 heteroatoms selected from N, O, and S, substituted with one or more $R_7$. In some embodiments, $R_5$ and $R_6$ together with the atoms to which they are attached form a 7-membered heterocyclyl comprising 1-4 heteroatoms selected from N, O, and S, substituted with one or more $R_7$. In some embodiments, $R_5$ and $R_6$ together with the atoms to which they are attached form a 8-membered heterocyclyl comprising 1-4 heteroatoms selected from N, O, and S, substituted with one or more $R_7$. In some embodiments, $R_5$ and $R_6$ together with the atoms to which they are attached form a 9-membered heterocyclyl comprising 1-4 heteroatoms selected from N, O, and S, substituted with one or more $R_7$. In some embodiments, $R_5$ and $R_6$ together with the atoms to which they are attached form a 10-membered heterocyclyl comprising 1-4 heteroatoms selected from N, O, and S, substituted with one or more $R_7$.

In some embodiments, $R_5$ and $R_6$ together with the atoms to which they are attached form a 4- to 10-membered heterocyclyl comprising 1-4 heteroatoms selected from N, O, and S, substituted with one $R_7$.

In some embodiments, $R_5$ and $R_6$ together with the atoms to which they are attached form a 4-membered heterocyclyl comprising 1-4 heteroatoms selected from N, O, and S, substituted with one $R_7$. In some embodiments, $R_5$ and $R_6$ together with the atoms to which they are attached form a 5-membered heterocyclyl comprising 1-4 heteroatoms selected from N, O, and S, substituted with one $R_7$. In some embodiments, $R_5$ and $R_6$ together with the atoms to which they are attached form a 6-membered heterocyclyl comprising 1-4 heteroatoms selected from N, O, and S, substituted with one $R_7$. In some embodiments, $R_5$ and $R_6$ together with the atoms to which they are attached form a 7-membered heterocyclyl comprising 1-4 heteroatoms selected from N, O, and S, substituted with one $R_7$. In some embodiments, $R_5$ and $R_6$ together with the atoms to which they are attached form a 8-membered heterocyclyl comprising 1-4 heteroatoms selected from N, O, and S, substituted with one $R_7$. In some embodiments, $R_5$ and $R_6$ together with the atoms to which they are attached form a 9-membered heterocyclyl comprising 1-4 heteroatoms selected from N, O, and S, substituted with one $R_7$. In some embodiments, $R_5$ and $R_6$ together with the atoms to which they are attached form a 10-membered heterocyclyl comprising 1-4 heteroatoms selected from N, O, and S, substituted with one $R_7$.

In some embodiments, $R_5$ and $R_6$ together with the atoms to which they are attached form a 4- to 10-membered heterocyclyl comprising 1-4 heteroatoms selected from N, O, and S.

In some embodiments, $R_5$ and $R_6$ together with the atoms to which they are attached form a 4-membered heterocyclyl comprising 1-4 heteroatoms selected from N, O, and S. In some embodiments, $R_5$ and $R_6$ together with the atoms to which they are attached form a 5-membered heterocyclyl comprising 1-4 heteroatoms selected from N, O, and S. In some embodiments, $R_5$ and $R_6$ together with the atoms to which they are attached form a 6-membered heterocyclyl comprising 1-4 heteroatoms selected from N, O, and S. In some embodiments, $R_5$ and $R_6$ together with the atoms to which they are attached form a 7-membered heterocyclyl comprising 1-4 heteroatoms selected from N, O, and S. In some embodiments, $R_5$ and $R_6$ together with the atoms to which they are attached form a 8-membered heterocyclyl comprising 1-4 heteroatoms selected from N, O, and S. In some embodiments, $R_5$ and $R_6$ together with the atoms to which they are attached form a 9-membered heterocyclyl comprising 1-4 heteroatoms selected from N, O, and S. In some embodiments, $R_5$ and $R_6$ together with the atoms to which they are attached form a 10-membered heterocyclyl comprising 1-4 heteroatoms selected from N, O, and S.

In some embodiments, $R_5$ and $R_6$ together with the atoms to which they are attached form a 5- to 10-membered heteroaryl comprising 1-4 heteroatoms selected from N, O, and S, optionally substituted with one or more $R_7$.

In some embodiments, $R_5$ and $R_6$ together with the atoms to which they are attached form a 5-membered heteroaryl comprising 1-4 heteroatoms selected from N, O, and S, optionally substituted with one or more $R_7$. In some embodiments, $R_5$ and $R_6$ together with the atoms to which they are attached form a 6-membered heteroaryl comprising 1-4 heteroatoms selected from N, O, and S, optionally substituted with one or more $R_7$. In some embodiments, $R_5$ and $R_6$ together with the atoms to which they are attached form a 7-membered heteroaryl comprising 1-4 heteroatoms selected from N, O, and S, optionally substituted with one or more $R_7$. In some embodiments, $R_5$ and $R_6$ together with the atoms to which they are attached form a 8-membered heteroaryl comprising 1-4 heteroatoms selected from N, O, and S, optionally substituted with one or more $R_7$. In some embodiments, $R_5$ and $R_6$ together with the atoms to which they are attached form a 9-membered heteroaryl comprising 1-4 heteroatoms selected from N, O, and S, optionally substituted with one or more $R_7$. In some embodiments, $R_5$ and $R_6$ together with the atoms to which they are attached form a 10-membered heteroaryl comprising 1-4 heteroatoms selected from N, O, and S, optionally substituted with one or more $R_7$.

In some embodiments, $R_5$ and $R_6$ together with the atoms to which they are attached form a 5- to 10-membered heteroaryl comprising 1-4 heteroatoms selected from N, O, and S, substituted with one or more $R_7$.

In some embodiments, $R_5$ and $R_6$ together with the atoms to which they are attached form a 5-membered heteroaryl comprising 1-4 heteroatoms selected from N, O, and S, substituted with one or more $R_7$. In some embodiments, $R_5$ and $R_6$ together with the atoms to which they are attached form a 6-membered heteroaryl comprising 1-4 heteroatoms selected from N, O, and S, substituted with one or more $R_7$. In some embodiments, $R_5$ and $R_6$ together with the atoms to which they are attached form a 7-membered heteroaryl comprising 1-4 heteroatoms selected from N, O, and S, substituted with one or more $R_7$. In some embodiments, $R_5$ and $R_6$ together with the atoms to which they are attached form a 8-membered heteroaryl comprising 1-4 heteroatoms selected from N, O, and S, substituted with one or more $R_7$. In some embodiments, $R_5$ and $R_6$ together with the atoms to which they are attached form a 9-membered heteroaryl comprising 1-4 heteroatoms selected from N, O, and S, substituted with one or more $R_7$. In some embodiments, $R_5$ and $R_6$ together with the atoms to which they are attached form a 10-membered heteroaryl comprising 1-4 heteroatoms selected from N, O, and S, substituted with one or more $R_7$.

In some embodiments, $R_5$ and $R_6$ together with the atoms to which they are attached form a 5- to 10-membered heteroaryl comprising 1-4 heteroatoms selected from N, O, and S, substituted with one $R_7$. In some embodiments, $R_5$ and $R_6$ together with the atoms to which they are attached form a 5-membered heteroaryl comprising 1-4 heteroatoms selected from N, O, and S, substituted with one $R_7$. In some embodiments, $R_5$ and $R_6$ together with the atoms to which they are attached form a 6-membered heteroaryl comprising 1-4 heteroatoms selected from N, O, and S, substituted with one $R_7$. In some embodiments, $R_5$ and $R_6$ together with the atoms to which they are attached form a 7-membered heteroaryl comprising 1-4 heteroatoms selected from N, O, and S, substituted with one $R_7$. In some embodiments, $R_5$ and $R_6$ together with the atoms to which they are attached form a 8-membered heteroaryl comprising 1-4 heteroatoms selected from N, O, and S, substituted with one $R_7$. In some embodiments, $R_5$ and $R_6$ together with the atoms to which they are attached form a 9-membered heteroaryl comprising 1-4 heteroatoms selected from N, O, and S, substituted with one $R_7$. In some embodiments, $R_5$ and $R_6$ together with the atoms to which they are attached form a 10-membered heteroaryl comprising 1-4 heteroatoms selected from N, O, and S, substituted with one $R_7$.

In some embodiments, $R_5$ and $R_6$ together with the atoms to which they are attached form a 5- to 10-membered heteroaryl comprising 1-4 heteroatoms selected from N, O, and S.

In some embodiments, $R_5$ and $R_6$ together with the atoms to which they are attached form a 5-membered heteroaryl comprising 1-4 heteroatoms selected from N, O, and S. In some embodiments, $R_5$ and $R_6$ together with the atoms to which they are attached form a 6-membered heteroaryl comprising 1-4 heteroatoms selected from N, O, and S. In some embodiments, $R_5$ and $R_6$ together with the atoms to which they are attached form a 7-membered heteroaryl comprising 1-4 heteroatoms selected from N, O, and S. In some embodiments, $R_5$ and $R_6$ together with the atoms to which they are attached form a 8-membered heteroaryl comprising 1-4 heteroatoms selected from N, O, and S. In some embodiments, $R_5$ and $R_6$ together with the atoms to which they are attached form a 9-membered heteroaryl comprising 1-4 heteroatoms selected from N, O, and S. In some embodiments, $R_5$ and $R_6$ together with the atoms to which they are attached form a 10-membered heteroaryl comprising 1-4 heteroatoms selected from N, O, and S.

In some embodiments, $R_5$ and $R_6$ together with the atoms to which they are attached form a piperidine, optionally substituted with one or more $R_7$.

In some embodiments, $R_5$ and $R_6$ together with the atoms to which they are attached form a piperidine, substituted with one or more $R_7$.

In some embodiments, $R_5$ and $R_6$ together with the atoms to which they are attached form a piperidine, substituted with one $R_7$.

In some embodiments, $R_5$ and $R_6$ together with the atoms to which they are attached form a piperidine.

In some embodiments, $R_5$ and $R_6$ together with the atoms to which they are attached form a tetrahydroquinoline, optionally substituted with one or more $R_7$.

In some embodiments, $R_5$ and $R_6$ together with the atoms to which they are attached form a tetrahydroquinoline, substituted with one or more $R_7$.

In some embodiments, $R_5$ and $R_6$ together with the atoms to which they are attached form a tetrahydroquinoline, substituted with one $R_7$.

In some embodiments, $R_5$ and $R_6$ together with the atoms to which they are attached form a tetrahydroquinoline.

In some embodiments, $R_5$ and $R_6$ together with the atoms to which they are attached form a tetrahydroisoquinoline, optionally substituted with one or more $R_7$.

In some embodiments, $R_5$ and $R_6$ together with the atoms to which they are attached form a tetrahydroisoquinoline, substituted with one or more $R_7$.

In some embodiments, $R_5$ and $R_6$ together with the atoms to which they are attached form a tetrahydroisoquinoline, substituted with one $R_7$.

In some embodiments, $R_5$ and $R_6$ together with the atoms to which they are attached form a tetrahydroisoquinoline.

In some embodiments, $R_5$ and $R_6$ together with the atoms to which they are attached form a tetrahydroimidazopyrazine, optionally substituted with one or more $R_7$.

In some embodiments, $R_5$ and $R_6$ together with the atoms to which they are attached form a tetrahydroimidazopyrazine, substituted with one or more $R_7$.

In some embodiments, $R_5$ and $R_6$ together with the atoms to which they are attached form a tetrahydroimidazopyrazine, substituted with one $R_7$.

In some embodiments, $R_5$ and $R_6$ together with the atoms to which they are attached form a tetrahydroimidazopyrazine.

In some embodiments, $R_5$ and $R_6$ together with the atoms to which they are attached form a tetrahydronaphthyridine, optionally substituted with one or more $R_7$.

In some embodiments, $R_5$ and $R_6$ together with the atoms to which they are attached form a tetrahydronaphthyridine, substituted with one or more $R_7$.

In some embodiments, $R_5$ and $R_6$ together with the atoms to which they are attached form a tetrahydronaphthyridine, substituted with one $R_7$.

In some embodiments, $R_5$ and $R_6$ together with the atoms to which they are attached form a tetrahydronaphthyridine.

In some embodiments, each $R_7$ is independently oxo, halogen, —OH, —$NH_2$, —CN, —$C(O)R_{10}$, —$C(O)OR_{10}$, —$C(O)N(R_{10})_2$, $C_{1-3}$ alkyl, $C_{2-6}$ alkenyl, $C_{2-6}$ alkynyl, $C_{1-6}$ alkoxy, —$NH(C_{1-6}$ alkyl), —$N(C_{1-6}$ alkyl$)_2$, —O—$(CH_2)_t$—$R_8$, —NH—$(CH_2)_t$—$R_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$.

In some embodiments, each $R_7$ is independently oxo, halogen, —OH, —$NH_2$, —CN, —$C(O)R_{10}$, —$C(O)OR_{10}$, —$C(O)N(R_{10})_2$, $C_{1-3}$ alkyl, $C_{2-6}$ alkenyl, $C_{2-6}$ alkynyl, $C_{1-6}$ alkoxy, —$NH(C_{1-6}$ alkyl), —$N(C_{1-6}$ alkyl$)_2$, —O—$(CH_2)_t$—$R_8$, —NH—$(CH_2)_t$—$R_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_7$ is oxo, halogen, —OH, —$NH_2$, —CN, —$C(O)R_{10}$, —$C(O)OR_{10}$, —$C(O)N(R_{10})_2$, —O—$(CH_2)_t$—$R_8$, or —NH—$(CH_2)_t$—$R_8$.

In some embodiments, $R_7$ is oxo, halogen, —OH, —$NH_2$, or —CN.

In some embodiments, $R_7$ is oxo.

In some embodiments, $R_7$ is halogen. In some embodiments, $R_7$ is F, Cl, Br, or I. In some embodiments, $R_7$ is F, Cl, or Br. In some embodiments, $R_7$ is F. In some embodiments, $R_7$ is Cl. In some embodiments, $R_7$ is Br. In some embodiments, $R_7$ is I.

In some embodiments, $R_7$ is —OH. In some embodiments, $R_7$ is —$NH_2$. In some embodiments, $R_7$ is —CN.

In some embodiments, $R_7$ is $-C(O)R_{10}$, $-C(O)OR_{10}$, $-C(O)N(R_{10})_2$, $-O-(CH_2)_t-R_8$, or $-NH-(CH_2)_t-R_8$.

In some embodiments, $R_7$ is $-C(O)R_{10}$. In some embodiments, $R_7$ is $-C(O)OR_{10}$. In some embodiments, $R_7$ is $-C(O)N(R_{10})_2$. In some embodiments, $R_7$ is $-O-(CH_2)_t-R_8$. In some embodiments, $R_7$ is $-NH-(CH_2)_t-R_8$.

In some embodiments, $R_7$ is $C_{1-6}$ alkoxy, $-NH(C_{1-6}$ alkyl), or $-N(C_{1-6}$ alkyl$)_2$.

In some embodiments, $R_7$ is $C_{1-6}$ alkoxy optionally substituted with one or more $R_{10}$.

In some embodiments, $R_7$ is $C_{1-6}$ alkoxy substituted with one or more $R_{10}$.

In some embodiments, $R_7$ is $C_{1-6}$ alkoxy substituted with one $R_{10}$. In some embodiments, $R_7$ is $C_{1-6}$ alkoxy substituted with two $R_{10}$.

In some embodiments, $R_7$ is $C_{1-6}$ alkoxy. In some embodiments, $R_7$ is methoxy. In some embodiments, $R_7$ is ethoxy. In some embodiments, $R_7$ is propoxy. In some embodiments, $R_7$ is butoxy. In some embodiments, $R_7$ is pentoxy. In some embodiments, $R_7$ is hexoxy. In some embodiments, $R_7$ is isopropoxy. In some embodiments, $R_7$ is isobutoxy. In some embodiments, $R_7$ is isopentoxy. In some embodiments, $R_7$ is isohexoxy. In some embodiments, $R_7$ is secbutoxy. In some embodiments, $R_7$ is secpentoxy. In some embodiments, $R_7$ is sechexoxy. In some embodiments, $R_7$ is tertbutoxy.

In some embodiments, $R_7$ is $-NH(C_{1-6}$ alkyl) or $-N(C_{1-6}$ alkyl$)_2$. In some embodiments, $R_7$ is $-NH(C_{1-6}$ alkyl). In some embodiments, $R_7$ is $-N(C_{1-6}$ alkyl$)_2$.

In some embodiments, $R_7$ is $C_{1-3}$ alkyl, $C_{2-6}$ alkenyl, $C_{2-6}$ alkynyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, cycloalkyl, heterocyclyl, aryl, or heteroaryl is optionally substituted with one or more $R_{10}$.

In some embodiments, $R_7$ is $C_{1-3}$ alkyl, $C_{2-6}$ alkenyl, $C_{2-6}$ alkynyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_7$ is $C_{1-3}$ alkyl, $C_{2-6}$ alkenyl, or $C_{2-6}$ alkynyl, wherein the alkyl, alkenyl, or alkynyl is optionally substituted with one or more $R_{10}$.

In some embodiments, $R_7$ is $C_{1-3}$ alkyl optionally substituted with one or more $R_{10}$. In some embodiments, $R_7$ is methyl optionally substituted with one or more $R_{10}$. In some embodiments, $R_7$ is ethyl optionally substituted with one or more $R_{10}$. In some embodiments, $R_7$ is propyl optionally substituted with one or more $R_{10}$. In some embodiments, $R_7$ is isopropyl optionally substituted with one or more $R_{10}$.

In some embodiments, $R_7$ is $C_{2-6}$ alkenyl optionally substituted with one or more $R_{10}$. In some embodiments, $R_7$ is $C_2$ alkenyl optionally substituted with one or more $R_{10}$. In some embodiments, $R_7$ is $C_3$ alkenyl optionally substituted with one or more $R_{10}$. In some embodiments, $R_7$ is $C_4$ alkenyl optionally substituted with one or more $R_{10}$. In some embodiments, $R_7$ is $C_5$ alkenyl optionally substituted with one or more $R_{10}$. In some embodiments, $R_7$ is $C_6$ alkenyl optionally substituted with one or more $R_{10}$.

In some embodiments, $R_7$ is $C_{2-6}$ alkynyl optionally substituted with one or more $R_{10}$. In some embodiments, $R_7$ is $C_2$ alkynyl optionally substituted with one or more $R_{10}$. In some embodiments, $R_7$ is $C_3$ alkynyl optionally substituted with one or more $R_{10}$. In some embodiments, $R_7$ is $C_4$ alkynyl optionally substituted with one or more $R_{10}$. In some embodiments, $R_7$ is $C_5$ alkynyl optionally substituted with one or more $R_{10}$. In some embodiments, $R_7$ is $C_6$ alkynyl optionally substituted with one or more $R_{10}$.

In some embodiments, $R_7$ is $C_{1-3}$ alkyl, $C_{2-6}$ alkenyl, or $C_{2-6}$ alkynyl, wherein the alkyl, alkenyl, or alkynyl is substituted with one or more $R_{10}$.

In some embodiments, $R_7$ is $C_{1-3}$ alkyl substituted with one or more $R_{10}$. In some embodiments, $R_7$ is methyl substituted with one or more $R_{10}$. In some embodiments, $R_7$ is ethyl substituted with one or more $R_{10}$. In some embodiments, $R_7$ is propyl substituted with one or more $R_{10}$. In some embodiments, $R_7$ is isopropyl substituted with one or more $R_{10}$.

In some embodiments, $R_7$ is $C_{2-6}$ alkenyl substituted with one or more $R_{10}$. In some embodiments, $R_7$ is $C_2$ alkenyl substituted with one or more $R_{10}$. In some embodiments, $R_7$ is $C_3$ alkenyl substituted with one or more $R_{10}$. In some embodiments, $R_7$ is $C_4$ alkenyl substituted with one or more $R_{10}$. In some embodiments, $R_7$ is $C_5$ alkenyl substituted with one or more $R_{10}$. In some embodiments, $R_7$ is $C_6$ alkenyl substituted with one or more $R_{10}$.

In some embodiments, $R_7$ is $C_{2-6}$ alkynyl substituted with one or more $R_{10}$. In some embodiments, $R_7$ is $C_2$ alkynyl substituted with one or more $R_{10}$. In some embodiments, $R_7$ is $C_3$ alkynyl substituted with one or more $R_{10}$. In some embodiments, $R_7$ is $C_4$ alkynyl substituted with one or more $R_{10}$. In some embodiments, $R_7$ is $C_5$ alkynyl substituted with one or more $R_{10}$. In some embodiments, $R_7$ is $C_6$ alkynyl substituted with one or more $R_{10}$.

In some embodiments, $R_7$ is $C_{1-3}$ alkyl, $C_{2-6}$ alkenyl, or $C_{2-6}$ alkynyl, wherein the alkyl, alkenyl, or alkynyl is substituted with one $R_{10}$.

In some embodiments, $R_7$ is $C_{1-3}$ alkyl substituted with one $R_{10}$. In some embodiments, $R_7$ is methyl substituted with one $R_{10}$. In some embodiments, $R_7$ is ethyl substituted with one $R_{10}$. In some embodiments, $R_7$ is propyl substituted with one $R_{10}$. In some embodiments, $R_7$ is isopropyl substituted with one $R_{10}$.

In some embodiments, $R_7$ is $C_{2-6}$ alkenyl substituted with one $R_{10}$. In some embodiments, $R_7$ is $C_2$ alkenyl substituted with one $R_{10}$. In some embodiments, $R_7$ is $C_3$ alkenyl substituted with one $R_{10}$. In some embodiments, $R_7$ is $C_4$ alkenyl substituted with one $R_{10}$. In some embodiments, $R_7$ is $C_5$ alkenyl substituted with one $R_{10}$. In some embodiments, $R_7$ is $C_6$ alkenyl substituted with one $R_{10}$.

In some embodiments, $R_7$ is $C_{2-6}$ alkynyl substituted with one $R_{10}$. In some embodiments, $R_7$ is $C_2$ alkynyl substituted with one $R_{10}$. In some embodiments, $R_7$ is $C_3$ alkynyl substituted with one $R_{10}$. In some embodiments, $R_7$ is $C_4$ alkynyl substituted with one $R_{10}$. In some embodiments, $R_7$ is $C_5$ alkynyl substituted with one $R_{10}$. In some embodiments, $R_7$ is $C_6$ alkynyl substituted with one $R_{10}$.

In some embodiments, $R_7$ is $C_{1-3}$ alkyl, $C_{2-6}$ alkenyl, or $C_{2-6}$ alkynyl.

In some embodiments, $R_7$ is $C_{1-3}$ alkyl. In some embodiments, $R_7$ is methyl. In some embodiments, $R_7$ is ethyl. In some embodiments, $R_7$ is propyl. In some embodiments, $R_7$ is isopropyl.

In some embodiments, $R_7$ is $C_{2-6}$ alkenyl. In some embodiments, $R_7$ is $C_2$ alkenyl. In some embodiments, $R_7$ is $C_3$ alkenyl. In some embodiments, $R_7$ is $C_4$ alkenyl. In some embodiments, $R_7$ is $C_5$ alkenyl. In some embodiments, $R_7$ is $C_6$ alkenyl.

In some embodiments, $R_7$ is $C_{2-6}$ alkynyl. In some embodiments, $R_7$ is $C_2$ alkynyl. In some embodiments, $R_7$ is $C_3$ alkynyl. In some embodiments, $R_7$ is $C_4$ alkynyl. In some embodiments, $R_7$ is $C_5$ alkynyl. In some embodiments, $R_7$ is $C_6$ alkynyl.

In some embodiments, $R_7$ is $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $R_{10}$.

In some embodiments, $R_7$ is $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_7$ is $C_{3-10}$ cycloalkyl or 3- to 10-membered heterocyclyl comprising 1-4 heteroatoms selected from N, O, and S, wherein the cycloalkyl or heterocyclyl is optionally substituted with one or more $R_{10}$.

In some embodiments, $R_7$ is $C_{3-10}$ cycloalkyl or 3- to 10-membered heterocyclyl comprising 1-4 heteroatoms selected from N, O, and S.

In some embodiments, $R_7$ is $C_{3-10}$ cycloalkyl optionally substituted with one or more $R_{10}$.

In some embodiments, $R_7$ is $C_3$ cycloalkyl optionally substituted with one or more $R_{10}$. In some embodiments, $R_7$ is $C_4$ cycloalkyl optionally substituted with one or more $R_{10}$. In some embodiments, $R_7$ is $C_5$ cycloalkyl optionally substituted with one or more $R_{10}$. In some embodiments, $R_7$ is $C_6$ cycloalkyl optionally substituted with one or more $R_{10}$. In some embodiments, $R_7$ is $C_7$ cycloalkyl optionally substituted with one or more $R_{10}$. In some embodiments, $R_7$ is $C_8$ cycloalkyl optionally substituted with one or more $R_{10}$. In some embodiments, $R_7$ is $C_9$ cycloalkyl optionally substituted with one or more $R_{10}$. In some embodiments, $R_7$ is $C_{10}$ cycloalkyl optionally substituted with one or more $R_{10}$.

In some embodiments, $R_7$ is $C_3$-$C_7$ monocyclic cycloalkyl optionally substituted with one or more $R_{10}$. In some embodiments, $R_7$ is $C_3$-$C_7$ monocyclic saturated cycloalkyl optionally substituted with one or more $R_{10}$. In some embodiments, $R_7$ is $C_3$-$C_7$ monocyclic partially saturated cycloalkyl optionally substituted with one or more $R_{10}$. In some embodiments, $R_7$ is $C_9$-$C_{10}$ bicyclic cycloalkyl optionally substituted with one or more $R_{10}$. In some embodiments, $R_7$ is $C_9$-$C_{10}$ bicyclic saturated cycloalkyl optionally substituted with one or more $R_{10}$. In some embodiments, $R_7$ is $C_9$-$C_{10}$ bicyclic partially saturated cycloalkyl optionally substituted with one or more $R_{10}$. In some embodiments, $R_7$ is $C_5$-$C_{10}$ polycyclic cycloalkyl optionally substituted with one or more $R_{10}$.

In some embodiments, $R_7$ is $C_{3-10}$ cycloalkyl substituted with one or more $R_{10}$.

In some embodiments, $R_7$ is $C_3$ cycloalkyl substituted with one or more $R_{10}$. In some embodiments, $R_7$ is $C_4$ cycloalkyl substituted with one or more $R_{10}$. In some embodiments, $R_7$ is $C_5$ cycloalkyl substituted with one or more $R_{10}$. In some embodiments, $R_7$ is $C_6$ cycloalkyl substituted with one or more $R_{10}$. In some embodiments, $R_7$ is $C_7$ cycloalkyl substituted with one or more $R_{10}$. In some embodiments, $R_7$ is $C_8$ cycloalkyl substituted with one or more $R_{10}$. In some embodiments, $R_7$ is $C_9$ cycloalkyl substituted with one or more $R_{10}$. In some embodiments, $R_7$ is $C_{10}$ cycloalkyl substituted with one or more $R_{10}$.

In some embodiments, $R_7$ is $C_3$-$C_7$ monocyclic cycloalkyl substituted with one or more $R_{10}$. In some embodiments, $R_7$ is $C_3$-$C_7$ monocyclic saturated cycloalkyl substituted with one or more $R_{10}$. In some embodiments, $R_7$ is $C_3$-$C_7$ monocyclic partially saturated cycloalkyl substituted with one or more $R_{10}$. In some embodiments, $R_7$ is $C_9$-$C_{10}$ bicyclic cycloalkyl substituted with one or more $R_{10}$. In some embodiments, $R_7$ is $C_9$-$C_{10}$ bicyclic saturated cycloalkyl substituted with one or more $R_{10}$. In some embodiments, $R_7$ is $C_9$-$C_{10}$ bicyclic partially saturated cycloalkyl substituted with one or more $R_{10}$. In some embodiments, $R_7$ is $C_8$-$C_{10}$ polycyclic cycloalkyl substituted with one or more $R_{10}$.

In some embodiments, $R_7$ is $C_{3-10}$ cycloalkyl substituted with one $R_{10}$.

In some embodiments, $R_7$ is $C_3$ cycloalkyl substituted with one $R_{10}$. In some embodiments, $R_7$ is $C_4$ cycloalkyl substituted with one $R_{10}$. In some embodiments, $R_7$ is $C_5$ cycloalkyl substituted with one $R_{10}$. In some embodiments, $R_7$ is $C_6$ cycloalkyl substituted with one $R_{10}$. In some embodiments, $R_7$ is $C_7$ cycloalkyl substituted with one $R_{10}$. In some embodiments, $R_7$ is $C_8$ cycloalkyl substituted with one $R_{10}$. In some embodiments, $R_7$ is $C_9$ cycloalkyl substituted with one $R_{10}$. In some embodiments, $R_7$ is $C_{10}$ cycloalkyl substituted with one $R_{10}$.

In some embodiments, $R_7$ is $C_3$-$C_7$ monocyclic cycloalkyl substituted with one $R_{10}$. In some embodiments, $R_7$ is $C_3$-$C_7$ monocyclic saturated cycloalkyl substituted with one $R_{10}$. In some embodiments, $R_7$ is $C_3$-$C_7$ monocyclic partially saturated cycloalkyl substituted with one $R_{10}$. In some embodiments, $R_7$ is $C_9$-$C_{10}$ bicyclic cycloalkyl substituted with one $R_{10}$. In some embodiments, $R_7$ is $C_9$-$C_{10}$ bicyclic saturated cycloalkyl substituted with one $R_{10}$. In some embodiments, $R_7$ is $C_9$-$C_{10}$ bicyclic partially saturated cycloalkyl substituted with one $R_{10}$. In some embodiments, $R_7$ is $C_5$-$C_{10}$ polycyclic cycloalkyl substituted with one $R_{10}$.

In some embodiments, $R_7$ is $C_{3-10}$ cycloalkyl.

In some embodiments, $R_7$ is $C_3$ cycloalkyl. In some embodiments, $R_7$ is $C_4$ cycloalkyl. In some embodiments, $R_7$ is $C_5$ cycloalkyl. In some embodiments, $R_7$ is $C_6$ cycloalkyl. In some embodiments, $R_7$ is $C_7$ cycloalkyl. In some embodiments, $R_7$ is $C_8$ cycloalkyl. In some embodiments, $R_7$ is $C_9$ cycloalkyl. In some embodiments, $R_7$ is $C_{10}$ cycloalkyl.

In some embodiments, $R_7$ is $C_3$-$C_7$ monocyclic cycloalkyl. In some embodiments, $R_7$ is $C_3$-$C_7$ monocyclic saturated cycloalkyl. In some embodiments, $R_7$ is $C_3$-$C_7$ monocyclic partially saturated cycloalkyl. In some embodiments, $R_7$ is $C_9$-$C_{10}$ bicyclic cycloalkyl. In some embodiments, $R_7$ is $C_9$-$C_{10}$ bicyclic saturated cycloalkyl. In some embodiments, $R_7$ is $C_9$-$C_{10}$ bicyclic partially saturated cycloalkyl. In some embodiments, $R_7$ is $C_5$-$C_{10}$ polycyclic cycloalkyl.

In some embodiments, $R_7$ is 3- to 10-membered heterocyclyl comprising 1-4 heteroatoms selected from N, O, and S, optionally substituted with one or more $R_{10}$. In some embodiments, $R_7$ is 3-membered heterocyclyl comprising 1-4 heteroatoms selected from N, O, and S, optionally substituted with one or more $R_{10}$. In some embodiments, $R_7$ is 4-membered heterocyclyl comprising 1-4 heteroatoms selected from N, O, and S, optionally substituted with one or more $R_{10}$. In some embodiments, $R_7$ is 5-membered heterocyclyl comprising 1-4 heteroatoms selected from N, O, and S, optionally substituted with one or more $R_{10}$. In some embodiments, $R_7$ is 6-membered heterocyclyl comprising 1-4 heteroatoms selected from N, O, and S, optionally substituted with one or more $R_{10}$. In some embodiments, $R_7$ is 7-membered heterocyclyl comprising 1-4 heteroatoms selected from N, O, and S, optionally substituted with one or more $R_{10}$. In some embodiments, $R_7$ is 8-membered heterocyclyl comprising 1-4 heteroatoms selected from N, O, and S, optionally substituted with one or more $R_{10}$. In some embodiments, $R_7$ is 9-membered heterocyclyl comprising 1-4 heteroatoms selected from N, O, and S, optionally substituted with one or more $R_{10}$. In some embodiments, $R_7$ is 10-membered heterocyclyl comprising 1-4 heteroatoms selected from N, O, and S, optionally substituted with one or more $R_{10}$.

In some embodiments, $R_7$ is 3- to 10-membered heterocyclyl comprising 1-4 heteroatoms selected from N, O, and S, substituted with one or more $R_{10}$. In some embodiments, $R_7$ is 3-membered heterocyclyl comprising 1-4 heteroatoms selected from N, O, and S, substituted with one or more $R_{10}$. In some embodiments, $R_7$ is 4-membered heterocyclyl comprising 1-4 heteroatoms selected from N, O, and S, substituted with one or more $R_{10}$. In some embodiments, $R_7$ is 5-membered heterocyclyl comprising 1-4 heteroatoms selected from N, O, and S, substituted with one or more $R_{10}$. In some embodiments, $R_7$ is 6-membered heterocyclyl comprising 1-4 heteroatoms selected from N, O, and S, substituted with one or more $R_{10}$. In some embodiments, $R_7$ is 7-membered heterocyclyl comprising 1-4 heteroatoms selected from N, O, and S, substituted with one or more $R_{10}$. In some embodiments, $R_7$ is 8-membered heterocyclyl comprising 1-4 heteroatoms selected from N, O, and S, substituted with one or more $R_{10}$. In some embodiments, $R_7$ is 9-membered heterocyclyl comprising 1-4 heteroatoms selected from N, O, and S, substituted with one or more $R_{10}$. In some embodiments, $R_7$ is 10-membered heterocyclyl comprising 1-4 heteroatoms selected from N, O, and S, substituted with one or more $R_{10}$.

In some embodiments, $R_7$ is 3- to 10-membered heterocyclyl comprising 1-4 heteroatoms selected from N, O, and S, substituted with one $R_{10}$. In some embodiments, $R_7$ is 3-membered heterocyclyl comprising 1-4 heteroatoms selected from N, O, and S, substituted with one $R_{10}$. In some embodiments, $R_7$ is 4-membered heterocyclyl comprising 1-4 heteroatoms selected from N, O, and S, substituted with one $R_{10}$. In some embodiments, $R_7$ is 5-membered heterocyclyl comprising 1-4 heteroatoms selected from N, O, and S, substituted with one $R_{10}$. In some embodiments, $R_7$ is 6-membered heterocyclyl comprising 1-4 heteroatoms selected from N, O, and S, substituted with one $R_{10}$. In some embodiments, $R_7$ is 7-membered heterocyclyl comprising 1-4 heteroatoms selected from N, O, and S, substituted with one $R_{10}$. In some embodiments, $R_7$ is 8-membered heterocyclyl comprising 1-4 heteroatoms selected from N, O, and S, substituted with one $R_{10}$. In some embodiments, $R_7$ is 9-membered heterocyclyl comprising 1-4 heteroatoms selected from N, O, and S, substituted with one $R_{10}$. In some embodiments, $R_7$ is 10-membered heterocyclyl comprising 1-4 heteroatoms selected from N, O, and S, substituted with one $R_{10}$.

In some embodiments, $R_7$ is 3- to 10-membered heterocyclyl comprising 1-4 heteroatoms selected from N, O, and S. In some embodiments, $R_7$ is 3-membered heterocyclyl comprising 1-4 heteroatoms selected from N, O, and S. In some embodiments, $R_7$ is 4-membered heterocyclyl comprising 1-4 heteroatoms selected from N, O, and S. In some embodiments, $R_7$ is 5-membered heterocyclyl comprising 1-4 heteroatoms selected from N, O, and S. In some embodiments, $R_7$ is 6-membered heterocyclyl comprising 1-4 heteroatoms selected from N, O, and S. In some embodiments, $R_7$ is 7-membered heterocyclyl comprising 1-4 heteroatoms selected from N, O, and S. In some embodiments, $R_7$ is 8-membered heterocyclyl comprising 1-4 heteroatoms selected from N, O, and S. In some embodiments, $R_7$ is 9-membered heterocyclyl comprising 1-4 heteroatoms selected from N, O, and S. In some embodiments, $R_7$ is 10-membered heterocyclyl comprising 1-4 heteroatoms selected from N, O, and S.

In some embodiments, $R_7$ is $C_{6-10}$ aryl or 5- to 10-membered heteroaryl comprising 1-4 heteroatoms selected from N, O, and S, wherein the aryl or heteroaryl is optionally substituted with one or more $R_{10}$.

In some embodiments, $R_7$ is $C_{6-10}$ aryl or 5- to 10-membered heteroaryl comprising 1-4 heteroatoms selected from N, O, and S.

In some embodiments, $R_7$ is $C_{6-10}$ aryl optionally substituted with one or more $R_{10}$.

In some embodiments, $R_7$ is $C_{6-8}$ aryl optionally substituted with one or more $R_{10}$. In some embodiments, $R_7$ is phenyl optionally substituted with one or more $R_{10}$.

In some embodiments, $R_7$ is $C_{6-8}$ aryl substituted with one or more $R_{10}$. In some embodiments, $R_7$ is phenyl substituted with one or more $R_{10}$.

In some embodiments, $R_7$ is $C_{6-8}$ aryl substituted with one $R_{10}$. In some embodiments, $R_7$ is phenyl substituted with one $R_{10}$.

In some embodiments, $R_7$ is $C_{6-10}$ aryl.

In some embodiments, $R_7$ is $C_{6-8}$ aryl. In some embodiments, $R_7$ is phenyl.

In some embodiments, $R_7$ is 5- to 10-membered heteroaryl comprising 1-4 heteroatoms selected from N, O, and S, optionally substituted with one or more $R_{10}$. In some embodiments, $R_7$ is 5-membered heteroaryl comprising 1-4 heteroatoms selected from N, O, and S, optionally substituted with one or more $R_{10}$. In some embodiments, $R_7$ is 6-membered heteroaryl comprising 1-4 heteroatoms selected from N, O, and S, optionally substituted with one or more $R_{10}$. In some embodiments, $R_7$ is 7-membered heteroaryl comprising 1-4 heteroatoms selected from N, O, and S, optionally substituted with one or more $R_{10}$. In some embodiments, $R_7$ is 8-membered heteroaryl comprising 1-4 heteroatoms selected from N, O, and S, optionally substituted with one or more $R_{10}$. In some embodiments, $R_7$ is 9-membered heteroaryl comprising 1-4 heteroatoms selected from N, O, and S, optionally substituted with one or more $R_{10}$. In some embodiments, $R_7$ is 10-membered heteroaryl comprising 1-4 heteroatoms selected from N, O, and S, optionally substituted with one or more $R_{10}$.

In some embodiments, $R_7$ is 5- to 10-membered heteroaryl comprising 1-4 heteroatoms selected from N, O, and S, substituted with one or more $R_{10}$. In some embodiments, $R_7$ is 5-membered heteroaryl comprising 1-4 heteroatoms selected from N, O, and S, substituted with one or more $R_{10}$. In some embodiments, $R_7$ is 6-membered heteroaryl comprising 1-4 heteroatoms selected from N, O, and S, substituted with one or more $R_{10}$. In some embodiments, $R_7$ is 7-membered heteroaryl comprising 1-4 heteroatoms selected from N, O, and S, substituted with one or more $R_{10}$. In some embodiments, $R_7$ is 8-membered heteroaryl comprising 1-4 heteroatoms selected from N, O, and S, substituted with one or more $R_{10}$. In some embodiments, $R_7$ is 9-membered heteroaryl comprising 1-4 heteroatoms selected from N, O, and S, substituted with one or more $R_{10}$. In some embodiments, $R_7$ is 10-membered heteroaryl comprising 1-4 heteroatoms selected from N, O, and S, substituted with one or more $R_{10}$.

In some embodiments, $R_7$ is 5- to 10-membered heteroaryl comprising 1-4 heteroatoms selected from N, O, and S, substituted with one $R_{10}$. In some embodiments, $R_7$ is 5-membered heteroaryl comprising 1-4 heteroatoms selected from N, O, and S, substituted with one $R_{10}$. In some embodiments, $R_7$ is 6-membered heteroaryl comprising 1-4 heteroatoms selected from N, O, and S, substituted with one $R_{10}$. In some embodiments, $R_7$ is 7-membered heteroaryl comprising 1-4 heteroatoms selected from N, O, and S, substituted with one $R_{10}$. In some embodiments, $R_7$ is 8-membered heteroaryl comprising 1-4 heteroatoms selected from N, O, and S, substituted with one $R_{10}$. In some embodiments, $R_7$ is 9-membered heteroaryl comprising 1-4 heteroatoms selected from N, O, and S, substituted with one $R_{10}$. In some embodiments, $R_7$ is 10-membered heteroaryl comprising 1-4 heteroatoms selected from N, O, and S, substituted with one $R_{10}$.

In some embodiments, $R_7$ is 5- to 10-membered heteroaryl comprising 1-4 heteroatoms selected from N, O, and S. In some embodiments, $R_7$ is 5-membered heteroaryl comprising 1-4 heteroatoms selected from N, O, and S. In some embodiments, $R_7$ is 6-membered heteroaryl comprising 1-4 heteroatoms selected from N, O, and S. In some embodiments, $R_7$ is 7-membered heteroaryl comprising 1-4 heteroatoms selected from N, O, and S. In some embodiments, $R_7$ is 8-membered heteroaryl comprising 1-4 heteroatoms selected from N, O, and S. In some embodiments, $R_7$ is 9-membered heteroaryl comprising 1-4 heteroatoms selected from N, O, and S. In some embodiments, $R_7$ is 10-membered heteroaryl comprising 1-4 heteroatoms selected from N, O, and S.

In some embodiments, $R_7$ is cyclopropyl, piperidine, tetrahydropyran, morpholine, phenyl, pyridine, pyrimidine, tetrazole, triazole, pyrazole, thiazole, oxazole, furan, pyrrole, isoxazole, 1,3-dihydro-2H-benzo[d]imidazol-2-one, indoline, indole, 2,3-diydrobenzofuran, 1H-benzo[d][1,2,3]triazole, 1H-indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_7$ is cyclopropyl, piperidine, tetrahydropyran, or morpholine.

In some embodiments, $R_7$ is phenyl, pyridine, pyrimidine, tetrazole, triazole, pyrazole, thiazole, oxazole, furan, pyrrole, isoxazole, 1,3-dihydro-2H-benzo[d]imidazol-2-one, indoline, indole, 2,3-diydrobenzofuran, 1H-benzo[d][1,2,3]triazole, 1H-indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_7$ is pyridine, pyrimidine, tetrazole, triazole, pyrazole, thiazole, oxazole, furan, pyrrole, isoxazole, 1,3-dihydro-2H-benzo[d]imidazol-2-one, indoline, indole, 2,3-diydrobenzofuran, 1H-benzo[d][1,2,3]triazole, 1H-indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_7$ is pyridine or pyrimidine.

In some embodiments, $R_7$ is tetrazole, triazole, pyrazole, thiazole, oxazole, furan, pyrrole, isoxazole, 1,3-dihydro-2H-benzo[d]imidazol-2-one, indoline, indole, 2,3-diydrobenzofuran, 1H-benzo[d][1,2,3]triazole, 1H-indazole, imidazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_7$ is tetrazole, triazole, pyrazole, thiazole, oxazole, furan, pyrrole, isoxazole, or imidazole.

In some embodiments, $R_7$ is 1,3-dihydro-2H-benzo[d]imidazol-2-one, indoline, indole, 2,3-diydrobenzofuran, 1H-benzo[d][1,2,3]triazole, 1H-indazole, imidazo[1,2-a]pyrazine, naphthalene, quinoline, 2,3-dihydrobenzo[b][1,4]dioxine, benzo[d]oxazol-2(3H)-one, benzo[d]isoxazole, or 9H-carbazole.

In some embodiments, $R_7$ is 1,3-dihydro-2H-benzo[d]imidazol-2-one, indoline, indole, 2,3-diydrobenzofuran, 1H-benzo[d][1,2,3]triazole, 1H-indazole, imidazo[1,2-a]pyrazine, naphthalene, quinoline, 2,3-dihydrobenzo[b][1,4]dioxine, or benzo[d]oxazol-2(3H)-one, benzo[d]isoxazole.

In some embodiments, $R_7$ is 9H-carbazole.

In some embodiments, $R_7$ is oxo, halogen, —OH, —NH$_2$, —CN, —C(O)R$_{10}$, C$_{1-6}$ alkyl, C$_{2-6}$ alkynyl, —O—(CH$_2$)$_f$—R$_8$, C$_{6-10}$ aryl, or 5- to 10-membered heteroaryl comprising 1-4 heteroatoms selected from N, O, and S, wherein the alkyl, alkynyl, aryl, or heteroaryl is optionally substituted with one or more $R_{10}$.

In some embodiments, $R_7$ is oxo, halogen, —OH, —NH$_2$, —CN, —C(O)R$_{10}$, C$_{1-6}$ alkyl, C$_{2-6}$ alkynyl, —O—(CH$_2$)$_f$—R$_8$, C$_{6-10}$ aryl, or 5- to 10-membered heteroaryl comprising 1-4 heteroatoms selected from N, O, and S, wherein the alkyl, alkynyl, aryl, or heteroaryl is substituted with one or more $R_{10}$.

In some embodiments, $R_8$ is —OH, C$_{1-6}$ alkoxy, C$_{1-6}$ alkoxy-OH, —NH$_2$, —NH(C$_{1-6}$ alkyl), —N(C$_{1-6}$ alkyl)$_2$, —SH, —S(C$_{1-6}$ alkyl), C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the alkoxy, alkyl, cycloalkyl, heterocyclyl, aryl or heteroaryl is optionally substituted by one or more $R_9$.

In some embodiments, $R_8$ is —OH, C$_{1-6}$ alkoxy, C$_{1-6}$ alkoxy-OH, —NH$_2$, —NH(C$_{1-6}$ alkyl), —N(C$_{1-6}$ alkyl)$_2$, —SH, —S(C$_{1-6}$ alkyl), C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S.

In some embodiments, $R_8$ is —OH, C$_{1-6}$ alkoxy, C$_{1-6}$ alkoxy-OH, —NH$_2$, —NH(C$_{1-6}$ alkyl), —N(C$_{1-6}$ alkyl)$_2$, —SH, or —S(C$_{1-6}$ alkyl), wherein the alkoxy or alkyl is optionally substituted by one or more $R_9$.

In some embodiments, $R_8$ is —OH, C$_{1-6}$ alkoxy, C$_{1-6}$ alkoxy-OH, —NH$_2$, —NH(C$_{1-6}$ alkyl), —N(C$_{1-6}$ alkyl)$_2$, —SH, or —S(C$_{1-6}$ alkyl), wherein the alkoxy or alkyl is substituted by one or more $R_9$.

In some embodiments, $R_8$ is —OH, C$_{1-6}$ alkoxy, C$_{1-6}$ alkoxy-OH, —NH$_2$, —NH(C$_{1-6}$ alkyl), —N(C$_{1-6}$ alkyl)$_2$, —SH, or —S(C$_{1-6}$ alkyl), wherein the alkoxy or alkyl is substituted by one $R_9$.

In some embodiments, $R_8$ is C$_{1-6}$ alkoxy optionally substituted by one or more $R_9$.

In some embodiments, $R_8$ is C$_{1-6}$ alkoxy-OH, wherein the alkoxy is optionally substituted by one or more $R_9$.

In some embodiments, $R_8$ is C$_{1-6}$ alkoxy substituted by one or more $R_9$.

In some embodiments, $R_8$ is C$_{1-6}$ alkoxy-OH, wherein the alkoxy is substituted by one or more $R_9$.

In some embodiments, $R_8$ is C$_{1-6}$ alkoxy substituted by one $R_9$.

In some embodiments, $R_8$ is C$_{1-6}$ alkoxy-OH, wherein the alkoxy is substituted by one $R_9$.

In some embodiments, $R_8$ is —NH(C$_{1-6}$ alkyl), wherein the alkyl is optionally substituted by one or more $R_9$.

In some embodiments, $R_8$ is —N(C$_{1-6}$ alkyl)$_2$, wherein the alkyl is optionally substituted by one or more $R_9$.

In some embodiments, $R_8$ is —NH(C$_{1-6}$ alkyl), wherein the alkyl is substituted by one or more $R_9$.

In some embodiments, $R_8$ is —N(C$_{1-6}$ alkyl)$_2$, wherein the alkyl is substituted by one or more $R_9$.

In some embodiments, $R_8$ is —NH(C$_{1-6}$ alkyl), wherein the alkyl is substituted by one $R_9$.

In some embodiments, $R_8$ is —N(C$_{1-6}$ alkyl)$_2$, wherein the alkyl is substituted by one $R_9$.

In some embodiments, $R_8$ is —S(C$_{1-6}$ alkyl), wherein the alkyl is optionally substituted by one or more $R_9$.

In some embodiments, $R_8$ is —S($C_{1-6}$ alkyl), wherein the alkyl is substituted by one or more $R_9$.

In some embodiments, $R_8$ is —S($C_{1-6}$ alkyl), wherein the alkyl is substituted by one $R_9$.

In some embodiments, $R_8$ is —OH, $C_{1-6}$ alkoxy, $C_{1-6}$ alkoxy-OH, —NH$_2$, —NH($C_{1-6}$ alkyl), —N($C_{1-6}$ alkyl)$_2$, —SH, —S($C_{1-6}$ alkyl).

In some embodiments, $R_8$ is —OH, $C_{1-6}$ alkoxy, or $C_{1-6}$ alkoxy-OH.

In some embodiments, $R_8$ is —OH.

In some embodiments, $R_8$ is $C_{1-6}$ alkoxy. In some embodiments, $R_8$ is methoxy. In some embodiments, $R_8$ is ethoxy. In some embodiments, $R_8$ is propoxy. In some embodiments, $R_8$ is butoxy. In some embodiments, $R_8$ is pentoxy. In some embodiments, $R_8$ is hexoxy. In some embodiments, $R_8$ is isopropoxy. In some embodiments, $R_8$ is isobutoxy. In some embodiments, $R_8$ is isopentoxy. In some embodiments, $R_8$ is isohexoxy. In some embodiments, $R_8$ is secbutoxy. In some embodiments, $R_8$ is secpentoxy. In some embodiments, $R_8$ is sechexoxy. In some embodiments, $R_8$ is tertbutoxy.

In some embodiments, $R_8$ is $C_{1-6}$ alkoxy-OH. In some embodiments, $R_8$ is methoxy-OH. In some embodiments, $R_8$ is ethoxy-OH. In some embodiments, $R_8$ is propoxy-OH. In some embodiments, $R_8$ is butoxy-OH. In some embodiments, $R_8$ is pentoxy-OH. In some embodiments, $R_8$ is hexoxy-OH. In some embodiments, $R_8$ is isopropoxy-OH. In some embodiments, $R_8$ is isobutoxy-OH. In some embodiments, $R_8$ is isopentoxy-OH. In some embodiments, $R_8$ is isohexoxy-OH. In some embodiments, $R_8$ is secbutoxy-OH. In some embodiments, $R_8$ is secpentoxy-OH. In some embodiments, $R_8$ is sechexoxy-OH. In some embodiments, $R_8$ is tertbutoxy-OH.

In some embodiments, $R_8$ is —NH$_2$, —NH($C_{1-6}$ alkyl), or —N($C_{1-6}$ alkyl)$_2$.

In some embodiments, $R_8$ is —NH$_2$.

In some embodiments, $R_8$ is —NH($C_{1-6}$ alkyl). In some embodiments, $R_8$ is —NH(methyl). In some embodiments, $R_8$ is —NH(ethyl). In some embodiments, $R_8$ is —NH(propyl). In some embodiments, $R_8$ is —NH(butyl). In some embodiments, $R_8$ is —NH(pentyl). In some embodiments, $R_8$ is —NH(hexyl). In some embodiments, $R_8$ is —NH(isopropyl). In some embodiments, $R_8$ is —NH(isobutyl). In some embodiments, $R_8$ is —NH(isopentyl). In some embodiments, $R_8$ is —NH(isohexyl). In some embodiments, $R_8$ is —NH(secbutyl). In some embodiments, $R_8$ is —NH(secpentyl). In some embodiments, $R_8$ is —NH(sechexyl). In some embodiments, $R_8$ is —NH(tertbutyl).

In some embodiments, $R_8$ is —N($C_{1-6}$ alkyl)$_2$. In some embodiments, $R_8$ is —N(methyl)$_2$. In some embodiments, $R_8$ is —N(ethyl)$_2$. In some embodiments, $R_8$ is —N(propyl)$_2$. In some embodiments, $R_8$ is —N(butyl)$_2$. In some embodiments, $R_8$ is —N(pentyl)$_2$. In some embodiments, $R_8$ is —N(hexyl)$_2$. In some embodiments, $R_8$ is —N(isopropyl)$_2$. In some embodiments, $R_8$ is —N(isobutyl)$_2$. In some embodiments, $R_8$ is —N(isopentyl)$_2$. In some embodiments, $R_8$ is —N(isohexyl)$_2$. In some embodiments, $R_8$ is —N(secbutyl)$_2$. In some embodiments, $R_8$ is —N(secpentyl)$_2$. In some embodiments, $R_8$ is —N(sechexyl)$_2$. In some embodiments, $R_8$ is —N(tertbutyl)$_2$.

In some embodiments, $R_8$ is —SH or —S($C_{1-6}$ alkyl).

In some embodiments, $R_8$ is —SH.

In some embodiments, $R_8$ is —S($C_{1-6}$ alkyl).

In some embodiments, $R_8$ is —S(methyl). In some embodiments, $R_8$ is —S(ethyl). In some embodiments, $R_8$ is —S(propyl). In some embodiments, $R_8$ is —S(butyl). In some embodiments, $R_8$ is —S(pentyl). In some embodiments, $R_8$ is —S(hexyl). In some embodiments, $R_8$ is —S(isopropyl).

In some embodiments, $R_8$ is —S(isobutyl). In some embodiments, $R_8$ is —S(isopentyl). In some embodiments, $R_8$ is —S(isohexyl). In some embodiments, $R_8$ is —S(secbutyl). In some embodiments, $R_8$ is —S(secpentyl). In some embodiments, $R_8$ is —S(sechexyl). In some embodiments, $R_8$ is —S(tertbutyl).

In some embodiments, $R_8$ is $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $R_9$.

In some embodiments, $R_8$ is $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_8$ is $C_{3-10}$ cycloalkyl or 3- to 10-membered heterocyclyl comprising 1-4 heteroatoms selected from N, O, and S, wherein the cycloalkyl or heterocyclyl is optionally substituted with one or more $R_9$.

In some embodiments, $R_8$ is $C_{3-10}$ cycloalkyl or 3- to 10-membered heterocyclyl comprising 1-4 heteroatoms selected from N, O, and S.

In some embodiments, $R_8$ is $C_{3-10}$ cycloalkyl optionally substituted with one or more $R_9$.

In some embodiments, $R_8$ is $C_3$ cycloalkyl optionally substituted with one or more $R_9$. In some embodiments, $R_8$ is $C_4$ cycloalkyl optionally substituted with one or more $R_9$. In some embodiments, $R_8$ is $C_5$ cycloalkyl optionally substituted with one or more $R_9$. In some embodiments, $R_8$ is $C_6$ cycloalkyl optionally substituted with one or more $R_9$. In some embodiments, $R_8$ is $C_7$ cycloalkyl optionally substituted with one or more $R_9$. In some embodiments, $R_8$ is $C_8$ cycloalkyl optionally substituted with one or more $R_9$. In some embodiments, $R_8$ is $C_9$ cycloalkyl optionally substituted with one or more $R_9$. In some embodiments, $R_8$ is $C_{10}$ cycloalkyl optionally substituted with one or more $R_9$.

In some embodiments, $R_8$ is $C_3$-$C_7$ monocyclic cycloalkyl optionally substituted with one or more $R_9$. In some embodiments, $R_8$ is $C_3$-$C_7$ monocyclic saturated cycloalkyl optionally substituted with one or more $R_9$. In some embodiments, $R_8$ is $C_3$-$C_7$ monocyclic partially saturated cycloalkyl optionally substituted with one or more $R_9$. In some embodiments, $R_8$ is $C_9$-$C_{10}$ bicyclic cycloalkyl optionally substituted with one or more $R_9$. In some embodiments, $R_8$ is $C_9$-$C_{10}$ bicyclic saturated cycloalkyl optionally substituted with one or more $R_9$. In some embodiments, $R_8$ is $C_9$-$C_{10}$ bicyclic partially saturated cycloalkyl optionally substituted with one or more $R_9$. In some embodiments, $R_8$ is $C_5$-$C_{10}$ polycyclic cycloalkyl optionally substituted with one or more $R_9$.

In some embodiments, $R_8$ is $C_{3-10}$ cycloalkyl substituted with one or more $R_9$.

In some embodiments, $R_8$ is $C_3$ cycloalkyl substituted with one or more $R_9$. In some embodiments, $R_8$ is $C_4$ cycloalkyl substituted with one or more $R_9$. In some embodiments, $R_8$ is $C_5$ cycloalkyl substituted with one or more $R_9$. In some embodiments, $R_8$ is $C_6$ cycloalkyl substituted with one or more $R_9$. In some embodiments, $R_8$ is $C_7$ cycloalkyl substituted with one or more $R_9$. In some embodiments, $R_8$ is $C_8$ cycloalkyl substituted with one or more $R_9$. In some embodiments, $R_8$ is $C_9$ cycloalkyl substituted with one or more $R_9$. In some embodiments, $R_8$ is $C_{10}$ cycloalkyl substituted with one or more $R_9$.

In some embodiments, $R_8$ is $C_3$-$C_7$ monocyclic cycloalkyl substituted with one or more $R_9$. In some embodiments, $R_8$ is $C_3$-$C_7$ monocyclic saturated cycloalkyl substituted with one or more $R_9$. In some embodiments, $R_8$ is $C_3$-$C_7$ monocyclic partially saturated cycloalkyl substituted with one or more $R_9$. In some embodiments, $R_8$ is $C_9$-$C_{10}$ bicyclic cycloalkyl substituted with one or more $R_9$. In some embodiments, $R_8$ is $C_9$-$C_{10}$ bicyclic saturated cycloalkyl substituted with one or more $R_9$. In some embodiments, $R_8$ is $C_9$-$C_{10}$ bicyclic partially saturated cycloalkyl substituted with one or more $R_9$. In some embodiments, $R_8$ is $C_5$-$C_{10}$ polycyclic cycloalkyl substituted with one or more $R_9$.

In some embodiments, $R_8$ is $C_{3-10}$ cycloalkyl substituted with one $R_9$.

In some embodiments, $R_8$ is $C_3$ cycloalkyl substituted with one $R_9$. In some embodiments, $R_8$ is $C_4$ cycloalkyl substituted with one $R_9$. In some embodiments, $R_8$ is $C_5$ cycloalkyl substituted with one $R_9$. In some embodiments, $R_8$ is $C_6$ cycloalkyl substituted with one $R_9$. In some embodiments, $R_8$ is $C_7$ cycloalkyl substituted with one $R_9$. In some embodiments, $R_8$ is $C_8$ cycloalkyl substituted with one $R_9$. In some embodiments, $R_8$ is $C_9$ cycloalkyl substituted with one $R_9$. In some embodiments, $R_8$ is $C_{10}$ cycloalkyl substituted with one $R_9$.

In some embodiments, $R_8$ is $C_3$-$C_7$ monocyclic cycloalkyl substituted with one $R_9$. In some embodiments, $R_8$ is $C_3$-$C_7$ monocyclic saturated cycloalkyl substituted with one $R_9$. In some embodiments, $R_8$ is $C_3$-$C_7$ monocyclic partially saturated cycloalkyl substituted with one $R_9$. In some embodiments, $R_8$ is $C_9$-$C_{10}$ bicyclic cycloalkyl substituted with one $R_9$. In some embodiments, $R_8$ is $C_9$-$C_{10}$ bicyclic saturated cycloalkyl substituted with one $R_9$. In some embodiments, $R_8$ is $C_9$-$C_{10}$ bicyclic partially saturated cycloalkyl substituted with one $R_9$. In some embodiments, $R_8$ is $C_5$-$C_{10}$ polycyclic cycloalkyl substituted with one $R_9$.

In some embodiments, $R_8$ is $C_{3-10}$ cycloalkyl.

In some embodiments, $R_8$ is $C_3$ cycloalkyl. In some embodiments, $R_8$ is $C_4$ cycloalkyl. In some embodiments, $R_8$ is $C_5$ cycloalkyl. In some embodiments, $R_8$ is $C_6$ cycloalkyl. In some embodiments, $R_8$ is $C_7$ cycloalkyl. In some embodiments, $R_8$ is $C_8$ cycloalkyl. In some embodiments, $R_8$ is $C_9$ cycloalkyl. In some embodiments, $R_8$ is $C_{10}$ cycloalkyl.

In some embodiments, $R_8$ is $C_3$-$C_7$ monocyclic cycloalkyl. In some embodiments, $R_8$ is $C_3$-$C_7$ monocyclic saturated cycloalkyl. In some embodiments, $R_8$ is $C_3$-$C_7$ monocyclic partially saturated cycloalkyl. In some embodiments, $R_8$ is $C_9$-$C_{10}$ bicyclic cycloalkyl. In some embodiments, $R_8$ is $C_9$-$C_{10}$ bicyclic saturated cycloalkyl. In some embodiments, $R_8$ is $C_9$-$C_{10}$ bicyclic partially saturated cycloalkyl. In some embodiments, $R_8$ is $C_5$-$C_{10}$ polycyclic cycloalkyl.

In some embodiments, $R_8$ is 3- to 10-membered heterocyclyl comprising 1-4 heteroatoms selected from N, O, and S, optionally substituted with one or more $R_9$. In some embodiments, $R_8$ is 3-membered heterocyclyl comprising 1-4 heteroatoms selected from N, O, and S, optionally substituted with one or more $R_9$. In some embodiments, $R_8$ is 4-membered heterocyclyl comprising 1-4 heteroatoms selected from N, O, and S, optionally substituted with one or more $R_9$. In some embodiments, $R_8$ is 5-membered heterocyclyl comprising 1-4 heteroatoms selected from N, O, and S, optionally substituted with one or more $R_9$. In some embodiments, $R_8$ is 6-membered heterocyclyl comprising 1-4 heteroatoms selected from N, O, and S, optionally substituted with one or more $R_9$. In some embodiments, $R_8$ is 7-membered heterocyclyl comprising 1-4 heteroatoms selected from N, O, and S, optionally substituted with one or more $R_9$. In some embodiments, $R_8$ is 8-membered heterocyclyl comprising 1-4 heteroatoms selected from N, O, and S, optionally substituted with one or more $R_9$. In some embodiments, $R_8$ is 9-membered heterocyclyl comprising 1-4 heteroatoms selected from N, O, and S, optionally substituted with one or more $R_9$. In some embodiments, $R_8$ is 10-membered heterocyclyl comprising 1-4 heteroatoms selected from N, O, and S, optionally substituted with one or more $R_9$.

In some embodiments, $R_8$ is 3- to 10-membered heterocyclyl comprising 1-4 heteroatoms selected from N, O, and S, substituted with one or more $R_9$. In some embodiments, $R_8$ is 3-membered heterocyclyl comprising 1-4 heteroatoms selected from N, O, and S, substituted with one or more $R_9$. In some embodiments, $R_8$ is 4-membered heterocyclyl comprising 1-4 heteroatoms selected from N, O, and S, substituted with one or more $R_9$. In some embodiments, $R_8$ is 5-membered heterocyclyl comprising 1-4 heteroatoms selected from N, O, and S, substituted with one or more $R_9$. In some embodiments, $R_8$ is 6-membered heterocyclyl comprising 1-4 heteroatoms selected from N, O, and S, substituted with one or more $R_9$. In some embodiments, $R_8$ is 7-membered heterocyclyl comprising 1-4 heteroatoms selected from N, O, and S, substituted with one or more $R_9$. In some embodiments, $R_8$ is 8-membered heterocyclyl comprising 1-4 heteroatoms selected from N, O, and S, substituted with one or more $R_9$. In some embodiments, $R_8$ is 9-membered heterocyclyl comprising 1-4 heteroatoms selected from N, O, and S, substituted with one or more $R_9$. In some embodiments, $R_8$ is 10-membered heterocyclyl comprising 1-4 heteroatoms selected from N, O, and S, substituted with one or more $R_9$.

In some embodiments, $R_8$ is 3- to 10-membered heterocyclyl comprising 1-4 heteroatoms selected from N, O, and S, substituted with one $R_9$. In some embodiments, $R_8$ is 3-membered heterocyclyl comprising 1-4 heteroatoms selected from N, O, and S, substituted with one $R_9$. In some embodiments, $R_8$ is 4-membered heterocyclyl comprising 1-4 heteroatoms selected from N, O, and S, substituted with one $R_9$. In some embodiments, $R_8$ is 5-membered heterocyclyl comprising 1-4 heteroatoms selected from N, O, and S, substituted with one $R_9$. In some embodiments, $R_8$ is 6-membered heterocyclyl comprising 1-4 heteroatoms selected from N, O, and S, substituted with one $R_9$. In some embodiments, $R_8$ is 7-membered heterocyclyl comprising 1-4 heteroatoms selected from N, O, and S, substituted with one $R_9$. In some embodiments, $R_8$ is 8-membered heterocyclyl comprising 1-4 heteroatoms selected from N, O, and S, substituted with one $R_9$. In some embodiments, $R_8$ is 9-membered heterocyclyl comprising 1-4 heteroatoms selected from N, O, and S, substituted with one $R_9$. In some embodiments, $R_8$ is 10-membered heterocyclyl comprising 1-4 heteroatoms selected from N, O, and S, substituted with one $R_9$.

In some embodiments, $R_8$ is 3- to 10-membered heterocyclyl comprising 1-4 heteroatoms selected from N, O, and S. In some embodiments, $R_8$ is 3-membered heterocyclyl comprising 1-4 heteroatoms selected from N, O, and S. In some embodiments, $R_8$ is 4-membered heterocyclyl comprising 1-4 heteroatoms selected from N, O, and S. In some embodiments, $R_8$ is 5-membered heterocyclyl comprising 1-4 heteroatoms selected from N, O, and S. In some embodiments, $R_8$ is 6-membered heterocyclyl comprising 1-4 heteroatoms selected from N, O, and S. In some embodiments, $R_8$ is 7-membered heterocyclyl comprising 1-4 heteroatoms selected from N, O, and S. In some embodiments, $R_8$ is 8-membered heterocyclyl comprising 1-4 heteroatoms selected from N, O, and S. In some embodiments, $R_8$ is 9-membered heterocyclyl comprising 1-4 heteroatoms selected from N, O, and S. In some embodiments, $R_8$ is 10-membered heterocyclyl comprising 1-4 heteroatoms selected from N, O, and S.

In some embodiments, $R_8$ is $C_{6-10}$ aryl or 5- to 10-membered heteroaryl comprising 1-4 heteroatoms selected from N, O, and S, wherein the aryl or heteroaryl is optionally substituted with one or more $R_9$.

In some embodiments, $R_8$ is $C_{6-10}$ aryl or 5- to 10-membered heteroaryl comprising 1-4 heteroatoms selected from N, O, and S.

In some embodiments, $R_8$ is $C_{6-10}$ aryl optionally substituted with one or more $R_9$.

In some embodiments, $R_8$ is $C_{6-8}$ aryl optionally substituted with one or more $R_9$. In some embodiments, $R_8$ is phenyl optionally substituted with one or more $R_9$.

In some embodiments, $R_8$ is $C_{6-8}$ aryl substituted with one or more $R_9$. In some embodiments, $R_8$ is phenyl substituted with one or more $R_9$.

In some embodiments, $R_8$ is $C_{6-8}$ aryl substituted with one $R_9$. In some embodiments, $R_8$ is phenyl substituted with one $R_9$.

In some embodiments, $R_8$ is $C_{6-10}$ aryl.

In some embodiments, $R_8$ is $C_{6-8}$ aryl. In some embodiments, $R_8$ is phenyl.

In some embodiments, $R_8$ is 5- to 10-membered heteroaryl comprising 1-4 heteroatoms selected from N, O, and S, optionally substituted with one or more $R_9$. In some embodiments, $R_8$ is 5-membered heteroaryl comprising 1-4 heteroatoms selected from N, O, and S, optionally substituted with one or more $R_9$. In some embodiments, $R_8$ is 6-membered heteroaryl comprising 1-4 heteroatoms selected from N, O, and S, optionally substituted with one or more $R_9$. In some embodiments, $R_8$ is 7-membered heteroaryl comprising 1-4 heteroatoms selected from N, O, and S, optionally substituted with one or more $R_9$. In some embodiments, $R_8$ is 8-membered heteroaryl comprising 1-4 heteroatoms selected from N, O, and S, optionally substituted with one or more $R_9$. In some embodiments, $R_8$ is 9-membered heteroaryl comprising 1-4 heteroatoms selected from N, O, and S, optionally substituted with one or more $R_9$. In some embodiments, $R_8$ is 10-membered heteroaryl comprising 1-4 heteroatoms selected from N, O, and S, optionally substituted with one or more $R_9$.

In some embodiments, $R_8$ is 5- to 10-membered heteroaryl comprising 1-4 heteroatoms selected from N, O, and S, substituted with one or more $R_9$. In some embodiments, $R_8$ is 5-membered heteroaryl comprising 1-4 heteroatoms selected from N, O, and S, substituted with one or more $R_9$. In some embodiments, $R_8$ is 6-membered heteroaryl comprising 1-4 heteroatoms selected from N, O, and S, substituted with one or more $R_9$. In some embodiments, $R_8$ is 7-membered heteroaryl comprising 1-4 heteroatoms selected from N, O, and S, substituted with one or more $R_9$. In some embodiments, $R_8$ is 8-membered heteroaryl comprising 1-4 heteroatoms selected from N, O, and S, substituted with one or more $R_9$. In some embodiments, $R_8$ is 9-membered heteroaryl comprising 1-4 heteroatoms selected from N, O, and S, substituted with one or more $R_9$. In some embodiments, $R_8$ is 10-membered heteroaryl comprising 1-4 heteroatoms selected from N, O, and S, substituted with one or more $R_9$.

In some embodiments, $R_8$ is 5- to 10-membered heteroaryl comprising 1-4 heteroatoms selected from N, O, and S, substituted with one $R_9$. In some embodiments, $R_8$ is 5-membered heteroaryl comprising 1-4 heteroatoms selected from N, O, and S, substituted with one $R_9$. In some embodiments, $R_8$ is 6-membered heteroaryl comprising 1-4 heteroatoms selected from N, O, and S, substituted with one $R_9$. In some embodiments, $R_8$ is 7-membered heteroaryl comprising 1-4 heteroatoms selected from N, O, and S, substituted with one $R_9$. In some embodiments, $R_8$ is 8-membered heteroaryl comprising 1-4 heteroatoms selected from N, O, and S, substituted with one $R_9$. In some embodiments, $R_8$ is 9-membered heteroaryl comprising 1-4 heteroatoms selected from N, O, and S, substituted with one $R_9$. In some embodiments, $R_8$ is 10-membered heteroaryl comprising 1-4 heteroatoms selected from N, O, and S, substituted with one $R_9$.

In some embodiments, $R_8$ is 5- to 10-membered heteroaryl comprising 1-4 heteroatoms selected from N, O, and S. In some embodiments, $R_8$ is 5-membered heteroaryl comprising 1-4 heteroatoms selected from N, O, and S. In some embodiments, $R_8$ is 6-membered heteroaryl comprising 1-4 heteroatoms selected from N, O, and S. In some embodiments, $R_8$ is 7-membered heteroaryl comprising 1-4 heteroatoms selected from N, O, and S. In some embodiments, $R_8$ is 8-membered heteroaryl comprising 1-4 heteroatoms selected from N, O, and S. In some embodiments, $R_8$ is 9-membered heteroaryl comprising 1-4 heteroatoms selected from N, O, and S. In some embodiments, $R_8$ is 10-membered heteroaryl comprising 1-4 heteroatoms selected from N, O, and S.

In some embodiments, $R_8$ is H, —OH, $C_{1-6}$ alkoxy, $C_{1-6}$ alkoxy-OH, —$NH_2$, —$N(C_{1-6}$ alkyl$)_2$, —$S(C_{1-6}$ alkyl), 3- to 10-membered heterocyclyl comprising 1-4 heteroatoms selected from N, O, and S, or 5- to 10-membered heteroaryl comprising 1-4 heteroatoms selected from N, O, and S, wherein the alkoxy, alkyl, heterocyclyl, or heteroaryl is optionally substituted by one or more $R_9$.

In some embodiments, $R_8$ is H, —OH, $C_{1-6}$ alkoxy, $C_{1-6}$ alkoxy-OH, —$NH_2$, —$N(C_{1-6}$ alkyl$)_2$, —$S(C_{1-6}$ alkyl), 3- to 10-membered heterocyclyl comprising 1-4 heteroatoms selected from N, O, and S, or 5- to 10-membered heteroaryl comprising 1-4 heteroatoms selected from N, O, and S, wherein the alkoxy, alkyl, heterocyclyl, or heteroaryl is substituted by one or more $R_9$.

In some embodiments, each $R_9$ is independently —$(CH_2)_u$-(5- to 10-membered heteroaryl comprising 1-4 heteroatoms selected from N, O, and S) or —$(CH_2)_u$—$(C_{6-10}$ aryl), wherein the heteroaryl or aryl is optionally substituted with one or more halogen, —CN, —OH, or —$NH_2$.

In some embodiments, $R_9$ is —$(CH_2)_u$-(5- to 10-membered heteroaryl comprising 1-4 heteroatoms selected from N, O, and S) or —$(CH_2)_u$—$(C_{6-10}$ aryl).

In some embodiments, $R_9$ is —$(CH_2)_u$-(5- to 10-membered heteroaryl comprising 1-4 heteroatoms selected from N, O, and S), wherein the heteroaryl is optionally substituted with one or more halogen, —CN, —OH, or —$NH_2$.

In some embodiments, $R_9$ is —$(CH_2)_u$-(5-membered heteroaryl), wherein the heteroaryl is optionally substituted with one or more halogen, —CN, —OH, or —$NH_2$. In some embodiments, $R_9$ is —$(CH_2)_u$-(6-membered heteroaryl), wherein the heteroaryl is optionally substituted with one or more halogen, —CN, —OH, or —$NH_2$. In some embodiments, $R_9$ is —$(CH_2)_u$-(7-membered heteroaryl), wherein the heteroaryl is optionally substituted with one or more halogen, —CN, —OH, or —$NH_2$. In some embodiments, $R_9$ is —$(CH_2)_u$-(8-membered heteroaryl), wherein the heteroaryl is optionally substituted with one or more halogen, —CN, —OH, or —$NH_2$. In some embodiments, $R_9$ is —$(CH_2)_u$-(9-membered heteroaryl), wherein the heteroaryl is optionally substituted with one or more halogen, —CN, —OH, or —NH$_2$. In some embodiments, R$_9$ is —(CH$_2$)$_u$-(10-membered heteroaryl), wherein the heteroaryl is optionally substituted with one or more halogen, —CN, —OH, or —NH$_2$.

In some embodiments, R$_9$ is —(CH$_2$)$_u$-(5- to 10-membered heteroaryl comprising 1-4 heteroatoms selected from N, O, and S), wherein the heteroaryl is substituted with one or more halogen, —CN, —OH, or —NH$_2$.

In some embodiments, R$_9$ is —(CH$_2$)$_u$-(5-membered heteroaryl comprising 1-4 heteroatoms selected from N, O, and S), wherein the heteroaryl is substituted with one or more halogen, —CN, —OH, or —NH$_2$. In some embodiments, R$_9$ is —(CH$_2$)$_u$-(6-membered heteroaryl comprising 1-4 heteroatoms selected from N, O, and S), wherein the heteroaryl is substituted with one or more halogen, —CN, —OH, or —NH$_2$. In some embodiments, R$_9$ is —(CH$_2$)$_u$-(7-membered heteroaryl comprising 1-4 heteroatoms selected from N, O, and S), wherein the heteroaryl is substituted with one or more halogen, —CN, —OH, or —NH$_2$. In some embodiments, R$_9$ is —(CH$_2$)$_u$-(8-membered heteroaryl comprising 1-4 heteroatoms selected from N, O, and S), wherein the heteroaryl is substituted with one or more halogen, —CN, —OH, or —NH$_2$. In some embodiments, R$_9$ is —(CH$_2$)$_u$-(9-membered heteroaryl comprising 1-4 heteroatoms selected from N, O, and S), wherein the heteroaryl is substituted with one or more halogen, —CN, —OH, or —NH$_2$. In some embodiments, R$_9$ is —(CH$_2$)$_u$-(10-membered heteroaryl comprising 1-4 heteroatoms selected from N, O, and S), wherein the heteroaryl is substituted with one or more halogen, —CN, —OH, or —NH$_2$.

In some embodiments, R$_9$ is —(CH$_2$)$_u$-(5- to 10-membered heteroaryl comprising 1-4 heteroatoms selected from N, O, and S), wherein the heteroaryl is substituted with one halogen, —CN, —OH, or —NH$_2$.

In some embodiments, R$_9$ is —(CH$_2$)$_u$-(5-membered heteroaryl comprising 1-4 heteroatoms selected from N, O, and S), wherein the heteroaryl is substituted with one halogen, —CN, —OH, or —NH$_2$. In some embodiments, R$_9$ is —(CH$_2$)$_u$-(6-membered heteroaryl comprising 1-4 heteroatoms selected from N, O, and S), wherein the heteroaryl is substituted with one halogen, —CN, —OH, or —NH$_2$. In some embodiments, R$_9$ is —(CH$_2$)$_u$-(7-membered heteroaryl comprising 1-4 heteroatoms selected from N, O, and S), wherein the heteroaryl is substituted with one halogen, —CN, —OH, or —NH$_2$. In some embodiments, R$_9$ is —(CH$_2$)$_u$-(8-membered heteroaryl comprising 1-4 heteroatoms selected from N, O, and S), wherein the heteroaryl is substituted with one halogen, —CN, —OH, or —NH$_2$. In some embodiments, R$_9$ is —(CH$_2$)$_u$-(9-membered heteroaryl comprising 1-4 heteroatoms selected from N, O, and S), wherein the heteroaryl is substituted with one halogen, —CN, —OH, or —NH$_2$. In some embodiments, R$_9$ is —(CH$_2$)$_u$-(10-membered heteroaryl comprising 1-4 heteroatoms selected from N, O, and S), wherein the heteroaryl is substituted with one halogen, —CN, —OH, or —NH$_2$.

In some embodiments, R$_9$ is —(CH$_2$)$_u$-(5- to 10-membered heteroaryl comprising 1-4 heteroatoms selected from N, O, and S).

In some embodiments, R$_9$ is —(CH$_2$)$_u$-(5-membered heteroaryl comprising 1-4 heteroatoms selected from N, O, and S). In some embodiments, R$_9$ is —(CH$_2$)$_u$-(6-membered heteroaryl comprising 1-4 heteroatoms selected from N, O, and S). In some embodiments, R$_9$ is —(CH$_2$)$_u$-(7-membered heteroaryl comprising 1-4 heteroatoms selected from N, O, and S). In some embodiments, R$_9$ is —(CH$_2$)$_u$-(8-membered heteroaryl comprising 1-4 heteroatoms selected from N, O, and S). In some embodiments, R$_9$ is —(CH$_2$)$_u$-(9-membered heteroaryl comprising 1-4 heteroatoms selected from N, O, and S). In some embodiments, R$_9$ is —(CH$_2$)$_u$-(10-membered heteroaryl comprising 1-4 heteroatoms selected from N, O, and S).

In some embodiments, R$_9$ is —(CH$_2$)$_u$—(C$_{6-10}$ aryl), wherein the aryl is optionally substituted with one or more halogen, —CN, —OH, or —NH$_2$. In some embodiments, R$_9$ is —(CH$_2$)$_u$—(C$_{6-8}$ aryl), wherein the aryl is optionally substituted with one or more halogen, —CN, —OH, or —NH$_2$. In some embodiments, R$_9$ is —(CH$_2$)$_u$-(phenyl), wherein the phenyl is optionally substituted with one or more halogen, —CN, —OH, or —NH$_2$.

In some embodiments, R$_9$ is —(CH$_2$)$_u$—(C$_{6-10}$ aryl), wherein the aryl is substituted with one or more halogen, —CN, —OH, or —NH$_2$. In some embodiments, R$_9$ is —(CH$_2$)$_u$—(C$_{6-8}$ aryl), wherein the aryl is substituted with one or more halogen, —CN, —OH, or —NH$_2$. In some embodiments, R$_9$ is —(CH$_2$)$_u$-(phenyl), wherein the phenyl is substituted with one or more halogen, —CN, —OH, or —NH$_2$.

In some embodiments, R$_9$ is —(CH$_2$)$_u$—(C$_{6-10}$ aryl), wherein the aryl is substituted with one halogen, —CN, —OH, or —NH$_2$. In some embodiments, R$_9$ is —(CH$_2$)$_u$—(C$_{6-8}$ aryl), wherein the aryl is substituted with one halogen, —CN, —OH, or —NH$_2$. In some embodiments, R$_9$ is —(CH$_2$)$_u$-(phenyl), wherein the phenyl is substituted with more halogen, —CN, —OH, or —NH$_2$.

In some embodiments, R$_9$ is —(CH$_2$)$_u$—(C$_{6-10}$ aryl). In some embodiments, R$_9$ is —(CH$_2$)$_u$—(C$_{6-8}$ aryl). In some embodiments, R$_9$ is —(CH$_2$)$_u$-(phenyl).

In some embodiments, R$_9$ is —(CH$_2$)$_u$-(5- to 10-membered heteroaryl comprising 1-4 heteroatoms selected from N, O, and S) or —(CH$_2$)$_u$—(C$_{6-10}$ aryl), wherein the heteroaryl or aryl is optionally substituted with one or more halogen or —OH.

In some embodiments, R$_9$ is —(CH$_2$)$_u$-(5- to 10-membered heteroaryl comprising 1-4 heteroatoms selected from N, O, and S) or —(CH$_2$)$_u$—(C$_{6-10}$ aryl), wherein the heteroaryl or aryl is substituted with one or more halogen or —OH.

In some embodiments, each R$_{10}$ is independently halogen, —OH, —NH$_2$, —CN, C$_{1-6}$ alkyl, C$_{2-6}$ alkenyl, C$_{2-6}$ alkynyl, C$_{1-6}$ haloalkyl, C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S.

In some embodiments, R$_{10}$ is halogen, —OH, —NH$_2$, or —CN.

In some embodiments, R$_{10}$ is halogen.

In some embodiments, R$_{10}$ is F, Cl, Br, or I. In some embodiments, R$_{10}$ is F, Cl, or Br.

In some embodiments, R$_{10}$ is F. In some embodiments, R$_{10}$ is Cl. In some embodiments, R$_{10}$ is Br. In some embodiments, R$_{10}$ is I.

In some embodiments, R$_{10}$ is —OH. In some embodiments, R$_{10}$ is —NH$_2$. In some embodiments, R$_{10}$ is —CN.

In some embodiments, R$_{10}$ is C$_{1-6}$ alkyl, C$_{2-6}$ alkenyl, C$_{2-6}$ alkynyl, C$_{1-6}$ haloalkyl, C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S.

In some embodiments, R$_{10}$ is C$_{1-6}$ alkyl, C$_{2-6}$ alkenyl, C$_{2-6}$ alkynyl, or C$_{1-6}$ haloalkyl.

In some embodiments, R$_{10}$ is C$_{1-6}$ alkyl, C$_{2-6}$ alkenyl, or C$_{2-6}$ alkynyl.

In some embodiments, $R_{10}$ is $C_{1-6}$ alkyl. In some embodiments, $R_{10}$ is methyl. In some embodiments, $R_{10}$ is ethyl. In some embodiments, $R_{10}$ is propyl. In some embodiments, $R_{10}$ is butyl. In some embodiments, $R_{10}$ is pentyl. In some embodiments, $R_{10}$ is hexyl. In some embodiments, $R_{10}$ is isopropyl. In some embodiments, $R_{10}$ is isobutyl. In some embodiments, $R_{10}$ is isopentyl. In some embodiments, $R_{10}$ is isohexyl. In some embodiments, $R_{10}$ is secbutyl. In some embodiments, $R_{10}$ is secpentyl. In some embodiments, $R_{10}$ is sechexyl. In some embodiments, $R_{10}$ is tertbutyl.

In some embodiments, $R_{10}$ is $C_{2-6}$ alkenyl. In some embodiments, $R_{10}$ is $C_2$ alkenyl. In some embodiments, $R_{10}$ is $C_3$ alkenyl. In some embodiments, $R_{10}$ is $C_4$ alkenyl. In some embodiments, $R_{10}$ is $C_5$ alkenyl. In some embodiments, $R_{10}$ is $C_6$ alkenyl.

In some embodiments, $R_{10}$ is $C_{2-6}$ alkynyl. In some embodiments, $R_{10}$ is $C_2$ alkynyl. In some embodiments, $R_{10}$ is $C_3$ alkynyl. In some embodiments, $R_{10}$ is $C_4$ alkynyl. In some embodiments, $R_{10}$ is $C_5$ alkynyl. In some embodiments, $R_{10}$ is $C_6$ alkynyl.

In some embodiments, $R_{10}$ is $C_{1-6}$ haloalkyl. In some embodiments, $R_{10}$ is halomethyl. In some embodiments, $R_{10}$ is haloethyl. In some embodiments, $R_{10}$ is halopropyl. In some embodiments, $R_{10}$ is halobutyl. In some embodiments, $R_{10}$ is halopentyl. In some embodiments, $R_{10}$ is halohexyl.

In some embodiments, $R_{10}$ is $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_{10}$ is $C_{3-10}$ cycloalkyl or 3- to 10-membered heterocyclyl comprising 1-4 heteroatoms selected from N, O, and S.

In some embodiments, $R_{10}$ is $C_{3-10}$ cycloalkyl.

In some embodiments, $R_{10}$ is $C_3$ cycloalkyl. In some embodiments, $R_{10}$ is $C_4$ cycloalkyl. In some embodiments, $R_{10}$ is $C_5$ cycloalkyl. In some embodiments, $R_{10}$ is $C_6$ cycloalkyl. In some embodiments, $R_{10}$ is $C_7$ cycloalkyl. In some embodiments, $R_{10}$ is $C_8$ cycloalkyl. In some embodiments, $R_{10}$ is $C_9$ cycloalkyl. In some embodiments, $R_{10}$ is $C_{10}$ cycloalkyl.

In some embodiments, $R_{10}$ is $C_3$-$C_7$ monocyclic cycloalkyl. In some embodiments, $R_{10}$ is $C_3$-$C_7$ monocyclic saturated cycloalkyl. In some embodiments, $R_{10}$ is $C_3$-$C_7$ monocyclic partially saturated cycloalkyl. In some embodiments, $R_{10}$ is $C_9$-$C_{10}$ bicyclic cycloalkyl. In some embodiments, $R_{10}$ is $C_9$-$C_{10}$ bicyclic saturated cycloalkyl. In some embodiments, $R_{10}$ is $C_9$-$C_{10}$ bicyclic partially saturated cycloalkyl. In some embodiments, $R_{10}$ is $C_5$-$C_{10}$ polycyclic cycloalkyl.

In some embodiments, $R_{10}$ is 3- to 10-membered heterocyclyl comprising 1-4 heteroatoms selected from N, O, and S. In some embodiments, $R_{10}$ is 3-membered heterocyclyl comprising 1-4 heteroatoms selected from N, O, and S. In some embodiments, $R_{10}$ is 4-membered heterocyclyl comprising 1-4 heteroatoms selected from N, O, and S. In some embodiments, $R_{10}$ is 5-membered heterocyclyl comprising 1-4 heteroatoms selected from N, O, and S. In some embodiments, $R_{10}$ is 6-membered heterocyclyl comprising 1-4 heteroatoms selected from N, O, and S. In some embodiments, $R_{10}$ is 7-membered heterocyclyl comprising 1-4 heteroatoms selected from N, O, and S. In some embodiments, $R_{10}$ is 8-membered heterocyclyl comprising 1-4 heteroatoms selected from N, O, and S. In some embodiments, $R_{10}$ is 9-membered heterocyclyl comprising 1-4 heteroatoms selected from N, O, and S. In some embodiments, $R_{10}$ is 10-membered heterocyclyl comprising 1-4 heteroatoms selected from N, O, and S.

In some embodiments, $R_{10}$ is $C_{6-10}$ aryl or 5- to 10-membered heteroaryl comprising 1-4 heteroatoms selected from N, O, and S.

In some embodiments, $R_{10}$ is $C_{6-10}$ aryl.

In some embodiments, $R_{10}$ is $C_{6-8}$ aryl. In some embodiments, $R_{10}$ is phenyl.

In some embodiments, $R_{10}$ is 5- to 10-membered heteroaryl comprising 1-4 heteroatoms selected from N, O, and S. In some embodiments, $R_{10}$ is 5-membered heteroaryl comprising 1-4 heteroatoms selected from N, O, and S. In some embodiments, $R_{10}$ is 6-membered heteroaryl comprising 1-4 heteroatoms selected from N, O, and S. In some embodiments, $R_{10}$ is 7-membered heteroaryl comprising 1-4 heteroatoms selected from N, O, and S. In some embodiments, $R_{10}$ is 8-membered heteroaryl comprising 1-4 heteroatoms selected from N, O, and S. In some embodiments, $R_{10}$ is 9-membered heteroaryl comprising 1-4 heteroatoms selected from N, O, and S. In some embodiments, $R_{10}$ is 10-membered heteroaryl comprising 1-4 heteroatoms selected from N, O, and S.

In some embodiments, $R_{10}$ is $C_{1-6}$ alkyl, $C_{1-6}$ haloalkyl, or 5- to 10-membered heteroaryl comprising 1-4 heteroatoms selected from N, O, and S.

In some embodiments, each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$.

In some embodiments, each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$.

In some embodiments, each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_{11}$ is H

In some embodiments, $R_{11}$ is $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$.

In some embodiments, $R_{11}$ is $C_{1-6}$ alkyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is methyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is ethyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is propyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is butyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is pentyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is hexyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is isopropyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is isobutyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is isopentyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is isohexyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is secbutyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is secpentyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is sechexyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is tertbutyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$.

In some embodiments, $R_{11}$ is $C_{1-6}$ alkyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is methyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is ethyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is propyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is butyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is pentyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is hexyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is isopropyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is isobutyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is isopentyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is isohexyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is secbutyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is secpentyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is sechexyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is tertbutyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$.

In some embodiments, $R_{11}$ is $C_{2-6}$ alkenyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is $C_2$ alkenyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is $C_3$ alkenyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is $C_4$ alkenyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, R$_{11}$ is C$_5$ alkenyl optionally substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$. In some embodiments, R$_{11}$ is C$_6$ alkenyl optionally substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$.

In some embodiments, R$_{11}$ is C$_{2-6}$ alkenyl substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$. In some embodiments, R$_{11}$ is C$_2$ alkenyl substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$. In some embodiments, R$_{11}$ is C$_3$ alkenyl substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$. In some embodiments, R$_{11}$ is C$_4$ alkenyl substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$. In some embodiments, R$_{11}$ is C$_5$ alkenyl substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$. In some embodiments, R$_{11}$ is C$_6$ alkenyl substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$.

In some embodiments, R$_{11}$ is C$_{2-6}$ alkynyl optionally substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$. In some embodiments, R$_{11}$ is C$_2$ alkynyl optionally substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$. In some embodiments, R$_{11}$ is C$_3$ alkynyl optionally substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, C$_{6-10}$ aryl, 5- to 10-membered heteroaryl comprising 1-4 heteroatoms selected from N, O, and S, C$_{1-6}$ alkyl, C$_{2-6}$ alkenyl, C$_{2-6}$ alkynyl, oxo, halogen, —CN, —OH, or —NH$_2$. In some embodiments, R$_{11}$ is C$_4$ alkynyl optionally substituted with one or more C$_{3-10}$ cycloalkyl, 3- to 10-membered heterocyclyl comprising 1-4 heteroatoms selected from N, O, and S, C$_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more C$_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is $C_5$ alkynyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is $C_6$ alkynyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$.

In some embodiments, $R_{11}$ is $C_{2-6}$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is $C_2$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is $C_3$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is $C_4$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is $C_5$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$. In some embodiments, $R_{11}$ is $C_6$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$.

In some embodiments, $R_{11}$ is $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_{11}$ is $C_{1-6}$ alkyl, $C_{2-6}$ alkenyl, or $C_{2-6}$ alkynyl, wherein the alkyl, alkenyl, or alkynyl is substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_{11}$ is $C_{1-6}$ alkyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is methyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is ethyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is propyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is butyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is pentyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is hexyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is isopropyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is isobutyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is isopentyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is isohexyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is secbutyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is secpentyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is sechexyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is tertbutyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_{11}$ is $C_{1-6}$ alkyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is methyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is ethyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is propyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is butyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is pentyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is hexyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is isopropyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is isobutyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is isopentyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is isohexyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is secbutyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is secpentyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is sechexyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is tertbutyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_{11}$ is $C_{2-6}$ alkenyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_2$ alkenyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_3$ alkenyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_4$ alkenyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_5$ alkenyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_6$ alkenyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_{11}$ is $C_{2-6}$ alkenyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_2$ alkenyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_3$ alkenyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_4$ alkenyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_5$ alkenyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_6$ alkenyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_{11}$ is $C_{2-6}$ alkynyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_2$ alkynyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_3$ alkynyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_4$ alkynyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_5$ alkynyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_6$ alkynyl optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_{11}$ is $C_{2-6}$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_2$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_3$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_4$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_5$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S. In some embodiments, $R_{11}$ is $C_6$ alkynyl substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S.

In some embodiments, $R_{11}$ is $C_{1-6}$ alkyl, $C_{2-6}$ alkenyl, or $C_{2-6}$ alkynyl.

In some embodiments, $R_{11}$ is $C_{1-6}$ alkyl. In some embodiments, $R_{11}$ is methyl. In some embodiments, $R_{11}$ is ethyl. In some embodiments, $R_{11}$ is propyl. In some embodiments, $R_{11}$ is butyl. In some embodiments, $R_{11}$ is pentyl. In some embodiments, $R_{11}$ is hexyl. In some embodiments, $R_{11}$ is isopropyl. In some embodiments, $R_{11}$ is isobutyl. In some embodiments, $R_{11}$ is isopentyl. In some embodiments, $R_{11}$ is isohexyl. In some embodiments, $R_{11}$ is secbutyl. In some embodiments, $R_{11}$ is secpentyl. In some embodiments, $R_{11}$ is sechexyl. In some embodiments, $R_{11}$ is tertbutyl.

In some embodiments, $R_{11}$ is $C_{2-6}$ alkenyl. In some embodiments, $R_{11}$ is $C_2$ alkenyl. In some embodiments, $R_{11}$ is $C_3$ alkenyl. In some embodiments, $R_{11}$ is $C_4$ alkenyl. In some embodiments, $R_{11}$ is $C_5$ alkenyl. In some embodiments, $R_{11}$ is $C_6$ alkenyl.

In some embodiments, $R_{11}$ is $C_{2-6}$ alkynyl. In some embodiments, $R_{11}$ is $C_2$ alkynyl. In some embodiments, $R_{11}$ is $C_3$ alkynyl. In some embodiments, $R_{11}$ is $C_4$ alkynyl. In some embodiments, $R_{11}$ is $C_5$ alkynyl. In some embodiments, $R_{11}$ is $C_6$ alkynyl.

In some embodiments, $R_{11}$ is H or $C_{1-6}$ alkyl optionally substituted with one or more 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the heterocyclyl, aryl, or heteroaryl is optionally substituted with one or more 5- to 10-membered heteroaryl comprising 1-4 heteroatoms selected from N, O, and S, $C_{1-6}$ alkyl, or oxo.

In some embodiments, $R_{11}$ is H or $C_{1-6}$ alkyl optionally substituted with one or more 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the heterocyclyl, aryl, or heteroaryl is substituted with one or more 5- to 10-membered heteroaryl comprising 1-4 heteroatoms selected from N, O, and S, $C_{1-6}$ alkyl, or oxo.

In some embodiments, $R_{11}$ is H or $C_{1-6}$ alkyl substituted with one or more 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the heterocyclyl, aryl, or heteroaryl is optionally substituted with one or more 5- to 10-membered heteroaryl comprising 1-4 heteroatoms selected from N, O, and S, $C_{1-6}$ alkyl, or oxo.

In some embodiments, two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S.

In some embodiments, two $R_{11}$ together with the atom to which they are attached form a 4- to 10-membered heterocyclyl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 4-membered heterocyclyl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 5-membered heterocyclyl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 6-membered heterocyclyl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 7-membered heterocyclyl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 8-membered heterocyclyl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 9-membered heterocyclyl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 10-membered heterocyclyl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 4- to 10-membered heterocyclyl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 4-membered heterocyclyl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 5-membered heterocyclyl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 6-membered heterocyclyl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 7-membered heterocyclyl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 8-membered heterocyclyl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 9-membered heterocyclyl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 10-membered heterocyclyl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 4- to 10-membered heterocyclyl comprising 1-4 heteroatoms selected from N, O, and S.

In some embodiments, two $R_{11}$ together with the atom to which they are attached form a 4-membered heterocyclyl comprising 1-4 heteroatoms selected from N, O, and S.

In some embodiments, two $R_{11}$ together with the atom to which they are attached form a 5-membered heterocyclyl comprising 1-4 heteroatoms selected from N, O, and S.

In some embodiments, two $R_{11}$ together with the atom to which they are attached form a 6-membered heterocyclyl comprising 1-4 heteroatoms selected from N, O, and S.

In some embodiments, two $R_{11}$ together with the atom to which they are attached form a 7-membered heterocyclyl comprising 1-4 heteroatoms selected from N, O, and S.

In some embodiments, two $R_{11}$ together with the atom to which they are attached form a 8-membered heterocyclyl comprising 1-4 heteroatoms selected from N, O, and S.

In some embodiments, two $R_{11}$ together with the atom to which they are attached form a 9-membered heterocyclyl comprising 1-4 heteroatoms selected from N, O, and S.

In some embodiments, two $R_{11}$ together with the atom to which they are attached form a 10-membered heterocyclyl comprising 1-4 heteroatoms selected from N, O, and S.

In some embodiments, two $R_{11}$ together with the atom to which they are attached form a 5- to 10-membered heteroaryl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 5-membered heteroaryl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 6-membered heteroaryl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 7-membered heteroaryl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 8-membered heteroaryl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 9-membered heteroaryl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 10-membered heteroaryl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 5- to 10-membered heteroaryl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 5-membered heteroaryl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 6-membered heteroaryl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 7-membered heteroaryl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 8-membered heteroaryl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 9-membered heteroaryl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 10-membered heteroaryl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 5- to 10-membered heteroaryl comprising 1-4 heteroatoms selected from N, O, and S.

In some embodiments, two $R_{11}$ together with the atom to which they are attached form a 5-membered heteroaryl comprising 1-4 heteroatoms selected from N, O, and S.

In some embodiments, two $R_{11}$ together with the atom to which they are attached form a 6-membered heteroaryl comprising 1-4 heteroatoms selected from N, O, and S.

In some embodiments, two $R_{11}$ together with the atom to which they are attached form a 7-membered heteroaryl comprising 1-4 heteroatoms selected from N, O, and S.

In some embodiments, two $R_{11}$ together with the atom to which they are attached form a 8-membered heteroaryl comprising 1-4 heteroatoms selected from N, O, and S.

In some embodiments, two $R_{11}$ together with the atom to which they are attached form a 9-membered heteroaryl comprising 1-4 heteroatoms selected from N, O, and S.

In some embodiments, two $R_{11}$ together with the atom to which they are attached form a 10-membered heteroaryl comprising 1-4 heteroatoms selected from N, O, and S.

In some embodiments, two $R_{11}$ together with the atom to which they are attached form a 4- to 10-membered heterocyclyl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

In some embodiments, two $R_{11}$ together with the atom to which they are attached form a 4- to 10-membered heterocyclyl comprising 1-4 heteroatoms selected from N, O, and S, substituted with one or more $C_{1-6}$ alkyl, $C_{2-6}$ alkenyl, $C_{2-6}$ alkynyl, halogen, —CN, —OH, or —NH$_2$.

In some embodiments, each n, m, and p is independently 0 or 1. In some embodiments, each n, m, and p is independently 0. In some embodiments, each n, m, and p is independently 1.

In some embodiments, n is 0 or 1. In some embodiments, n is 0. In some embodiments, n is 1.

In some embodiments, m is 0 or 1. In some embodiments, m is 0. In some embodiments, m is 1.

In some embodiments, p is 0 or 1. In some embodiments, p is 0. In some embodiments, p is 1.

In some embodiments, t is 1, 2, or 3. In some embodiments, t is 1. In some embodiments, t is 2. In some embodiments, t is 3.

In some embodiments, u is 0, 1, 2, or 3. In some embodiments, u is 0. In some embodiments, u is 1. In some embodiments, u is 2. In some embodiments, u is 3.

In some embodiments, when $R_5$ and $R_6$ together with the atoms to which they are attached form a heterocyclyl or heteroaryl substituted with two $R_7$, then one $R_7$ is not —O-methyl.

In some embodiments, when $R_5$ and $R_6$ together with the atoms to which they are attached form a heterocyclyl substituted with two $R_7$, then one $R_7$ is not —O-methyl.

In some embodiments, when $R_5$ and $R_6$ together with the atoms to which they are attached form a heteroaryl substituted with two $R_7$, then one $R_7$ is not —O-methyl.

In some embodiments, when $R_5$ and $R_6$ together with the atoms to which they are attached form a heterocyclyl or heteroaryl substituted with two $R_7$ and both $R_7$ are —O-methyl, then one $R_2$ or $R_3$ is not —O-methyl.

In some embodiments, when $R_5$ and $R_6$ together with the atoms to which they are attached form a heterocyclyl or heteroaryl substituted with two $R_7$ and both $R_7$ are —O-methyl, then $R_x$ or $R_y$ is 5- to 10-membered heteroaryl comprising 1-4 heteroatoms selected from N, O, and S.

In some embodiments, one of $R_2$ and $R_3$ is not —O-methyl.

In some embodiments, $R_x$ or $R_y$ is 5- to 10-membered heteroaryl comprising 1-4 heteroatoms selected from N, O, and S.

In some embodiments, the compound is of Formula (I-a) or (I-b):

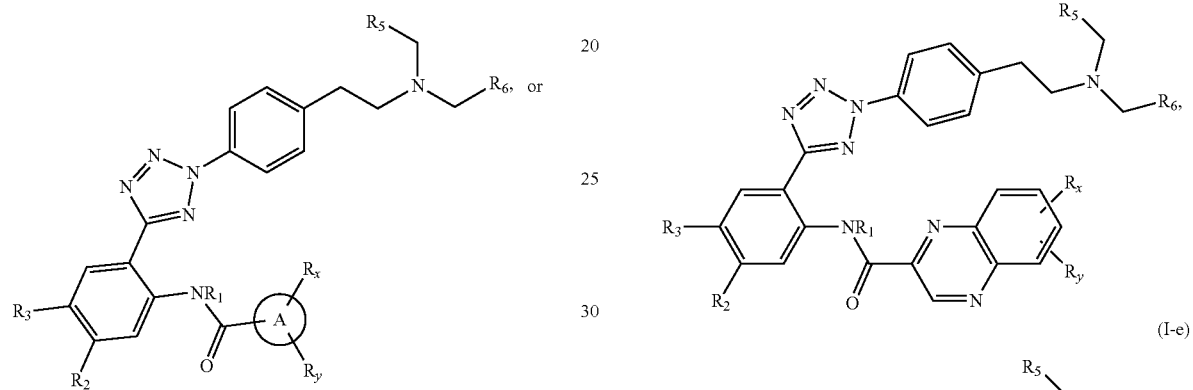

(I-a)

(I-b)

or a pharmaceutically acceptable prodrug, solvate, enantiomer, stereoisomer, tautomer, or salt thereof.

In some embodiments, the compound is of Formula (I-a) or a pharmaceutically acceptable prodrug, solvate, enantiomer, stereoisomer, tautomer, or salt thereof.

In some embodiments, the compound is of Formula (I-b) or a pharmaceutically acceptable prodrug, solvate, enantiomer, stereoisomer, tautomer, or salt thereof.

In some embodiments, the compound is of Formula (I-c), (I-d), (I-e), or (I-f):

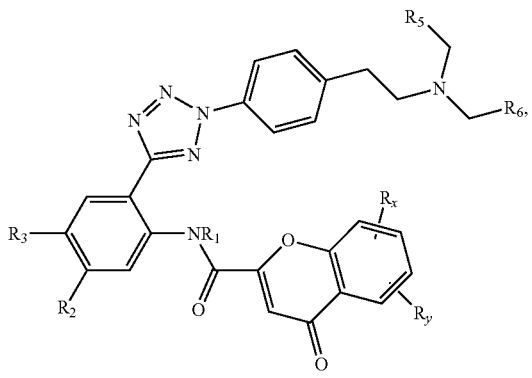

(I-c)

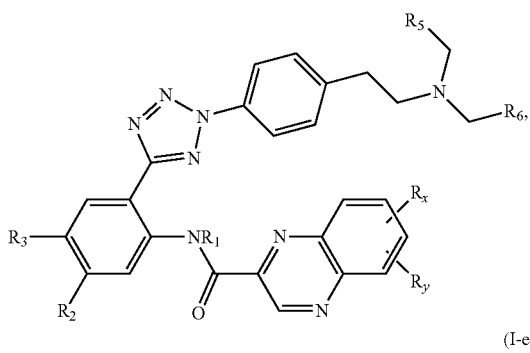

(I-d)

(I-e)

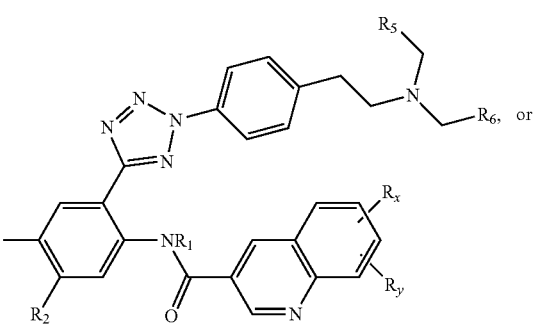

(I-f)

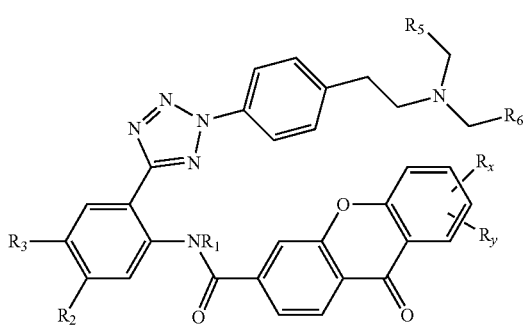

or a pharmaceutically acceptable prodrug, solvate, enantiomer, stereoisomer, tautomer, or salt thereof.

In some embodiments, the compound is of Formula (I-c) or a pharmaceutically acceptable prodrug, solvate, enantiomer, stereoisomer, tautomer, or salt thereof.

In some embodiments, the compound is of Formula (I-d) or a pharmaceutically acceptable prodrug, solvate, enantiomer, stereoisomer, tautomer, or salt thereof.

In some embodiments, the compound is of Formula (I-e) or a pharmaceutically acceptable prodrug, solvate, enantiomer, stereoisomer, tautomer, or salt thereof.

In some embodiments, the compound is of Formula (I-f) or a pharmaceutically acceptable prodrug, solvate, enantiomer, stereoisomer, tautomer, or salt thereof.

In some embodiments, the compound is of Formula (I-a') or (I-b'):

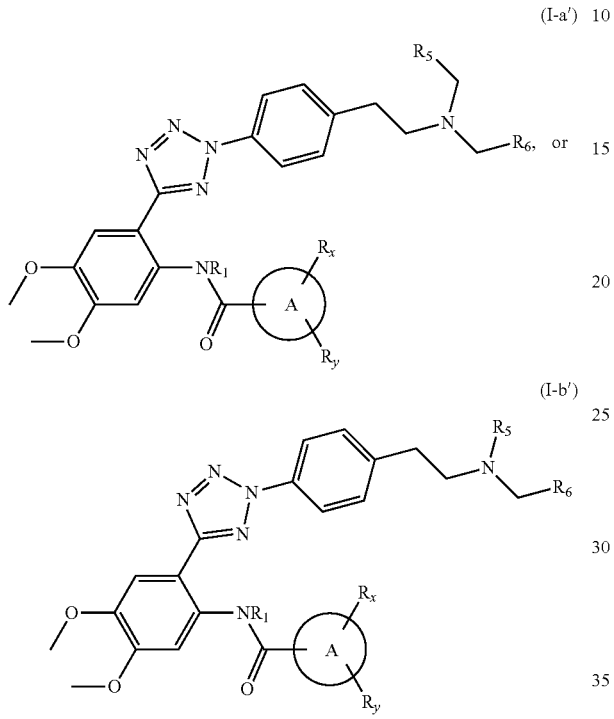

(I-a')

(I-b')

or a pharmaceutically acceptable prodrug, solvate, enantiomer, stereoisomer, tautomer, or salt thereof.

In some embodiments, the compound is of Formula (I-a') or a pharmaceutically acceptable prodrug, solvate, enantiomer, stereoisomer, tautomer, or salt thereof.

In some embodiments, the compound is of Formula (I-b') or a pharmaceutically acceptable prodrug, solvate, enantiomer, stereoisomer, tautomer, or salt thereof.

In some embodiments, the compound is of Formula (II-a):

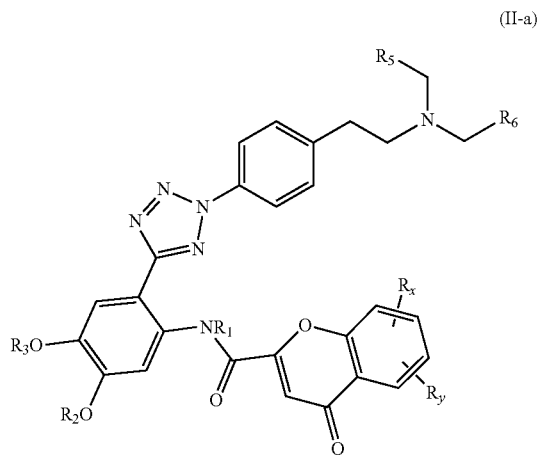

(II-a)

or a pharmaceutically acceptable prodrug, solvate, enantiomer, stereoisomer, tautomer, or salt thereof.

In some embodiments, the compound is of Formula (II-a) or a pharmaceutically acceptable prodrug, solvate, enantiomer, stereoisomer, tautomer, or salt thereof.

In some embodiments, the compound is of Formula (II-a'):

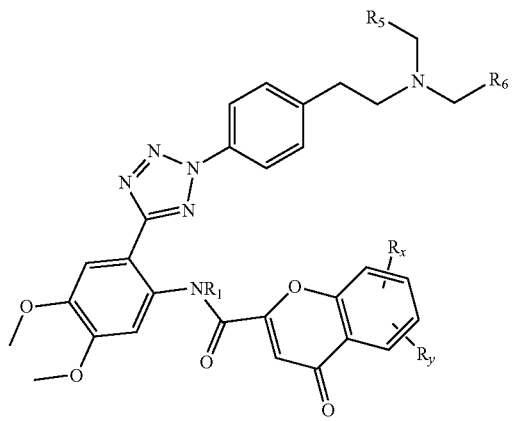

(II-a')

or a pharmaceutically acceptable prodrug, solvate, enantiomer, stereoisomer, tautomer, or salt thereof.

In some embodiments, the compound is of Formula (II-a') or a pharmaceutically acceptable prodrug, solvate, enantiomer, stereoisomer, tautomer, or salt thereof.

It is understood that, for a compound of any of the Formulae disclosed herein, A, $R_X$, $R_Y$, $R_1$, $R_2$, $R_3$, $R_5$, $R_6$, $R_7$, $R_8$, $R_9$, $R_{10}$, $R_{11}$, n, m, p, t, and u can each be, where applicable, selected from the groups described herein, and any group described herein for any of A, $R_X$, $R_Y$, $R_1$, $R_2$, $R_3$, $R_5$, $R_6$, $R_7$, $R_8$, $R_9$, $R_{10}$, $R_{11}$, n, m, p, t, and u can be combined, where applicable, with any group described herein for one or more of the remainder of A, $R_X$, $R_Y$, $R_1$, $R_2$, $R_3$, $R_5$, $R_6$, $R_7$, $R_8$, $R_9$, $R_{10}$, $R_{11}$, n, m, p, t, and u.

In some embodiments, the compound is selected from the compounds described in Table 1 and prodrugs and pharmaceutically acceptable salts thereof.

In some embodiments, the compound is selected from the compounds described in Table 1 and pharmaceutically acceptable salts thereof.

In some embodiments, the compound is selected from the prodrugs of compounds described in Table 1 and pharmaceutically acceptable salts thereof.

In some embodiments, the compound is selected from the compounds described in Table 1.

In some embodiments, the compound is selected from the compounds described in Table 2 and prodrugs and pharmaceutically acceptable salts thereof.

In some embodiments, the compound is selected from the compounds described in Table 2 and pharmaceutically acceptable salts thereof.

In some embodiments, the compound is selected from the prodrugs of compounds described in Table 2 and pharmaceutically acceptable salts thereof.

In some embodiments, the compound is selected from the compounds described in Table 2.

TABLE 1

| Compound No. | Structure |
|---|---|
| 1 | (chemical structure) |
| 2 | (chemical structure) |
| 3 | (chemical structure) |
| 4 | (chemical structure) |

TABLE 1-continued

| Compound No. | Structure |
|---|---|
| 5 | 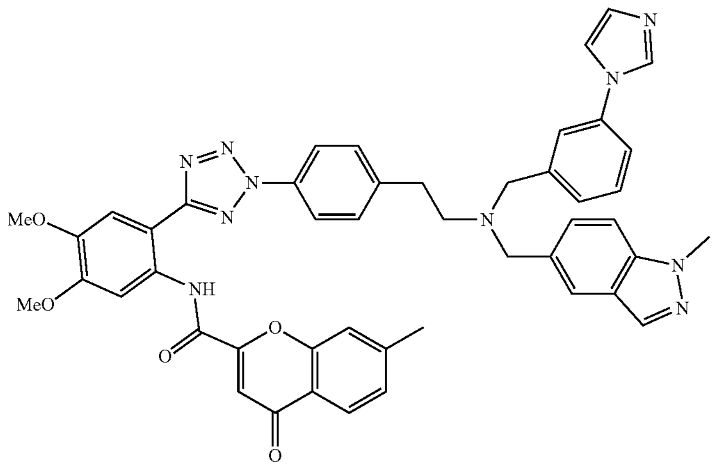 [SMILES: COc1cc(NC(=O)c2cc(=O)c3ccc(C)cc3o2)c(-c2nnn(-c3ccc(CCN(Cc4cccc(-n5ccnc5)c4)Cc4ccc5c(cnn5C)c4)cc3)n2)cc1OC] |
| 6 | 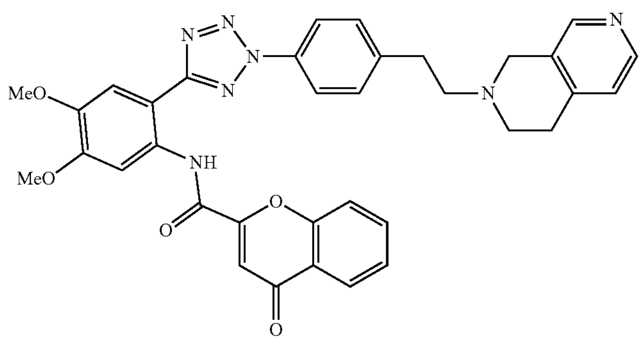 [SMILES: COc1cc(NC(=O)c2cc(=O)c3ccccc3o2)c(-c2nnn(-c3ccc(CCN4CCc5ccncc5C4)cc3)n2)cc1OC] |
| 7 | 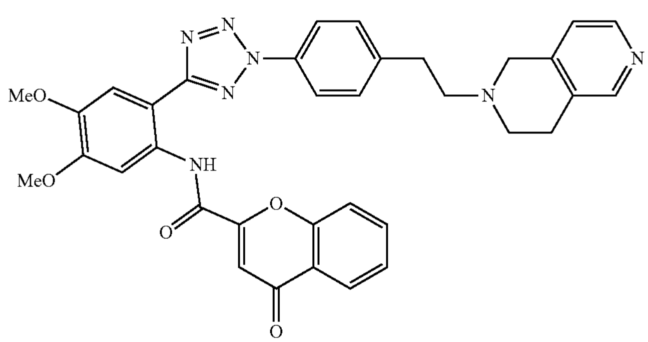 [SMILES: COc1cc(NC(=O)c2cc(=O)c3ccccc3o2)c(-c2nnn(-c3ccc(CCN4CCc5cnccc5C4)cc3)n2)cc1OC] |
| 8 | 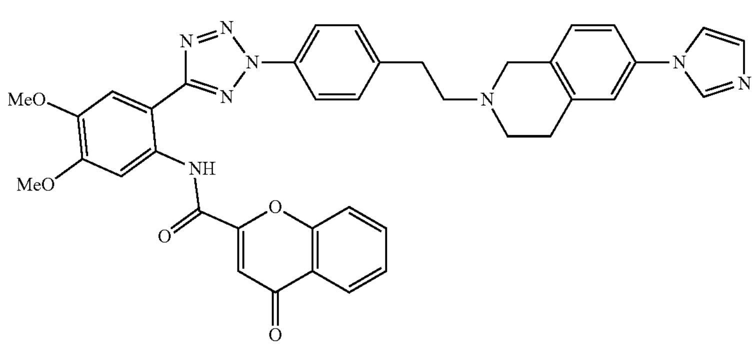 [SMILES: COc1cc(NC(=O)c2cc(=O)c3ccccc3o2)c(-c2nnn(-c3ccc(CCN4CCc5cc(-n6ccnc6)ccc5C4)cc3)n2)cc1OC] |

TABLE 1-continued

| Compound No. | Structure |
| --- | --- |
| 9 | 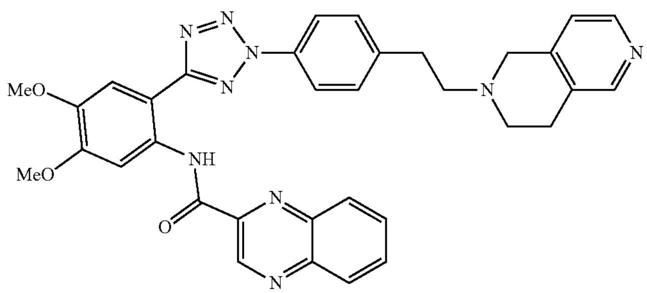 [SMILES: COc1cc(NC(=O)c2cnc3ccccc3n2)c(-c2nnn(-c3ccc(CCN4CCc5cnccc5C4)cc3)n2)cc1OC] |
| 10 | 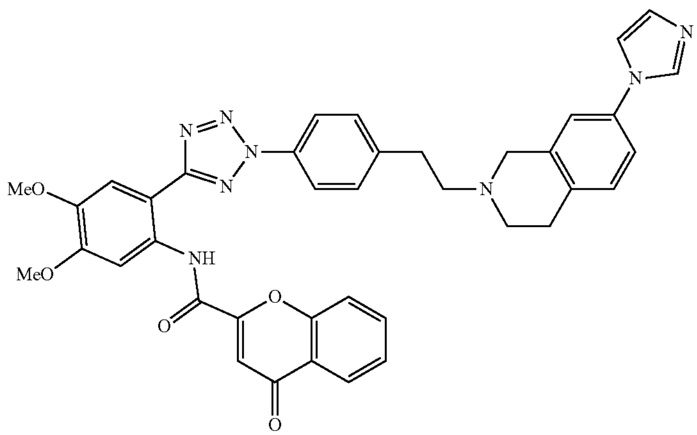 [SMILES: COc1cc(NC(=O)c2cc(=O)c3ccccc3o2)c(-c2nnn(-c3ccc(CCN4CCc5ccc(-n6ccnc6)cc5C4)cc3)n2)cc1OC] |
| 11 | 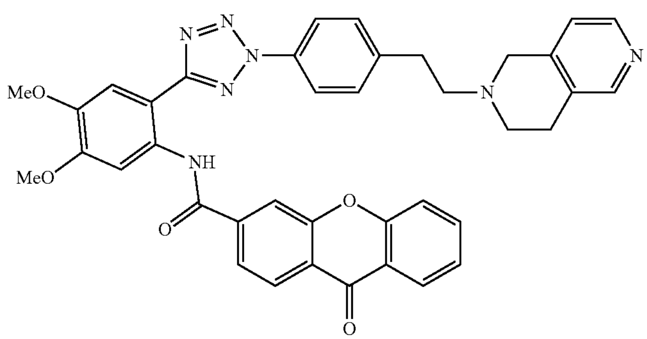 [SMILES: COc1cc(NC(=O)c2ccc3c(=O)c4ccccc4oc3c2)c(-c2nnn(-c3ccc(CCN4CCc5cnccc5C4)cc3)n2)cc1OC] |
| 12 | 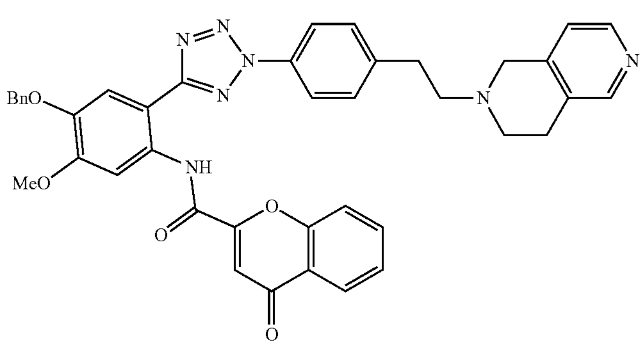 [SMILES: COc1cc(NC(=O)c2cc(=O)c3ccccc3o2)c(-c2nnn(-c3ccc(CCN4CCc5cnccc5C4)cc3)n2)cc1OCc1ccccc1] |

TABLE 1-continued

| Compound No. | Structure |
|---|---|
| 13 | 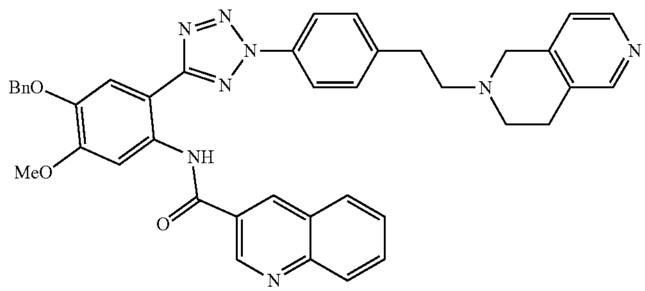 [SMILES: COc1cc(NC(=O)c2cnc3ccccc3c2)c(-c2nnn(-c3ccc(CCN4CCc5cnccc5C4)cc3)n2)cc1OCc1ccccc1] |
| 14 | 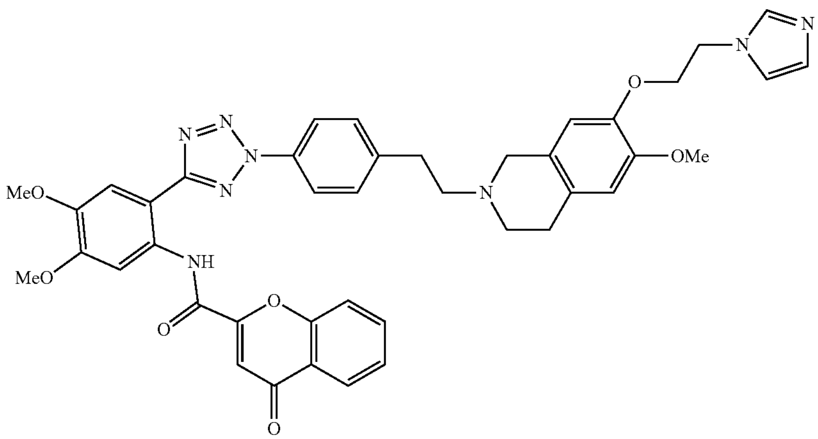 [SMILES: COc1cc(NC(=O)c2cc(=O)c3ccccc3o2)c(-c2nnn(-c3ccc(CCN4CCc5cc(OC)c(OCCn6ccnc6)cc5C4)cc3)n2)cc1OC] |
| 15 | 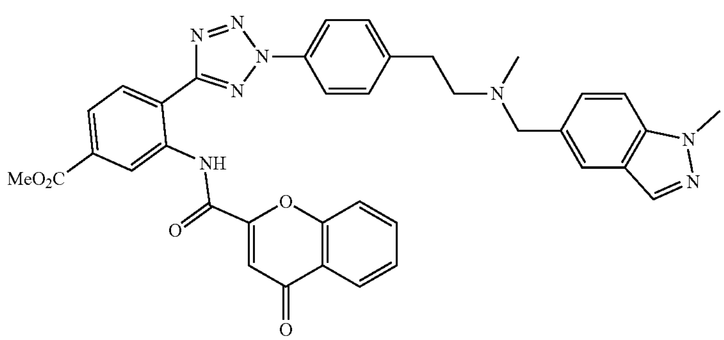 [SMILES: COC(=O)c1ccc(-c2nnn(-c3ccc(CCN(C)Cc4ccc5c(cnn5C)c4)cc3)n2)c(NC(=O)c2cc(=O)c3ccccc3o2)c1] |
| 16 | 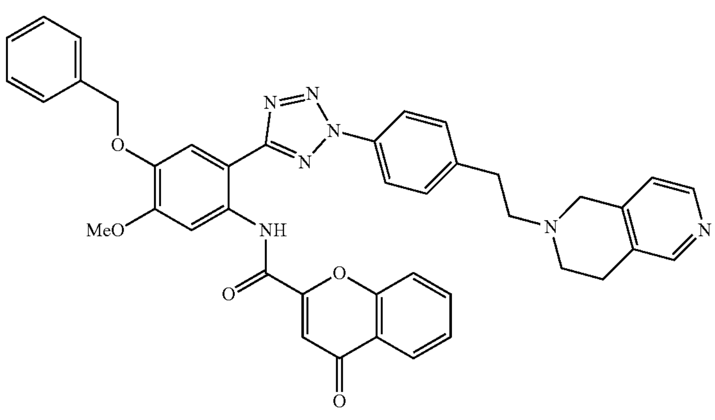 [SMILES: COc1cc(NC(=O)c2cc(=O)c3ccccc3o2)c(-c2nnn(-c3ccc(CCN4CCc5cnccc5C4)cc3)n2)cc1OCc1ccccc1] |

TABLE 1-continued
| Compound No. | Structure |
|---|---|
| 17 | 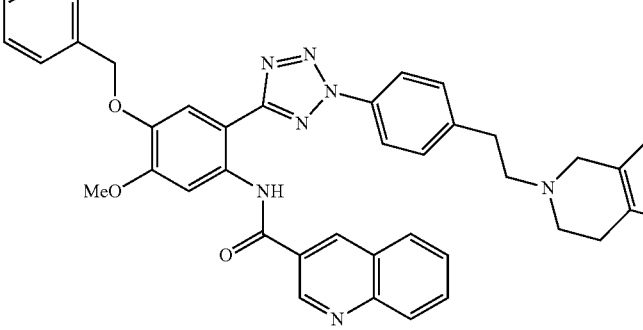 |
| 18 | 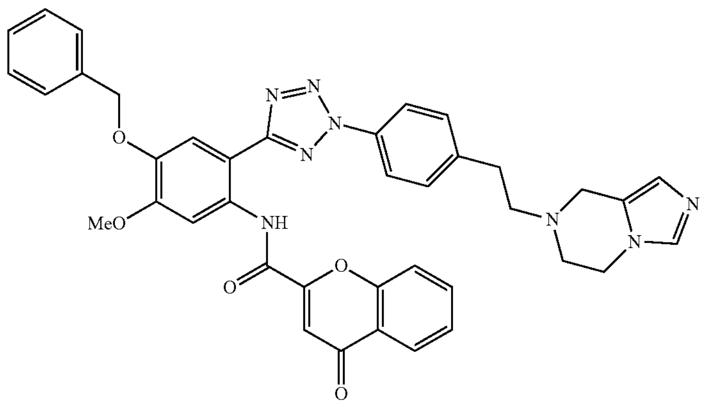 [SMILES: COc1cc(NC(=O)c2cc(=O)c3ccccc3o2)c(-c2nnn(-c3ccc(CCN4CCn5cncc5C4)cc3)n2)cc1OCc1ccccc1] |
TABLE 2
| Compound No. | Structure |
|---|---|
| 19 | 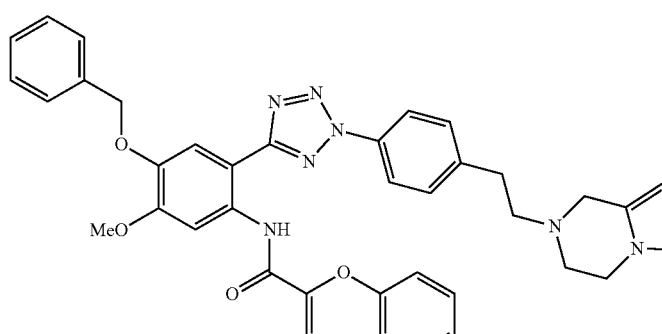 |
| 20 | 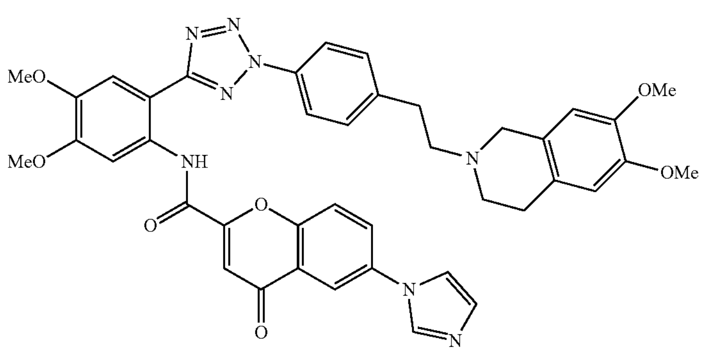 [SMILES: COc1cc2c(cc1OC)CN(CCc1ccc(-n3nnc(-c4cc(OC)c(OC)cc4NC(=O)c4cc(=O)c5cc(-n6ccnc6)ccc5o4)n3)cc1)CC2] |

TABLE 2-continued
| Compound No. | Structure |
|---|---|
| 21 | 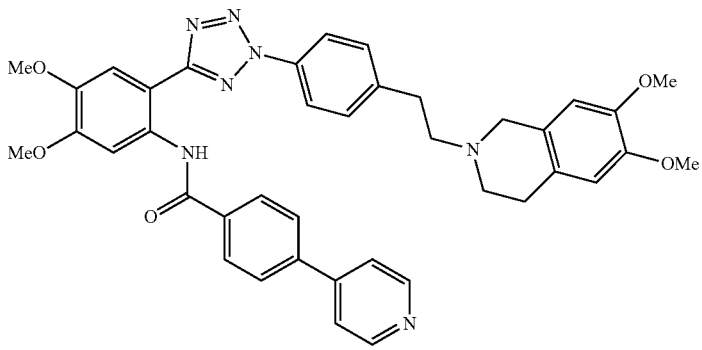 [SMILES: COc1cc2c(cc1OC)CN(CCc1ccc(-n3nnc(-c4cc(OC)c(OC)cc4NC(=O)c4ccc(-c5ccncc5)cc4)n3)cc1)CC2] |
| 22 | 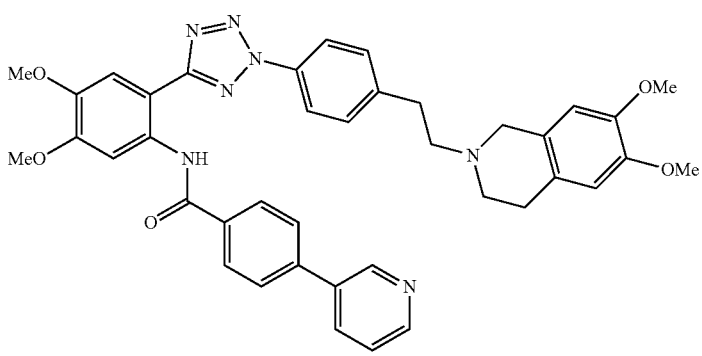 [SMILES: COc1cc2c(cc1OC)CN(CCc1ccc(-n3nnc(-c4cc(OC)c(OC)cc4NC(=O)c4ccc(-c5cccnc5)cc4)n3)cc1)CC2] |
| 23 | 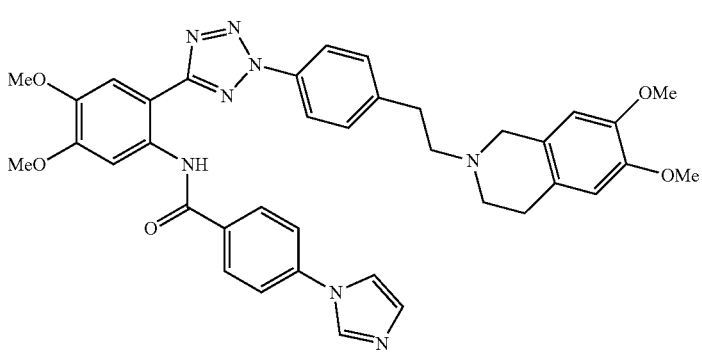 [SMILES: COc1cc2c(cc1OC)CN(CCc1ccc(-n3nnc(-c4cc(OC)c(OC)cc4NC(=O)c4ccc(-n5ccnc5)cc4)n3)cc1)CC2] |
| 24 | 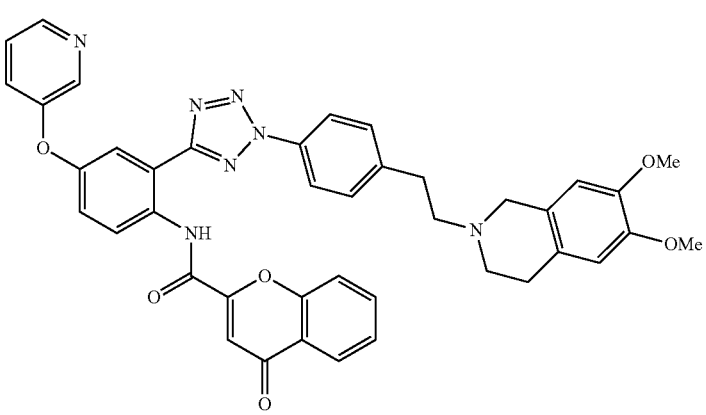 [SMILES: COc1cc2c(cc1OC)CN(CCc1ccc(-n3nnc(-c4cc(Oc5cccnc5)ccc4NC(=O)c4cc(=O)c5ccccc5o4)n3)cc1)CC2] |

TABLE 2-continued

| Compound No. | Structure |
| --- | --- |
| 25 | 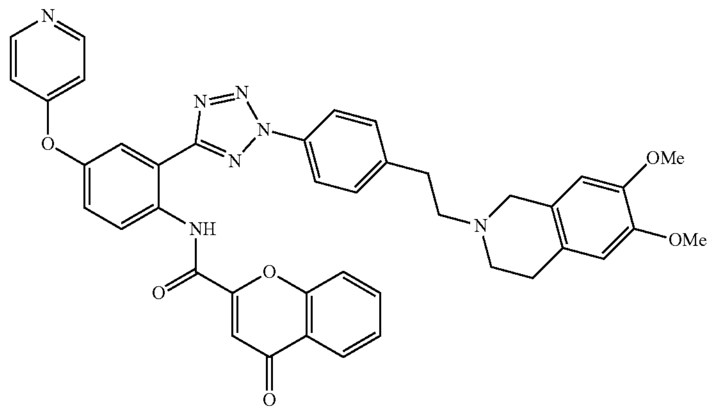 [SMILES: COc1cc2c(cc1OC)CN(CCc1ccc(-n3nnc(-c4cc(Oc5ccncc5)ccc4NC(=O)c4cc(=O)c5ccccc5o4)n3)cc1)CC2] |
| 26 | 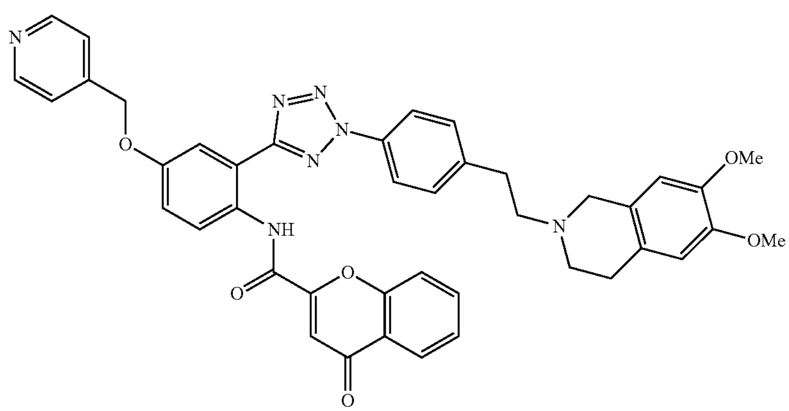 [SMILES: COc1cc2c(cc1OC)CN(CCc1ccc(-n3nnc(-c4cc(OCc5ccncc5)ccc4NC(=O)c4cc(=O)c5ccccc5o4)n3)cc1)CC2] |
| 27 | 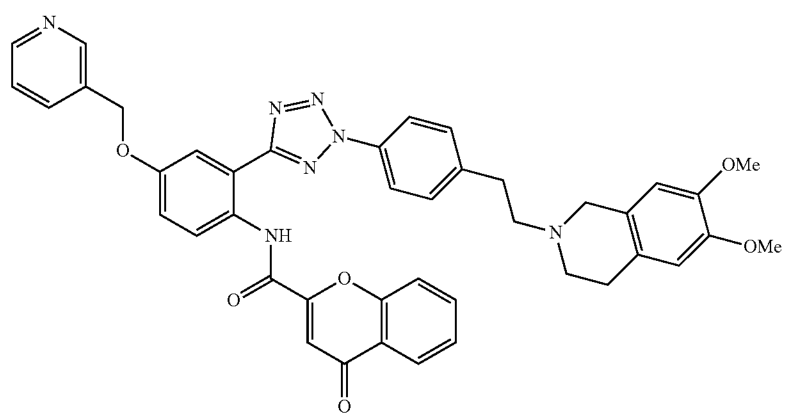 [SMILES: COc1cc2c(cc1OC)CN(CCc1ccc(-n3nnc(-c4cc(OCc5cccnc5)ccc4NC(=O)c4cc(=O)c5ccccc5o4)n3)cc1)CC2] |
| 28 | 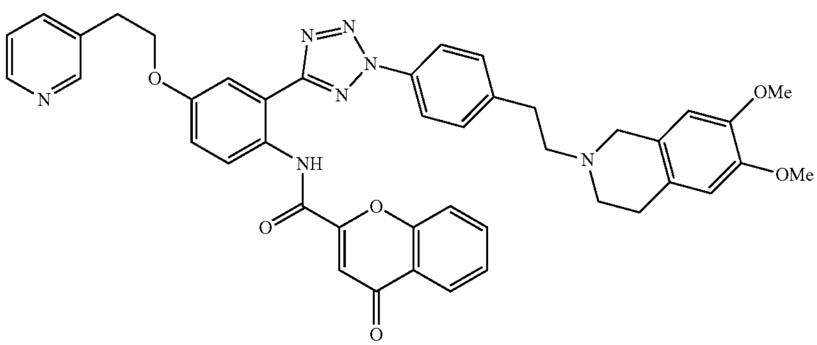 [SMILES: COc1cc2c(cc1OC)CN(CCc1ccc(-n3nnc(-c4cc(OCCc5cccnc5)ccc4NC(=O)c4cc(=O)c5ccccc5o4)n3)cc1)CC2] |

TABLE 2-continued

| Compound No. | Structure |
|---|---|
| 29 | 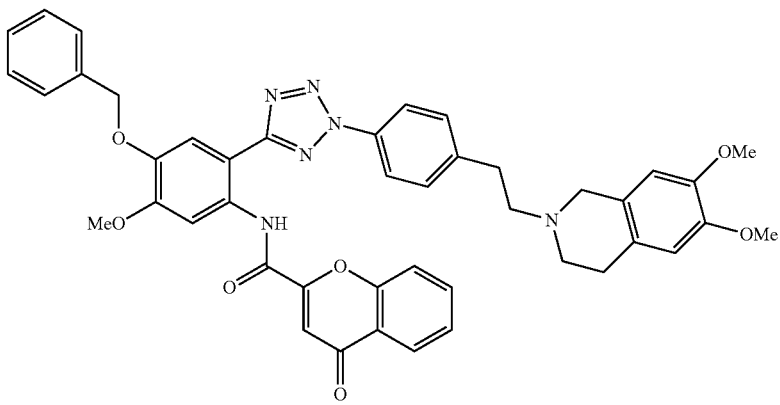 [SMILES: COc1cc2c(cc1OC)CN(CCc1ccc(-n3nnc(-c4cc(OCc5ccccc5)c(OC)cc4NC(=O)c4cc(=O)c5ccccc5o4)n3)cc1)CC2] |
| 30 | 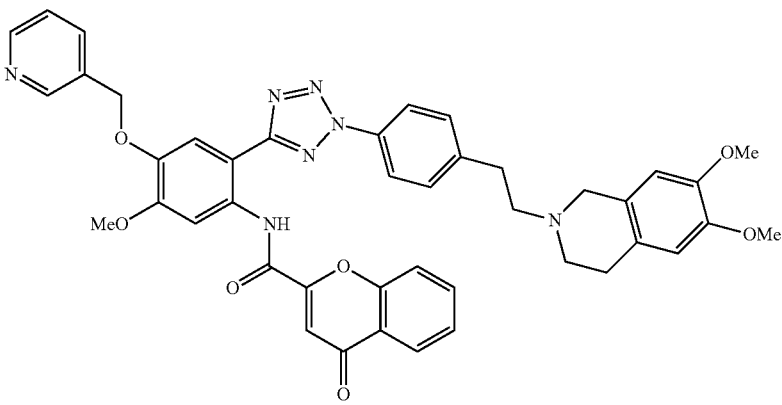 [SMILES: COc1cc2c(cc1OC)CN(CCc1ccc(-n3nnc(-c4cc(OCc5cccnc5)c(OC)cc4NC(=O)c4cc(=O)c5ccccc5o4)n3)cc1)CC2] |

The present disclosure also encompasses compounds of the disclosure as defined herein which comprise one or more isotopic substitutions.

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Table 1 and prodrugs and pharmaceutically acceptable salts thereof.

In some embodiments, the compound is an isotopic derivative of any one of the compounds described in Table 1 and pharmaceutically acceptable salts thereof.

In some embodiments, the compound is an isotopic derivative of any one of prodrugs of the compounds described in Table 1 and pharmaceutically acceptable salts thereof.

In some embodiments, the compound is an isotopic derivative of any one of the compounds described in Table 1.

In some embodiments, the compound is an isotopic derivative of any one of the compounds described in Table 2 and prodrugs and pharmaceutically acceptable salts thereof.

In some embodiments, the compound is an isotopic derivative of any one of the compounds described in Table 2 and pharmaceutically acceptable salts thereof.

In some embodiments, the compound is an isotopic derivative of any one of prodrugs of the compounds described in Table 2 and pharmaceutically acceptable salts thereof.

In some embodiments, the compound is an isotopic derivative of any one of the compounds described in Table 2.

It is understood that the isotopic derivative can be prepared using any of a variety of art-recognized techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

In some embodiments, the compound is a deuterium labeled compound of any one of the compounds described in Table 1 and prodrugs and pharmaceutically acceptable salts thereof.

In some embodiments, the compound is a deuterium labeled compound of any one of the compounds described in Table 1 and pharmaceutically acceptable salts thereof.

In some embodiments, the compound is a deuterium labeled compound of any one of the prodrugs of the compounds described in Table 1 and pharmaceutically acceptable salts thereof.

In some embodiments, the compound is a deuterium labeled compound of any one of the compounds described in Table 1.

In some embodiments, the compound is a deuterium labeled compound of any one of the compounds described in Table 2 and prodrugs and pharmaceutically acceptable salts thereof.

In some embodiments, the compound is a deuterium labeled compound of any one of the compounds described in Table 2 and pharmaceutically acceptable salts thereof.

In some embodiments, the compound is a deuterium labeled compound of any one of the prodrugs of the compounds described in Table 2 and pharmaceutically acceptable salts thereof.

In some embodiments, the compound is a deuterium labeled compound of any one of the compounds described in Table 2.

It is understood that the deuterium labeled compound comprises a deuterium atom having an abundance of deuterium that is substantially greater than the natural abundance of deuterium, which is 0.015%.

In some embodiments, the deuterium labeled compound has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). As used herein, the term "deuterium enrichment factor" means the ratio between the deuterium abundance and the natural abundance of a deuterium.

It is understood that the deuterium labeled compound can be prepared using any of a variety of art-recognized techniques. For example, the deuterium labeled compound can generally be prepared by carrying out the procedures disclosed in the Schemes and/or in the Examples described herein, by substituting a deuterium labeled reagent for a non-deuterium labeled reagent.

A compound of the disclosure or a pharmaceutically acceptable prodrug, solvate, enantiomer, stereoisomer, tautomer, or salt thereof that contains the aforementioned deuterium atom(s) is within the scope of the disclosure. Further, substitution with deuterium (i.e., $^2$H) may afford certain therapeutic advantages resulting from greater metabolic stability, e.g., increased in vivo half-life or reduced dosage requirements.

In some embodiments, the compound is a $^{18}$F labeled compound.

In some embodiments, the compound is a $^{123}$I labeled compound, a $^{124}$I labeled compound, a $^{125}$I labeled compound, a $^{129}$I labeled compound, a $^{131}$I labeled compound, a $^{135}$I labeled compound, or any combination thereof.

In some embodiments, the compound is a $^3$SS labeled compound, a $^{14}$S labeled compound, a SS labeled compound, a $^{16}$S labeled compound, or any combination thereof.

It is understood that the $^{18}$F, $^{123}$I, $^{124}$I, $^{125}$I, $^{129}$I, $^{131}$I, $^{135}$I, $^3$S, $^{34}$S, $^{35}$S, and/or $^{36}$S labeled compound, can be prepared using any of a variety of art-recognized techniques. For example, the deuterium labeled compound can generally be prepared by carrying out the procedures disclosed in the Schemes and/or in the Examples described herein, by substituting a $^{18}$F, $^{123}$I, $^{124}$I, $^{125}$I, $^{129}$I, $^{131}$I, $^{135}$I, $^3$S, $^{34}$S, $^{35}$S, and/or $^{36}$S labeled reagent for a non-isotope labeled reagent.

A compound of the disclosure or a pharmaceutically acceptable prodrug, solvate, enantiomer, stereoisomer, tautomer, or salt thereof that contains one or more of the aforementioned $^{18}$F, $^{123}$I, $^{124}$I, $^{125}$I, $^{129}$I, $^{131}$I, $^{135}$I, $^3$S $^{34}$S $^{35}$S, and $^{36}$S atom(s) is within the scope of the disclosure. Further, substitution with isotope (e.g., $^{18}$F, $^{123}$I, $^{124}$I, $^{125}$I, $^{129}$I, $^{131}$I, $^{135}$I, $^3$S, $^{34}$S, $^{35}$S, and/or $^{36}$S) may afford certain therapeutic advantages resulting from greater metabolic stability, e.g., increased in vivo half-life or reduced dosage requirements.

Definitions

Unless otherwise stated, the following terms used in the specification and claims have the meanings set out below.

As use herein, the phrase "compound of the disclosure" refers to those compounds which are disclosed herein, both generically and specifically.

For the avoidance of doubt it is to be understood that, where in this specification a group is qualified by "described herein", the said group encompasses the first occurring and broadest definition as well as each and all of the particular definitions for that group.

The various functional groups and substituents making up the compounds of any of the Formulae disclosed herein are typically chosen such that the molecular weight of the compound does not exceed 1000 daltons. More usually, the molecular weight of the compound will be less than 900, for example less than 800, or less than 750, or less than 700, or less than 650 daltons.

More conveniently, the molecular weight is less than 600 and, for example, is 550 daltons or less.

As used herein, "alkyl", "$C_1$, $C_2$, $C_3$, $C_4$, $C_5$ or $C_6$ alkyl", "$C_1$-$C_6$ alkyl", or "$C_{1-6}$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated hydrocarbon monocyclic or polycyclic (e.g., fused, bridged, or spiro rings) system having 3 to 30 carbon atoms (e.g., $C_3$-$C_{12}$ (or $C_{3-12}$), $C_3$-$C_{10}$ (or $C_{3-10}$), or $C_3$-$C_8$ (or $C_{3-8}$)). Examples of cycloalkyl include, but are not limited to, cyclopropyl, cyclobutyl, cyclopentyl, cyclohexyl, cycloheptyl, cyclooctyl, 1,2,3,4-tetrahydronaphthalenyl, and adamantyl.

As used herein, the term "heterocycloalkyl" or "heterocyclyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur. The nitrogen atom may be substituted or unsubstituted (i.e., N or NR wherein R is H or other substituents, as defined). The nitrogen and sulphur heteroatoms may optionally be oxidised (i.e., N→O and S(O)$_p$, where p=1 or 2). It is to be noted that total number of S and O atoms in the aromatic heterocyclyl is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl).

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocyclyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O⁻.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae disclosed herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used.

The processes generally provide the desired final compound at or near the end of the overall process, although it may be desirable in certain instances to further convert the compound to a pharmaceutically acceptable prodrug, solvate, enantiomer, stereoisomer, tautomer, or salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; Greene, T. W., Wuts, P. G. M., *Protective Groups in Organic Synthesis*, $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, $3^{rd}$ edition, John Wiley & Sons: New York, 1999.

It is to be understood that, unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable prodrug, solvate, enantiomer, stereoisomer, tautomer, or salt thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) modulating the state, disorder or condition, i.e., arresting, reducing or delaying the development of the disease or a relapse thereof (in case of maintenance treatment) or at least one clinical or subclinical symptom thereof, or (2) relieving or attenuating the disease, i.e., causing regression of the state, disorder or condition or at least one of its clinical or subclinical symptoms.

It is to be understood that a compound of the present disclosure, or a pharmaceutically acceptable prodrug, solvate, enantiomer, stereoisomer, tautomer, or salt thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the disclosure.

It is to be understood that, for the compounds of the present disclosure being capable of further forming salts, all of these forms are also contemplated within the scope of the claimed disclosure.

It is to be understood that the compounds of any Formula disclosed herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulphate, bisulphate, sulphamate, nitrate, phosphate, citrate, methanesulphonate, trifluoroacetate, glutamate, glucuronate, glutarate, malate, maleate, succinate, fumarate, tartrate, tosylate, salicylate, lactate, naphthalenesulphonate, and acetate (e.g., trifluoroacetate).

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulphonic, acetic, ascorbic, benzene sulphonic, benzoic, bicarbonic, carbonic, citric, edetic, ethane disulphonic, 1,2-ethane sulphonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulphonic, maleic, malic, mandelic, methane sulphonic, napsylic, nitric, oxalic, pamoic, pantothenic, phenylacetic, phosphoric, polygalacturonic, propionic, salicylic, stearic, subacetic, succinic, sulphamic, sulphanilic, sulphuric, tannic, tartaric, toluene sulphonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulphonic acid, 2-naphthalenesulphonic acid, 4-toluenesulphonic acid, camphorsulphonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

A suitable pharmaceutically acceptable salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulphuric, phosphoric, trifluoroacetic, formic, citric methane sulphonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. It is also to be understood that certain compounds of any of the Formulae disclosed herein may exist in solvated as well as unsolvated forms such as, for example, hydrated forms. Nonlimiting examples of hydrates include monohydrates, dihydrates, trihydrate, semihydrate, etc. Nonlimiting examples of solvates include ethanol solvates, acetone solvates, etc. It is to be understood that the disclosure encompasses all such solvated forms that possess P-glycoprotein and/or cytochrome P450 (e.g., CYP3A4 and CYP3A5 isoforms) modulatory activity.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

It will be understood that the compounds of any of the Formulae disclosed herein and any pharmaceutically acceptable salts thereof, comprise stereoisomers, mixtures of stereoisomers, polymorphs of all isomeric forms of said compounds.

As used herein, the term "isomerism" means compounds that have identical molecular formulae but differ in the sequence of bonding of their atoms or in the arrangement of their atoms in space. Compounds that have the same molecular formula but differ in the nature or sequence of bonding of their atoms or the arrangement of their atoms in space are termed "isomers". Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centers (E- and Z-isomers). It is to be understood that the present disclosure encompasses all optical, diastereoisomers and geometric isomers and mixtures thereof that possess P-glycoprotein and/or cytochrome P450 (e.g., CYP3A4 and CYP3A5 isoforms) modulatory activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism. Of the various types of tautomerism that are possible, two are commonly observed.

In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

For the avoidance of doubt, where a compound can exist in one of several tautomeric forms, and only one is specifically described or shown, all others are nevertheless embraced by any of the Formulae disclosed herein. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

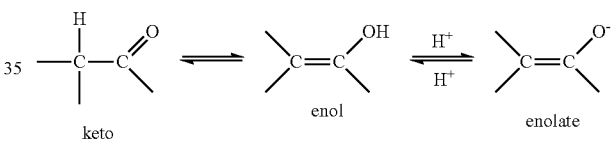

Compounds of any of the Formulae disclosed herein containing an amine function may also form N-oxides. A reference herein to a compound of any of the Formulae disclosed herein that contains an amine function also includes the N-oxide. Where a compound contains several amine functions, one or more than one nitrogen atom may be oxidized to form an N-oxide. Particular examples of N-oxides are the N-oxides of a tertiary amine or a nitrogen atom of a nitrogen-containing heterocyclyl. N-oxides can be formed by treatment of the corresponding amine with an oxidizing agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulphonamides, tetrazoles, sulphonates and phosphonates. See, e.g., Patani and LaVoie, *Chem. Rev.* 96, 3147-3176, 1996.

It is also to be understood that certain compounds of any of the Formulae disclosed herein may exhibit polymorphism, and that the disclosure encompasses all such forms, or mixtures thereof, which possess P-glycoprotein and/or cytochrome P450 (e.g., CYP3A4 and CYP3A5 isoforms) modulatory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

The compounds of any of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the ester or amide group in any of the Formulae disclosed herein.

Accordingly, the present disclosure includes those compounds of any of the Formulae disclosed herein as defined hereinbefore when made available by organic synthesis and when made available within the human or animal body by way of cleavage of a prodrug thereof. Accordingly, the present disclosure includes those compounds of any of the Formulae disclosed herein that are produced by organic synthetic means and also such compounds that are produced in the human or animal body by way of metabolism of a precursor compound, that is a compound of any of the Formulae disclosed herein may be a synthetically-produced compound or a metabolically-produced compound.

A suitable pharmaceutically acceptable prodrug of a compound of any of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of any of the Formulae disclosed herein that possesses a hydroxy group is, for example, an in vivo cleavable ester or ether thereof. An in vivo cleavable ester or ether of a compound of any of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any of the Formulae disclosed herein that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of any of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vivo effects of a compound of any of the Formulae disclosed herein may be exerted in part by one or more metabolites that are formed within the human or animal body after administration of a compound of any of the Formulae disclosed herein. As stated hereinbefore, the in vivo effects of a compound of any of the Formulae disclosed herein may also be exerted by way of metabolism of a precursor compound (a prodrug).

Suitably, the present disclosure excludes any individual compounds not possessing the biological activity defined herein.

Methods of Synthesis

In some aspects, the present disclosure provides a method of preparing a compound of the present disclosure.

In some aspects, the present disclosure provides a method of preparing a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying schemes and examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilized.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, *"Protective Groups in Organic Synthesis"* by Theodora Green (John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide.

Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of any of the Formulae disclosed herein has been synthesized by any one of the processes defined herein, the processes may then further comprise the additional steps of: (i) removing any protecting groups present; (ii) converting the compound into another compound of a Formula disclosed herein; (iii) forming a pharmaceutically acceptable salt, hydrate or solvate thereof, and/or (iv) forming a prodrug thereof.

The resultant compounds of a Formula disclosed herein can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulphoxides, such as dimethyl sulphoxide (DMSO); nitro compounds, such as nitromethane or nitrobenzene; esters, such as ethyl acetate or methyl acetate, or mixtures of the said solvents or mixtures with water.

Reaction times are generally in the range between a fraction of a minute and several days, depending on the reactivity of the respective compounds and the respective reaction conditions. Suitable reaction times are readily determinable by methods known in the art, for example reaction monitoring.

Moreover, by utilizing the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying schemes and examples. The skilled person will easily recognize which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesized by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "*Greene's Protective Groups in Organic Synthesis*", 4th edition (2006) (John Wiley & Sons).

General routes for the preparation of a compound of the application are described in Schemes 1-6 herein. A person of skill in the art will understand that the general reagents used throughout the below schemes could be substituted with other standard reagents (e.g., a couple reaction utilizing HATU could also utilize any suitable couple agent in replacement of HATU).

In some embodiments, the compounds of the instant disclosure were prepared according to a similar route disclosed in WO/2005/033097. For example, the tetrazole intermediates may be prepared following the reaction of phenylsulfonylhydrazones of appropriately substituted aromatic aldehydes with aryldiazonium salts, prepared in situ from aniline intermediate. Reduction of the nitro group followed by coupling of the resultant aniline with a suitable thioester may afford the compounds of the instant disclosure. In some embodiments, the aniline intermediate required to prepare the tetrazole intermediate may be prepared by a variety of means, as described in the Scheme 1.

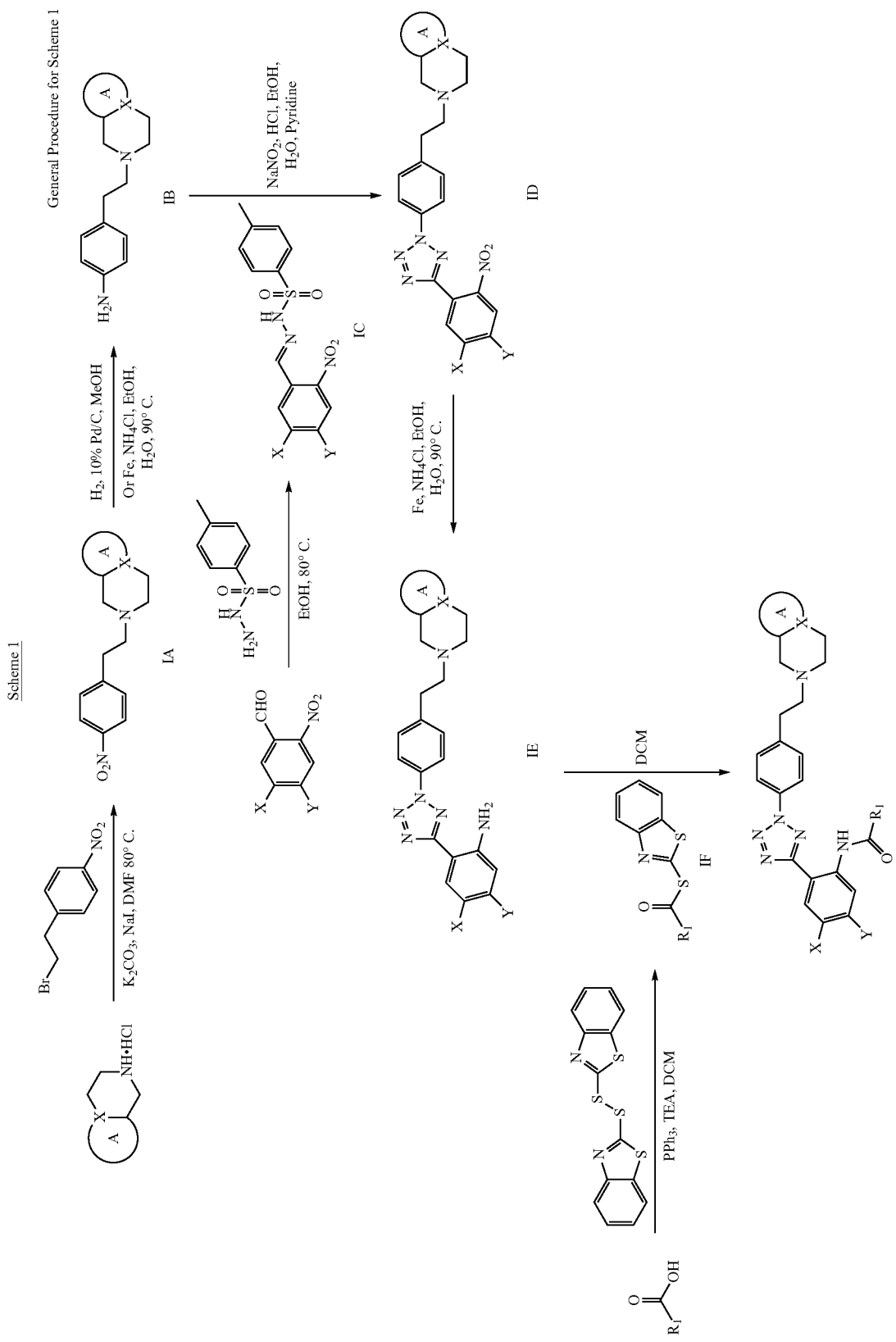
Scheme 1
General Procedure for Scheme 1

Intermediate IB may be prepared by alkylation of appropriately substituted tetrahydroisoquinoline followed by hydrogenation under suitable conditions. The reaction of p-tolylsulfonylhydrazone (IC), prepared from appropriately substituted aromatic 2-nitrobenzaldehyde and p-tolylsulfonylhydrazide, with aryldiazonium salt, prepared in situ from aniline IB, yields tetrazole intermediate ID. Reduction of the nitro group followed by coupling of the resultant aniline with a suitable thioester IF affords the target compound.

In some embodiments, the compounds of the instant disclosure were prepared according to a similar route disclosed in WO/2005/033097.

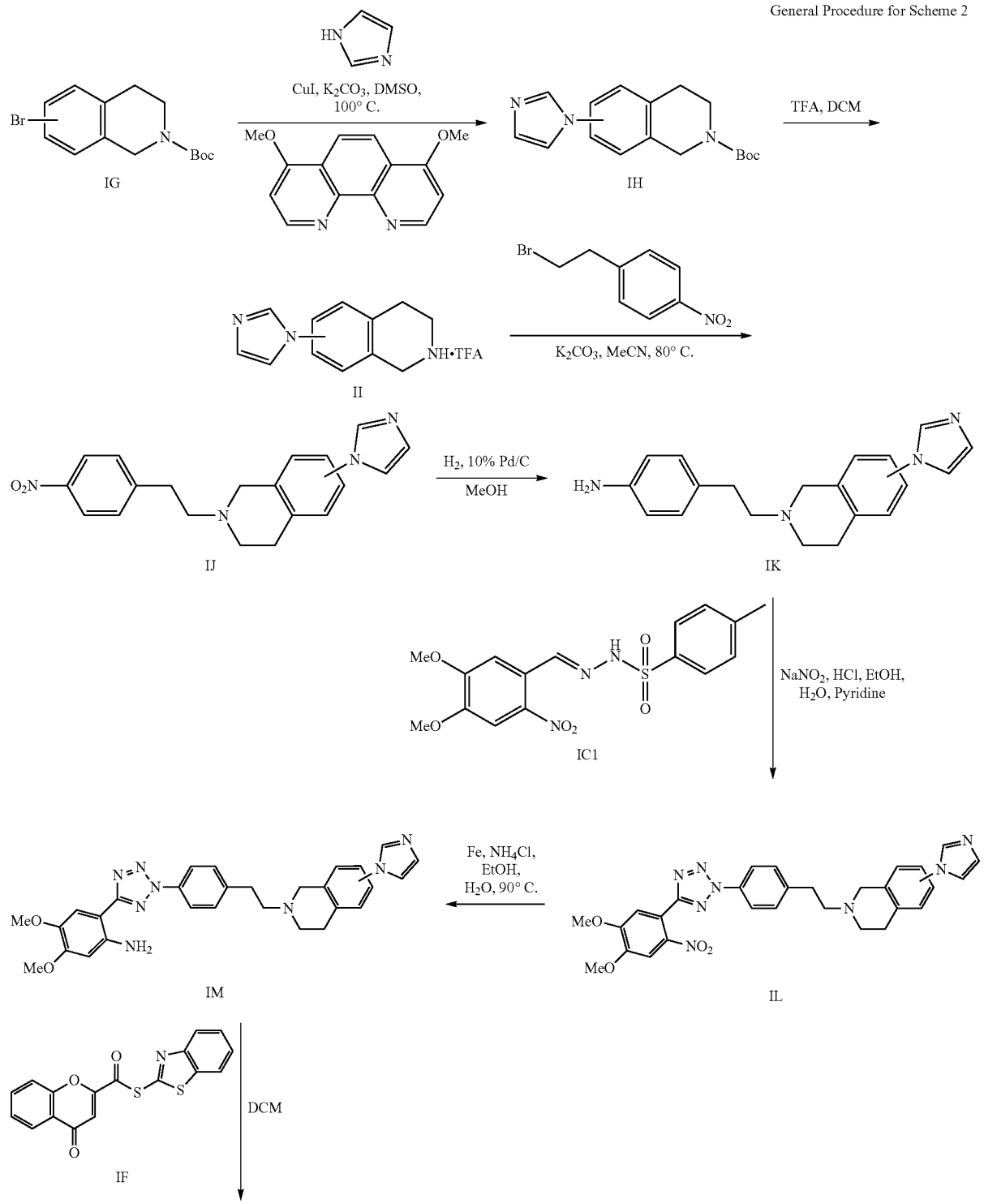

Scheme 2

General Procedure for Scheme 2

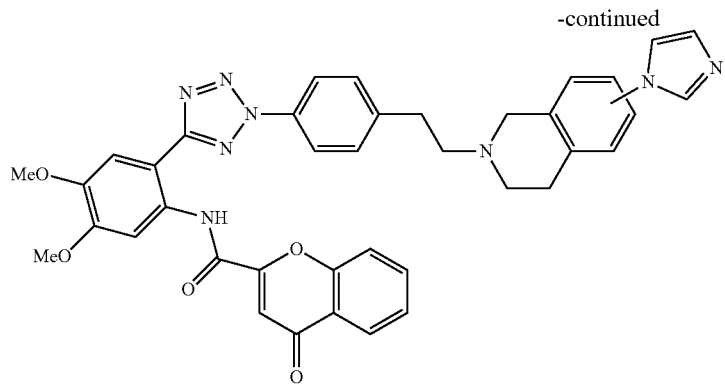
Intermediate IH is prepared through carbon-nitrogen bond formation between appropriately substituted aromatic bromide IG and imidazole, using catalysis (e.g., copper catalysis). Removal of the Boc protecting group affords intermediate II. The target compound is afforded through the route described in Scheme 1 with minor modifications.
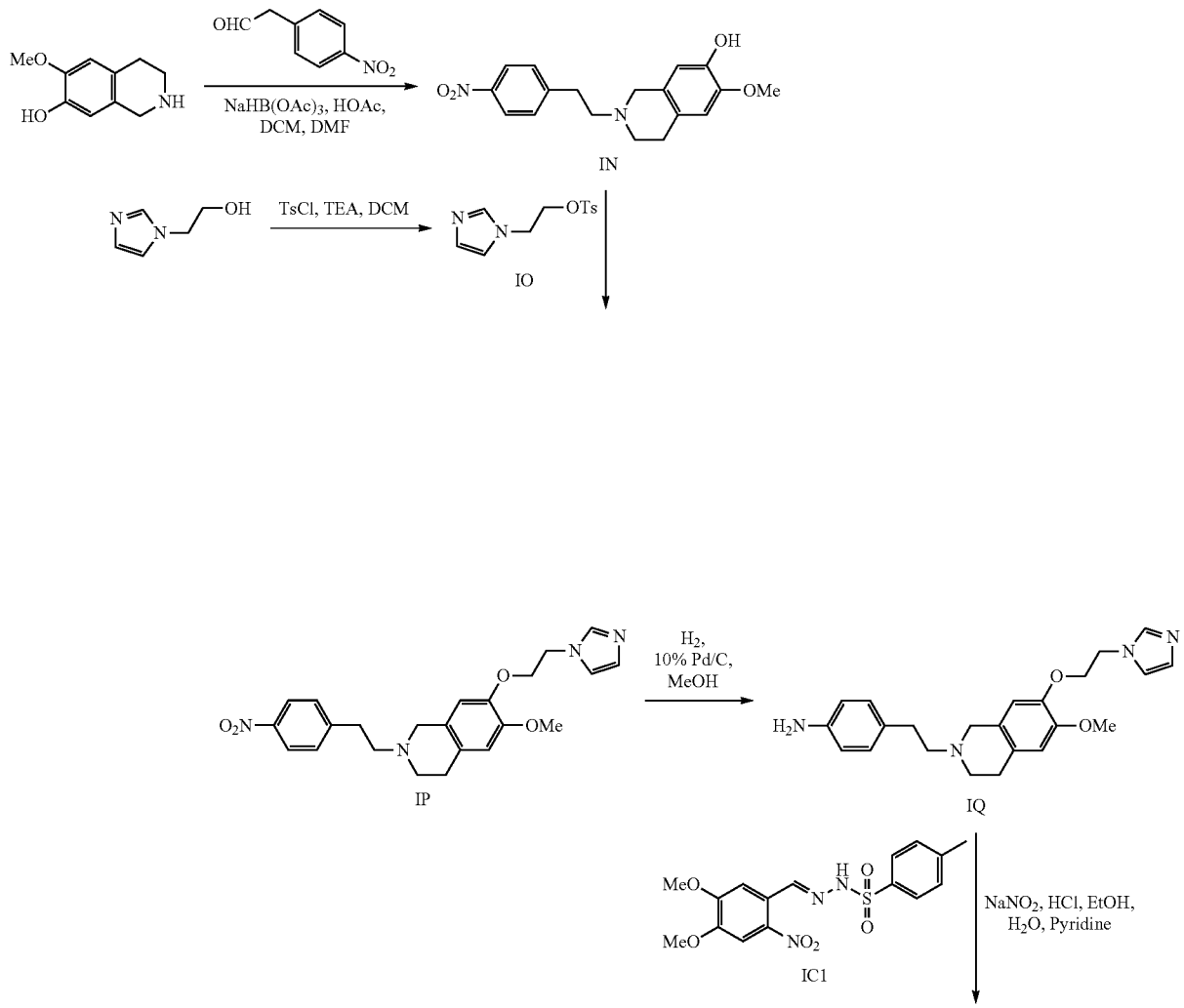

147

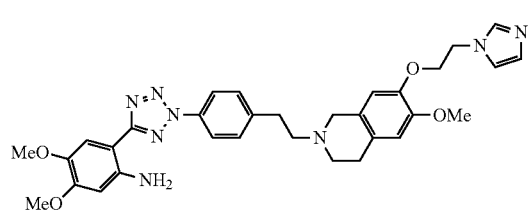

IS

-continued

H₂,
10% Pd/C,
MeOH

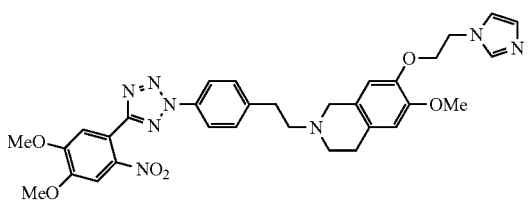

IR

148

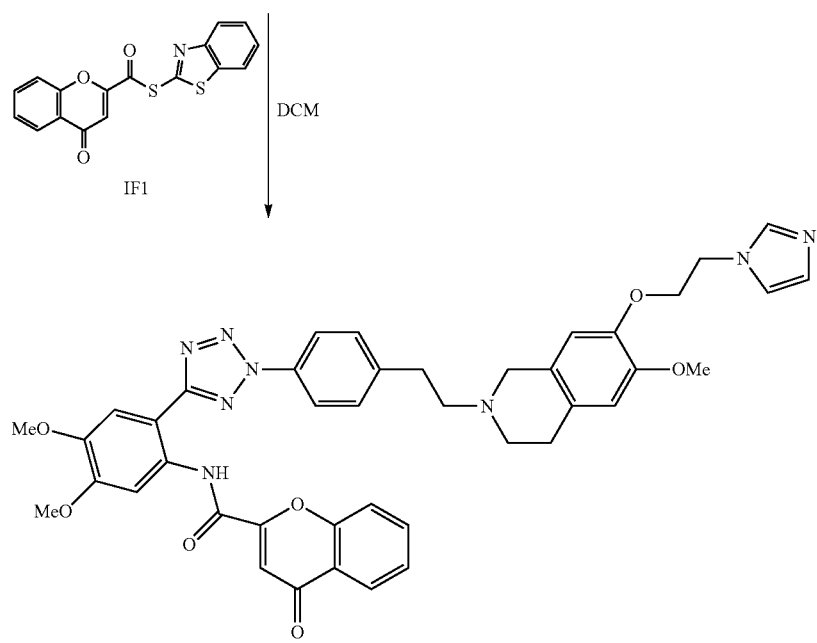

IF1

DCM

Intermediate IN is prepared with the reductive amination of 7-hydroxy-6-methoxy-1,2,3,4-tetrahydroisoquinoline (e.g., with (4-nitrophenyl)acetaldehyde). Alkylation of the phenol IN with tosylate intermediate IO affords intermediate IP. The target compound is afforded through the route described in Scheme 1 with minor modifications.

Scheme 4

General Procedure for Scheme 4

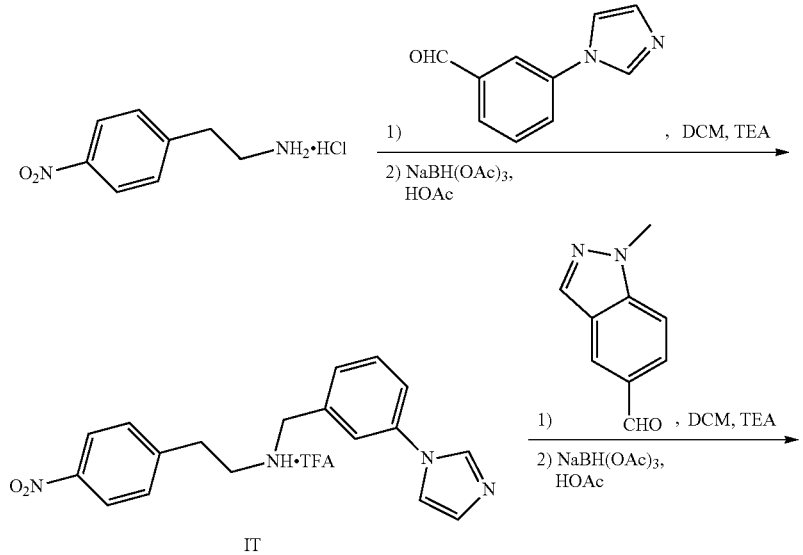

IT

-continued
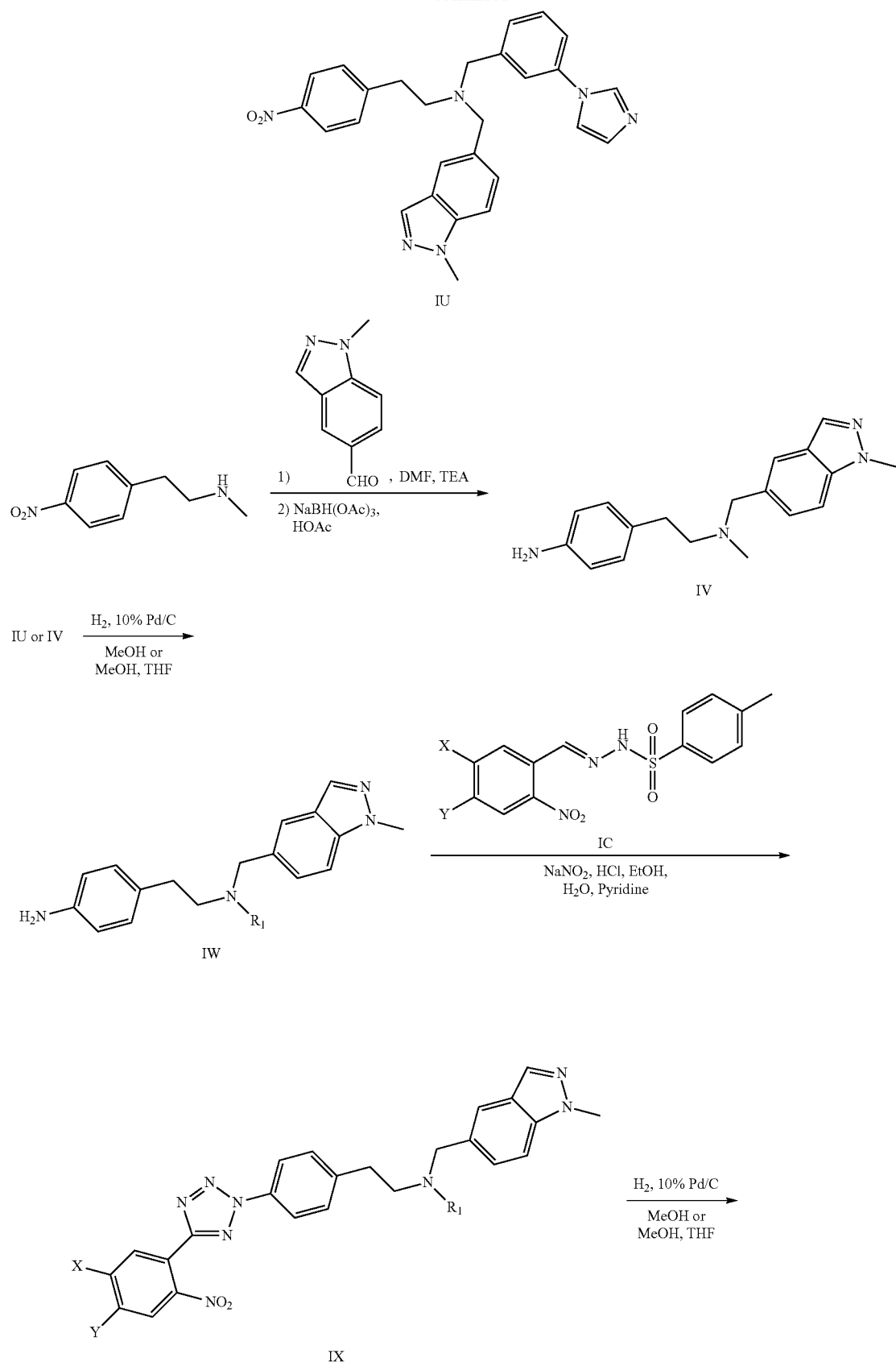

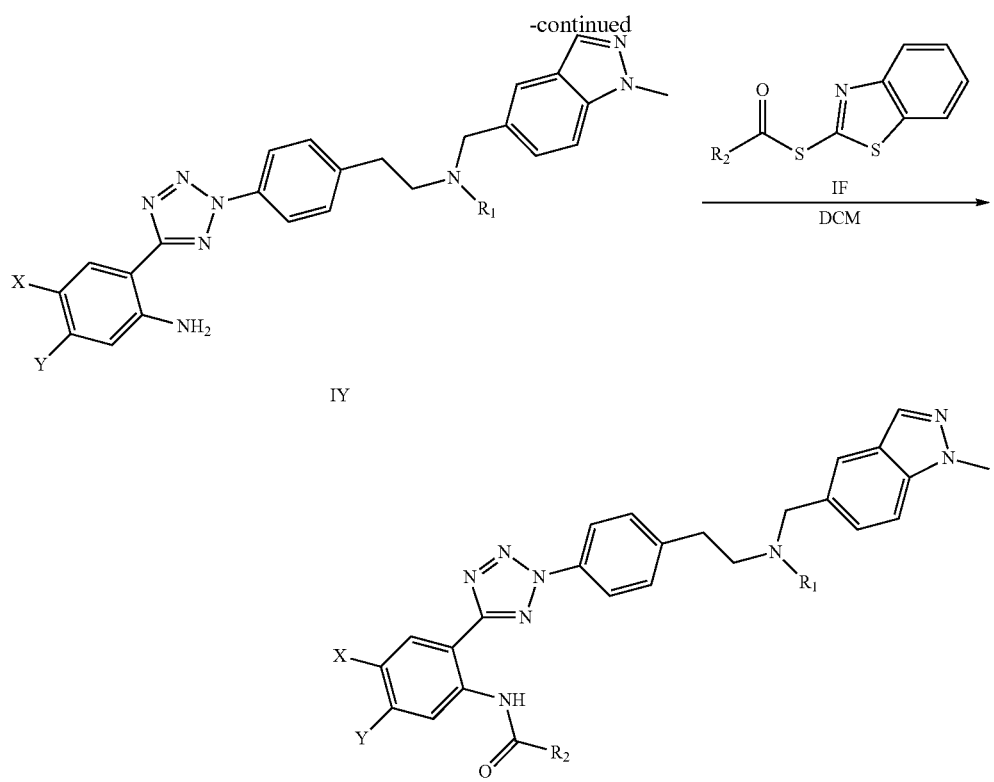

IY

Intermediate IU is prepared via sequential reductive amination, starting from (4-nitrophenyl)ethylamine hydrochloride, first using 3(1H-imidazol-1-yl)benzaldehyde followed by 1-methyl-1H-indazole-5-carbaldehyde. In some embodiments, the order of reductive amination may be reversed. Intermediate IV is prepared via reductive amination reaction of N-methyl-4-nitrophenylethylamine (e.g., with 1-methyl-1H-indazole-5-carbaldehyde). The target compound is afforded through the route described in Scheme 1 with minor modifications (e.g., the reduction of IX to intermediate IY may be carried out under palladium conditions).

Scheme 5

General Procedure for Scheme 5

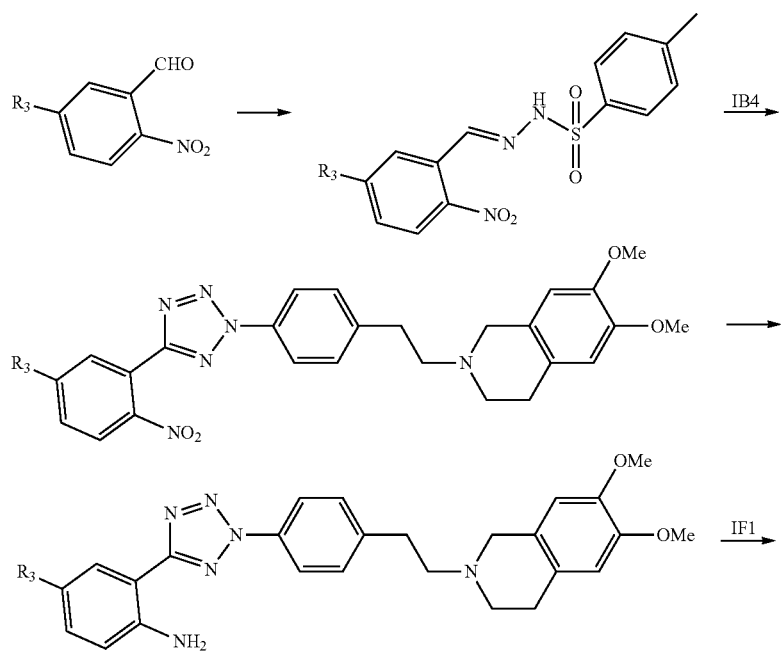

-continued

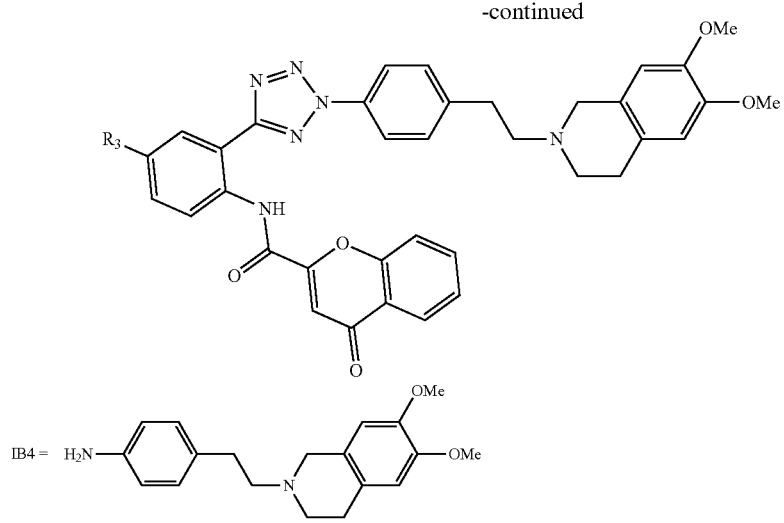

The synthetic route for the synthesis of compounds of the instant disclosure wherein R₂=H is presented in Scheme 5. The reaction of a p-tolylsulfonylhydrazone derivative, prepared from appropriately substituted aromatic 2-nitrobenzaldehyde and p-tolylsulfonylhydrazide, with aryldiazonium salt, prepared in situ from aniline IB4 (e.g., U.S. Pat. No. 7,625,926 B2), yields the tetrazole intermediate. The tetrazole phenol is then alkylated to afford the Intermediate which is then carried forward. Reduction of the nitro group followed by coupling of the resultant aniline with thioester IF1 affords the target compounds.

General Procedure for Scheme 6

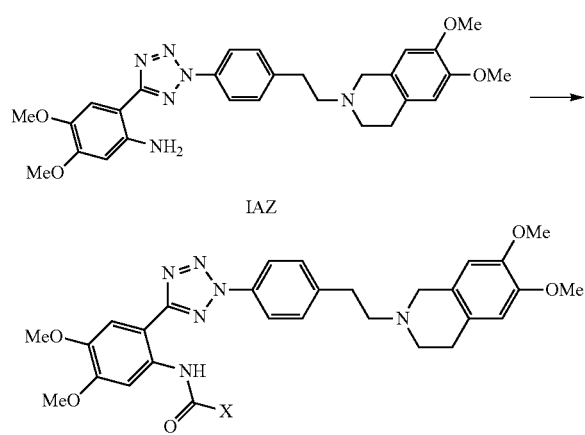

The synthetic route for the synthesis of compounds of the present disclosure is provided in Scheme 6. Intermediate 1AZ is prepared according to a similar route disclosed in WO/2005/033097. The coupling of 1AZ with various thioesters IF (prepared from the corresponding acids) affords the target compounds.

It should be understood that in the description and formulae shown above, the various groups are as defined herein, except where otherwise indicated. Furthermore, for synthetic purposes, the compounds in the Schemes are mere representatives with elected substituents to illustrate the general synthetic methodology of a compound disclosed herein.

It is understood that a neutral compound of any of the Formulae disclosed herein may be converted to a salt (e.g., sodium salt) using routine techniques in the art (e.g., pH adjustment and, optionally, extraction (e.g., into an organic phase)). Further, a salt (e.g., sodium salt) of a compound of any of the Formulae disclosed herein may be converted to a neutral compound using routine techniques in the art (e.g., pH adjustment and, optionally, extraction (e.g., into an aqueous phase)).

Biological Assays

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Various in vitro or in vivo biological assays may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

P-glycoprotein inhibitory activity may be determined by an assay wherein P-glycoprotein overexpressed cell lines are treated with increasing concentrations of a compound of the present disclosure and therapeutic agent for three days, followed by an MTT assay.

Cell growth percentage may be calculated with the following equation:

Cell growth percentage=$(T-T_0)/(C-T_0)\times 100\%$, wherein T is OD of the test well exposure to Compound; C is OD of the control well without Compound treatment; and $T_0$ is OD at time zero. Cell growth inhibition curve and $EC_{50}$ (measure of P-glycoprotein inhibition) may be obtained and fit to a nonlinear regression model using GraphPad Prism software (v6.0).

Cytochrome P450 activity may be determined by a P450-Glo™ assay (Promega) with human liver microsomes wherein the compounds of the present disclosure are dosed at different concentrations in buffer and incubated. Dose-response curve and $IC_{50}$ data may be obtained and fit to a nonlinear regression model using GraphPad Prism software (v6.0).

In vivo activity in mice of the instant compounds may be determined by administering (e.g., orally) compound to the mice at different concentrations.

Blood samples may be obtained via peripheral veins at determined time points and analyzed by LC-MS/MS.

In some embodiments, the biological assay is described in the Examples herein.

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of any of the Formulae disclosed herein, or a pharmaceutically acceptable prodrug, solvate, enantiomer, stereoisomer, tautomer, or salt thereof, and one or more pharmaceutically acceptable carriers or excipients. In some embodiments, the present disclosure provides a pharmaceutical composition comprising at least one compound selected from Table 1, or a pharmaceutically acceptable prodrug, solvate, enantiomer, stereoisomer, tautomer, or salt thereof, and one or more pharmaceutically acceptable carriers or excipients.

As used herein, the term "composition" is intended to encompass a product comprising the specified ingredients in the specified amounts, as well as any product which results, directly or indirectly, from combination of the specified ingredients in the specified amounts.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

It is to be understood that the present disclosure also provides pharmaceutical compositions comprising any compound described herein in combination with at least one pharmaceutically acceptable excipient or carrier.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulphite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated. Therapeutically effective amounts for a given situation can be determined by routine experimentation that is within the skill and judgment of the clinician.

As used herein, the term "effective amount", refers to an amount of a pharmaceutical agent to treat, ameliorate, or prevent an identified disease or condition, or to exhibit a detectable therapeutic or modulatory effect. The effect can be detected by any assay method known in the art. The precise effective amount for a subject will depend upon the subject's body weight, size, and health; the nature and extent of the condition; and the therapeutic or combination of therapeutics selected for administration. Effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. It is to be understood that, for any compound, the effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing). In one embodiment, the compound is administered orally. One skilled in the art will recognize the advantages of certain routes of administration.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor© EL or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulphated P-cyclodextrin (S-β-CD), maltosyl-β-cyclodextrin, β-cyclodextrin sulphobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and F-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure can also be formulated for intravenous (bolus or infusion), intraperitoneal, topical, subcutaneous, intramuscular or transdermal (e.g., patch) administration, all using forms well known to those of ordinary skill in the pharmaceutical arts.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives.

Transmucosal administration can be accomplished through the use of nasal sprays or suppositories. For transdermal administration, the active compounds are formulated into ointments, salves, gels, or creams as generally known in the art.

According to a further aspect of the disclosure there is provided a pharmaceutical composition which comprises a compound of the disclosure as defined hereinbefore, or a pharmaceutically acceptable prodrug, solvate, enantiomer, stereoisomer, tautomer, or salt thereof, in association with a pharmaceutically acceptable diluent or carrier.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. In preferred aspects, dosages can range from about 1 mg/kg per day to about 1000 mg/kg per day.

In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

The compositions of the disclosure may be obtained by conventional procedures using conventional pharmaceutical excipients, well known in the art. Thus, compositions intended for oral use may contain, for example, one or more coloring, sweetening, flavoring and/or preservative agents.

An effective amount of a compound of the present disclosure for use in therapy is an amount sufficient to modulate P-glycoprotein activity related to a condition referred to herein, slow the progression of the condition and/or reduce the symptoms associated with the condition.

The size of the dose for therapeutic or prophylactic purposes of a compound of any of the Formulae disclosed herein will naturally vary according to the nature and severity of the conditions, the age and sex of the animal or patient and the route of administration, according to well-known principles of medicine.

Methods of Use

In some aspects, the present disclosure provides a method of modulating P-glycoprotein activity (e.g., in vitro or in vivo) and/or cytochrome P450 activity (e.g., in vitro or in vivo), comprising contacting a cell with an effective amount of a compound of the present disclosure or a pharmaceutically acceptable prodrug, solvate, enantiomer, stereoisomer, tautomer, or salt thereof.

In some aspects, the present disclosure provides a method of modulating P-glycoprotein activity (e.g., in vitro or in vivo), comprising contacting a cell with an effective amount of a compound of the present disclosure or a pharmaceutically acceptable prodrug, solvate, enantiomer, stereoisomer, tautomer, or salt thereof.

In some aspects, the present disclosure provides a method of modulating cytochrome P450 activity (e.g., in vitro or in vivo), comprising contacting a cell with an effective amount of a compound of the present disclosure or a pharmaceutically acceptable prodrug, solvate, enantiomer, stereoisomer, tautomer, or salt thereof.

In some embodiments, the P-glycoprotein activity is overexpressed. In some embodiments, the P-glycoprotein activity is under expressed.

In some embodiments, the cytochrome P450 activity is overexpressed. In some embodiments, the cytochrome P450 activity is under expressed.

In some embodiments, the cytochrome P450 activity is CYP3A4 activity.

In some embodiments, the cytochrome P450 activity is CYP3A5 activity.

In some embodiments, the modulation is inhibition.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable prodrug, solvate, enantiomer, stereoisomer, tautomer, or salt thereof, or a pharmaceutical composition of the present disclosure.

In some aspects, the present disclosure provides a method of treating or preventing a disease or disorder disclosed herein in a subject in need thereof, comprising administering to the subject an effective amount of a compound of the present disclosure or a pharmaceutically acceptable prodrug, solvate, enantiomer, stereoisomer, tautomer, or salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable prodrug, solvate, enantiomer, stereoisomer, tautomer, or salt thereof, or a pharmaceutical composition of the present disclosure.

In some aspects, the present disclosure provides a method of treating a disease or disorder disclosed herein in a subject in need thereof, comprising administering to the subject an effective amount of a compound of the present disclosure or a pharmaceutically acceptable prodrug, solvate, enantiomer, stereoisomer, tautomer, or salt thereof, or a pharmaceutical composition of the present disclosure.

In some embodiments, when the methods relate to preventing or prevention of a disease or disorder, the method comprises administering an effective amount of a compound of the present disclosure or a pharmaceutically acceptable prodrug, solvate, enantiomer, stereoisomer, tautomer, or salt thereof, or a pharmaceutical composition of the present disclosure.

In some embodiments, when the methods relate to treating or treatment of a disease or disorder, the method comprises administering a therapeutically effective amount or effective amount of a compound of the present disclosure or a pharmaceutically acceptable prodrug, solvate, enantiomer, stereoisomer, tautomer, or salt thereof, or a pharmaceutical composition of the present disclosure.

In some embodiments, the disease or disorder is associated with an implicated P-glycoprotein activity (e.g., overactivity or abnormal activity). In some embodiments, the disease or disorder is a disease or disorder in which P-glycoprotein activity is implicated (e.g., abnormal or elevated). In some embodiments, the disease or disorder is a disease or disorder in which multi-drug resistance is implicated due to P-glycoprotein activity. In some embodiments, the disease or disorder is a disease or disorder in which P-glycoprotein activity is implicated due to multi-drug resistance following cancer treatment.

In some embodiments, the disease or disorder is associated with an implicated cytochrome P450 activity (e.g., overactivity or abnormal activity). In some embodiments, the disease or disorder is a disease or disorder in which cytochrome P450 activity is implicated (e.g., abnormal or elevated). In some embodiments, the disease or disorder is a disease or disorder in which multi-drug resistance is implicated due to cytochrome P450 activity. In some embodiments, the disease or disorder is a disease or disorder in which cytochrome P450 activity is implicated due to multi-drug resistance following cancer treatment.

In some embodiments, the disease or disorder is a cell proliferative disorder.

In some embodiments, the cell proliferative disorder is a cancer.

In some embodiments, the cancer involves abnormal cell growth with the potential to invade or spread to other parts of the body.

In some embodiments, the cancer is a malignant tumor or neoplasm.

In some embodiments, the cancer is breast cancer, pancreatic cancer, non-small cell lung cancer, small cell lung cancer, ovarian cancer, epithelial ovarian cancer, AIDS-related Kaposi sarcoma, soft tissue sarcoma, leiomyosarcoma, esophageal cancer, melanoma, lymphoma, uterine cancer, peritoneal cancer, fallopian tube cancer, endometrial cancer, cervical cancer, thyroid cancer, gastric cancer, gastroesophageal junction cancer, urothelial cancer, bladder cancer, oropharynx cancer, hypopharynx cancer, larynx cancer, head and neck cancer, germ cell cancer/tumors, prostate cancer, colon cancer, rectal cancer, kidney cancer, cholangiocarcinoma (bile duct cancer), glioblastoma, squamous cell carcinoma, glioma, leukemia, or non-Hodgkin lymphoma.

In some embodiments, the cancer is breast cancer. In some embodiments, the breast cancer is metastatic breast cancer. In some embodiments, the breast cancer is carcinoma of the breast. In some embodiments, the breast cancer is triple-negative breast cancer.

In some embodiments, the cancer is lung cancer. In some embodiments, the lung cancer is non-small cell lung cancer. In some embodiments, the lung cancer is small cell lung cancer.

In some embodiments, the cancer is prostate cancer. In some embodiments, the prostate cancer is metastatic hormone resistant prostate cancer, castration naïve prostate cancer, or castration resistant prostate cancer. In some embodiments, the prostate cancer is metastatic hormone resistant prostate cancer. In some embodiments, the prostate cancer is carcinoma of the prostate.

In some embodiments, the cancer is ovarian cancer. In some embodiments, the cancer is carcinoma of the ovary.

In some embodiments, the cancer is AIDS-related Kaposi sarcoma.

In some embodiments, the cancer is pancreatic cancer. In some embodiments, the pancreatic cancer is adenocarcinoma of the pancreas.

In some embodiments, the cancer is bladder cancer, breast cancer, cervical cancer, esophageal cancer, gastric cancer, epithelial ovarian cancer, fallopian tube cancer, primary peritoneal cancer, head and neck cancer, squamous cell carcinoma of the head and neck (SCCHN), non-small cell lung cancer (NSCLC), castration naïve prostate cancer, castration resistant prostate cancer, metastatic hormone resistant prostate cancer (mHRPC), small cell lung cancer, soft tissue sarcoma, or uterine cancer.

In some embodiments, the cancer is breast cancer, non-small cell lung cancer, prostate cancer (including metastatic hormone resistant prostate cancer, castration naïve prostate cancer, or castration resistant prostate cancer), squamous cell carcinoma of the head and neck, or gastric cancer.

In some embodiments, the cancer is colorectal cancer.

In some embodiments, the cancer is an advanced malignancy. In some embodiments, the cancer is a primary or secondary cancer.

In some embodiments, the cancer is a solid tumor.

In some embodiments, the solid tumor is histologically or cytologically confirmed.

In some embodiments, the solid tumor is metastatic or unresectable.

In some embodiments, the subject is predisposed to the state, disorder, or condition (e.g., presence of a genetic variant).

In some aspects, the present disclosure provides a method of treating or preventing a cancer in a subject in need thereof, comprising administering to the subject a therapeutically effective amount of a compound of the present disclosure or a pharmaceutically acceptable prodrug, solvate, enantiomer, stereoisomer, tautomer, or salt thereof, or a pharmaceutical composition of the present disclosure.

In some aspects, the present disclosure provides a method of treating or preventing a cancer in a subject in need thereof, comprising administering to the subject an effective amount of a compound of the present disclosure or a pharmaceutically acceptable prodrug, solvate, enantiomer, stereoisomer, tautomer, or salt thereof, or a pharmaceutical composition of the present disclosure.

In some aspects, the present disclosure provides a method of treating a cancer in a subject in need thereof, comprising administering to the subject a therapeutically effective amount of a compound of the present disclosure or a pharmaceutically acceptable prodrug, solvate, enantiomer, stereoisomer, tautomer, or salt thereof, or a pharmaceutical composition of the present disclosure.

In some aspects, the present disclosure provides a method of treating a cancer in a subject in need thereof, comprising administering to the subject an effective amount of a compound of the present disclosure or a pharmaceutically acceptable prodrug, solvate, enantiomer, stereoisomer, tautomer, or salt thereof, or a pharmaceutical composition of the present disclosure.

In some aspects, the present disclosure provides a compound of the present disclosure or a pharmaceutically acceptable prodrug, solvate, enantiomer, stereoisomer, tautomer, or salt thereof for use in modulating P-glycoprotein activity (e.g., in vitro or in vivo) and/or cytochrome P450 activity (e.g., in vitro or in vivo).

In some aspects, the present disclosure provides a compound of the present disclosure or a pharmaceutically acceptable prodrug, solvate, enantiomer, stereoisomer, tautomer, or salt thereof for use in modulating P-glycoprotein activity (e.g., in vitro or in vivo).

In some aspects, the present disclosure provides a compound of the present disclosure or a pharmaceutically acceptable prodrug, solvate, enantiomer, stereoisomer, tautomer, or salt thereof for use in modulating cytochrome P450 activity (e.g., in vitro or in vivo).

In some aspects, the present disclosure provides a compound of the present disclosure or a pharmaceutically acceptable prodrug, solvate, enantiomer, stereoisomer, tautomer, or salt thereof for use in treating or preventing a disease or disorder disclosed herein.

In some aspects, the present disclosure provides a compound of the present disclosure or a pharmaceutically acceptable prodrug, solvate, enantiomer, stereoisomer, tautomer, or salt thereof for use in treating a disease or disorder disclosed herein.

In some aspects, the present disclosure provides a compound of the present disclosure or a pharmaceutically acceptable prodrug, solvate, enantiomer, stereoisomer, tautomer, or salt thereof for use in treating or preventing a cancer in a subject in need thereof.

In some aspects, the present disclosure provides a compound of the present disclosure or a pharmaceutically acceptable prodrug, solvate, enantiomer, stereoisomer, tautomer, or salt thereof for use in treating a cancer in a subject in need thereof.

In some aspects, the present disclosure provides use of a compound of the present disclosure or a pharmaceutically acceptable prodrug, solvate, enantiomer, stereoisomer, tautomer, or salt thereof in the manufacture of a medicament for modulating P-glycoprotein activity (e.g., in vitro or in vivo) and/or cytochrome P450 activity (e.g., in vitro or in vivo).

In some aspects, the present disclosure provides use of a compound of the present disclosure or a pharmaceutically acceptable prodrug, solvate, enantiomer, stereoisomer, tautomer, or salt thereof in the manufacture of a medicament for modulating P-glycoprotein activity (e.g., in vitro or in vivo).

In some aspects, the present disclosure provides use of a compound of the present disclosure or a pharmaceutically acceptable prodrug, solvate, enantiomer, stereoisomer, tautomer, or salt thereof in the manufacture of a medicament for modulating cytochrome P450 activity (e.g., in vitro or in vivo).

In some aspects, the present disclosure provides use of a compound of the present disclosure or a pharmaceutically acceptable prodrug, solvate, enantiomer, stereoisomer, tautomer, or salt thereof in the manufacture of a medicament for treating or preventing a disease or disorder disclosed herein.

In some aspects, the present disclosure provides use of a compound of the present disclosure or a pharmaceutically acceptable prodrug, solvate, enantiomer, stereoisomer, tautomer, or salt thereof in the manufacture of a medicament for treating a disease or disorder disclosed herein.

In some aspects, the present disclosure provides use of a compound of the present disclosure or a pharmaceutically acceptable prodrug, solvate, enantiomer, stereoisomer, tautomer, or salt thereof in the manufacture of a medicament for treating or preventing a cancer in a subject in need thereof.

In some aspects, the present disclosure provides use of a compound of the present disclosure or a pharmaceutically acceptable prodrug, solvate, enantiomer, stereoisomer, tautomer, or salt thereof in the manufacture of a medicament for treating a cancer in a subject in need thereof.

The present disclosure therefore provides a method of modulating P-glycoprotein activity in vitro or in vivo and/or cytochrome P450 activity in vitro or in vivo, comprising contacting a cell with an effective amount of a compound, or a pharmaceutically acceptable prodrug, solvate, enantiomer, stereoisomer, tautomer, or salt thereof, as defined herein.

The present disclosure provides compounds that function as modulators of P-glycoprotein activity and/or cytochrome P450 activity. The present disclosure therefore provides a method of modulating P-glycoprotein activity in vitro or in vivo and/or cytochrome P450 activity in vitro or in vivo, comprising contacting a cell with an effective amount of a compound, or a pharmaceutically acceptable prodrug, solvate, enantiomer, stereoisomer, tautomer, or salt thereof, as defined herein.

The present disclosure provides compounds that function as modulators of P-glycoprotein activity. The present disclosure therefore provides a method of modulating P-glycoprotein activity in vitro or in vivo, comprising contacting a cell with an effective amount of a compound, or a pharmaceutically acceptable prodrug, solvate, enantiomer, stereoisomer, tautomer, or salt thereof, as defined herein.

The present disclosure therefore provides a method of modulating cytochrome P450 activity in vitro or in vivo, comprising contacting a cell with an effective amount of a compound, or a pharmaceutically acceptable prodrug, solvate, enantiomer, stereoisomer, tautomer, or salt thereof, as defined herein.

The present disclosure provides compounds that function as modulators of cytochrome P450 activity. The present disclosure therefore provides a method of modulating cytochrome P450 activity in vitro or in vivo, comprising contacting a cell with an effective amount of a compound, or a pharmaceutically acceptable prodrug, solvate, enantiomer, stereoisomer, tautomer, or salt thereof, as defined herein.

In some embodiments, the compounds of the present disclosure improve oral bioavailability of therapeutics which are substrates of P-glycoprotein and/or cytochrome P450.

In some embodiments, the compounds of the present disclosure improve oral bioavailability of therapeutics which are substrates of P-glycoprotein.

In some embodiments, the compounds of the present disclosure improve oral bioavailability of therapeutics which are substrates of cytochrome P450.

In some embodiments, the compounds of the present disclosure increase brain distribution of therapeutics which are substrates of P-glycoprotein and/or cytochrome P450.

In some embodiments, the compounds of the present disclosure increase brain distribution of therapeutics which are substrates of P-glycoprotein.

In some embodiments, the compounds of the present disclosure increase brain distribution of therapeutics which are substrates of cytochrome P450.

Effectiveness of compounds of the disclosure can be determined by industry-accepted assays/disease models according to standard practices of elucidating the same as described in the art and are found in the current general knowledge.

The present disclosure also provides a method of treating a disease or disorder in which P-glycoprotein activity and/or cytochrome P450 activity is implicated in a subject in need of such treatment, comprising administering to said patient a therapeutically effective amount of a compound, or a pharmaceutically acceptable prodrug, solvate, enantiomer, stereoisomer, tautomer, or salt thereof, or a pharmaceutical composition as defined herein.

The present disclosure also provides a method of treating a disease or disorder in which P-glycoprotein activity is implicated in a subject in need of such treatment, comprising administering to said patient a therapeutically effective amount of a compound, or a pharmaceutically acceptable prodrug, solvate, enantiomer, stereoisomer, tautomer, or salt thereof, or a pharmaceutical composition as defined herein.

The present disclosure also provides a method of treating a disease or disorder in which cytochrome P450 activity is implicated in a subject in need of such treatment, comprising administering to said patient a therapeutically effective amount of a compound, or a pharmaceutically acceptable prodrug, solvate, enantiomer, stereoisomer, tautomer, or salt thereof, or a pharmaceutical composition as defined herein.

The present disclosure also provides a method of treating a disease or disorder in which P-glycoprotein activity and/or cytochrome P450 activity is implicated in a subject in need of such treatment, comprising administering to said patient an effective amount of a compound, or a pharmaceutically acceptable prodrug, solvate, enantiomer, stereoisomer, tautomer, or salt thereof, or a pharmaceutical composition as defined herein.

The present disclosure also provides a method of treating a disease or disorder in which P-glycoprotein activity is implicated in a subject in need of such treatment, comprising administering to said patient an effective amount of a compound, or a pharmaceutically acceptable prodrug, solvate, enantiomer, stereoisomer, tautomer, or salt thereof, or a pharmaceutical composition as defined herein.

The present disclosure also provides a method of treating a disease or disorder in which cytochrome P450 activity is implicated in a subject in need of such treatment, comprising administering to said patient an effective amount of a compound, or a pharmaceutically acceptable prodrug, solvate, enantiomer, stereoisomer, tautomer, or salt thereof, or a pharmaceutical composition as defined herein.

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering a compound of any of the Formulae disclosed herein with another therapeutic agent (which also includes a therapeutic regimen) that also has therapeutic benefit.

In the instances wherein the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which P-glycoprotein activity and/or cytochrome P450 activity is implicated comprising a compound of the disclosure as defined hereinbefore, or a pharmaceutically acceptable prodrug, solvate, enantiomer, stereoisomer, tautomer, or salt thereof, and another suitable agent. According to this aspect of the disclosure there is provided a combination for use in the treatment of a disease in which P-glycoprotein activity is implicated comprising a compound of the disclosure as defined hereinbefore, or a pharmaceutically acceptable prodrug, solvate, enantiomer, stereoisomer, tautomer, or salt thereof, and another suitable agent. According to this aspect of the disclosure there is provided a combination for use in the treatment of a disease in which cytochrome P450 activity is implicated comprising a compound of the disclosure as defined hereinbefore, or a pharmaceutically acceptable prodrug, solvate, enantiomer, stereoisomer, tautomer, or salt thereof, and another suitable agent.

According to a further aspect of the disclosure there is provided a pharmaceutical composition which comprises a compound of the disclosure, or a pharmaceutically acceptable prodrug, solvate, enantiomer, stereoisomer, tautomer, or salt thereof, in combination with another suitable agent, in association with a pharmaceutically acceptable diluent or carrier.

In addition to its use in therapeutic medicine, compounds of any of the Formulae disclosed herein and pharmaceutically acceptable salts thereof are also useful as pharmacological tools in the development and standardization of in vitro and in vivo test systems for the evaluation of the effects of modulators of P-glycoprotein and/or cytochrome P450 in laboratory animals such as dogs, rabbits, monkeys, rats and mice, as part of the search for new therapeutic agents.

In addition to its use in therapeutic medicine, compounds of any of the Formulae disclosed herein and pharmaceutically acceptable salts thereof are also useful as pharmacological tools in the development and standardization of in vitro and in vivo test systems for the evaluation of the effects of modulators of P-glycoprotein in laboratory animals such as dogs, rabbits, monkeys, rats and mice, as part of the search for new therapeutic agents.

In addition to its use in therapeutic medicine, compounds of any of the Formulae disclosed herein and pharmaceutically acceptable salts thereof are also useful as pharmacological tools in the development and standardization of in vitro and in vivo test systems for the evaluation of the effects of modulators of cytochrome P450 in laboratory animals such as dogs, rabbits, monkeys, rats and mice, as part of the search for new therapeutic agents.

In any of the above-mentioned pharmaceutical composition, process, method, use, medicament, and manufacturing features of the instant disclosure, any of the alternate embodiments of macromolecules of the present disclosure described herein also apply.

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The disclosure having been described, the following examples are offered by way of illustration and not limitation.

EXAMPLES

For exemplary purpose, neutral compounds of any of the Formulae disclosed herein are synthesized and tested in the examples. It is understood that the neutral compounds of any of the Formulae disclosed herein may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Nuclear magnetic resonance (NMR) spectra were recorded at 400 MHz or 300 MHz as stated and at 300.3 K unless otherwise stated; the chemical shifts (δ) are reported in parts per million (ppm). Spectra were recorded using a Bruker or Varian instrument with 8, 16 or 32 scans.

LC-MS chromatograms and spectra were recorded using an Agilent 1200 or Shimadzu LC-20 AD&MS 2020 instrument using a C-18 column such as a Luna-C18 2.0×30 mm or Xbridge Shield RPC18 2.1×50 mm. Injection volumes were 0.7-8.0 μl and the flow rates were typically 0.8 or 1.2 ml/min. Detection methods were diode array (DAD) or evaporative light scattering (ELSD) as well as positive ion electrospray ionization. MS range was 100-1000 Da. Solvents were gradients of water and acetonitrile both containing a modifier (typically 0.01-0.04%) such as trifluoroacetic acid or ammonium carbonate.

Abbreviations

ACN Acetonitrile
$CDCl_3$ Chloroform-d
DCM Dichloromethane
DIPEA N,N-Diisopropylethylamine
DMAP 4-Dimethylaminopyridine
DMF N,N-dimethylformamide
DMSO Dimethylsulphoxide
DMSO-$d_6$ Hexadeuterodimethylsulfoxide
dppf 1,1'-Bis(diphenylphosphino)ferrocene
eq. Equivalents
ESI Electrospray ionisation
EtOAc Ethyl acetate
FCC Flash column chromatography
H Hour(s)
HATU 1-[Bis(dimethylamino)methylene]-1H-1,2,3-triazolo[4,5-b]pyridinium 3-oxid hexafluorophosphate
$^1$H NMR Proton nuclear magnetic resonance spectroscopy
HPLC High performance liquid chromatography
LC-MS Liquid chromatography-mass spectrometry
MeOD Methanol-$d_4$
MeOH Methanol
min Minute(s)
$Na_2SO_4$ Sodium sulfate
$Pd(PPh_3)_4$ Tetrakis(triphenylphosphine)palladium(0)
pet. ether Petroleum ether
ppm Parts per million
RM Reaction mixture
TEA Triethylamine
TFA Trifluoroacetic acid
THF Tetrahydrofuran
TLC Thin layer chromatography
Y Yield Example 1. Synthesis of Intermediates Synthesis of IA (Scheme 1; General Procedure AA)

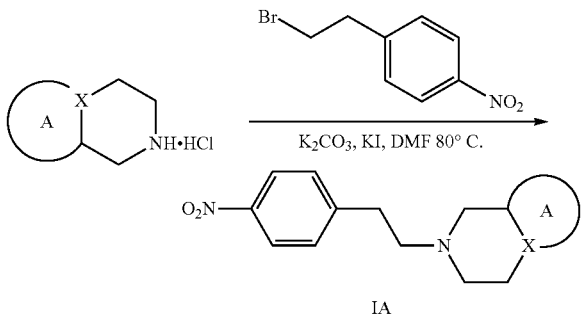

A round-bottom flask was charged with the amine (15.3 mmol, 1.02 eq.), 1-(2-bromoethyl)-4-nitrobenzene (3.45 g, 15.0 mmol, 1.0 eq.), sodium iodide (2.73 g, 18 mmol, 1.2 eq.), anhydrous potassium carbonate (6.26 g, 45 mmol, 3.0 eq.), and DMF (50 mL). and the reaction mixture was heated to 80° C. and stirred for 4 h, then stirred at room temperature overnight. Upon reaction completion, the mixture was diluted with DCM (250 mL) and washed with water (2×200 mL) and brine (2×100 mL). The organic layer was separated, dried over anhydrous $Na_2SO_4$, filtered, and concentrated under vacuum to afford Intermediate IA, which was used without further purification.

Synthesis of 7-(4-Nitrophenethyl)-5,6,7,8-tetrahydroimidazo[1,5-a]pyrazine (IA1) (Scheme 1)

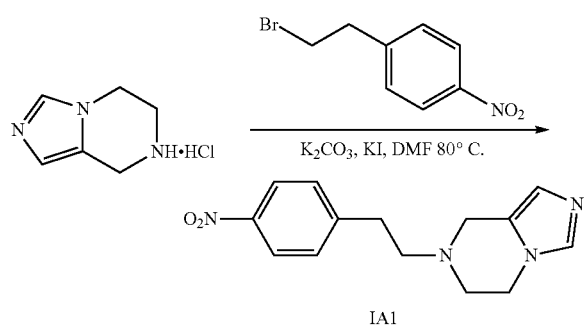

2.60 g of 5,6,7,8-tetrahydroimidazo[1,5-a]pyrazine hydrochloride was used as the amine to synthesize 3.02 g of the title compound (74% yield) according to the General Procedure AA. $^1$H NMR (400 MHz, DMSO-$d_6$): δ 2.79 (t, J=7.2 Hz, 2H), 2.85 (t, J=5.6 Hz, 2H), 2.98 (t, J=7.2 Hz, 2H), 3.65 (s, 2H), 3.98 (t, J=5.6 Hz, 2H), 6.62 (d, J=0.8 Hz, 1H), 7.50 (d, J=0.8 Hz, 1H), 7.55-7.58 (m, 2H), 8.14-8.16 (m, 2H); LC/MS (ESI, m/z): 273.10 [M+H]$^+$.

Synthesis of 2-(4-Nitrophenethyl)-1,2,3,4-tetrahydro-2,6-naphthyridine (IA2) (Scheme 1)

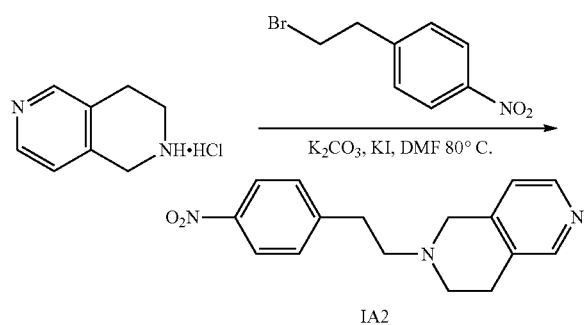

2.43 g of 1,2,3,4-tetrahydro-2,6-naphthyridine hydrochloride was used to synthesize 2.73 g of the title compound (64% yield) according to the General Procedure AA. $^1$H NMR (400 MHz, DMSO-$d_6$): δ 2.77-2.79 (m, 6H), 2.97-2.99 (m, 2H), 3.64 (s, 2H), 7.06 (d, J=3.0 Hz, 1H), 7.55 (d, J=8.0 Hz, 2H), 8.14 (d, J=8.0 Hz, 2H), 8.25 (d, J=8.0 Hz, 1H)), 8.31 (s, 1H). LC/MS (ESI, m/z): 284.15 [M+H]$^+$.

Synthesis of 2-(4-Nitrophenethyl)-1,2,3,4-tetrahydro-2,7-naphthyridine (IA3) (Scheme 1)

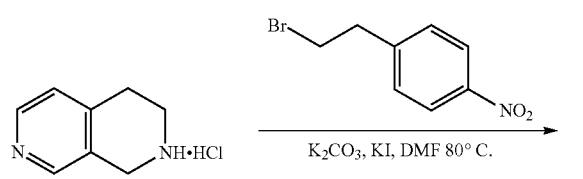

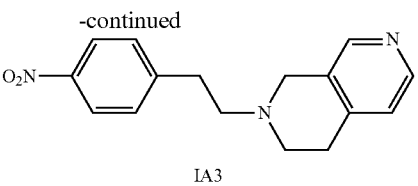

2.43 g of 1,2,3,4-tetrahydro-2,7-naphthyridine hydrochloride was used to synthesize 2.59 g of the title compound (61% yield) according to the General Procedure AA. $^1$H NMR (400 MHz, DMSO-$d_6$): δ 2.73-2.79 (m, 6H), 2.97-3.01 (m, 2H), 3.65 (s, 2H), 7.10 (d, J=8.0 Hz, 1H), 7.55 (d, J=12.0 Hz, 2H), 8.13 (d, J=12.0 Hz, 2H), 8.24 (d, J=8.0 Hz, 2H). LC/MS (ESI, m/z): 284.11 [M+H]$^+$.

Synthesis of 4-(2-(5,6-Dihydroimidazo[1,5-a]pyrazin-7(8H)-yl)ethyl)aniline (IB1) (Scheme 1)

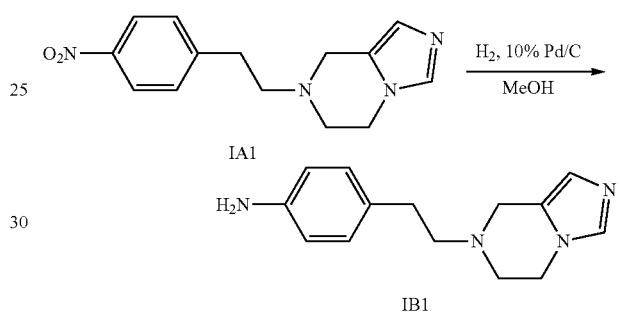

To a clean, dry hydrogenation flask were added Intermediate IA1 (1.36 g, 5.0 mmol, 1.0 eq.), 10% palladium on activated carbon (265 mg, 0.25 mmol Pd, 0.05 eq.), and MeOH (60 mL). The flask was then charged with hydrogen at 50 psi and shook for 3 h. The reaction mixture was filtered on Celite and concentrated under vacuum to afford 985 mg of the product (81% yield), which was used without further purification. $^1$H NMR (400 MHz, DMSO-$d_6$): δ 2.62 (s, 4H), 2.81 (t, J=5.6 Hz, 2H), 3.62 (s, 2H), 3.99 (t, J=5.4 Hz, 2H), 4.82 (s, 2H), 6.47-6.50 (m, 2H), 6.62 (d, J=0.8 Hz, 1H), 6.87-6.90 (m, 2H), 7.50 (d, J=0.4 Hz, 1H). LC/MS (ESI, m/z): 243.20 [M+H]$^+$.

Synthesis of Intermediate IB (Scheme 1; General Procedure BB)

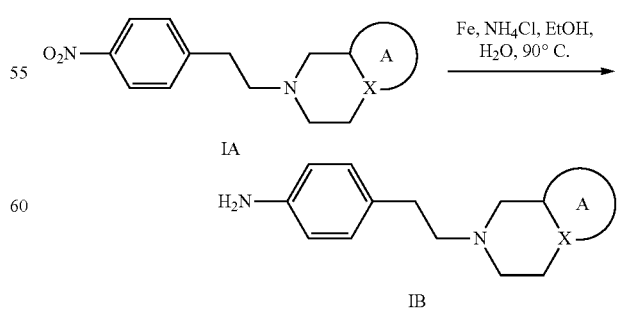

A clean, dry 40 mL vial was charged with Intermediate IA (2.6 mmol, 1.0 eq.), iron (1.46 g, 26.0 mmol, 10 eq.), ammonium chloride (1.35 g, 26 mmol, 10 eq.), EtOH (10.0 mL), and water (1.5 mL). The mixture reaction was stirred at 90° C. for 1 h and checked for completion (by LC/MS). The mixture was then filtered, while hot, on Celite, and the solid was washed with EtOH. The filtrate was then evaporated, diluted with DCM (200 mL), washed with saturated sodium bicarbonate (2×200 mL) and brine (1×100 mL), then dried over anhydrous sodium sulfate, filtered, and concentrated under vacuum to afford intermediate IB, which was used without further purification.

Synthesis of 4-(2-(3,4-Dihydro-2,6-naphthyridin-2 (1H)-yl)ethyl)aniline (IB2) (Scheme 1)

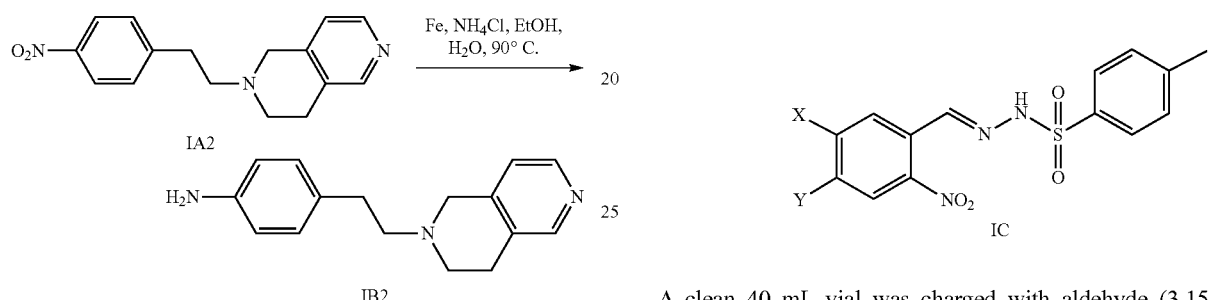

736 mg of Intermediate IA2 was used to synthesize 540 mg of the title compound (82% yield) according to the General Procedure BB. $^1$H NMR (400 MHz, DMSO-$d_6$): δ 2.60-2.63 (m, 4H), 2.64-2.66 (m, 2H), 2.71-2.81 (m, 2H), 3.61 (s, 2H), 4.84 (s, 2H), 6.47 (d, J=8.0 Hz, 2H), 6.88 (d, J=8.0 Hz, 2H), 7.07 (d, J=4.0 Hz, 1H), 8.25 (d, J=8.0 Hz, 1H), 8.31 (s, 1H). LC/MS (ESI, m/z): 254.20 [M+H]$^+$.

Synthesis of 4-(2-(3,4-Dihydro-2,7-naphthyridin-2 (1H)-yl)ethyl)aniline (IB3) (Scheme 1)

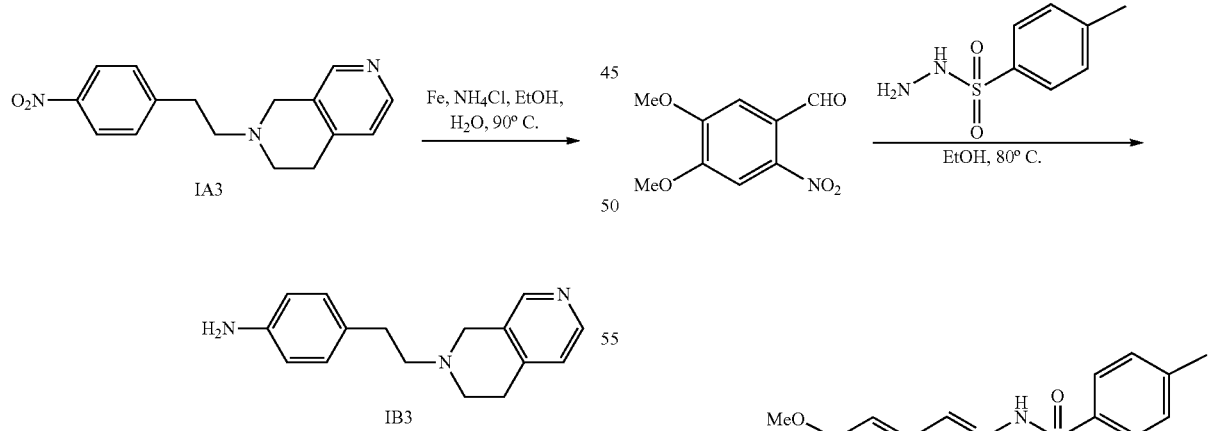

736 mg of Intermediate IA3 was used to synthesize 513 mg of the title compound (78% yield) according to the General Procedure BB. $^1$H NMR (400 MHz, DMSO-$d_6$): δ 2.67-2.69 (m, 4H), 2.70-2.72 (m, 2H), 2.78-2.81 (m, 2H), 3.62 (s, 2H), 4.84 (s, 2H), 6.48 (d, J=8.0 Hz, 2H), 6.88 (d, J=8.0 Hz, 2H), 7.10 (d, J=8.0 Hz, 1H), 8.26 (d, J=8.0 Hz, 2H). LC/MS (ESI, m/z): 254.13 [M+H]$^+$.

Synthesis of Intermediate IC (Scheme 1; General Procedure CC)

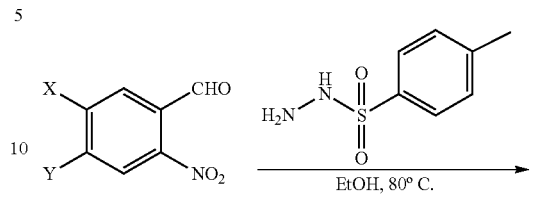

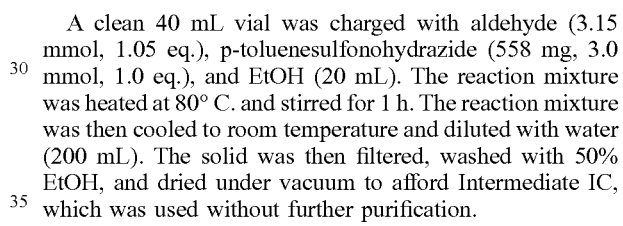

A clean 40 mL vial was charged with aldehyde (3.15 mmol, 1.05 eq.), p-toluenesulfonohydrazide (558 mg, 3.0 mmol, 1.0 eq.), and EtOH (20 mL). The reaction mixture was heated at 80° C. and stirred for 1 h. The reaction mixture was then cooled to room temperature and diluted with water (200 mL). The solid was then filtered, washed with 50% EtOH, and dried under vacuum to afford Intermediate IC, which was used without further purification.

Synthesis of 1-(4,5-Dimethoxy-2-nitrobenzylidene)-2-(p-tosyl)hydrazine (IC1) (Scheme 1)

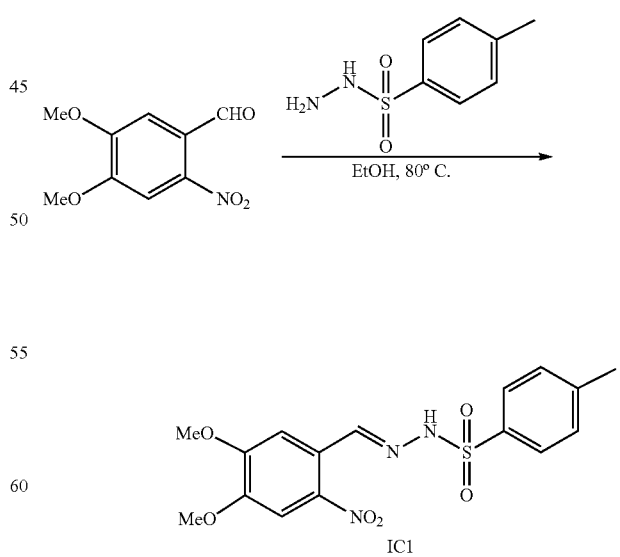

665 mg of veratraldehyde was used to synthesize 795 mg of the title compound (84% yield) according to the General Procedure CC.

Synthesis of 1-(5-(Benzyloxy)-4-methoxy-2-nitrobenzylidene)-2-(p-tosyl)hydrazine (IC2) (Scheme 1)

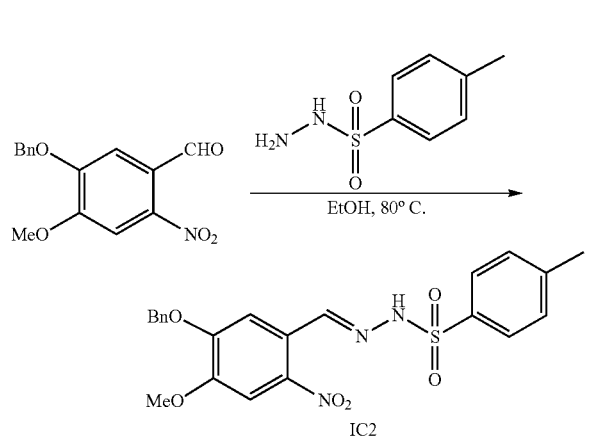

904 mg of 5-(Benzyloxy)-4-methoxy-2-nitrobenzaldehyde was used to synthesize 1.02 g of the title compound (87% yield) according to the General Procedure CC. $^1$H NMR (400 MHz, DMSO-$d_6$): δ 2.36 (s, 3H), 3.89 (s, 3H), 5.23 (s, 2H), 7.23 (s, 1H), 7.44 (m, 7H), 7.62 (s, 1H), 7.78 (d, J=8.0 Hz, 2H), 8.33 (s, 1H), 11.75 (s, 1H). LC/MS (ESI, m/z): 456.31 [M+H]$^+$.

Synthesis of Methyl 3-nitro-4-((2-(p-tosyl)hydrazinylidene)methyl)benzoate (IC3) (Scheme 1)

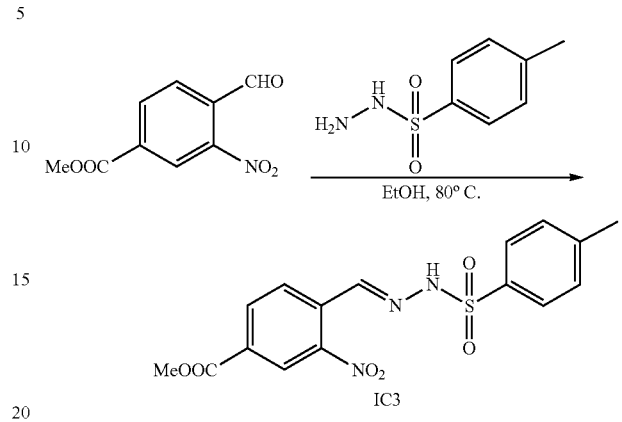

658 mg of Methyl 4-formyl-3-nitrobenzoate, was used to synthesize 836 mg of the title compound (89% yield) according to the General Procedure CC.

Synthesis of Intermediate ID (Scheme 1; General Procedure DD)

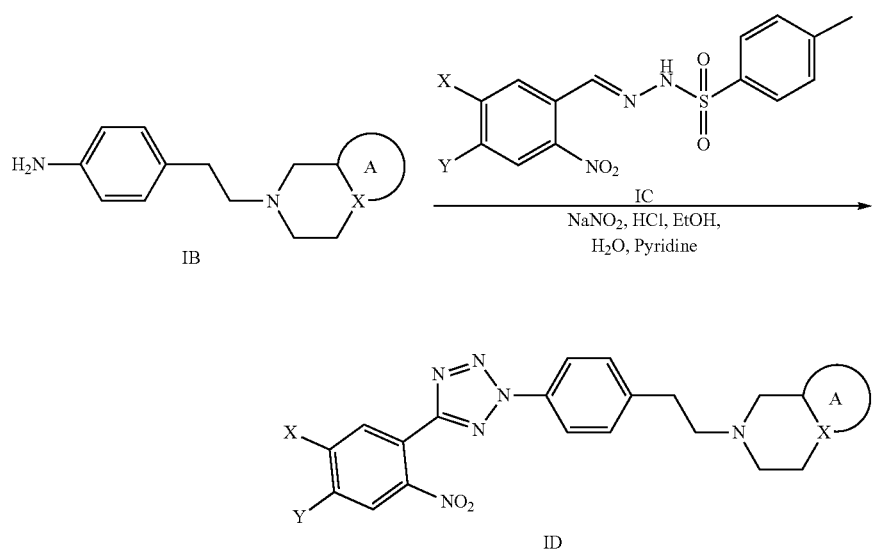

A clean, dry 40 mL vial was charged with Intermediate IB (2.0 mmol, 1.0 eq.), sodium nitrite (170 mg, 2.46 mmol, 1.23 eq.), H$_2$O (1.6 mL), and EtOH (3.2 mL). The mixture was vortexed and cooled below 0° C. 36% HCl (0.50 mL) was then added to the mixture, and the mixture was vigorously stirred for about 5 min. In another clean, dry 40 mL vial, Intermediate IC (2.0 mmol, 1.0 eq) was dissolved in pyridine (8.0 mL), and this solution was gradually added to the vial containing intermediate IB. The mixture was then stirred at room temperature overnight, and upon completion, the mixture diluted with DCM (150 mL), and washed with water and brine (2×100 mL), then dried over anhydrous Na$_2$SO$_4$, filtered, and concentrated under vacuum to afford the product, which was purified by flash chromatography on silica gel (MeOH/DCM).

Synthesis of 7-(4-(5-(4,5-Dimethoxy-2-nitrophenyl)-2H-tetrazol-2-yl)phenethyl)-5,6,7,8-tetrahydroimidazo[1,5-a]pyrazine (ID1) (Scheme 1)

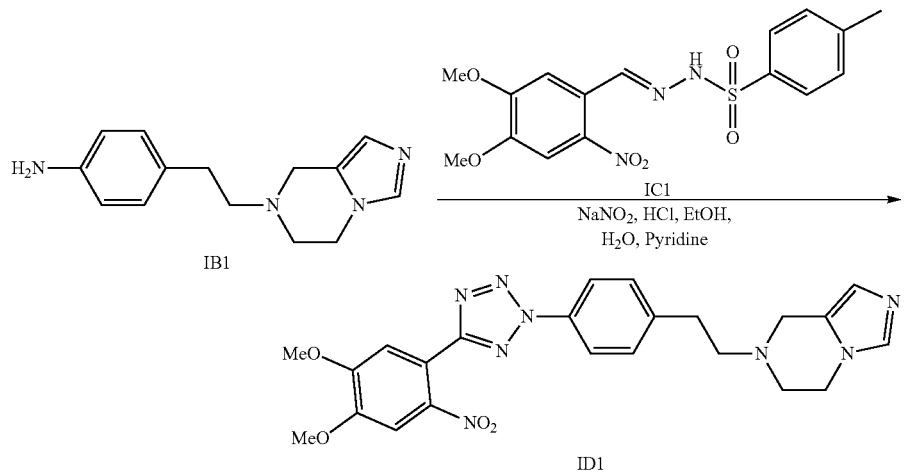

484 mg of Intermediate IB1 and 630 mg of Intermediate IC1 were used to synthesize 461 mg of the title compound (48% yield) according to the General Procedure DD. $^1$H NMR (400 MHz, DMSO-$d_6$): δ 2.81 (t, J=7.2 Hz, 2H), 2.88 (t, J=6.0 Hz, 2H), 2.96 (t, J=7.2 Hz, 2H), 3.69 (s, 2H), 3.96, 3.97 (2s, 6H), 4.01 (t, J=5.4 Hz, 2H), 6.66 (s, 1H), 7.47 (s, 1H), 7.54 (s, 1H), 6.58-6.61 (m, 2H), 7.77 (s, 1H), 8.03-8.05 (m, 2H); LC/MS (ESI, m/z): 477.18 [M+H]$^+$.

Synthesis of 2-(4-(5-(4,5-Dimethoxy-2-nitrophenyl)-2H-tetrazol-2-yl)phenethyl)-1,2,3,4-tetrahydro-2,6-naphthyridine (ID2) (Scheme 1)

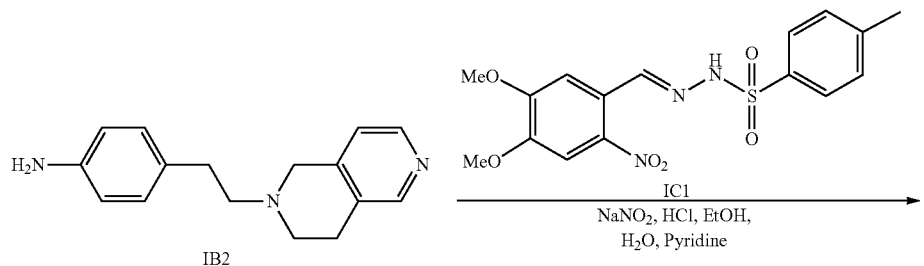

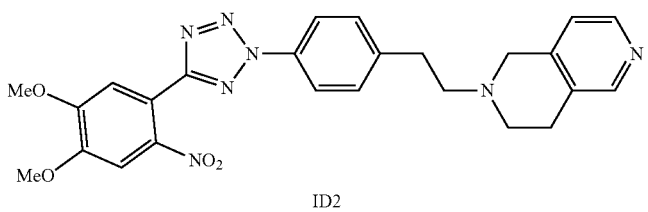

506 mg of Intermediate IB2 and 630 mg of Intermediate IC1 were used to synthesize 451 mg of the title compound (46% yield) according to the General Procedure DD. $^1$H NMR (400 MHz, CDCl$_3$): δ 3.26 (bs, 2H), 3.43 (bs, 2H), 3.51 (bs, 2H), 3.65 (bs, 2H), 4.02 (s, 6H), 4.66 (s, 2H), 7.41 (d, J=8.0 Hz, 1H), 7.53 (s, 2H), 7.56 (s, 2H), 8.00 (d, J=8.0 Hz, 2H), 8.73 (s, 2H). LC/MS (ESI, m/z): 488.20 [M+H]$^+$.

Synthesis of 2-(4-(5-(5-(Benzyloxy)-4-methoxy-2-nitrophenyl)-2H-tetrazol-2-yl)phenethyl)-1,2,3,4-tetrahydro-2,6-naphthyridine (ID3) (Scheme 1)

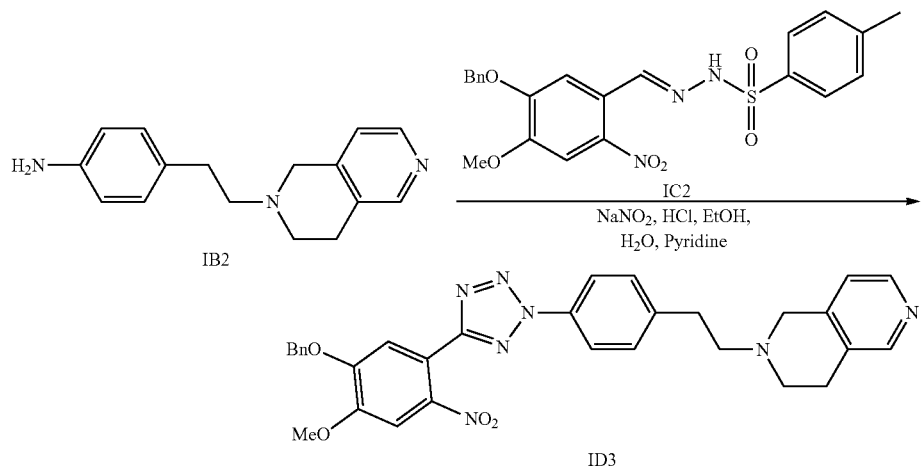

506 mg of Intermediate IB2 and 785 mg of Intermediate IC2 were used to synthesize 550 mg of the title compound (49% yield) according to the General Procedure DD. $^1$H NMR (400 MHz, DMSO-$d_6$): δ 3.03 (m, 8H), 3.93 (m, 2H), 3.97 (s, 3H), 5.30 (s, 2H), 7.12-7.80 (m, 11H), 8.05-8.36 (m, 3H). LC/MS (ESI, m/z): 564.33 [M+H]$^+$.

Synthesis of 2-(4-(5-(4,5-Dimethoxy-2-nitrophenyl)-2H-tetrazol-2-yl)phenethyl)-1,2,3,4-tetrahydro-2,7-naphthyridine (ID4) (Scheme 1)

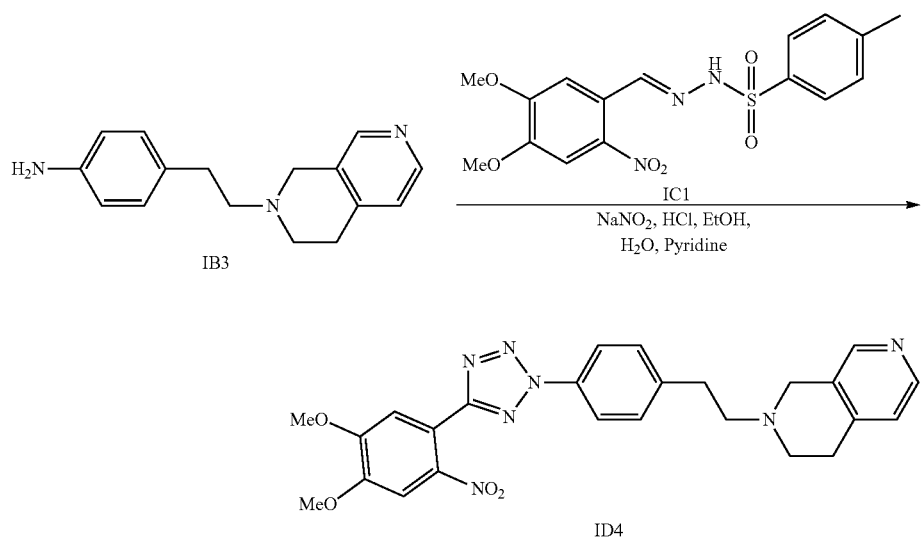

506 mg of Intermediate IB3 and 630 mg of Intermediate IC1 were used to synthesize 437 mg of the title compound (45% yield) according to the General Procedure DD. $^1$H NMR (400 MHz, CD$_3$OD): δ 3.35 (s, 2H), 3.36-3.38 (m, 2H), 3.46-3.49 (m, 2H), 3.67-3.71 (m, 2H), 3.79-3.82 (m, 2H), 4.00 (s, 6H), 4.76 (s, 2H), 7.41 (s, 1H), 7.64 (d, J=8.0 Hz, 2H), 7.70 (s, 1H), 7.75 (d, J=8.0 Hz, 1H), 8.16 (d, J=8.0 Hz, 2H), 8.65 (bs, 2H). LC/MS (ESI, m/z): 488.13 [M+H]$^+$.

Synthesis of Intermediate IE (Scheme 1; General Procedure EE)

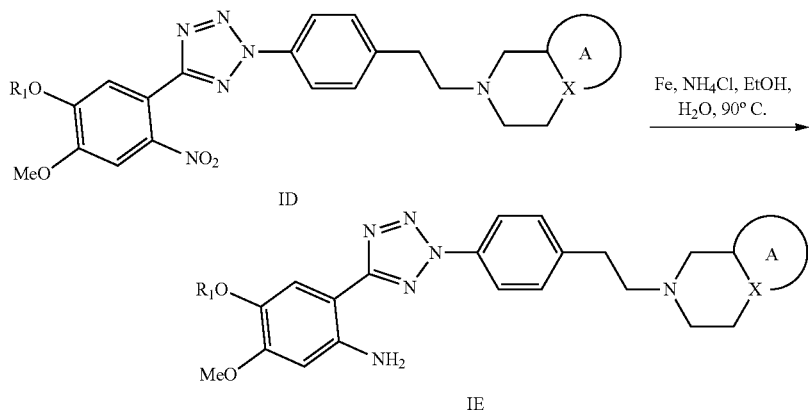

A clean, dry 40 mL vial was charged with Intermediate ID (0.8 mmol, 1.0 eq.), iron (308 mg, 8.0 mmol, 10 eq.), ammonium chloride (415 mg, 8.0 mmol, 10 eq.), EtOH (6.0 mL), and water (1.0 mL). The mixture reaction was stirred at 90° C. for 1 h and checked for completion. The mixture was then filtered, while hot, on Celite, and the solid was washed with EtOH. The filtrate was then evaporated, diluted with DCM (100 mL), washed with saturated sodium bicarbonate (2×100 mL) and brine (1×50 mL), then dried over anhydrous sodium sulfate, filtered, and concentrated under vacuum to afford intermediate IE, which was purified by flash chromatography on silica gel (MeOH/DCM).

Synthesis of 2-(2-(4-(2-(5,6-Dihydroimidazo[1,5-a]pyrazin-7(8H)-yl)ethyl)phenyl)-2H-tetrazol-S-yl)-4,5-dimethoxyaniline (IE1) (Scheme 1)

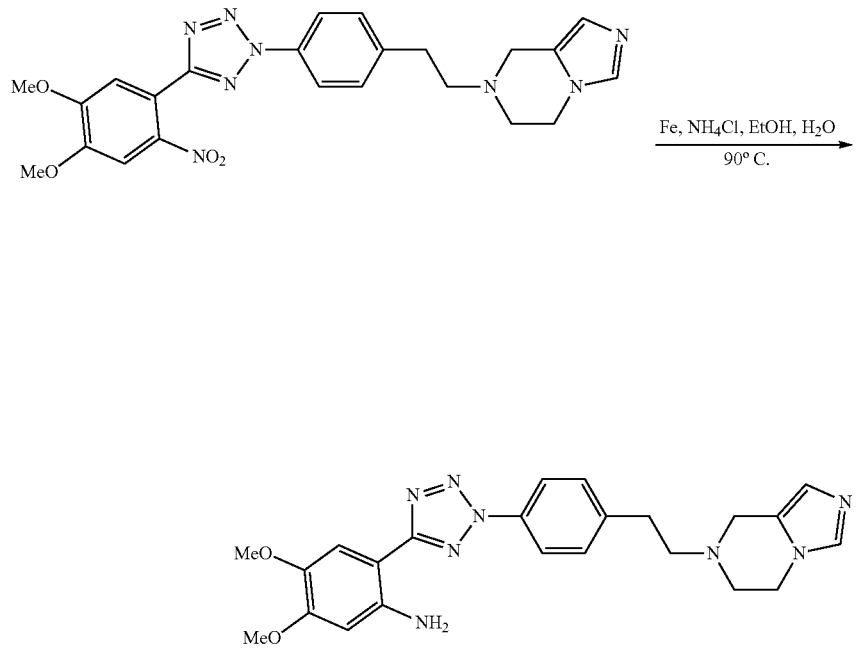

381 mg of Intermediate ID1 was used to synthesize 265 mg of the title compound (74% yield) according to the General Procedure EE. $^1$H NMR (400 MHz, DMSO-$d_6$): δ 2.80 (t, J=7.2 Hz, 2H), 2.88 (t, J=5.6 Hz, 2H), 2.95 (t, J=7.4 Hz, 2H), 3.68 (s, 2H), 3.75 (s, 3H), 3.78 (s, 3H), 4.01 (t, J=5.6 Hz, 2H), 6.11 (s, 2H), 6.56 (s, 1H), 6.64 (d, J=0.8 Hz, 1H), 7.51 (d, J=0.4 Hz, 1H), 7.53-7.58 (m, 3H), 8.09-8.12 (m, 2H); LC/MS (ESI, m/z): 447.08 [M+H]$^+$.

Synthesis of 2-(2-(4-(2-(3,4-Dihydro-2,6-naphthyridin-2(1H)-yl)ethyl)phenyl)-2H-tetrazol-5-yl)-4,5-dimethoxyaniline (IE2) (Scheme 1)

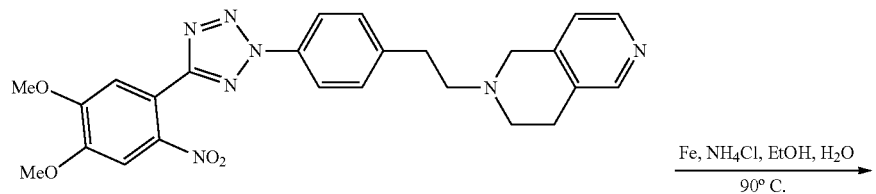

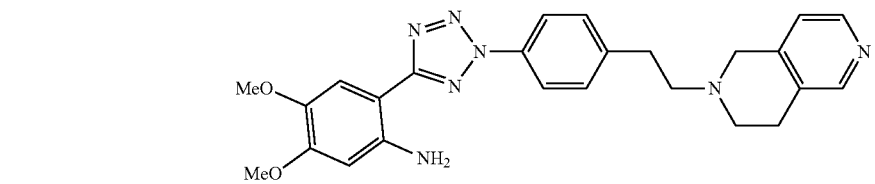

390 mg of Intermediate ID2 was used to synthesize 221 mg of the title compound (60% yield) according to the General Procedure EE. $^1$H NMR (400 MHz, CDCl$_3$): δ 2.83-2.85 (m, 4H), 2.86-2.88 (m, 2H), 2.91-3.03 (m, 2H), 3.74 (s, 2H), 3.91 (s, 3H), 3.96 (s, 3H), 5.30 (bs, 2H), 6.36 (s, 1H), 7.04 (d, J=4.0 Hz, 1H), 7.43 (d, J=8.0 Hz, 2H), 7.71 (s, 1H), 8.09 (d, J=8.0 Hz, 2H), 8.33 (s, 2H). LC/MS (ESI, m/z): 458.09 [M+H]$^+$.

Synthesis of 4-(Benzyloxy)-2-(2-(4-(2-(3,4-dihydro-2,6-naphthyridin-2(1H)-yl)ethyl)phenyl)-2H-tetrazol-5-yl)-5-methoxyaniline (IE3) (Scheme 1)

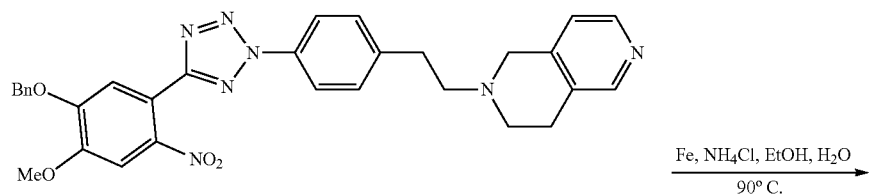

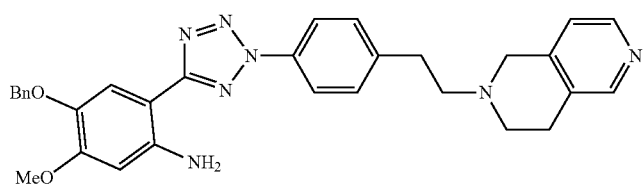

450 mg of Intermediate ID3 was used to synthesize 267 mg of the title compound (63% yield) according to the General Procedure EE. $^1$H NMR (400 MHz, DMSO-d$_6$): δ 2.80-3.10 (m, 8H), 3.70-4.00 (m, 2H), 3.85 (s, 3H), 5.03 (s, 2H), 6.15 (bs, 1H), 6.58 (s, 1H), 7.14 (d, J=4.8 Hz, 1H), 7.37 (m, 4H), 7.48 (m, 2H), 7.59 (d, J=8.8 Hz, 2H), 7.63 (s, 1H), 8.12 (d, J=8.4 Hz, 2H), 8.32 (d, J=5.2 Hz, 1H), 8.37 (s, 1H). LC/MS (ESI, m/z): 534.19 [M+H]$^+$.

Synthesis of 2-(2-(4-(2-(3,4-Dihydro-2,7-naphthyridin-2(1H)-yl)ethyl)phenyl)-2H-tetrazol-5-yl)-4,5-dimethoxyaniline (IE4) (Scheme 1)

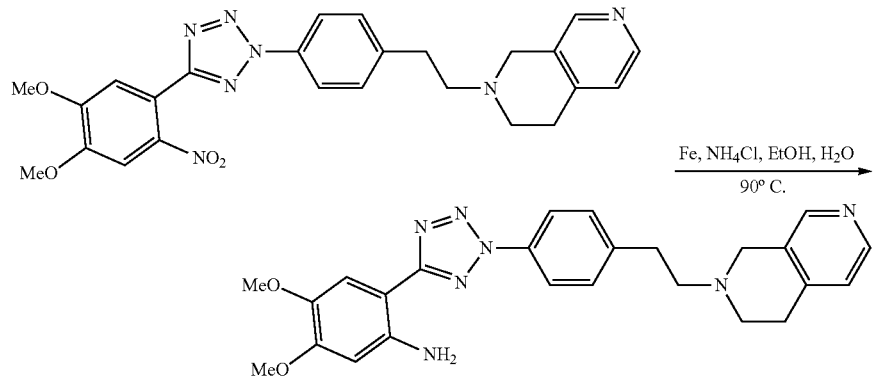

390 mg of Intermediate ID4 was used to synthesize 236 mg of the title compound (64% yield) according to the General Procedure EE. $^1$H NMR (400 MHz, CD$_3$OD): δ 3.32 (s, 2H), 3.33-3.44 (m, 2H), 3.46-3.48 (m, 2H), 3.67-3.77 (m, 2H), 3.78-3.80 (m, 2H), 4.00 (s, 3H), 4.02 (s, 3H), 4.65 (s, 2H), 7.27 (s, 1H), 7.75 (d, J=8.0 Hz, 2H), 7.95 (s, 1H), 8.15 (d, J=8.0 Hz, 1H), 8.29 (d, J=8.0 Hz, 2H), 8.80 (d, J=4.0 Hz, 1H), 8.95 (s, 1H). LC/MS (ESI, m/z): 458.14 [M+H]$^+$.

Synthesis of Intermediate IF (Scheme 1; General Procedure FF)

To a stirred solution of acid (10 mmol, 1.0 eq.), 2,2'-benzothiazolyl disulfide (3.65 g, 11 mmol, 1.1 eq.), PPh$_3$ (2.88 g, 11 mmol, 1.1 eq.) in DCM (50 mL) at room temperature, TEA (1.36 mL, 10 mmol, 1 eq.) was added. The mixture was stirred overnight at room temperature. Heptane (200 mL) was added and the solid formed was filtered, rinsed with acetone, and dried under vacuum to afford the desired thioester which was used without further purification.

Synthesis of S-(Benzo[d]thiazol-2-yl)$_4$-oxo-4H-chromene-2-carbothioate (IF1)

Using general procedure FF and chromone-2-carboxylic acid (1.9 g) as the acid, 2.59 g of the title compound was obtained (76% yield).

Synthesis of S-(benzo[d]thiazol-2-yl)quinoline-3-carbothioate (IF2)

Using general procedure FF and quinoline-3-carboxylic acid (1.73 g) as the acid, 2.34 g of the title compound was obtained (73% yield).

Synthesis of S-(Benzo[d]thiazol-2-yl) quinoxaline-2-carbothioate (IF3)

Using general procedure FF and quinoxaline-2-carboxylic acid (1.74 g) as the acid, 2.07 g of the title compound was obtained (64% yield).

Synthesis of S-(benzo[d]thiazol-2-yl) 9-oxo-9,10-dihydroacridine-4-carbothioate (IF4)

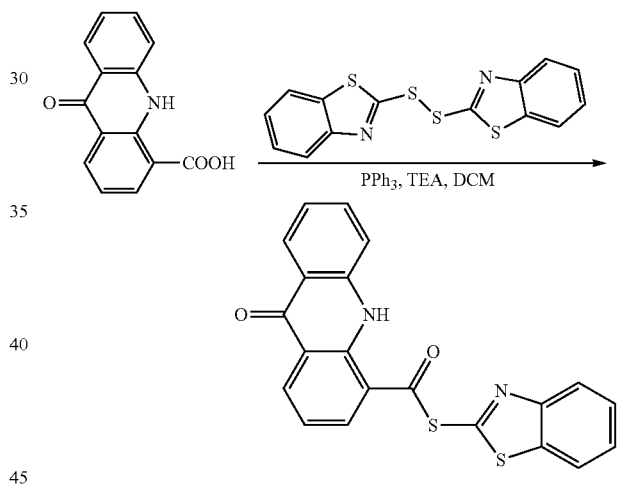

Using general procedure FF and 9-oxo-9,10-dihydroacridine-4-carboxylic acid (2.39 g) as the acid, 7.2 g of the title compound was obtained (70% yield).

Synthesis of S-(Benzo[d]thiazol-2-yl) 7-methyl-4-oxo-4H-chromene-2-carbothioate (IF5)

Using general procedure FF and 7-methyl chromone-2-carboxylic acid (2.04 g) as the acid, 4.41 g of the title compound was obtained (83% yield).

Synthesis of S-(Benzo[d]thiazol-2-yl) 4-oxo-6-(pyridin-3-yl)-4H-chromene-2-carbothioate (IF6)

Using general procedure FF and A23 (0.45 g) as the acid, 0.52 g of the title compound was obtained (74% yield). $^1$H NMR (400 MHz, DMSO-d$_6$): δ 6.96 (s, 1H), 7.42-7.56 (m, 3H), 7.86 (d, J=12.0 Hz, 1H), 7.94 (d, J=8.0 Hz, 1H), 8.06 (d, J=8.0 Hz, 1H), 8.19-8.30 (m, 3H), 8.63 (d, J=4.0 Hz, 1H), 8.98 (d, J=8.0 Hz, 1H). LC/MS (ESI, m/z): 417.22 [M+H]$^+$.

1-(2-Hydroxy-5-(pyridin-3-yl)phenyl)ethan-1-one (A11)

A clean, dry 40 mL vial was charged with 1-(5-bromo-2-hydroxyphenyl)ethan-1-one (1.0 g, 4.65 mmol), pyridin-3-ylboronic acid (0.85 g, 6.97 mmol), Pd(PPh$_3$)$_4$ (0.24 g, 0.23 mmol), Na$_2$CO$_3$ (1.48 g, 14.04 mmol), water (6 mL) and DME (18 mL), and the mixture was purged with argon for 2 min. The reaction mixture was stirred at 95° C. for 5 h. Upon completion (monitored by LC/MS), the mixture was diluted with ethyl acetate (100 mL) and washed with water (100 mL) and brine (100 mL). The organic layer was separated, dried (Na$_2$SO$_4$), and concentrated under reduced pressure to afford the crude residue, which was purified by flash column chromatography on silica gel (0-100% n-heptane/ethyl acetate) to afford A11 (0.75 g, 76%). $^1$H NMR (400 MHz, DMSO-d$_6$): δ 2.75 (s, 3H), 7.09 (d, J=8.0 Hz, 1H), 7.46-7.49 (m, 1H), 7.89 (d, J=4.0 Hz, 1H), 8.08-8.11 (m, 1H), 8.17 (d, J=4.0 Hz, 1H), 8.55 (d, J=4.0 Hz, 1H), 8.93 (d, J=4.0 Hz, 1H), 12.01 (s, 1H). LC/MS (ESI, m/z): 214.22 [M+H]$^+$.

4-Oxo-6-(pyridin-3-yl)-4H-chromene-2-carboxylic acid (A12)

A clean, dry 40 mL vial was charged with A11 (0.7 g, 3.28 mmol), diethyl oxalate (1.43 g, 9.84 mmol), a solution of NaOMe in MeOH (0.25 mL, 6.56 mmol, 25% w/w) and dioxane (5 mL). The resulting solution was stirred at 120° C. for 12 h. Then, an aqueous solution of HCl (1.48 mL, 50.84 mmol, 6 M) was added to the reaction mixture and stirring was continued at 80° C. for another 12 h. Upon completion (monitored by LC/MS), the solid formed was filtered, washed with water, dried under reduced pressure, washed with DCM, and dried under reduced pressure to afford A12 (0.5 g, 57%). $^1$H NMR (400 MHz, DMSO-d$_6$): δ 6.96 (s, 1H), 7.92 (d, J=8.0 Hz, 1H), 8.06-8.08 (m, 1H), 8.09 (s, 1H), 8.45 (s, 1H), 8.89 (d, J=4.0 Hz, 2H), 9.35 (s, 1H). LC/MS (ESI, m/z): 268.17 [M+H]$^+$.

Synthesis of S-(Benzo[d]thiazol-2-yl) 6-(1H-imidazol-1-yl)-4-oxo-4H-chromene-2-carbothioate (IF7)

Using general procedure FF and A14 (0.4 g) as the acid, 0.49 g of the title compound was obtained (77% yield). $^1$H NMR (400 MHz, DMSO-d$_6$): δ 6.93 (s, 1H), 7.31 (s, 1H), 7.42-7.5 (m, 4H), 7.94 (d, J=8.0 Hz, 2H), 8.07 (d, J=8.0 Hz, 2H), 8.21-8.23 (m, 1H). LC/MS (ESI, m/z): 406.31 [M+H]$^+$.

1-(2-Hydroxy-5-(1H-imidazol-1-yl)phenyl)ethan-1-one (A13)

A clean, dry 40 mL vial was charged with 1-(2-hydroxy-5-iodophenyl)ethan-1-one (1.0 g, 3.81 mmol), imidazole (0.39 g, 5.72 mmol), CuI (0.073 g, 0.38 mmol), 4,7-dimethoxy-1,10-phenanthroline (0.1 g, 0.42 mmol), anhydrous K$_2$CO$_3$ (1.58 g, 11.44 mmol) and DMSO (10 mL). The reaction mixture was purged with argon for 2 min and stirred overnight at 100° C. Upon completion (monitored by LC/MS), the mixture was filtered, diluted with ethyl acetate (50 mL), and washed with water (2×50 mL) followed by brine (50 mL). The organic layer was separated, dried (Na$_2$SO$_4$), and concentrated under reduced pressure to afford A13 (0.65 g, 84%) which was used without further purification. $^1$H NMR (400 MHz, DMSO-d$_6$): δ 2.53 (s, 3H), 6.33 (s, 1H), 6.97-7.06 (m, 2H), 7.33 (s, 1H), 7.46 (s, 1H), 7.78 (s, 1H), 11.95 (s, 1H). LC/MS (ESI, m/z): 203.10 [M+H]$^+$.

6-(1H-Imidazol-1-yl)-4-oxo-4H-chromene-2-carboxylic acid (A14)

A clean, dry 40 mL vial was charged with A13 (0.6 g, 2.97 mmol), diethyl oxalate (1.30 g, 8.91 mmol), a solution of NaOMe in MeOH (0.11 mL, 5.94 mmol, 25% w/w) and dioxane (7 mL). The resulting solution was stirred at 120° C. for 12 h. Then, an aqueous solution of HCl (1.4 mL, 46.0 mmol, 6 M) was added to the reaction mixture and the stirring was continued at 80° C. for another 12 h. Upon completion (monitored by LC/MS), the solid formed was filtered, washed with water, dried under reduced pressure, washed with DCM, and dried under reduced pressure to afford A14 (0.42 g, 55%). $^1$H NMR (400 MHz, DMSO-d$_6$): δ 6.99 (s, 1H), 7.90-8.11 (m, 3H), 8.31 (d, J=8.0 Hz, 1H), 8.41 (s, 1H), 8.47 (s, 1H), 9.77 (bs, 1H). LC/MS (ESI, m/z): 257.13 [M+H]$^+$.

Synthesis of S-(benzo[d]thiazol-2-yl) 4-(pyridin-4-yl)benzothioate (IF8)

Using general procedure FF and 4-(pyridin-4-yl) benzoic acid (0.6 g) as the acid, 0.77 g of the title compound was obtained (73% yield). $^1$H NMR (400 MHz, DMSO-d$_6$): δ 7.76 (d, J=4.0 Hz, 3H), 7.92 (d, J=8.0 Hz, 3H), 8.06 (d, J=8.0 Hz, 3H), 8.68 (d, J=4.0 Hz, 3H). LC/MS (ESI, m/z): 349.21 [M+H]$^+$.

Synthesis of S-(Benzo[d]thiazol-2-yl) 4-(pyridin-3-yl)benzothioate (IF9)

Using general procedure FF and 4-(pyridin-3-yl)benzoic acid (0.6 g) as the acid, 0.72 g of the title compound was obtained (69% yield). $^1$H NMR (400 MHz, DMSO-d$_6$): δ 7.43-7.55 (m, 3H), 7.86 (d, J=12.0 Hz, 2H), 7.94 (d, J=8.0 Hz, 2H), 8.05-8.17 (m, 4H), 8.62 (d, J=4.0 Hz, 1H), 8.96 (s, 1H). LC/MS (ESI, m/z): 349.23 [M+H]$^+$.

Synthesis of S-(Benzo[d]thiazol-2-yl) 4-(1H-imidazol-1-yl)benzothioate (IF10)

Using general procedure FF and 4-(1H-imidazol-1-yl) benzoic acid (0.7 g) as the acid, 0.82 g of the title compound was obtained (65% yield). $^1$H NMR (400 MHz, DMSO-d$_6$): δ 7.15 (d, J=16.0 Hz, 1H), 7.42-7.55 (m, 2H), 7.79-7.96 (m, 4H), 8.05 (d, J=8.0 Hz, 2H), 8.26 (d, J=8.0 Hz, 1H), 8.37 (s, 1H). LC/MS (ESI, m/z): 338.13 [M+H]$^+$.

Synthesis of Compounds of the Instant Disclosure (Scheme 1; General Procedure GG)

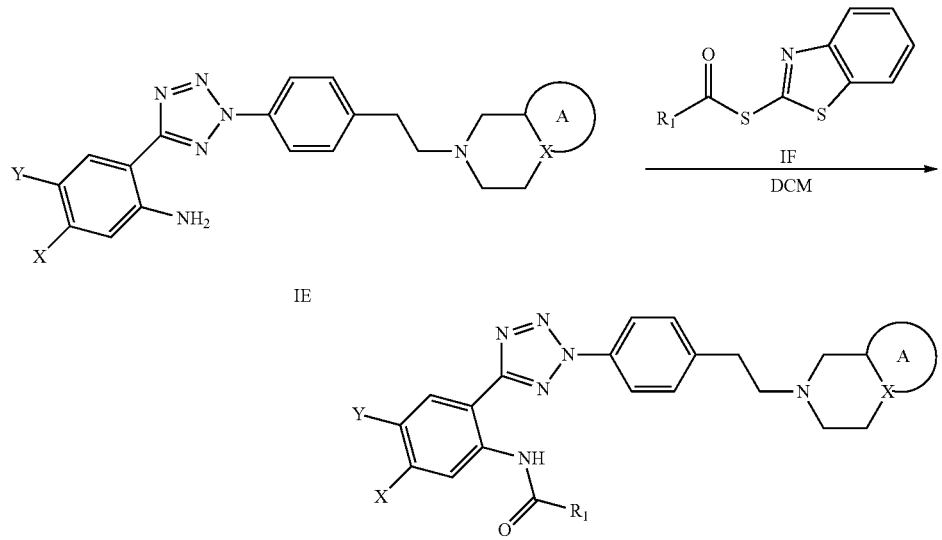

A clean, dry 40 mL vial was charged with Intermediate IE (0.3 mmol, 1.0 eq.), Intermediate IF (0.4 mmol, 1.3 eq.), and DCM (10 mL). The reaction mixture was stirred at room temperature for 3 h, and upon reaction completion, the mixture was concentrated under vacuum and purified by flash chromatography on silica gel (MeOH/DCM) to give the compounds of the instant disclosure.

Synthesis of Intermediate IH (Scheme 2; General Procedure HH)

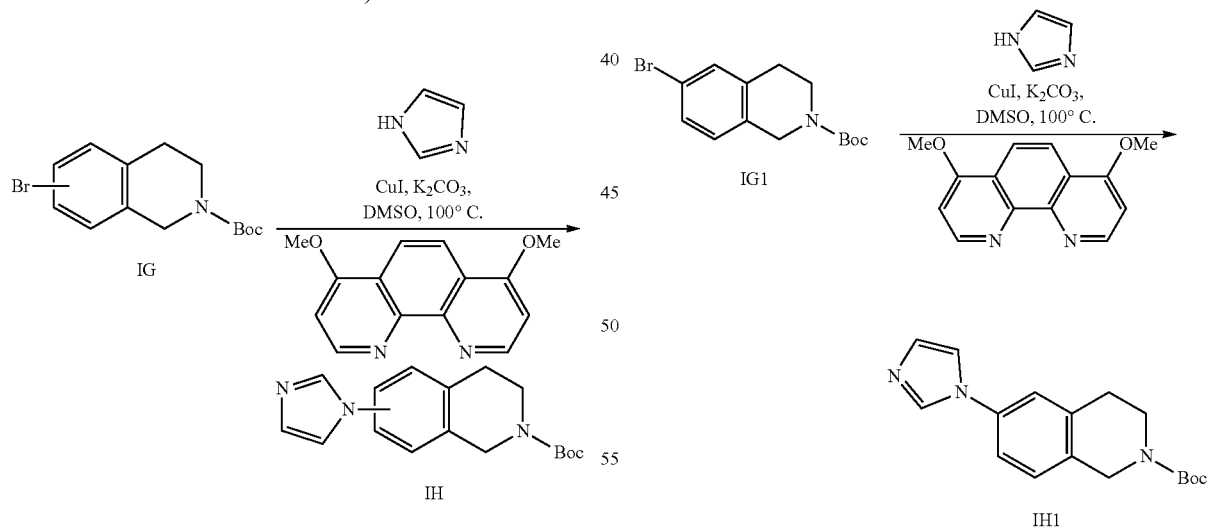

A clean, dry 40 mL vial was charged with bromide IG (3.2 mmol, 1.0 eq.), imidazole (327 mg, 4.8 mmol, 1.5 eq.), copper iodide (61 mg, 0.32 mmol, 0.1 eq.), 4,7-dimethoxy-1,10-phenanthroline (85 mg, 0.35 mmol, 0.11 eq.), potassium carbonate (1.33 g, 9.6 mmol, 3.0 eq.), and DMSO (10 mL) under nitrogen. The reaction mixture was stirred at 100° C. overnight. Upon completion, the reaction mixture was diluted with water (50 mL) and extracted with EtOAc (100 mL). The organic layer was then washed with brine (2×50 mL), dried over anhydrous sulfate, and concentrated under vacuum to give Intermediate IH1, which was used without further purification.

Synthesis of tert-Butyl 6-(1H-imidazol-1-yl)-3,4-dihydroisoquinoline-2(1H)-carboxylate (IH1) (Scheme 2)

998 mg of tert-butyl 6-bromo-3,4-dihydroisoquinoline-2(1H)-carboxylate (IG1) was used to synthesize 839 mg of the title compound (88% yield) according to the General Procedure HH. $^1$H NMR (400 MHz, CD$_3$OD): δ 1.52 (s, 9H), 3.27 (t, J=12.0 Hz, 2H), 3.58 (t, J=12.0 Hz, 2H), 4.51 (s, 2H), 7.54-7.56 (m, 1H), 7.68-7.73 (m, 2H), 7.82 (s, 1H), 8.13 (s, 1H), 9.55 (s, 1H). LC/MS (ESI, m/z): 300.09 [M+H]$^+$.

Synthesis of tert-Butyl 7-(1H-imidazol-1-yl)-3,4-dihydroisoquinoline-2(1H)-carboxylate (IH2) (Scheme 2)

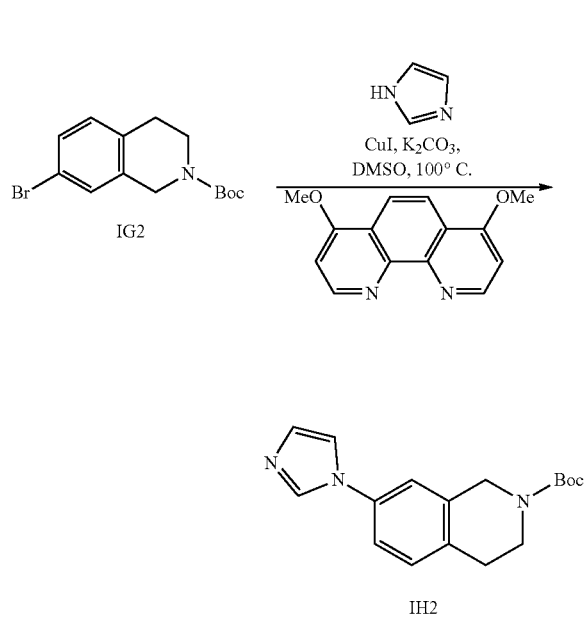

998 mg of tert-butyl 7-bromo-3,4-dihydroisoquinoline-2(1H)-carboxylate (IG2) was used to synthesize 805 mg of the title compound (84% yield) according to the General Procedure HH. $^1$H NMR (400 MHz, DMSO-d$_6$): δ 1.43 (s, 9H), 2.81 (t, J=12.0 Hz, 2H), 3.55 (t, J=12.0 Hz, 2H), 4.51 (s, 2H), 7.09 (s, 1H), 7.29 (d, J=8.0 Hz, 1H), 7.44-7.46 (m, 2H), 7.70 (s, 1H), 8.21 (s, 1H). LC/MS (ESI, m/z): 300.09 [M+H]$^+$.

Synthesis of Intermediate II (Scheme 2; General Procedure II)

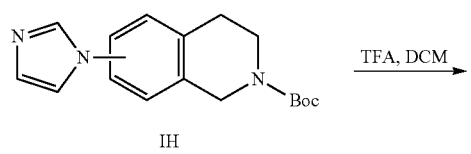

A clean, dry 40 mL vial was charged with intermediate IH (2.6 mmol, 1.0 eq.) and a mixture of TFA and DCM (1:2 v/v, 6.0 mL). The reaction mixture was stirred at room temperature for 5 h. The solution was then diluted with MeOH (50 mL) and concentrated under vacuum to afford intermediate II, which was used without further purification.

Synthesis of 6-(1H-Imidazol-1-yl)-1,2,3,4-tetrahydroisoquinoline trifluoroacetate (II1) (Scheme 2)

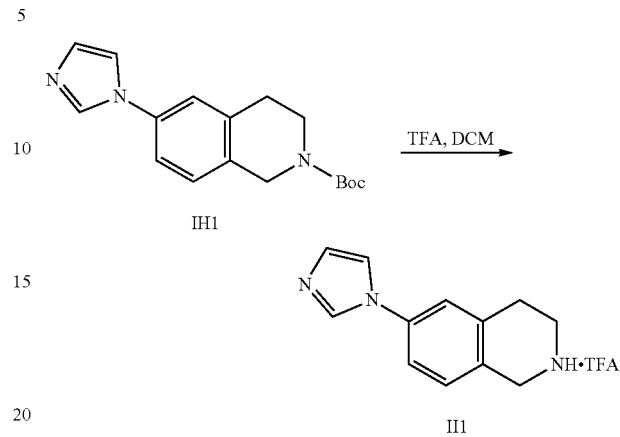

777 mg of Intermediate IH1 was used to synthesize 758 mg of the title compound (93% yield) according to the General Procedure II.

Synthesis of 7-(1H-Imidazol-1-yl)-1,2,3,4-tetrahydroisoquinoline trifluoroacetate (II2) (Scheme 2)

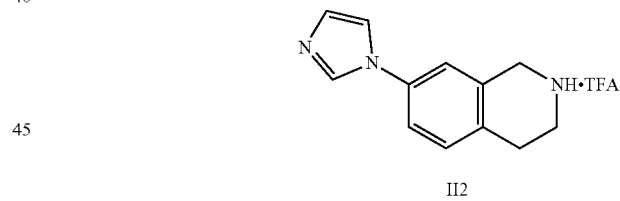

777 mg of Intermediate IH2 was used to synthesize 770 mg of the title compound (95% yield) according to the General Procedure IT.

Synthesis of Intermediate IJ (Scheme 2; General Procedure JJ)

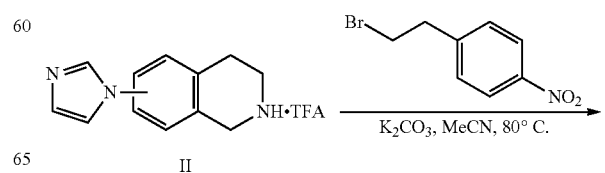

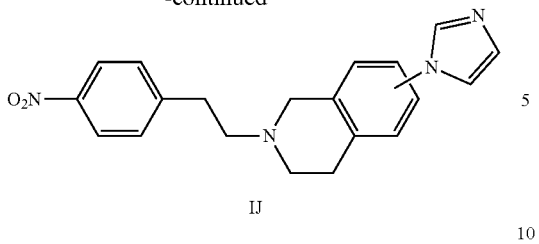

IJ

A clean, dry 40 mL vial was charged with Intermediate II (2.4 mmol, 1.0 eq.), 1-(2-bromoethyl)-4-nitrobenzene (552 mg, 2.4 mmol, 1.0 eq.), anhydrous potassium carbonate (1.00 g, 7.2 mmol, 3.0 eq.), and MeCN (20 mL). The reaction mixture was heated at 80° C. and stirred overnight. The mixture was diluted with DCM (150 mL) and washed with water (2×100 mL) and brine (2×50 mL). The organic layer was separated, dried over anhydrous $Na_2SO_4$, filtered, and concentrated under vacuum. The residue was then purified by flash chromatography on silica gel (MeOH/DCM) to afford Intermediate IJ.

Synthesis of 6-(1H-Imidazol-1-yl)-2-(4-nitrophenethyl)-1,2,3,4-tetrahydroisoquinoline (IJ1) (Scheme 2)

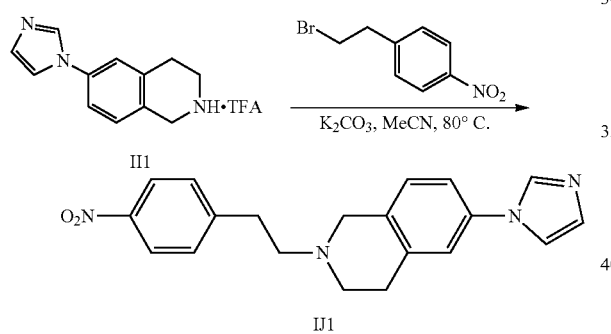

751 mg of Intermediate II1 was used to synthesize 429 mg of the title compound (51% yield) according to the General Procedure JJ. $^1$H NMR (400 MHz, DMSO-$d_6$): δ 2.70-2.75 (m, 4H), 2.82-2.91 (m, 4H), 3.62 (s, 2H), 6.58 (d, J=8.0 Hz, 2H), 7.22 (d, J=8.0 Hz, 2H), 7.25 (s, 1H), 7.29 (s, 1H), 7.36-7.39 (m, 2H), 7.69 (s, 1H), 8.19 (s, 1H). LC/MS (ESI, m/z): 349.11 [M+H]$^+$.

Synthesis of 7-(1H-imidazol-1-yl)-2-(4-nitrophenethyl)-1,2,3,4-tetrahydroisoquinoline (IJ2) (Scheme 2)

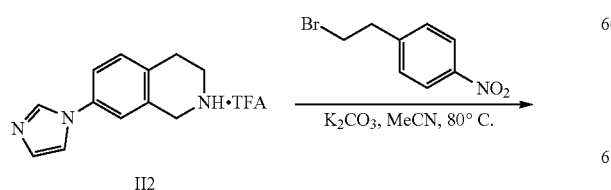

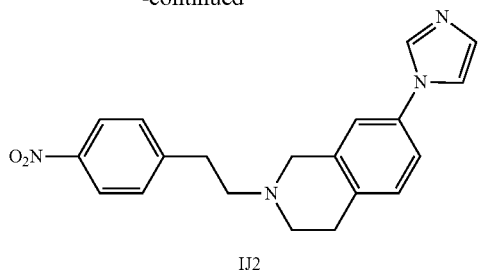

IJ2

751 mg of Intermediate II2 was used to synthesize 403 mg of the title compound (48% yield) according to the General Procedure JJ. $^1$H NMR (400 MHz, CDCl$_3$): δ 2.84-2.87 (m, 4H), 2.97-3.06 (m, 4H), 3.75 (s, 2H), 7.16-7.20 (m, 4H), 7.26 (s, 1H), 7.41 (d, J=12.0 Hz, 2H), 7.83 (s, 1H), 8.16 (d, J=8.0 Hz, 2H). LC/MS (ESI, m/z): 349.08 [M+H]$^+$.

Synthesis of Intermediate IK (Scheme 2; General Procedure KK)

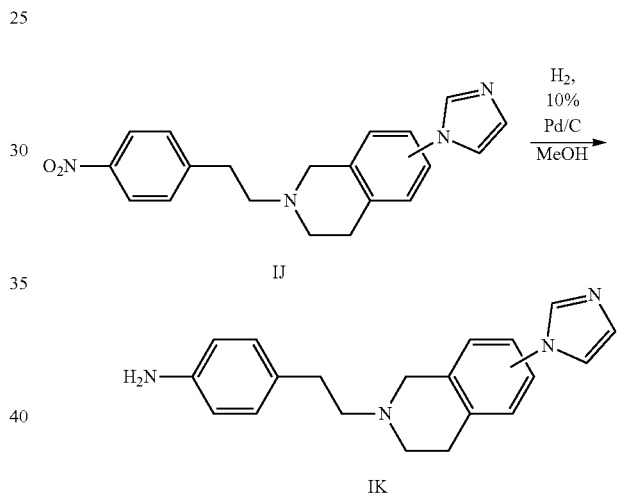

To a clean, dry hydrogenation flask were added Intermediate IJ (1.0 mmol, 1.0 eq.), 10% palladium on activated carbon (53 mg, 0.05 mmol Pd, 0.05 eq.), and MeOH (25 mL). The flask was then charged with hydrogen at 50 psi and shook for 3 h. The reaction mixture was then filtered on Celite and concentrated under vacuum to afford Intermediate IK, which was used without further purification.

Synthesis of 4-(2-(6-(1H-Imidazol-1-yl)-3,4-dihydroisoquinolin-2(1H)-yl)ethyl)aniline (IK1) (Scheme 2)

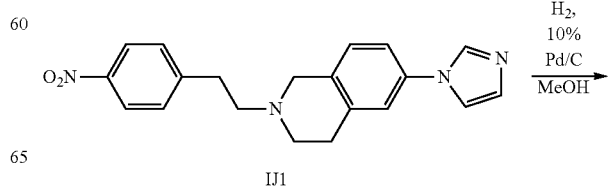

IJ1

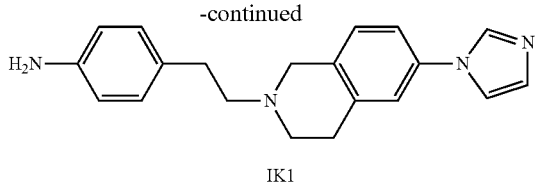

IK1

348 mg of Intermediate IJ1 was used to synthesize 267 mg of the title compound (84% yield) according to the General Procedure KK. $^1$H NMR (400 MHz, DMSO-$d_6$): δ 2.61-2.66 (m, 4H), 2.70 (t, J=12.0 Hz, 2H), 2.85 (t, J=12.0 Hz, 2H), 3.63 (s, 2H), 4.83 (s, 2H), 6.48 (d, J=8.0 Hz, 2H), 6.89 (d, J=8.0 Hz, 2H), 7.08 (s, 1H), 7.18 (d, J=8.0 Hz, 1H), 7.37-7.39 (m, 2H), 7.69 (s, 1H), 8.19 (s, 1H). LC/MS (ESI, m/z): 319.18 [M+H]$^+$.

Synthesis of 4-(2-(7-(1H-Imidazol-1-yl)-3,4-dihydroisoquinolin-2(1H)-yl)ethyl)aniline (IK2) (Scheme 2)

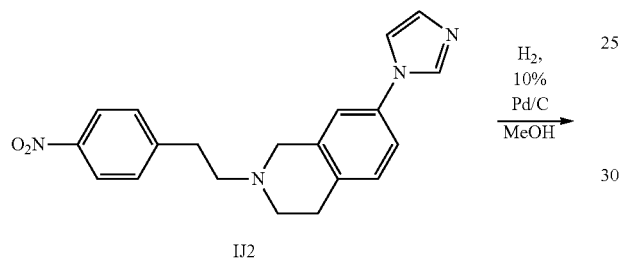

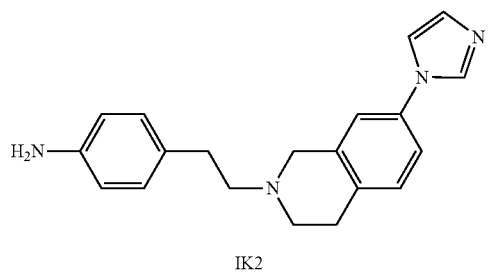

IK2

348 mg of Intermediate IJ2 was used to synthesize 251 mg of the title compound (79% yield) according to the General Procedure KK. $^1$H NMR (400 MHz, CDCl$_3$): δ 2.74-2.78 (m, 2H), 2.81-2.86 (m, 4H), 2.98 (t, J=12.0 Hz, 2H), 3.60 (bs, 2H), 3.75 (s, 2H), 6.65 (d, J=8.0 Hz, 2H), 7.04 (d, J=8.0 Hz, 2H), 7.16 (s, 3H), 7.20 (s, 1H), 7.28 (s, 1H), 7.83 (s, 1H). LC/MS (ESI, m/z): 319.22 [M+H]$^+$.

Synthesis of Intermediate IL (Scheme 2; General Procedure LL)

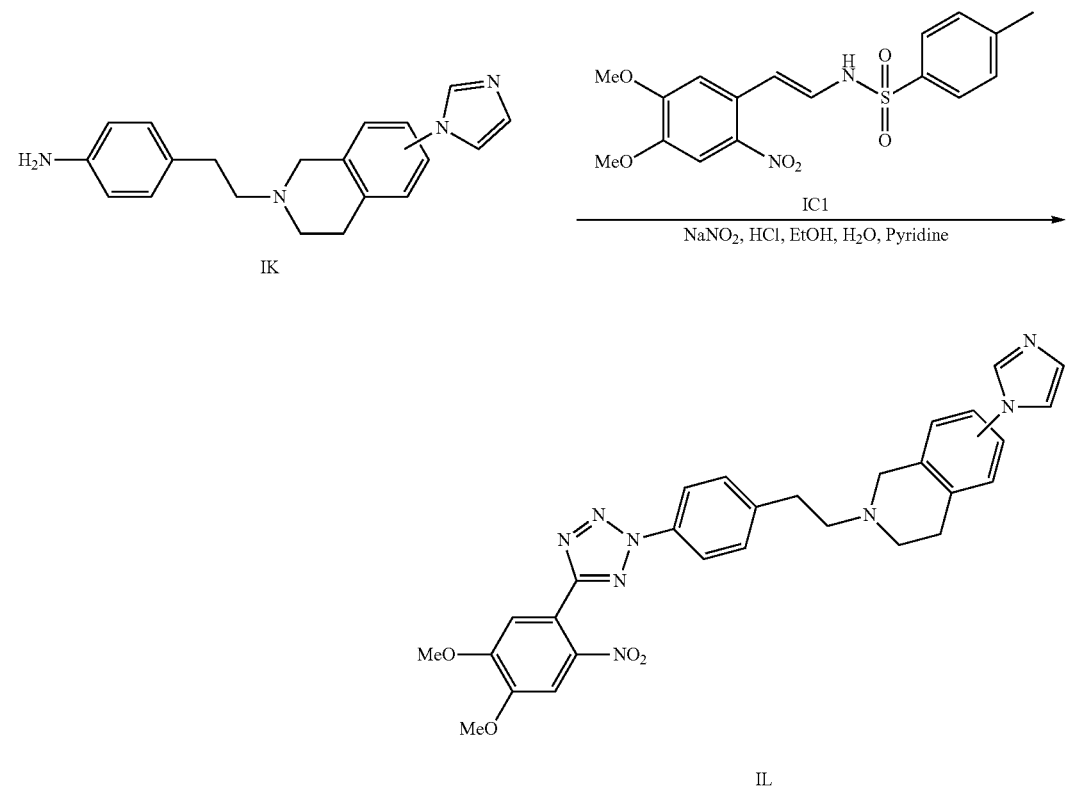

A clean, dry 40 mL vial was charged with Intermediate IK (0.75 mmol, 1.0 eq.), sodium nitrite (64 mg, 0.92 mmol, 1.23 eq.), H₂O (1.2 mL), and EtOH (2.4 mL). The mixture was vortexed and cooled below 0° C. 36% HCl (0.20 mL) was then added to the mixture, and the mixture was vigorously stirred for about 5 min. In another clean, dry 40 mL vial, Intermediate IC (0.75 mmol, 1.0 eq) was dissolved in pyridine (4.0 mL), and this solution was gradually added to the vial containing intermediate IK. The mixture was then stirred at room temperature overnight, and upon completion, the mixture diluted with DCM (100 mL), and washed with water and brine (2×50 mL), then dried over anhydrous Na₂SO₄, filtered, and concentrated under vacuum to afford IL, which was used without further purification.

Synthesis of 2-(4-(5-(4,5-Dimethoxy-2-nitrophenyl)-2H-tetrazol-2-yl)phenethyl)-6-(1H-imidazol-1-yl)-1,2,3,4-tetrahydroisoquinoline (IL1)

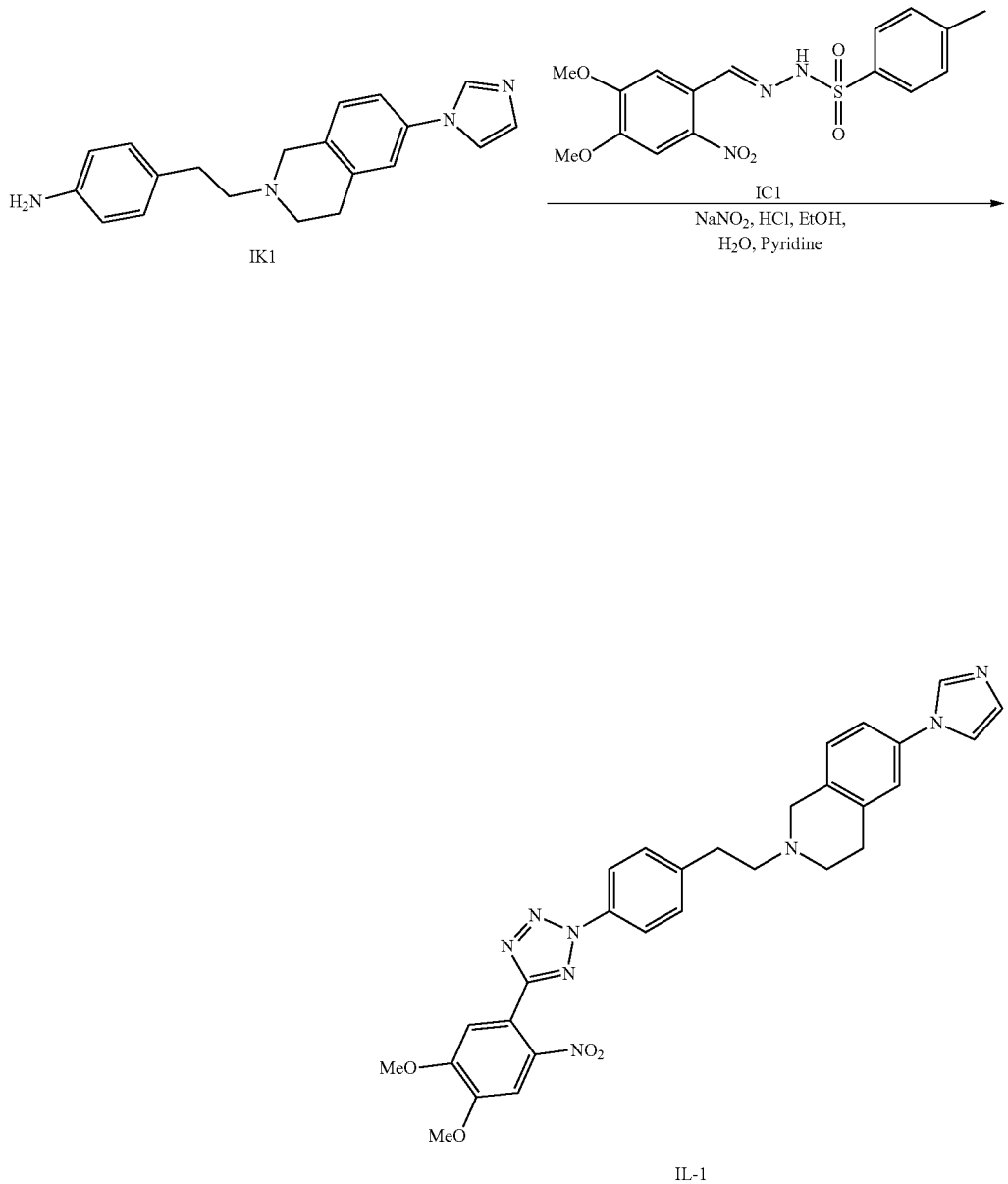

239 mg of Intermediate IK1 and 236 mg of Intermediate IC1 were used to synthesize 278 mg of the title compound (67% yield) according to the General Procedure LL. ¹H NMR (400 MHz, DMSO-d₆): δ 3.15-3.29 (m, 4H), 3.38-3.46 (m, 5H), 3.95 (s, 6H), 4.36 (s, 1H), 7.17 (s, 1H), 7.34 (d, J=8.0 Hz, 1H), 7.46 (s, 1H), 7.55-7.59 (m, 2H), 7.64 (d, J=8.0 Hz, 2H), 7.76 (d, J=8.0 Hz, 2H), 8.09 (d, J=8.0 Hz, 2H), 8.38 (s, 1H). LC/MS (ESI, m/z): 553.18 [M+H]⁺.

Synthesis of 2-(4-(5-(4,5-Dimethoxy-2-nitrophenyl)-2H-tetrazol-2-yl)phenethyl)-7-(1H-imidazol-1-yl)-1,2,3,4-tetrahydroisoquinoline (IL2)

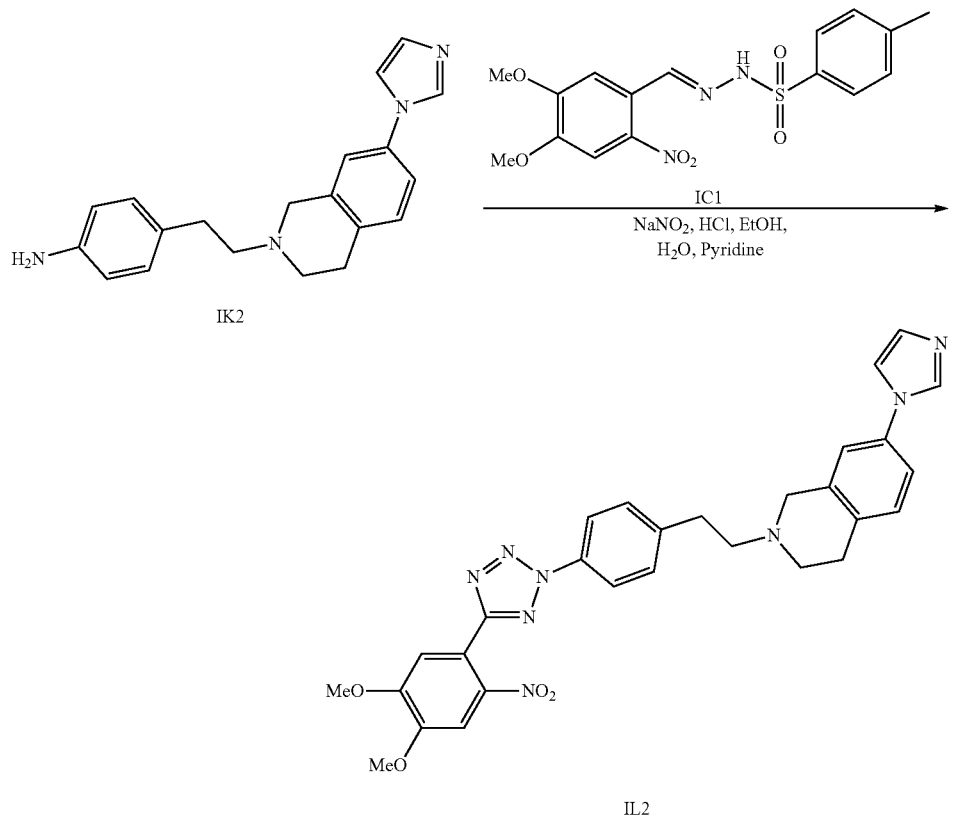

239 mg of Intermediate IK1 and 236 mg of Intermediate IC1 were used to synthesize 253 mg of the title compound (61% yield) according to the General Procedure LL. $^1$H NMR (400 MHz, DMSO-$d_6$): δ 3.13-3.30 (m, 4H), 3.37-3.45 (m, 5H), 3.95 (s, 6H), 4.36 (s, 1H), 7.10 (s, 1H), 7.35-4.44 (m, 2H), 7.55-7.61 (m, 2H), 7.62 (d, J=8.0 Hz, 2H), 7.74 (d, J=8.0 Hz, 2H), 8.09 (d, J=8.0 Hz, 2H), 8.42 (s, 1H). LC/MS (ESI, m/z): 553.20 [M+H]$^+$.

Synthesis of Intermediate IM (Scheme 2; General Procedure MM)

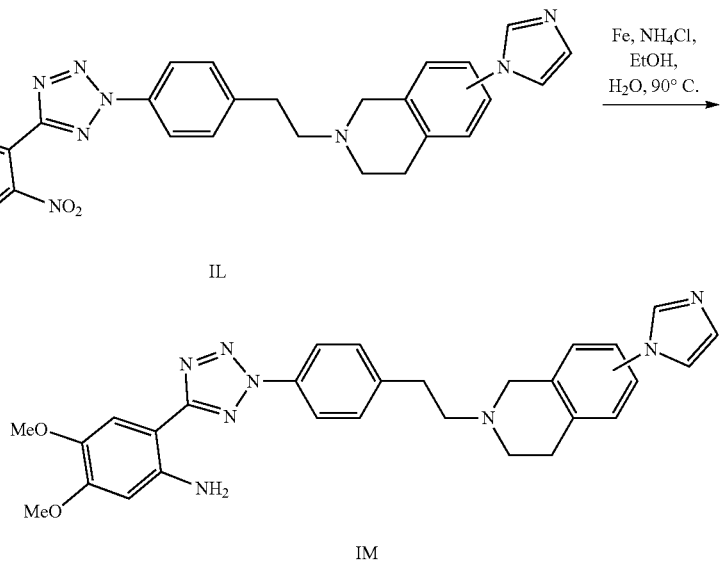

A clean, dry 40 mL vial was charged with Intermediate IL (0.4 mmol, 1.0 eq.), iron (154 mg, 4.0 mmol, 10 eq.), ammonium chloride (208 mg, 4.0 mmol, 10 eq.), EtOH (6.0 mL), and water (1.0 mL). The mixture reaction was stirred at 90° C. for 1 h and checked for completion. The mixture was then filtered, while hot, on Celite, and the solid was washed with EtOH. The filtrate was then evaporated, diluted with DCM (75 mL), washed with saturated sodium bicarbonate (2×50 mL) and brine (1×50 mL), then dried over anhydrous sodium sulfate, filtered, and concentrated under vacuum. The residue was purified by flash chromatography on silica gel (MeOH/DCM) to afford intermediate IM.

Synthesis of 2-(2-(4-(2-(6-(1H-Imidazol-1-yl)-3,4-dihydroisoquinolin-2(1H)-yl)ethyl)phenyl)-2H-tetrazol-5-yl)-4,5-dimethoxyaniline (IM1)

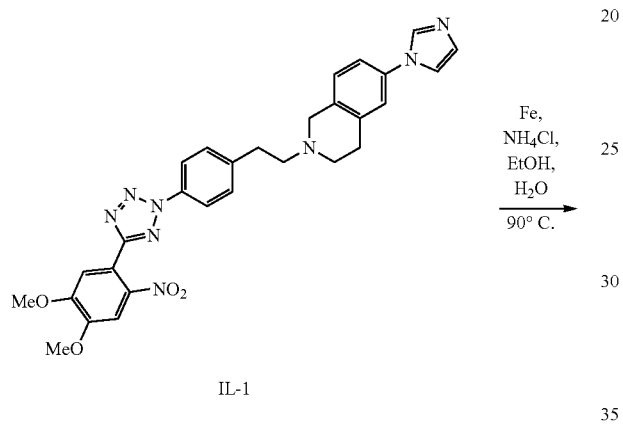

Synthesis of 2-(2-(4-(2-(7-(1H-Imidazol-1-yl)-3,4-dihydroisoquinolin-2(1H)-yl)ethyl)phenyl)-2H-tetrazol-5-yl)-4,5-dimethoxyaniline (IM2)

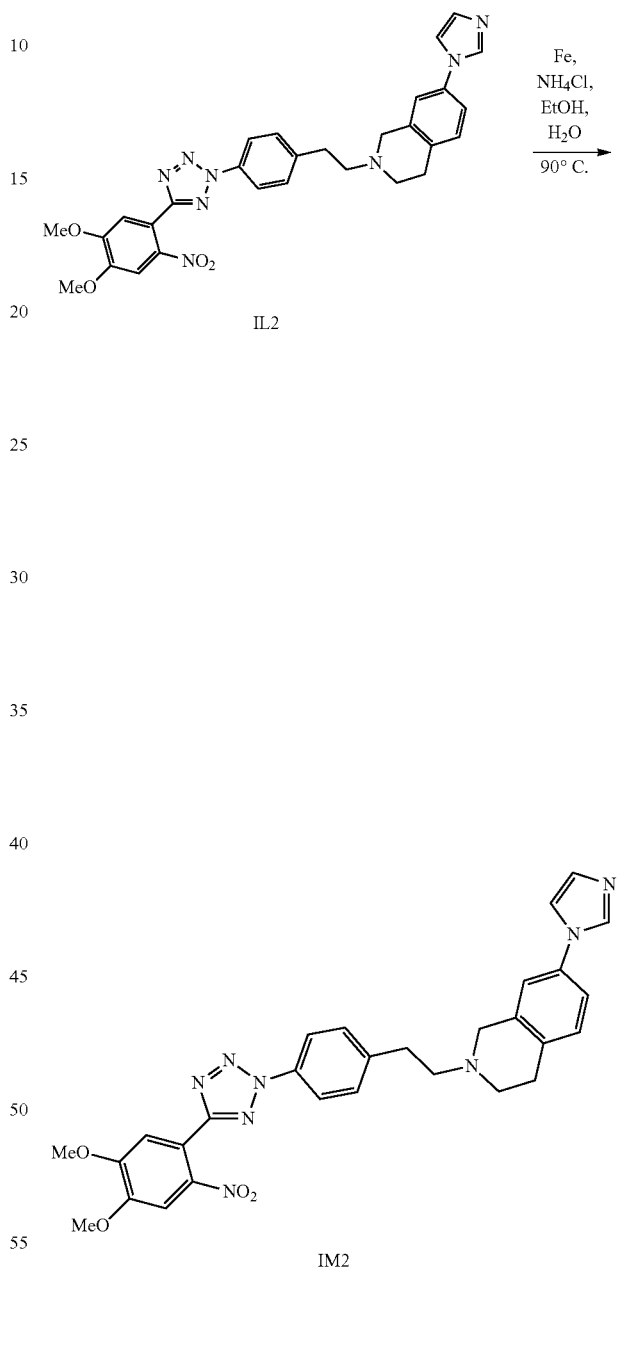

221 mg of Intermediate IL1 was used to synthesize 92 mg of the title compound (44% yield) according to the General Procedure MM. $^1$H NMR (400 MHz, CDCl$_3$): δ 2.85-2.89 (m, 4H), 2.99-3.03 (m, 4H), 3.78 (s, 2H), 3.91 (s, 3H), 3.94 (s, 3H), 5.31 (s, 2H), 7.16-7.20 (m, 4H), 7.26-7.28 (m, 2H), 7.45 (d, J=8.0 Hz, 2H), 7.72 (s, 1H), 7.84 (s, 1H), 8.10 (d, J=8.0 Hz, 2H). LC/MS (ESI, m/z): 523.09 [M+H]$^+$.

221 mg of Intermediate IL2 was used to synthesize 101 mg of the title compound (48% yield) according to the General Procedure MM. $^1$H NMR (400 MHz, CDCl$_3$): δ 2.88 (s, 4H), 3.01 (s, 4H), 3.78 (s, 2H), 3.92 (s, 6H), 5.32 (bs, 2H), 7.17-7.20 (m, 4H), 7.28 (s, 2H), 7.46 (d, J=4.0 Hz, 2H), 7.72 (s, 1H), 7.84 (s, 1H), 8.10 (d, J=8.0 Hz, 2H). LC/MS (ESI, m/z): 523.10 [M+H]$^+$.

Synthesis of Compounds of the Present Disclosure
(Scheme 2; General Procedure NN)

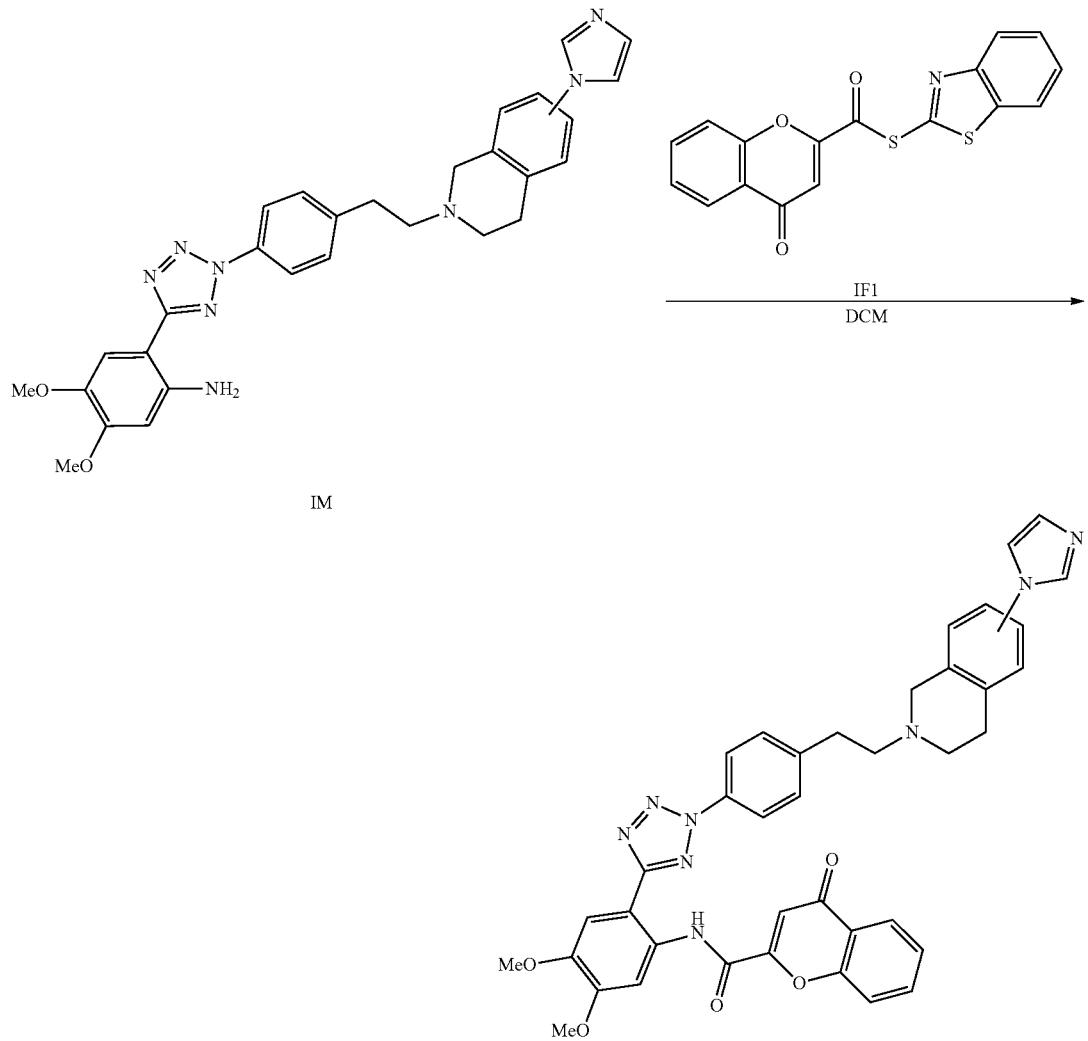

IM

A clean, dry 40 mL vial was charged with Intermediate IM (0.15 mmol, 1.0 eq.), Intermediate IF1 (0.2 mmol, 1.33 eq.), and DCM (8.0 mL). The reaction mixture was stirred at room temperature for 3 h, and upon reaction completion, the mixture was concentrated under vacuum and purified by flash chromatography on silica gel (MeOH/DCM) to give the compounds of the present disclosure.

Synthesis of 6-Methoxy-2-(4-nitrophenethyl)-1,2,3,4-tetrahydroisoquinolin-7-ol (IN) (Scheme 3)

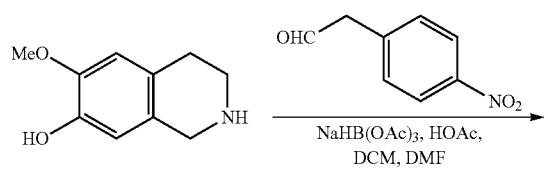

-continued

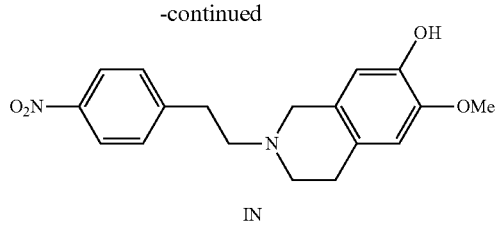

IN

A round-bottom flask was charged with 6-methoxy-1,2,3,4-tetrahydroisoquinolin-7-ol (2.95 g, 16.5 mmol, 1.0 eq.), 2-(4-nitrophenyl)acetaldehyde (2.99 g, 18.1 mmol, 1.1 eq.), and 50% DCM/DMF (60 mL). A drop of HOAc was added to the reaction mixture, and the mixture was stirred at room temperature for 4 h. Sodium triacetoxyborohydride (10.4 g, 49.5 mmol, 3 eq) was then added to the mixture, and the mixture was stirred at room temperature overnight. The product was precipitated by adding DCM (300 mL) to the mixture. Filtration, and drying of resulting solid under vacuum afforded 2.64 g of Intermediate IN (49% yield).

Synthesis of 2-(1H-Imidazol-1-yl)ethyl 4-methylbenzenesulfonate (10) (Scheme 3)

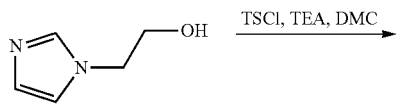

A round-bottom flask was charged with 2-(1H-imidazol-1-yl)ethan-1-ol (1.02 g, 9.1 mmol, 1.0 eq.), p-toluenesulfonyl chloride (1.91 g, 10 mmol, 1.1 eq.), and DCM (20 mL). TEA (2.54 mL, 18.2 mmol, 2.0 eq.) was added to the reaction mixture at 0° C., and the reaction mixture was stirred overnight. The mixture was then diluted with DCM (100 mL), washed with saturated sodium bicarbonate (2×100 mL) and brine (50 mL), dried using anhydrous sodium sulfate, filtered, and concentrated under vacuum to give 1.58 g of Intermediate IO (65% yield), which was used without further purification.

Synthesis of 7-(2-(1H-Imidazol-1-yl)ethoxy)-6-methoxy-2-(4-nitrophenethyl)-1,2,3,4-tetrahydroisoquinoline (IP) (Scheme 3)

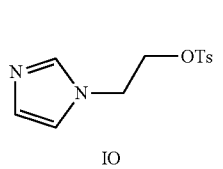

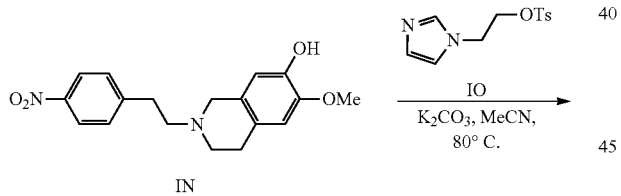

A round-bottom flask was charged with Intermediate IN (1.0 g, 3.0 mmol, 1.0 eq.), Intermediate IO (811 mg, 3.0 mmol, 1.0 eq.), anhydrous potassium carbonate (2.1 g, 15.0 mmol, 3.0 eq.), and MeCN (20 mL). The reaction mixture was heated at 80° C. and stirred overnight. The mixture was diluted with DCM (150 mL) and washed with water (2×100 mL) and brine (2×50 mL). The organic layer was separated, dried over anhydrous Na$_2$SO$_4$, filtered, and concentrated under vacuum. The residue was then purified by reverse-phase HPLC (0.1% TFA in water/MeCN) to afford 750 mg of Intermediate IP (58% yield).

Synthesis of 4-(2-(7-(2-(1H-Imidazol-1-yl)ethoxy)-6-methoxy-3,4-dihydroisoquinolin-2(1H)-yl)ethyl)aniline (IQ) (Scheme 3)

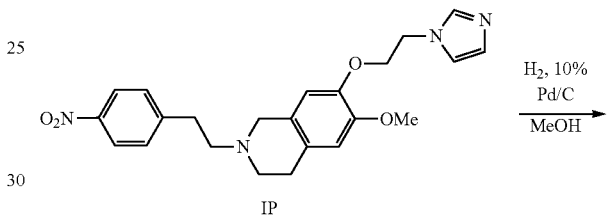

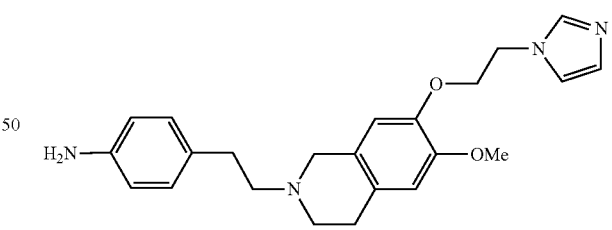

To a clean, dry hydrogenation flask were added Intermediate IP (717 mg, 1.7 mmol, 1.0 eq.), 10% palladium on activated carbon (90 mg, 0.085 mmol Pd, 0.05 eq.), and MeOH (30 mL). The flask was then charged with hydrogen at 50 psi and shook for 3 h. The reaction mixture was then filtered on Celite and concentrated under vacuum to afford 566 mg of Intermediate IQ (85% yield), which was used without further purification.

Synthesis of 7-(2-(1H-Imidazol-1-yl)ethoxy)-2-(4-(5-(4,5-dimethoxy-2-nitrophenyl)-2H-tetrazol-2-yl)phenethyl)-6-methoxy-1,2,3,4-tetrahydroisoquinoline (IR) (Scheme 3)

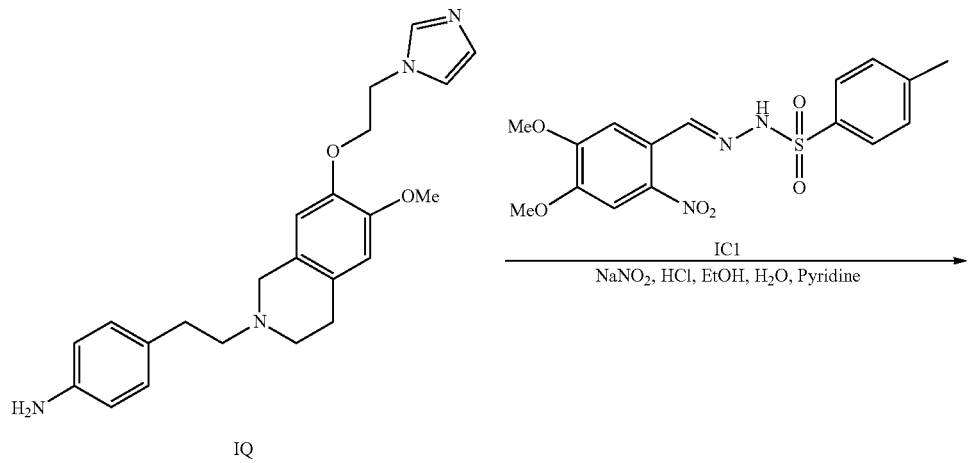

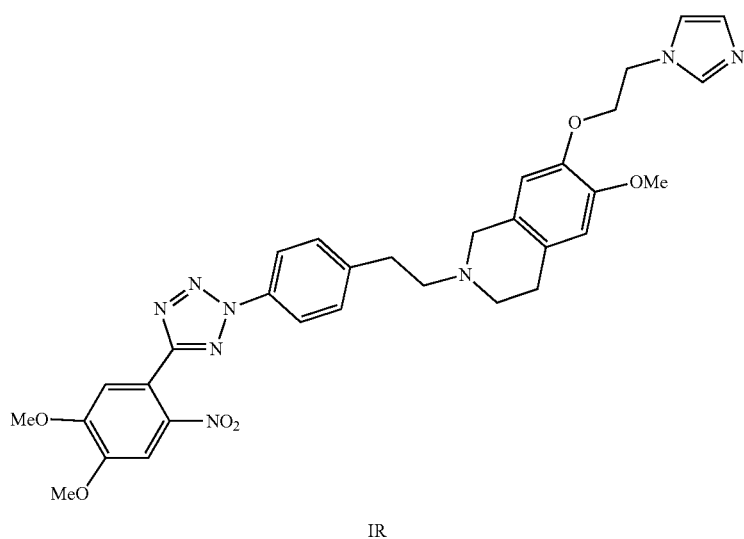

A clean, dry 40 mL vial was charged with Intermediate IQ (549 mg, 1.4 mmol, 1.0 eq.), sodium nitrite (120 mg, 1.87 mmol, 1.23 eq.), H₂O (1.8 mL), and EtOH (3.6 mL). The mixture was vortexed and cooled below 0° C. 36% HCl (0.40 mL) was then added to the mixture, and the mixture was vigorously stirred for about 5 min. In another clean, dry 40 mL vial, Intermediate IC (441 mg, 1.4 mmol, 1.0 eq) was dissolved in pyridine (7.0 mL), and this solution was gradually added to the vial containing intermediate IQ. The mixture was then stirred at room temperature overnight, and upon completion, the mixture diluted with DCM (100 mL), and washed with water and brine (2×50 mL), then dried over anhydrous Na₂SO₄, filtered, and concentrated under vacuum, and purified by reverse-phase HPLC (0.1% TFA in water/MeCN) to afford 210 mg of intermediate IR (24% yield).

Synthesis of 2-(2-(4-(2-(7-(2-(1H-Imidazol-1-yl)
ethoxy)-6-methoxy-3,4-dihydroisoquinolin-2(1H)-
yl)ethyl)phenyl)-2H-tetrazol-5-yl)-4,5-dimethoxya-
niline (IS) (Scheme 3)

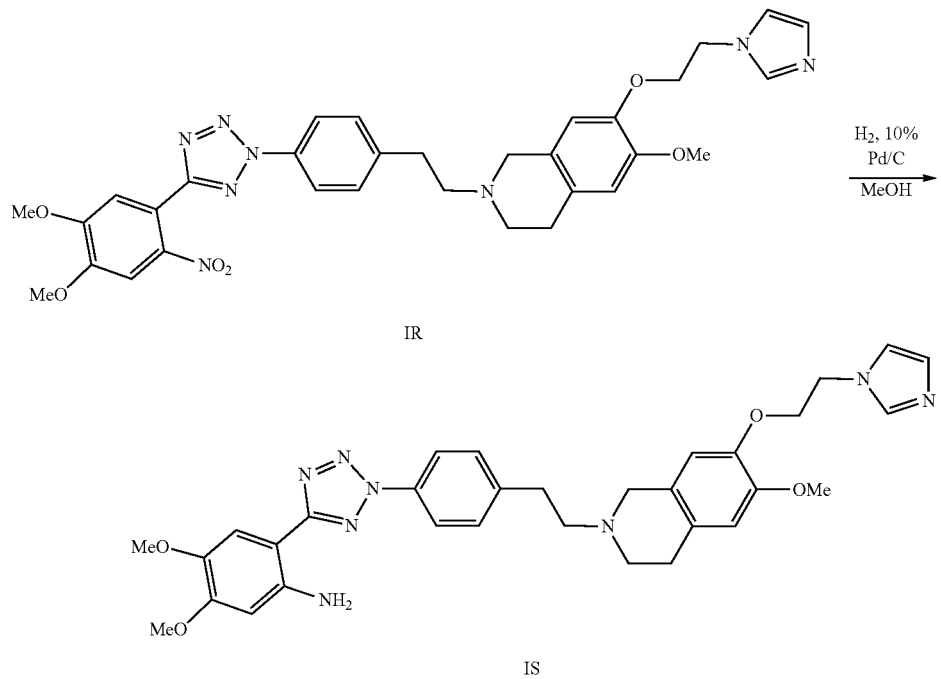

To a clean, dry hydrogenation flask were added Intermediate IR (188 mg, 0.3 mmol, 1.0 eq.), 10% palladium on activated carbon (32 mg, 0.03 mmol Pd, 0.1 eq.), and MeOH (15 mL). The flask was then charged with hydrogen at 50 psi and shook for 3 h. The reaction mixture was then filtered on Celite, concentrated under vacuum, and the residue obtained was purified by reverse-phase HPLC (0.1% TFA in water/MeCN) to afford 140 mg of intermediate IS (78% yield).

Synthesis of N-(3-(1H-Imidazol-1-yl)benzyl)-2-(4-
nitrophenyl)ethan-1-amine trifluoroacetate (IT)
(Scheme 4)

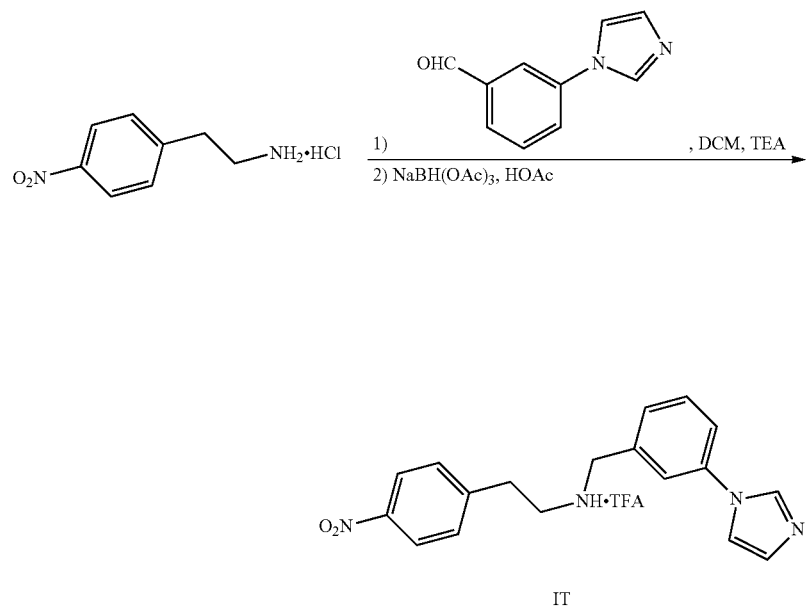

A clean, dry 40 mL vial was charged with 2-(4-nitrophenyl)ethan-1-amine hydrochloride (1.01 g, 5.0 mmol, 1.0 eq.), 3-(1H-imidazol-1-yl)benzaldehyde (860 mg, 5.0 mmol, 1.0 eq.), DCM (12 mL), and TEA (2.75 mL, 20.0 mmol, 4.0 eq.). The mixture was stirred at room temperature for 3 h. To the mixture, were added HOAc (1.44 mL, 25.0 mmol, 5.0 eq) followed by sodium triacetoxyborohydride (3.17 g, 15 mmol, 3.0 eq.), and the mixture was stirred for 2 h until reaction completion. The mixture was quenched with MeOH, concentrated under vacuum, and purified by reverse phase HPLC (0.1 TFA in water/MeCN) to afford 2.01 g of Intermediate IT as a TFA salt (92% yield).

Synthesis of N-(3-(1H-Imidazol-1-yl)benzyl)-N-((1-methyl-1H-indazol-5-yl)methyl)-2-(4-nitrophenyl)ethan-1-amine (IU) (Scheme 4)

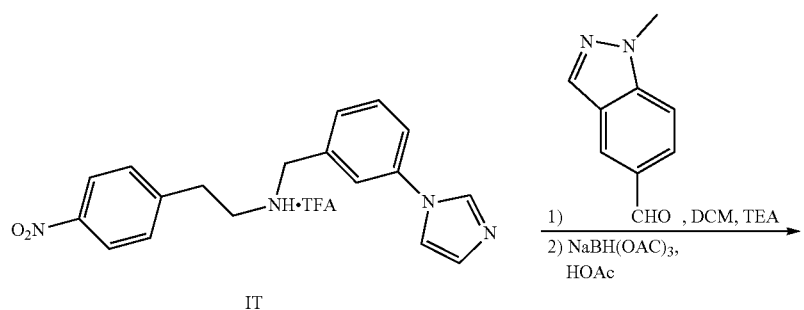

IT

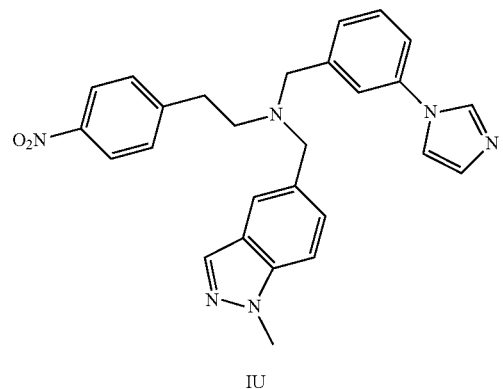

IU

A clean, dry 40 mL vial was charged with the secondary amine IT (1.96 g, 4.5 mmol, 1.0 eq.), 1-methyl-1H-indazole-5-carbaldehyde (860 mg, 5.0 mmol, 1.0 eq.), DCM (25 mL), and TEA (2.50 mL, 18.0 mmol, 4.0 eq.). The mixture was stirred at room temperature for 3 h. To the mixture, were added HOAc (1.30 mL, 22.5 mmol, 5.0 eq) followed by sodium triacetoxyborohydride (2.85 g, 13.5 mmol, 3.0 eq.), and the mixture was stirred for 3 h until reaction completion. The mixture was quenched with MeOH, diluted with DCM (150 mL), washed with saturated sodium bicarbonate (2×100 mL) and brine (50 mL), dried over anhydrous sodium sulfate, filtered, and concentrated under vacuum. The residue obtained was purified by flash chromatography on silica gel (EtOAc/Heptane) to afford 1.26 g of Intermediate IU (60% yield).

Synthesis of N-methyl-N-((1-methyl-1H-indazol-5-yl)methyl)-2-(4-nitrophenyl)ethan-1-amine (IV) (Scheme 4)

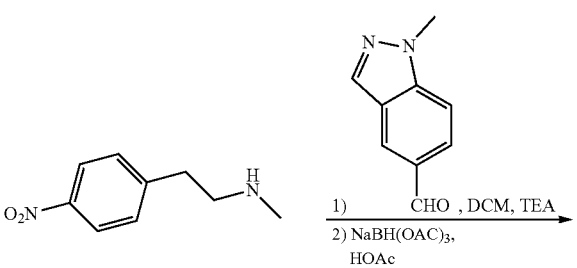

-continued

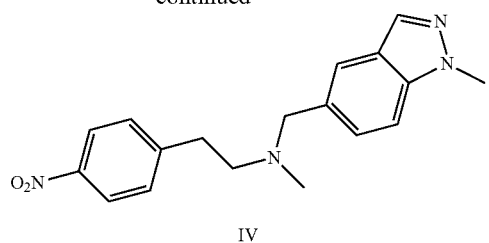

IV

A clean, dry 40 mL vial was charged with A-methyl-2-(4-nitrophenyl)ethan-1-amine (500 mg, 2.77 mmol, 1.0 eq.), 1-methyl-1H-indazole-5-carbaldehyde (450 mg, 2.77 mmol, 1.0 eq.), DMF (15 mL), and TEA (1.0 mL, 6.94 mmol, 2.5 eq.). The mixture was stirred at room temperature for 3 h. To the mixture, were added HOAc (0.50 mL, 8.31 mmol, 3.0 eq.) followed by sodium triacetoxyborohydride (1.76 g, 8.31 mmol, 3.0 eq.) and stirring continued overnight at room temperature. Upon completion of the reaction, the reaction mixture was quenched with MeOH, diluted with DCM (150 mL), and washed with water (2×100 mL) and brine (2×50 mL). The organic layer was dried over $Na_2SO_4$, filtered, and concentrated to afford the crude product which was then purified by flash chromatography on silica gel (MeOH/DCM) to afford 420 mg of Intermediate IV (47% yield).

Synthesis of Intermediate IW (Scheme 4; General Procedure OO)

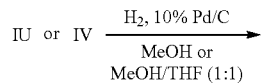

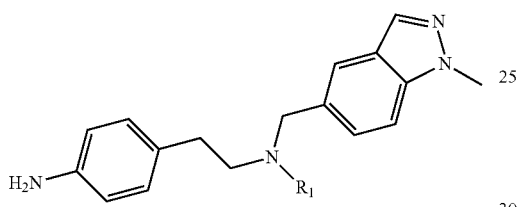

IW

To a clean, dry hydrogenation flask were added Intermediate IU or Intermediate IV (1.2-2.0 mmol, 1.0 eq.), 10% palladium on activated carbon (64-106 mg, 0.06-0.10 mmol Pd, 0.05 eq.), and either MeOH or 1:1 MeOH/THF (50 mL). The flask was then charged with hydrogen at 50 psi and shook for 3-5 h. The reaction mixture was then filtered on Celite and concentrated under vacuum to afford Intermediate IW, which was used without further purification.

Synthesis of 4-(2-((3-(1H-Imidazol-1-yl)benzyl)((1-methyl-1H-indazol-5-yl)methyl)amino)ethyl)aniline (IW1) (Scheme 4)

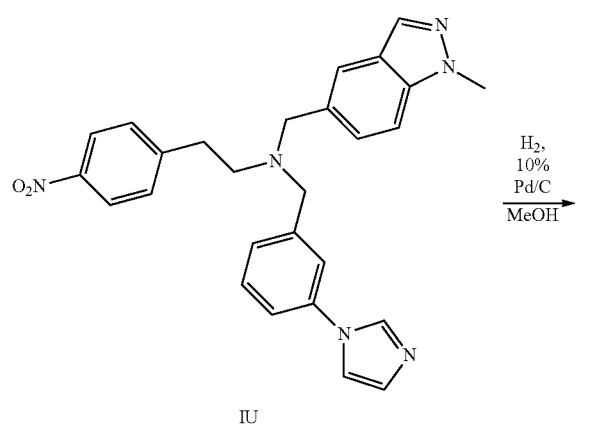

IU

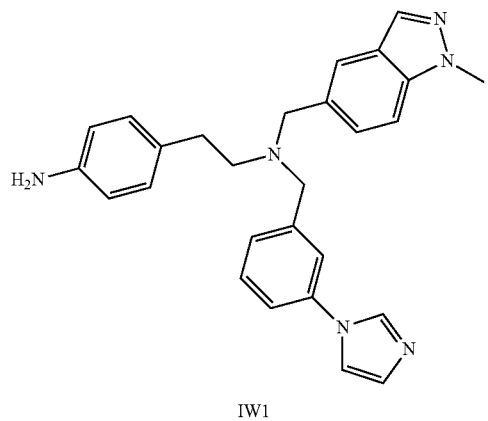

IW1

932 mg of Intermediate IU was hydrogenated in MeOH using 106 mg Pd/C to afford 823 mg of the title compound (94% yield) according to the General Procedure OO Synthesis of 4-(2-(Methyl((1-methyl-1H-indazol-5-yl)methyl)amino)ethyl)aniline (IW2) (Scheme

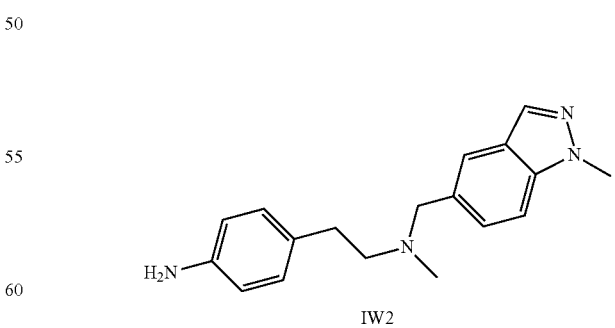

IW2

400 mg of Intermediate IV was hydrogenated in 1:1 MeOH/THF using 63 mg Pd/C to afford 320 mg of the title compound (91% yield) according to the General Procedure OO.

Synthesis of Intermediate IX (Scheme 4; General Procedure PP)

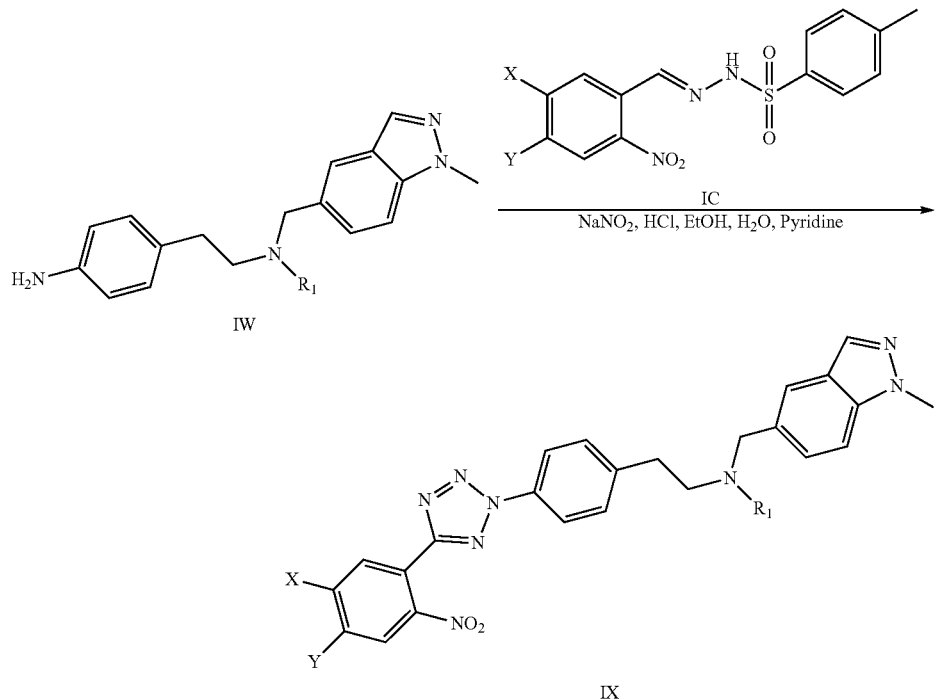

A clean, dry 40 mL vial was charged with Intermediate IW (1.0 mmol, 1.0 eq.), sodium nitrite (85 mg, 1.23 mmol, 1.23 eq.), H$_2$O (1.8 mL), and EtOH (3.2 mL). The mixture was vortexed and cooled below 0° C. 36% HCl (0.25 mL) was then added to the mixture, and the mixture was vigorously stirred for about 5 min. In another clean, dry 40 mL vial, Intermediate IC (1.0 mmol, 1.0 eq) was dissolved in pyridine (5.0 mL), and this solution was gradually added to the vial containing intermediate IW. The mixture was then stirred at room temperature overnight, and upon completion, the mixture was diluted with DCM (100 mL) and washed with water followed by brine (2×50 mL), then dried over anhydrous Na$_2$SO$_4$, filtered, and concentrated under vacuum. The residue was purified by reverse-phase HPLC (0.1 TFA in water/MeOH) or by flash chromatography on silica gel (MeOH/DCM) to afford Intermediate IX.

Synthesis of N-(3-(1H-Imidazol-1-yl)benzyl)-2-(4-(5-(4,5-dimethoxy-2-nitrophenyl)-2H-tetrazol-2-yl)phenyl)-N-((1-methyl-1H-indazol-5-yl)methyl)ethan-1-amine (IX1) (Scheme 4)

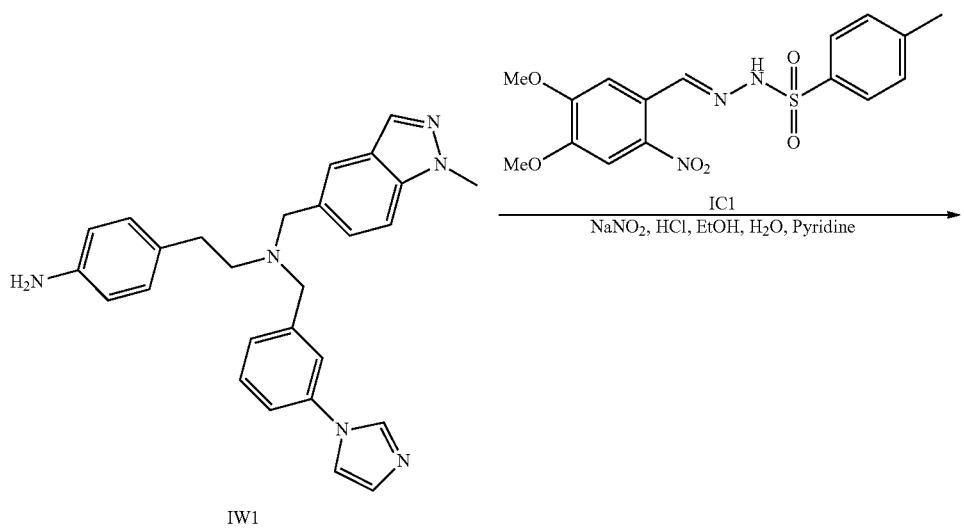

-continued

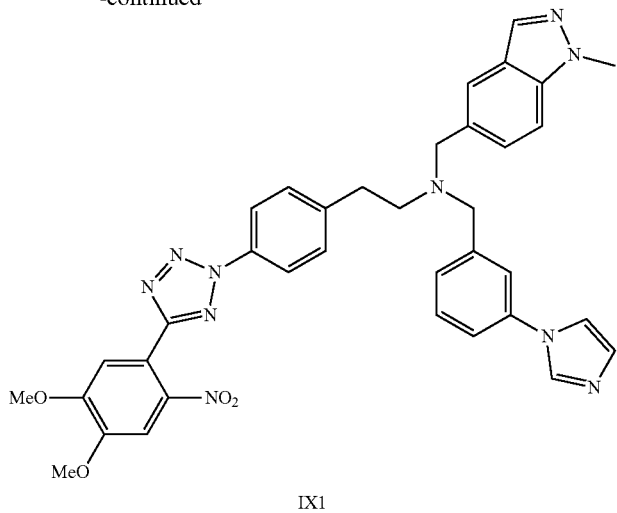

IX1

436 mg of Intermediate IW1 and 315 mg of Intermediate IC1 were used to synthesize 404 mg of the title compound (60% yield) according to the General Procedure PP.

Synthesis of Methyl 4-(2-(4-(2-(methyl((1-methyl-1H-indazol-5-yl)methyl)amino)ethyl)phenyl)-2H-tetrazol-5-yl)-3-nitrobenzoate (IX2) (Scheme 4)

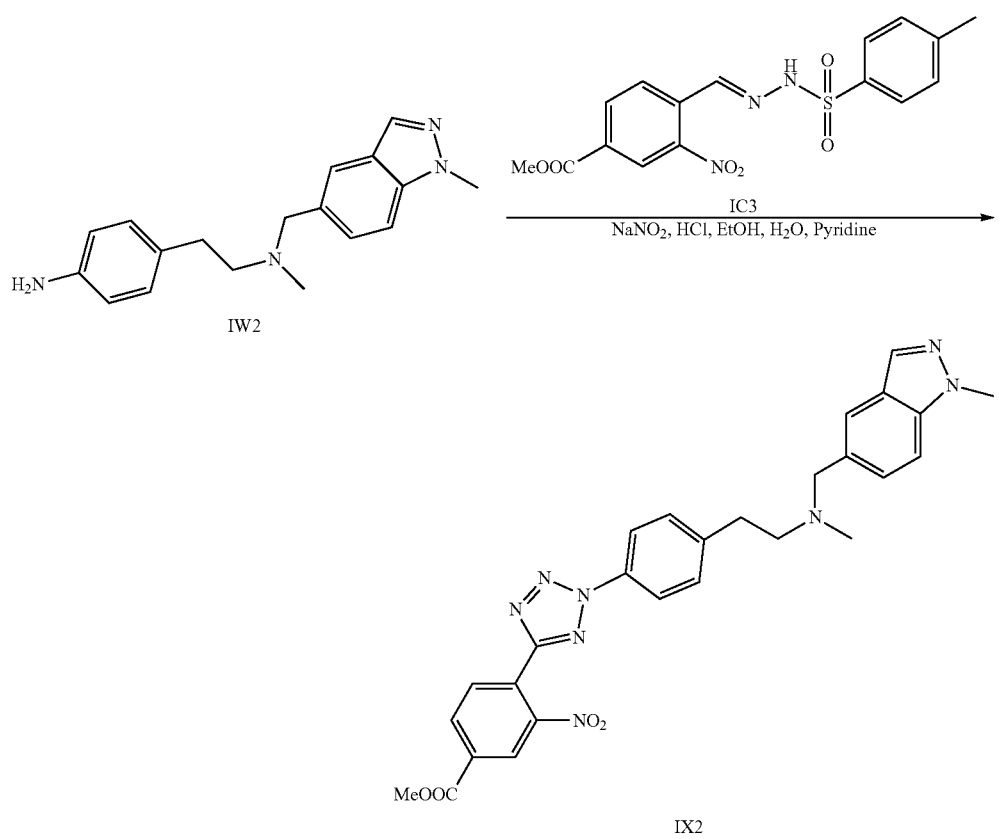

294 mg of Intermediate IW2 and 313 mg of Intermediate IC3 were used to synthesize 290 mg of the title compound (55% yield) according to the General Procedure PP.

Synthesis of Intermediate IY (Scheme 4; General Procedure QQ)

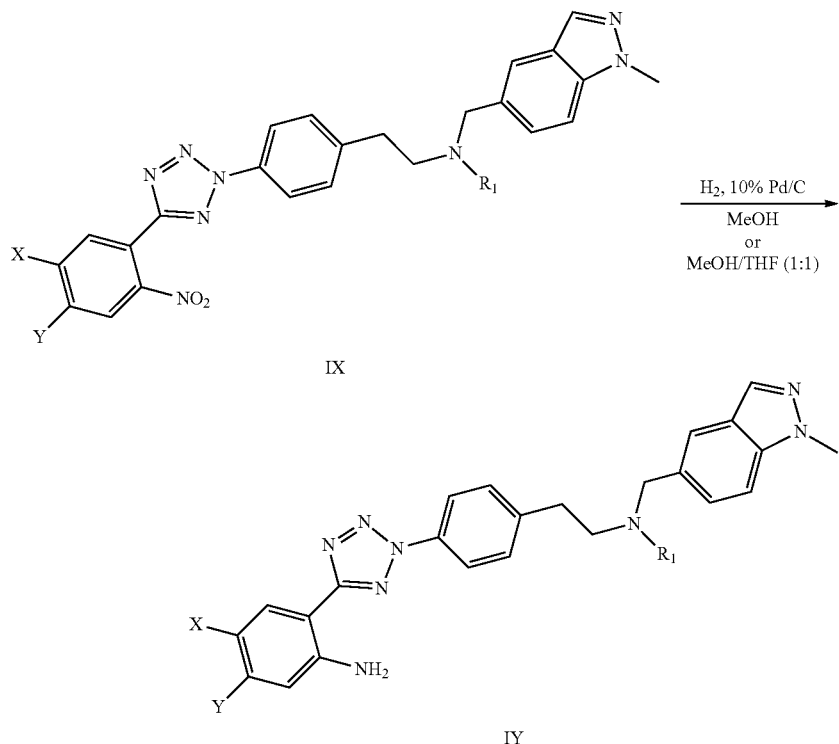

To a clean, dry hydrogenation flask were added Intermediate IX (0.56 mmol, 1.0 eq.), 10% palladium on activated carbon (30 mg, 0.028 mmol Pd, 0.05 eq.), and either MeOH or 1:1 MeOH/THF (25 mL). The flask was then charged with hydrogen at 50 psi and shook for 3 h. The reaction mixture was then filtered on Celite and concentrated under vacuum to afford Intermediate IY, which was used without further purification.

Synthesis of 2-(2-(4-(2-((3-(1H-Imidazol-1-yl)benzyl)((1-methyl-1H-indazol-5-yl)methyl)amino)ethyl)phenyl)-2H-tetrazol-5-yl)-4,5-dimethoxyaniline (IY1) (Scheme 4)

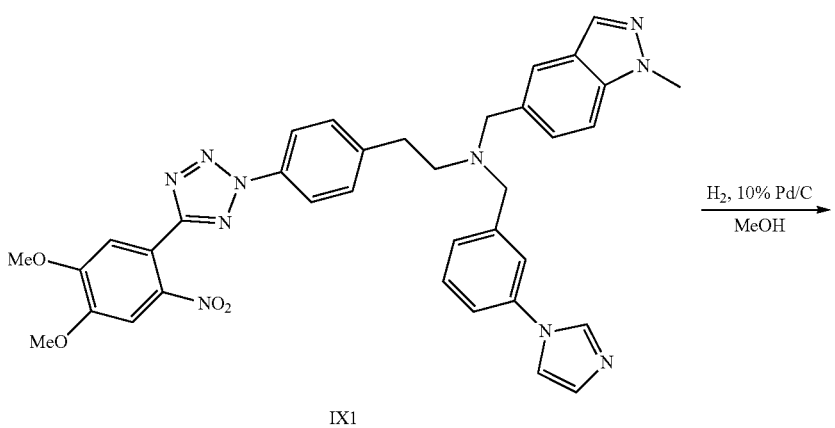

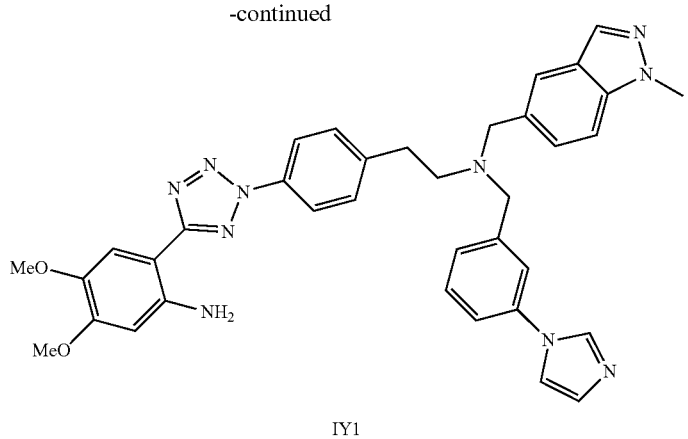

IY1

375 mg of Intermediate IX1 was hydrogenated in MeOH to afford 333 mg of the title compound (93% yield) according to the General Procedure QQ.

Synthesis of Methyl 3-amino-4-(2-(4-(2-(methyl((1-methyl-1H-indazol-5-yl)methyl)amino)ethyl)phenyl)-2H-tetrazol-5-yl) benzoate (IY2) (Scheme 4)

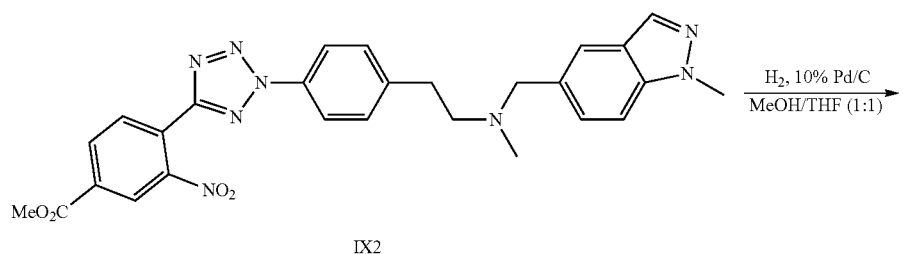

IX2

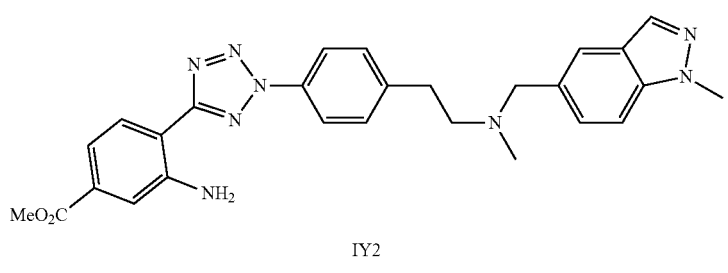

IY2

295 mg of Intermediate IX2 was hydrogenated in 1:1 MeOH/THF to afford 150 mg of the title compound (54% yield) according to the General Procedure QQ.

General Procedure RR for the Synthesis of the Final Compounds (Scheme 4)

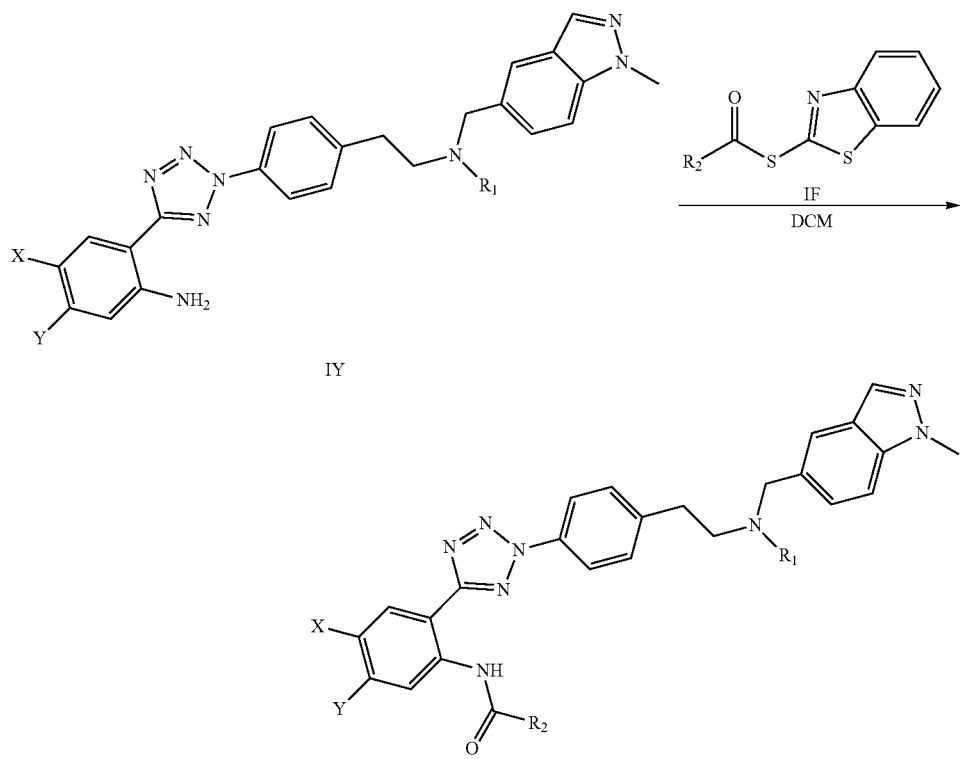

A clean, dry 40 mL vial was charged with Intermediate IY (0.15-0.30 mmol, 1.0 eq.), Intermediate IF (0.20-0.40 mmol, 1.33 eq.), and DCM (10.0 mL). The reaction mixture was stirred at room temperature for 3 h, and upon reaction completion, the mixture was concentrated under vacuum and purified by reverse-phase HPLC (0.1% TFA in water/MeCN). The product was then dissolved in 10% MeOH/DCM, followed by extraction with 1.0 M NaOH, drying over anhydrous sodium sulfate, filtration, and removal of the solvent under vacuum to give the final product as a free base. Alternatively, the product was purified by flash chromatography on silica gel (MeOH/DCM) to give the product as a free base.

Synthesis of 2-Nitro-5-(pyridin-3-yloxy)benzaldehyde (A2)

A clean, dry 40 mL vial was charged with 5-fluoro-2-nitrobenzaldehyde A1 (0.9 g, 5.32 mmol), pyridin-3-ol (0.75 g, 7.98 mmol), anhydrous $K_2CO_3$ (2.2 g, 15.97 mmol) and anhydrous acetonitrile (25 mL). The reaction mixture was stirred at 90° C. for 4 h. Upon completion (monitored by LC/MS), the mixture was filtered, and concentrated under reduced pressure to afford the residue, which was purified by flash column chromatography on silica gel (0-100% n-heptane/ethyl acetate) to afford A2 (0.76 g, 58%). $^1$H NMR (400 MHz, DMSO-$d_6$): δ 7.32 (d, J=4.0 Hz, 1H), 7.42-7.45 (m, 1H), 7.54-7.58 (m, 1H), 7.71-7.74 (m, 1H), 8.23 (d, J=8.0 Hz, 1H), 8.54-8.56 (m, 2H), 10.26 (s, 1H). LC/MS (ESI, m/z): 245.21 $[M+H]^+$.

Synthesis of (E/Z)-4-Methyl-N'-(2-nitro-5-(pyridin-3-yloxy)benzylidene)benzenesulfonohydrazide (IC5)

A clean, dry 40 mL vial was charged with A2 (0.65 g, 2.66 mmol), p-toluenesulfonhydrazide (0.49 g, 2.66 mmol), and EtOH (20 mL). The reaction mixture was stirred at 80° C. for 1 h. After cooling to room temperature, the reaction mixture was diluted with water. The solid obtained was filtered, washed with 50% aq EtOH, and dried under reduced pressure to afford IC5 (0.72 g, 65%), which was used without further purification. $^1$H NMR (400 MHz, DMSO-$d_6$): δ 2.39 (s, 3H), 7.16 (d, J=4.0 Hz, 1H), 7.24-7.27 (m, 1H), 7.35 (d, J=8.0 Hz, 2H), 7.59-7.62 (m, 3H), 7.70-7.74 (m, 1H), 8.12 (d, J=12.0 Hz, 1H), 8.32 (s, 1H), 8.55 (s, 1H), 8.61-8.62 (m, 1H), 11.93 (s, 1H). LC/MS (ESI, m/z): 413.34 $[M+H]^+$.

Synthesis of 6,7-Dimethoxy-2-(4-(5-(2-nitro-5-(pyridin-3-yloxy)phenyl)-2H-tetrazol-2-yl)phenethyl)-1,2,3,4-tetrahydroisoquinoline (ID9)

A clean, dry 40 mL vial was charged with IB4 (0.26 g, 0.84 mmol), sodium nitrite (0.071 g, 1.03 mmol), $H_2O$ (2 mL), and EtOH (6 mL). The mixture was vortexed and cooled to ~−15° C. (ice/salt bath). A 36% HCl solution (0.3 mL) was then added to the mixture, and the mixture was vigorously stirred for about 5 min. In another clean, dry 40 mL vial, IC9 (0.35 g, 0.84 mmol) was dissolved in pyridine (5 mL), and this solution was gradually added to the vial containing IB4. The mixture was stirred overnight at room temperature. Upon completion (monitored by LC/MS), the mixture was diluted with DCM (75 mL), washed with water followed by brine (2×50 mL), dried ($Na_2SO_4$), and concentrated under reduced pressure to afford the crude residue, which was purified by flash column chromatography on silica gel (0-5% MeOH/DCM) to afford ID9 (0.20 g, 41%). $^1$H NMR (400 MHz, DMSO-d$_6$): δ 2.71-2.76 (m, 6H), 2.93 (t, J=12.0 Hz, 2H), 3.55 (s, 2H), 3.69 (s, 3H), 3.70 (s, 3H), 6.63 (d, J=8.0 Hz, 2H), 7.41-7.44 (m, 1H), 7.53-7.59 (m, 4H), 7.74-7.78 (m, 1H), 7.99 (d, J=8.0 Hz, 2H), 8.22 (d, J=8.0 Hz, 1H), 8.52-8.60 (m, 2H). LC/MS (ESI, m/z): 580.21 [M+H]$^+$.

Synthesis of 2-(2-(4-(2-(6,7-Dimethoxy-3,4-dihydroisoquinolin-2(1H)-yl)ethyl)phenyl)-2H-tetrazol-5-yl)-4-(pyridin-3-yloxy)aniline (IE9)

A clean, dry 40 mL vial was charged with ID9 (0.18 g, 0.31 mmol), iron (0.17 g, 3.10 mmol), ammonium chloride (0.16 g, 3.10 mmol), EtOH (7 mL), and water (1.5 mL). The mixture reaction was stirred at 90° C. for 1 h. Upon completion (monitored by LC/MS), the mixture was filtered while hot through a plug of Celite and washed with DCM. The filtrate was washed with saturated NaHCO$_3$ (2×50 mL), brine (1×50 mL), dried (Na$_2$SO$_4$), and concentrated under reduced pressure to afford the crude residue, which was purified by flash column chromatography on silica gel (0-5% MeOH/DCM) to afford IE9 (0.14 g, 82%). $^1$H NMR (400 MHz, DMSO-d$_6$): δ 2.71-2.76 (m, 6H), 2.93 (t, J=12.0 Hz, 2H), 3.55 (s, 2H), 3.69 (s, 3H), 3.70 (s, 3H), 6.39 (s, 2H), 6.63 (d, j=8.0 Hz, 2H), 7.00-7.13 (m, 2H), 7.35-7.37 (m, 2H), 7.55 (d, J=8.0 Hz, 2H), 7.74 (s, 1H), 8.09 (d, J=12.0 Hz, 2H), 8.29-8.36 (m, 2H). LC/MS (ESI, m/z): 550.18 [M+H]$^+$.

Synthesis of 2-Nitro-5-(pyridin-4-yloxy)benzaldehyde (A3)

A clean, dry 40 mL vial was charged with 5-fluoro-2-nitrobenzaldehyde A1 (1.69 g, 10 mmol), pyridin-4-ol (1.05 g, 11 mmol), anhydrous K$_2$CO$_3$ (2.09 g, 15 mmol) and anhydrous acetonitrile (15 mL). The reaction mixture was stirred at 100° C. for 4 h. Upon completion (monitored by LC/MS), the mixture was filtered, and concentrated under reduced pressure to afford the residue, which was crystallized from EtOH to afford A3 (1.42 g, 58%). $^1$H NMR (400 MHz, DMSO-d$_6$): δ 6.30 (d, J=8.0 Hz, 2H), 8.04-8.09 (m, 2H), 8.17 (d, J=8.0 Hz, 2H), 8.34 (d, J=8.8 Hz, 1H), 10.30 (s, 1H). LC/MS (ESI, m/z): 245.00 [M+H]$^+$.

Synthesis of (E/Z)-4-Methyl-N'-(2-nitro-5-(pyridin-4-yloxy)benzylidene)benzenesulfonohydrazide (IC4)

A clean, dry 40 mL vial was charged with A3 (0.732 g, 3.0 mmol), p-toluenesulfonhydrazide (0.558 g, 3.0 mmol), and EtOH (20 mL). The reaction mixture was stirred at 80° C. for 3 h. After cooling to room temperature, the reaction mixture was diluted with water. The solid obtained was filtered, washed with 50% aq EtOH, and dried under reduced pressure to afford IC4 (0.767 g, 62%), which was used without further purification. $^1$H NMR (400 MHz, DMSO-d$_6$): δ 2.37 (s, 3H), 6.33 (d, J=8.0 Hz, 2H), 7.42 (d, J=8.0 Hz, 2H), 7.74 (d, j=2.8 Hz, 1H), 7.78, 7.80 (2s, 2H), 7.83 (d, j=2.8 Hz, 1H), 8.08 (d, j=8.0 Hz, 2H), 8.20 (d, j=9.2 Hz, 1H), 8.31 (s, 1H), 12.04 (s, 1H). LC/MS (ESI, m/z): 413.08 [M+H]$^+$.

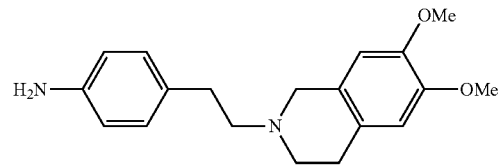

Synthesis of 6,7-Dimethoxy-2-(4-(5-(2-nitro-5-(pyridin-4-yloxy)phenyl)-2H-tetrazol-2-yl)phenethyl)-1,2,3,4-tetrahydroisoquinoline (ID10)

A clean, dry 40 mL vial was charged with IB4 (609 g, 1.95 mmol), sodium nitrite (0.0165 g, 2.43 mmol), H$_2$O (2.5 mL), and EtOH (7.5 mL). The mixture was vortexed and cooled to ~−15° C. (ice/salt bath). A 36% HCl solution (0.75 mL) was then added to the mixture, and the mixture was vigorously stirred for about 5 min. In another clean, dry 40 mL vial, IC4 (0.803 g, 1.95 mmol) was dissolved in pyridine (5 mL), and this solution was gradually added to the vial containing IB4. The mixture was stirred overnight at room temperature. Upon completion (monitored by LC/MS), the mixture was diluted with DCM (75 mL), washed with water followed by brine (2×50 mL), dried (Na$_2$SO$_4$), and concentrated under reduced pressure to afford the crude residue, which was purified by flash column chromatography on silica gel (0-10% MeOH/DCM) to afford ID10 (0.351 g, 31%). $^1$H NMR (400 MHz, DMSO-d$_6$): δ 2.72-2.78 (m, 6H), 2.97 (t, j=7.4 Hz, 2H), 3.56 (s, 2H), 3.70 (2s, 6H), 6.31 (m, 2H), 6.63 (s, 1H), 6.66 (s, 1H), 7.61 (d, j=8.8 Hz, 2H), 8.04-8.09 (m, 3H), 8.17-8.21 (m, 2H), 8.27 (d, j=2.4 Hz, 1H), 8.36 (d, j=8.8 Hz, 1H). LC/MS (ESI, m/z): 580.19 [M+H]$^+$.

Synthesis of 2-(2-(4-(2-(6,7-Dimethoxy-3,4-dihydroisoquinolin-2(1H)-yl)ethyl)phenyl)-2H-tetrazol-5-yl)-4-(pyridin-4-yloxy)aniline (IE10)

A clean, dry 40 mL vial was charged with ID10 (0.260 g, 0.45 mmol), iron (0.249 g, 4.50 mmol), ammonium chloride (0.048 g, 0.90 mmol), EtOH (5 mL), and water (0.75 mL). The mixture reaction was stirred at 90° C. for 2 h. Upon completion (monitored by LC/MS), the mixture was filtered while hot through a plug of Celite and washed with EtOH (3×) followed by DCM (3×). The filtrate was diluted with DCM up to 150 mL, washed with saturated NaHCO$_3$ (1×100 mL), brine (1×100 mL), dried (Na$_2$SO$_4$), and concentrated under reduced pressure to afford IE10 (0.172 g, 69%), which was used without further purification. $^1$H NMR (400 MHz, DMSO-d$_6$): δ 2.70-2.80 (m, 6H), 2.97 (t, J=7.4 Hz, 2H), 3.57 (s, 2H), 3.70 (2s, 6H), 6.22 (m, 2H), 6.64 (s, 1H), 6.66 (s, 1H), 6.68 (bs, 2H), 7.06 (d, J=8.8 Hz, 1H), 7.43 (dd, j=8.8, 2.8 Hz, 1H), 7.59 (d, J=8.8 Hz, 2H), 7.91-7.93 (m, 2H), 8.07 (d, j=6.8 Hz, 1H), 8.16 (d, j=8.4 Hz, 2H). LC/MS (ESI, m/z): 550.09 [M+H]$^+$.

Synthesis of N'-(5-Hydroxy-2-nitrobenzylidene)-4-methylbenzenesulfonohydrazide (IC6)

A clean, dry 40 mL vial was charged with 5-hydroxy-2-nitrobenzaldehyde A4 (0.75 g, 4.49 mmol), p-toluenesulfonhydrazide (0.83 g, 4.49 mmol), and EtOH (20 mL). The reaction mixture was stirred at 80° C. for 1 h. The reaction mixture was stirred at 80° C. for 1 h. The solid obtained was filtered, washed with 50% aq EtOH, and dried under reduced pressure to afford IC6 (0.85 g, 65%), which was used without further purification. $^1$H NMR (400 MHz, DMSO-d$_6$): δ 2.38 (s, 3H), 6.92 (d, J=12.0 Hz, 1H), 7.17 (s, 1H), 7.42 (d, J=8.0 Hz, 2H), 7.75 (d, J=8.0 Hz, 2H), 7.99 (d, j=12.0 Hz, 1H), 8.40 (s, 1H), 11.06 (s, 1H), 11.88 (s, 1H). LC/MS (ESI, m/z): 336.19 [M+H]$^+$.

Synthesis of 3-(2-(4-(2-(6,7-Dimethoxy-3,4-dihydroisoquinolin-2(1H)-yl)ethyl)phenyl)-2H-tetrazol-5-yl)-4-nitrophenol (ID12)

A clean, dry 40 mL vial was charged with IB4 (0.36 g, 1.17 mmol), sodium nitrite (0.09 g, 1.44 mmol), H$_2$O (2 mL), and EtOH (6 mL). The mixture was vortexed and cooled to ~−15° C. (ice/salt bath). A 36% HCl solution (0.3 mL) was then added to the mixture, and the mixture was vigorously stirred for about 5 min. In another clean, dry 40 mL vial, IC6 (0.39 g, 1.17 mmol) was dissolved in pyridine (5 mL), and this solution was gradually added to the vial containing IB4. The mixture was stirred overnight at room temperature. Upon completion (monitored by LC/MS), the mixture was concentrated under reduced pressure to afford ID12 (0.38 g, 64%), which was used without further purification. LC/MS (ESI, m/z): 503.24 [M+H]$^+$.

Synthesis of 6,7-Dimethoxy-2-(4-(5-(2-nitro-5-(pyridin-4-ylmethoxy)phenyl)-2H-tetrazol-2-yl)phenethyl)-1,2,3,4-tetrahydroisoquinoline (ID12-1)

A clean, dry 40 mL vial was charged with ID12 (0.38 g, 0.75 mmol), 4-(bromomethyl)pyridine (0.19 g, 1.13 mmol), anhydrous K$_2$CO$_3$ (0.31 g, 2.27 mmol) and anhydrous DMF (5 mL). The mixture was stirred at 85° C. overnight. Upon completion (monitored by LC/MS), the mixture was diluted with DCM (75 mL), washed with water, brine (2×50 mL), dried (Na$_2$SO$_4$), and concentrated under reduced pressure to afford the crude residue, which was purified by flash column chromatography on silica gel (0-5% MeOH/DCM) to afford ID12-1 (0.24 g, 34%). $^1$H NMR (400 MHz, DMSO-d$_6$): δ 2.65-2.72 (m, 6H), 2.89-2.91 (m, 2H), 3.54 (s, 2H), 3.71 (s, 6H), 5.24 (s, 2H), 6.65 (s, 1H), 6.69 (s, 1H), 7.32-7.55 (m, 5H), 7.65 (d, J=8.0 Hz, 2H), 7.98 (d, J=8.0 Hz, 2H), 8.25 (d, J=8.0 Hz, 2H). LC/MS (ESI, m/z): 594.09 [M+H]$^+$.

Synthesis of 2-(2-(4-(2-(6,7-Dimethoxy-3,4-dihydroisoquinolin-2(1H)-yl)ethyl)phenyl)-2H-tetrazol-5-yl)-4-(pyridin-4-ylmethoxy)aniline (IE12)

A clean, dry 40 mL vial was charged with ID12-1 (0.19 g, 0.32 mmol), iron (0.17 g, 3.20 mmol), ammonium chloride (0.16 g, 3.20 mmol), EtOH (7 mL), and water (1.5 mL). The mixture reaction was stirred at 90° C. for 1 h. Upon completion (monitored by LC/MS), the mixture was filtered while hot through a plug of Celite and washed with DCM. The filtrate was washed with saturated NaHCO$_3$ (2×50 mL), brine (1×50 mL), dried (Na$_2$SO$_4$), and concentrated under reduced pressure to afford the crude residue, which was purified by flash column chromatography on silica gel (0-5% MeOH/DCM) to afford IE12 (0.10 g, 93%). $^1$H NMR (400 MHz, DMSO-d$_6$): δ 2.65-2.72 (m, 6H), 2.91 (t, J=12.0 Hz, 2H), 3.54 (s, 2H), 3.71 (s, 6H), 5.24 (s, 2H), 6.69 (s, 2H), 6.71 (d, J=12.0 Hz, 2H), 7.29 (s, 2H), 7.31-7.54 (m, 3H), 7.63 (d, J=8.0 Hz, 2H), 8.01 (d, J=8.0 Hz, 2H), 8.24 (d, J=8.0 Hz, 2H). LC/MS (ESI, m/z): 564.16 [M+H]$^+$.

Synthesis of 2-Nitro-5-(pyridin-3-ylmethoxy)benzaldehyde (A5)

A clean, dry 40 mL vial was charged with 5-hydroxy-2-nitrobenzaldehyde A4 (1.0 g, 5.98 mmol), 3-(bromomethyl)pyridine (1.54 g, 8.98 mmol), anhydrous K$_2$CO$_3$ (2.47 g, 17.96 mmol) and DMF (25 mL). The reaction mixture was stirred overnight at 90° C. Upon completion (monitored by LC/MS), the mixture was diluted with DCM (50 mL) and washed with water (2×75 mL) followed by brine (2×75 mL). The organic layer was separated, dried (Na$_2$SO$_4$), and concentrated under reduced pressure to afford the crude residue, which was purified by flash column chromatography on silica gel (0-100% EtOAc/n-heptane) to afford A5 (0.75 g, 49%). $^1$H NMR (400 MHz, DMSO-d$_6$): δ 5.26 (s, 2H), 7.23 (d, J=8.0 Hz, 1H), 7.45-7.46 (m, 3H), 7.59 (d, J=12.0 Hz, 1H), 8.59 (d, J=4.0 Hz, 2H), 9.83 (s, 1H). LC/MS (ESI, m/z): 259.19 [M+H]$^+$.

Synthesis of 4-Methyl-N'-(2-nitro-5-(pyridin-3-ylmethoxy)benzylidene)benzenesulfonohydrazide (IC8)

A clean, dry 40 mL vial was charged with A5 (0.65 g, 2.51 mmol), p-toluenesulfonohydrazide (0.46 g, 2.51 mmol), and EtOH (20 mL). The reaction mixture was stirred at 80° C. for 1 h, cooled to room temperature, and diluted with water (50 mL). The solid obtained was filtered, washed with 50% aq EtOH, and dried under reduced pressure to afford IC8 (0.78 g, 73%), which was used without further purification. $^1$H NMR (400 MHz, DMSO-d$_6$): δ 2.36 (s, 3H), 5.31 (s, 2H), 7.24-7.28 (m, 2H), 7.41-7.48 (m, 3H), 7.77 (d, J=8.0 Hz, 2H), 7.90 (d, J=4.0 Hz, 1H), 8.09 (d, J=8.0 Hz, 1H), 8.38 (s, 1H), 8.59 (d, J=4.0 Hz, 1H), 8.71 (s, 1H), 11.91 (s, 1H). LC/MS (ESI, m/z): 427.23 [M+H]$^+$.

Synthesis of 6,7-Dimethoxy-2-(4-(5-(2-nitro-5-(pyridin-3-ylmethoxy)phenyl)-2H-tetrazol-2-yl)phenethyl)-1,2,3,4-tetrahydroisoquinoline (ID8)

A clean, dry 40 mL vial was charged with IB4 (0.26 g, 0.84 mmol), sodium nitrite (0.071 g, 1.04 mmol), H$_2$O (2 mL), and EtOH (6 mL). The mixture was vortexed and cooled to ~−15° C. (ice/salt bath). A 36% HCl solution (0.26 mL) was then added to the mixture, and the mixture was vigorously stirred for about 5 min. In another clean, dry 40 mL vial, IC8 (0.36 g, 0.84 mmol) was dissolved in pyridine (5 mL), and this solution was gradually added to the vial containing IB4. The mixture was stirred overnight at room temperature. Upon completion (monitored by LC/MS), the mixture was diluted with DCM (75 mL), washed with water, brine (2×50 mL), dried (Na$_2$SO$_4$), and concentrated under reduced pressure to afford the crude residue, which was purified by flash column chromatography on silica gel (5% MeOH/DCM) to afford ID8 (0.21 g, 42%). $^1$H NMR (400 MHz, DMSO-d$_6$): δ 2.72-2.77 (m, 6H), 2.95 (t, J=12.0 Hz, 2H), 3.56 (s, 2H), 3.70 (s, 6H), 5.39 (s, 2H), 6.63 (d, J=12.0 Hz, 2H), 7.45-7.50 (m, 2H), 7.59-7.61 (m, 3H), 7.92-7.94 (m, 1H), 8.03 (d, J=8.0 Hz, 2H), 8.21 (d, J=8.0 Hz, 1H), 8.58 (d, J=8.0 Hz, 1H), 8.73 (s, 1H). LC/MS (ESI, m/z): 594.15 [M+H]$^+$.

Synthesis of 2-(2-(4-(2-(6,7-Dimethoxy-3,4-dihydroisoquinolin-2(1H)-yl)ethyl)phenyl)-2H-tetrazol-5-yl)-4-(pyridin-3-ylmethoxy)aniline (IE8)

A clean, dry 40 mL vial was charged with ID8 (0.19 g, 0.32 mmol), iron (0.17 g, 3.20 mmol), ammonium chloride (0.16 g, 3.20 mmol), EtOH (7 mL), and water (1.5 mL). The mixture reaction was stirred at 90° C. for 1 h. The mixture was filtered while hot through a plug of Celite and washed with DCM. The filtrate was washed with saturated NaHCO$_3$ (2×50 mL), brine (1×50 mL), dried (Na$_2$SO$_4$), and concentrated under reduced pressure to afford the crude residue, which was purified by flash column chromatography on silica gel (5% MeOH/DCM) to afford IE8 (0.10 g, 84% yield). $^1$H NMR (400 MHz, DMSO-d$_6$): δ 2.70-2.75 (m, 6H), 2.93 (t, J=12.0 Hz, 2H), 3.56 (s, 2H), 3.70 (s, 6H), 5.04 (s, 2H), 6.45 (s, 2H), 6.64 (d, J=8.0 Hz, 2H), 7.35-7.60 (m, 5H), 7.89 (s, 1H), 8.05 (d, J=8.0 Hz, 2H), 8.45 (d, J=8.0 Hz, 2H), 8.75 (s, 1H). LC/MS (ESI, m/z): 564.16 [M+H]$^+$.

Synthesis of 2-Nitro-5-(2-(pyridin-3-yl)ethoxy)benzaldehyde (A6)

A clean, dry vial equipped with a stir bar was charged with 5-hydroxy-2-nitrobenzaldehyde A4 (418 mg, 2.5 mmol), 3-(2-bromoethyl)pyridine hydrobromide (950 mg, 3.5 mmol), anhydrous K$_2$CO$_3$ (1.04 g, 7.5 mmol), and DMF (8 mL). The reaction mixture was stirred overnight at 80° C. The mixture was then filtered and concentrated under reduced pressure to afford the crude residue.

Purification by flash column chromatography on silica gel (0-15% MeOH/DCM) afforded A6 as viscous oil (380 mg, 56%). $^1$H NMR (400 MHz, DMSO-d$_6$): δ 3.12 (t, J=6.4 Hz, 2H), 4.45 (t, J=6.6 Hz, 2H), 7.33 (d, J=0.8 Hz, 1H), 7.36 (m, 2H), 7.78 (dt, J=8.0, 2.0 Hz, 1H), 8.17 (d, J=9.2 Hz, 1H), 8.45 (dd, J=4.8, 1.6 Hz, 1H), 8.56 (d, J=2.0 Hz, 1H), 10.28 (s, 1H); LC/MS (ESI, m/z): 273.00 [M+H]$^+$.

Synthesis of (E/Z)-4-Methyl-N'-(2-nitro-5-(2-(pyridin-3-yl)ethoxy)benzylidene)benzenesulfonohydrazide (IC11)

A clean, dry 40 mL vial equipped with a stir bar was charged with A6 (353 mg, 1.3 mmol), p-toluenesulfonohydrazide (242 mg, 1.3 mmol), and EtOH (15 mL). The reaction mixture was stirred at 80° C. for 3 h. The precipitation of a yellow solid was observed. Upon cooling to room temperature, the reaction mixture was diluted with water (200 mL). The solid obtained was collected, washed with water, and dried under reduced pressure to afford IC11 as an off-white solid (315 mg, 55%), which was used in the subsequent reaction without further purification. $^1$H NMR (400 MHz, DMSO-d$_6$): δ 2.36 (s, 3H), 3.12 (t, J=6.6 Hz, 2H), 4.35 (t, J=6.6 Hz, 2H), 7.09 (d, J=2.8 Hz, 1H), 7.18 (dd, J=6.4, 2.8 Hz, 1H), 7.37 (m, 3H), 7.77 (m, 2H), 7.78 (dt, J=8.0, 1.9 Hz, 1H), 8.17 (d, J=9.2 Hz, 1H), 8.36 (s, 1H), 8.48 (dd, J=4.8, 1.6 Hz, 1H), 8.59 (d, J=2.0 Hz, 1H), 11.89 (s, 1H); LC/MS (ESI, m/z): 441.08 [M+H]$^+$.

Synthesis of 6,7-Dimethoxy-2-(4-(5-(2-nitro-5-(2-(pyridin-3-yl)ethoxy)phenyl)-2H-tetrazol-2-yl)phenethyl)-1,2,3,4-tetrahydroisoquinoline (ID11)

A clean, dry 40 mL vial equipped with a stir bar was charged with IB4 (203 mg, 0.65 mmol), sodium nitrite (55 mg, 0.81 mmol), H$_2$O (1 mL), and EtOH (3 mL). The mixture was vortexed and cooled to ~−15° C. (ice/salt bath). A 36% HCl solution (0.25 mL) was added to the mixture and the mixture was vigorously stirred for about 5 min. In another clean, dry 40 mL vial, IC11 (286 mg, 0.65 mmol) was dissolved in pyridine (5 mL), and this solution was gradually added to the vial containing intermediate IB4. The mixture was then stirred overnight at room temperature. Upon completion (monitored by LC/MS), the solvent was removed in vacuo to afford the crude residue, which was purified by flash column chromatography on silica gel (0-10% MeOH/DCM) to afford ID11 as reddish solid (115 mg, 29%). $^1$H NMR (400 MHz, DMSO-d$_6$): δ. LC/MS (ESI, m/z): 608.29 [M+H]$^+$.

Synthesis of 2-(2-(4-(2-(6,7-Dimethoxy-3,4-dihydroisoquinolin-2(1H)-yl)ethyl)phenyl)-2H-tetrazol-5-yl)-4-(2-(pyridin-3-yl)ethoxy)aniline (IE11)

A clean, dry 40 mL vial equipped with a stir bar was charged with ID11 (91 mg, 0.15 mmol), iron (83 mg, 1.5 mmol), ammonium chloride (16 mg, 0.3 mmol), EtOH (3 mL), and water (0.5 mL). The reaction mixture was stirred at 90° C. for 2 h. Upon completion (monitored by LC/MS), the mixture was filtered and the solid obtained was washed with EtOH (3×) followed by DCM (3×). The filtrate was then diluted with DCM up to 150 mL and washed with saturated NaHCO$_3$ (1×100 mL), brine (1×100 mL), and dried (Na$_2$SO$_4$). The solvent was removed in vacuo to afford IE11 as yellow solid (55 mg, 63%), which was used without further purification. $^1$H NMR (400 MHz, DMSO-d$_6$): δ 2.74 (m, 5H), 2.98 (t, J=6.8 Hz, 1H), 3.06 (t, J=6.4 Hz, 2H), 3.18 (d, J=5.2 Hz, 2H), 3.61 (bs, 1H), 3.71 (2s, 6H), 4.08 (t, J=5.2 Hz, 1H), 4.20 (t, J=6.4 Hz, 2H), 6.01 (bs, 2H), 6.65 (s, 1H), 6.67 (s, 1H), 6.87 (m, 1H), 6.94 (dd, J=9.0, 3.0 Hz, 1H), 7.35 (dd, J=8.2, 5.0 Hz, 1H), 7.57 (m, 3H), 7.77 (m, 1H), 8.12 (d, J=8.4 Hz, 2H), 8.45 (d, J=3.6 Hz, 1H), 8.56 (s, 1H). LC/MS (ESI, m/z): 578.19 [M+H]$^+$.

Synthesis of 5-(Benzyloxy)-4-methoxy-2-nitrobenzaldehyde (A8)

A clean, dry 40 mL vial equipped with a stir bar was charged with 5-(benzyloxy)-4-methoxybenzaldehyde A7 (1.21 g, 5.0 mmol) and DCM (12 mL). The solution was cooled to 0° C., and conc. nitric acid (70%, 6 mL) was gradually added. The reaction mixture was stirred for 30 min at 0° C., then another portion of conc. nitric acid (70%, 6 mL) was added to the vial. The mixture was stirred overnight at room temperature. Upon completion (monitored by LC/MS), the mixture was diluted with EtOAc (200 mL), washed with water (2×200 mL), brine (1×100 mL), dried (Na$_2$SO$_4$), and concentrated under reduced pressure to afford the crude residue, which was recrystallized from EtOAc/n-heptane to afford A8 as yellow solid (0.89 g, 62%). $^1$H NMR (400 MHz, DMSO-d$_6$): δ 3.98 (s, 3H), 5.32 (s, 2H), 7.44 (m, 6H), 7.73 (s, 1H), 10.20 (s, 1H). LC/MS (ESI, m/z): 288.24 [M+H]$^+$.

Synthesis of 2-(4-(5-(5-(Benzyloxy)-4-methoxy-2-nitrophenyl)-2H-tetrazol-2-yl)phenethyl)-6,7-dimethoxy-1,2,3,4-tetrahydroisoquinoline (ID6)

A clean, dry 40 mL vial equipped with a stir bar was charged with IB4 (0.17 g, 0.55 mmol), sodium nitrite (0.046 g, 0.67 mmol), H$_2$O (2 mL), and EtOH (6 mL). The mixture was vortexed and cooled to ~−15° C. (ice/salt bath). A 36% HCl solution (0.2 mL) was added to the mixture and the mixture was vigorously stirred for about 5 min. In another clean, dry 40 mL vial, IC2 (0.25 g, 0.55 mmol) was dissolved in pyridine (5 mL), and this solution was gradually added to the vial containing intermediate IB4. The mixture was then stirred overnight at room temperature. Upon completion (monitored by LC/MS), the mixture was diluted with DCM (75 mL), and washed with water, brine (2×50 mL), dried (Na$_2$SO$_4$), and concentrated under reduced pressure to afford the crude residue, which was purified by flash column chromatography on silica gel (0-5% MeOH/DCM) to afford ID6 as reddish solid (0.19 g, 55%). $^1$H NMR (400 MHz, DMSO-d$_6$): δ 2.67-2.84 (m, 7H), 2.95 (t, J=12.0 Hz, 1H), 3.56 (s, 2H), 3.70 (s, 6H), 3.97 (s, 3H), 5.30 (s, 2H), 6.63 (d, J=12.0 Hz, 2H), 7.25-7.50 (m, 6H), 7.58 (s, 1H), 7.61 (s, 1H), 7.79 (s, 1H), 8.02 (d, J=12.0 Hz, 2H). LC/MS (ESI, m/z): 623.22 [M+H]$^+$.

Synthesis of 4-(Benzyloxy)-2-(2-(4-(2-(6,7-dimethoxy-3,4-dihydroisoquinolin-2(1H)-yl)ethyl)phenyl)-2H-tetrazol-5-yl)-5-methoxyaniline (IE6)

A clean, dry 40 mL vial equipped with a stir bar was charged with ID6 (0.18 g, 0.30 mmol), iron (0.17 g, 3.04 mmol), ammonium chloride (0.16 g, 3.04 mmol), EtOH (7 mL), and water (1.5 mL). The reaction mixture was stirred at 90° C. for 1 h. Upon completion (monitored by LC/MS), the mixture was filtered while hot through a Celite pad and washed with DCM. The filtrate was washed with saturated NaHCO$_3$ (2×50 mL), brine (1×50 mL), dried (Na$_2$SO$_4$), and concentrated under reduced pressure to afford the crude residue, which was purified by flash column chromatography on silica gel (0-5% MeOH/DCM) to afford IE6 (0.15 g, 84%). $^1$H NMR (400 MHz, DMSO-d$_6$): δ 2.71-2.76 (m, 6H), 2.93 (t, J=12.0 Hz, 2H), 3.56 (s, 2H), 3.70 (s, 6H), 3.81 (s, 3H), 5.02 (s, 2H), 6.14 (s, 2H), 6.58 (s, 1H), 6.63 (d, J=12.0 Hz, 2H), 7.33-7.48 (m, 5H), 7.55 (d, J=8.0 Hz, 2H), 7.63 (s, 1H), 8.02 (d, J=12.0 Hz, 2H). LC/MS (ESI, m/z): 593.14 [M+H]$^+$.

Synthesis of 2-(4-(5-(5-(Benzyloxy)-4-methoxy-2-nitrophenyl)-2H-tetrazol-2-yl)phenethyl)-1,2,3,4-tetrahydro-2,6-naphthyridine (ID3)

A clean, dry 40 mL vial equipped with a stir bar was charged with IB2 (381 mg, 1.5 mmol), sodium nitrite (128 mg, 1.86 mmol), H$_2$O (1.5 mL), and EtOH (3 mL). The mixture was vortexed and cooled to ~−15° C. (ice/salt bath). A 36% HCl solution (0.40 mL) was then added to the mixture, and the mixture was vigorously stirred for about 5 min. In another clean, dry 40 mL vial, compound IC2 (683 mg, 1.5 mmol) was dissolved in pyridine (8 mL), and this solution was gradually added to the vial containing IB2. The mixture was stirred overnight at room temperature. Upon completion (monitored by LC/MS), the mixture was diluted with DCM (150 mL), washed with water (2×100 mL), brine (1×100 mL), dried (Na$_2$SO$_4$), and concentrated under reduced pressure to afford the crude residue, which was purified by flash column chromatography on silica gel (0-5% MeOH/DCM). The desired product obtained after column chromatography purification was dissolved in MeOH (acidified with HCl) and further purified by reverse phase HPLC (10-100% MeCN/water (acidified with 0.01% HCl)) to afford the desired product in salt form. This product was suspended in 10% MeOH/DCM (100 mL) and washed with 1 N NaOH (2×50 mL), brine (1×50 mL), dried (Na$_2$SO$_4$), and concentrated under reduced pressure to afford ID3 as reddish solid (362 mg, 21%). $^1$H NMR (400 MHz, DMSO-d$_6$): δ 3.03 (m, 8H), 3.93 (m, 2H), 3.97 (s, 3H), 5.30 (s, 2H), 7.12-7.80 (m, 11H), 8.05-8.36 (m, 3H). LC/MS (ESI, m/z): 564.33 [M+H]$^+$.

Synthesis of 4-(Benzyloxy)-2-(2-(4-(2-(3,4-dihydro-2,6-naphthyridin-2(1H)-yl)ethyl)phenyl)-2H-tetrazol-5-yl)-5-methoxyaniline (IE3)

A clean, dry 40 mL vial equipped with a stir bar was charged with ID3 (282 mg, 0.5 mmol), iron (280 mg, 5.0 mmol), ammonium chloride (53 mg, 1.0 mmol), EtOH (3.5 mL), and water (0.5 mL). The reaction mixture was stirred at 90° C. for 1.5 h. Upon completion (monitored by LC/MS), the mixture was filtered, and the solid obtained was washed with EtOH and DCM three times. The filtrate was then diluted with DCM up to 150 mL, washed with saturated NaHCO$_3$ (2×100 mL), brine (1×100 mL), dried (Na$_2$SO$_4$), and concentrated under reduced pressure to afford the crude residue. This residue was dissolved in MeOH (acidified with HCl) and purified by reverse phase HPLC (10-80% MeCN/water (acidified with 0.01% HCl)) to afford the desired product in salt form. This product was suspended in 10% MeOH/DCM (100 mL) and washed with 1 N NaOH (2×50 mL), brine (1×50 mL), dried (Na$_2$SO$_4$), and concentrated under reduced pressure to afford IE3 as reddish solid (206 mg, 77%). $^1$H NMR (400 MHz, DMSO-d$_6$): δ 2.80-3.10 (m, 8H), 3.70-4.00 (m, 2H), 3.85 (s, 3H), 5.03 (s, 2H), 6.15 (bs, 1H), 6.58 (s, 1H), 7.14 (d, J=4.8 Hz, 1H), 7.37 (m, 4H), 7.48 (m, 2H), 7.59 (d, J=8.8 Hz, 2H), 7.63 (s, 1H), 8.12 (d, J=8.4 Hz, 2H), 8.32 (d, J=5.2 Hz, 1H), 8.37 (s, 1H). LC/MS (ESI, m/z): 534.19 [M+H]$^+$.

Synthesis of 5-Hydroxy-4-methoxy-2-nitrobenzaldehyde (A9)

A clean, dry 40 mL vial equipped with a stir bar was charged with A8 (900 mg, 3.13 mmol), cooled to 0° C. and then TFA (10 mL) was added. The reaction mixture was stirred overnight at 60° C. Upon completion (monitored by LC/MS), the mixture was concentrated under reduced pressure to afford the crude residue, which was purified by flash column chromatography on silica gel (0-100% ethyl acetate/n-heptane) affording A9 as brown solid (550 mg, 89%). $^1$H NMR (400 MHz, DMSO-d$_6$): δ 3.95 (s, 3H), 7.21 (s, 1H), 7.68 (s, 1H), 10.17 (s, 1H), 11.02 (s, 1H). LC/MS (ESI, m/z): 198.12 [M+H]$^+$.

Synthesis of 4-Methoxy-2-nitro-5-(pyridin-3-ylmethoxy)benzaldehyde (A10)

A clean, dry 40 mL vial was charged with A9 (0.5 g, 2.53 mmol), 3-(2-bromomethyl)pyridine HBr (0.95 g, 3.80 mmol), anhydrous K$_2$CO$_3$ (1.05 g, 7.59 mmol) and anhydrous DMF (20 mL). The reaction mixture was stirred at 90° C. for 4 h. Upon completion (monitored by LC/MS), the mixture was filtered, and diluted with 100 mL DCM. The organic layer was washed with water (2×100 mL), brine (1×100 mL), dried (Na$_2$SO$_4$), and concentrated under reduced pressure to afford the crude residue, which was purified by flash column chromatography on silica gel (0-100% ethyl acetate/n-heptane) to afford A10 as yellow solid (0.51 g, 70%). $^1$H NMR (400 MHz, DMSO-$d_6$): δ 3.96 (s, 3H), 5.36 (s, 2H), 7.43-7.47 (m, 1H), 7.52 (s, 1H), 7.73 (s, 1H), 7.87 (d, J=8.0 Hz, 1H), 8.57 (d, J=4.0 Hz, 1H), 8.68 (s, 1H), 10.19 (s, 1H). LC/MS (ESI, m/z): 288.99 [M+H]$^+$.

Synthesis of (E/Z)—N'-(4-Methoxy-2-nitro-5-(pyridin-3-ylmethoxy)benzylidene)-4-methylbenzenesulfonohydrazide (IC7)

A clean, dry 40 mL vial equipped with a stir bar was charged with A10 (500 mg, 1.73 mmol), p-toluenesulfonohydrazide (323 mg, 1.73 mmol), and EtOH (15 mL). The reaction mixture was stirred at 80° C. for 3 h. The precipitation of a yellow solid was observed. Upon cooling to room temperature, the reaction mixture was diluted with water (200 mL). The solid obtained was collected, washed with water, and dried under reduced pressure to afford IC7 as a yellow solid (670 mg, 85%), which was used in the subsequent reaction without further purification. $^1$H NMR (400 MHz, DMSO-$d_6$): δ 2.35 (s, 3H), 3.88 (s, 3H), 5.27 (s, 2H), 7.30 (s, 1H), 7.39 (d, J=8.0 Hz, 2H), 7.44-7.47 (m, 1H), 7.61 (s, 1H), 7.78 (d, J=8.0 Hz, 2H), 7.87-7.90 (m, 1H), 8.33 (s, 1H), 8.60 (d, J=4.0 Hz, 1H), 8.70 (s, 1H), 11.73 (s, 1H). LC/MS (ESI, m/z): 457.08 [M+H]$^+$.

Synthesis of 6,7-Dimethoxy-2-(4-(5-(4-methoxy-2-nitro-5-(pyridin-3-ylmethoxy)phenyl)-2H-tetrazol-2-yl)phenethyl)-1,2,3,4-tetrahydroisoquinoline (ID7)

A clean, dry 40 mL vial equipped with a stir bar was charged with IB4 (376 mg, 1.20 mmol), sodium nitrite (102 mg, 1.48 mmol), H$_2$O (2 mL), and EtOH (6 mL). The mixture was vortexed and cooled below 0° C. A 36% HCl solution (0.4 mL) was added to the mixture and the mixture was vigorously stirred for about 5 min. In another clean, dry 40 mL vial, IC7 (550 mg, 1.20 mmol) was dissolved in pyridine (8 mL), and this solution was gradually added to the vial containing intermediate IB4. The mixture was then stirred overnight at room temperature. Upon completion (monitored by LC/MS), the solvent was removed in vacuo to afford the crude residue, which was purified by flash column chromatography on silica gel (0-5% MeOH/DCM) to afford ID7 as brownish yellow solid (290 mg, 38%). $^1$H NMR (400 MHz, DMSO-$d_6$): δ 2.70 (s, 4H), 2.72 (t, J=12.0 Hz, 2H), 2.93 (t, J=12.0 Hz, 2H), 3.55 (s, 2H), 3.69 (s, 6H), 3.95 (s, 3H), 5.34 (s, 2H), 6.62 (d, J=12.0 Hz, 2H), 7.44-7.47 (m, 1H), 7.57 (d, J=8.0 Hz, 1H), 7.64 (s, 1H), 7.79 (s, 1H), 7.89-7.92 (m, 1H), 8.01 (d, J=12.0 Hz, 2H), 8.57 (d, J=4.0 Hz, 1H), 8.70 (s, 1H). LC/MS (ESI, m/z): 624.20 [M+H]$^+$.

Synthesis of 2-(2-(4-(2-(6,7-Dimethoxy-3,4-dihydroisoquinolin-2(1H)-yl)ethyl)phenyl)-2H-tetrazol-5-yl)-5-methoxy-4-(pyridin-3-ylmethoxy)aniline (IE7)

A clean, dry 40 mL vial equipped with a stir bar was charged with ID7 (250 mg, 0.40 mmol), iron (223 mg, 4.0 mmol), ammonium chloride (43 mg, 0.8 mmol), EtOH (10 mL), and water (1.5 mL). The reaction mixture was stirred at 90° C. for 1 h. Upon completion (monitored by LC/MS), the mixture was filtered and the solid obtained was washed with EtOH (3×) followed by DCM (3×). The filtrate was then diluted with DCM up to 150 mL and washed with saturated NaHCO$_3$ (1×100 mL), brine (1×100 mL), and dried (Na$_2$SO$_4$). The solvent was removed in vacuo to afford IE7 as pale-yellow solid (175 mg, 73%), which was used without further purification. $^1$H NMR (400 MHz, DMSO-$d_6$): δ 2.70 (s, 4H), 2.72 (t, J=12.0 Hz, 2H), 2.91 (t, J=12.0 Hz, 2H), 3.55 (s, 2H), 3.68 (s, 6H), 3.79 (s, 3H), 5.06 (s, 2H), 6.16 (s, 2H), 6.57 (s, 1H), 6.61 (d, J=12.0 Hz, 2H), 7.40-7.43 (m, 1H), 7.52 (d, J=8.0 Hz, 2H), 7.64 (s, 1H), 7.85-7.88 (m, 1H), 8.06 (d, J=8.0 Hz, 2H), 8.52 (d, J=8.0 Hz, 1H), 8.66 (s, 1H). LC/MS (ESI, m/z): 594.19 [M+H]$^+$.

Synthesis of 7-(4-(5-(5-(Benzyloxy)-4-methoxy-2-nitrophenyl)-2H-tetrazol-2-yl)phenethyl)-5,6,7,8-tetrahydroimidazo[1,5-a]pyrazine (ID5)

A clean, dry 40 mL vial equipped with a stir bar was charged with IB1 (0.20 g, 0.82 mmol), sodium nitrite (0.069 g, 1.0 mmol), H$_2$O (2 mL), and EtOH (6 mL). The mixture was vortexed and cooled to ~−15° C. (ice/salt bath). A 36% HCl solution (0.25 mL) was added to the mixture and the mixture was vigorously stirred for about 5 min. In another clean, dry 40 mL vial, compound IC2 (0.37 g, 0.82 mmol) was dissolved in pyridine (5 mL), and this solution was gradually added to the vial containing IB1. The mixture was then stirred at room temperature overnight. Upon completion (monitored by LC/MS), the crude mixture was diluted with DCM (75 mL) and washed with water, brine (2×50 mL), and dried (Na$_2$SO$_4$). The solvent was removed in vacuo to afford the crude residue, which was purified by flash column chromatography on silica gel (0-5% MeOH/DCM) to afford ID5 (0.15 g, 33%). $^1$H NMR (400 MHz, DMSO-$d_6$): δ 2.79-2.89 (m, 4H), 2.94 (t, J=12.0 Hz, 2H), 3.68 (s, 2H), 3.97-4.02 (m, 5H), 5.30 (s, 2H), 6.63 (s, 1H), 7.37-7.50 (m, 6H), 7.58 (s, 1H), 7.61 (s, 2H), 7.79 (s, 1H), 8.02 (d, J=12.0 Hz, 2H). LC/MS (ESI, m/z): 553.21 [M+H]$^+$.

Synthesis of 4-(Benzyloxy)-2-(2-(4-(2-(5,6-dihydroimidazo[1,5-a]pyrazin-7(8H)-yl)ethyl)phenyl)-2H-tetrazol-5-yl)-5-methoxyaniline (IE5)

A clean, dry 40 mL vial equipped with a stir bar was charged with ID5 (0.13 g, 0.23 mmol), iron (0.13 g, 2.35 mmol), ammonium chloride (0.12 g, 2.35 mmol), EtOH (7 mL), and water (1.5 mL). The reaction mixture was stirred at 90° C. and monitored by LC/MS. Upon completion (after 1 h), the mixture was filtered while hot through a plug of Celite and washed with DCM. The filtrate was washed with saturated NaHCO$_3$ (2×50 mL), brine (1×50 mL), dried (Na$_2$SO$_4$), and concentrated to afford the crude residue, which was purified by flash column chromatography on silica gel (0-5% MeOH/DCM) to afford IE5 (0.085 g, 71%). $^1$H NMR (400 MHz, DMSO-$d_6$): δ 2.79-2.89 (m, 4H), 2.94 (t, J=12.0 Hz, 2H), 3.68 (s, 2H), 3.97 (s, 3H), 3.99 (t, J=12.0 Hz, 2H), 5.30 (s, 2H), 6.63 (s, 1H), 7.37-7.50 (m, 8H), 7.59 (s, 1H), 7.61 (s, 2H), 7.79 (s, 1H), 8.03 (d, J=8.0 Hz, 2H). LC/MS (ESI, m/z): 523.18 [M+H]$^+$.

Example 2: Synthesis of A-(2-(2-(4-(2-(5,6-Dihydroimidazo[1,5-a]pyrazin-7(8H)-yl)ethyl)phenyl)-2H-tetrazol-5-yl)-4,5-dimethoxyphenyl)-4-oxo-4H-chromene-2-carboxamide (Scheme 1, Compound No. 1)

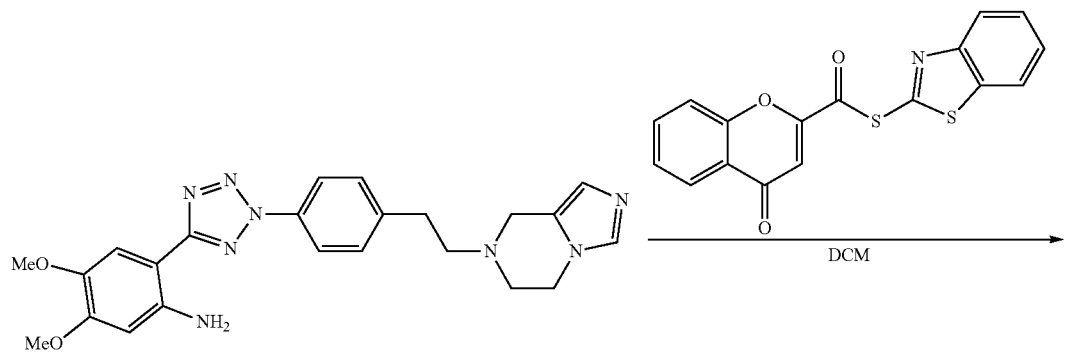

134 mg of Intermediate IE1 and 136 mg of Intermediate IF1 were used to synthesize 85 mg of the title compound (46% yield) according to the General Procedure GG. $^1$H NMR (400 MHz, DMSO-$d_6$): δ 2.80 (m, 2H), 2.91 (m, 4H), 3.70 (s, 2H), 3.76 (s, 3H), 3.79 (s, 3H), 4.02 (t, J=5.4 Hz, 2H), 6.67 (s, 1H), 6.82 (s, 1H), 7.45-7.55 (m, 6H), 7.77 (t, j=7.8 Hz, 1H), 7.92 (d, j=8.0 Hz, 2H), 7.99 (d, j=8.0 Hz, 1H), 8.06 (s, 1H), 11.72 (s, 1H); LC/MS (ESI, m/z): 619.20 [M+H]$^+$.

Example 3: Synthesis of N-(2-(2-(4-(2-(3,4-Dihydro-2,6-naphthyridin-2(1H)-yl)ethyl)phenyl)-2H-tetrazol-5-yl)-4,5-dimethoxyphenyl)-4-oxo-4H-chromene-2-carboxamide (Scheme 1, Compound No. 7)

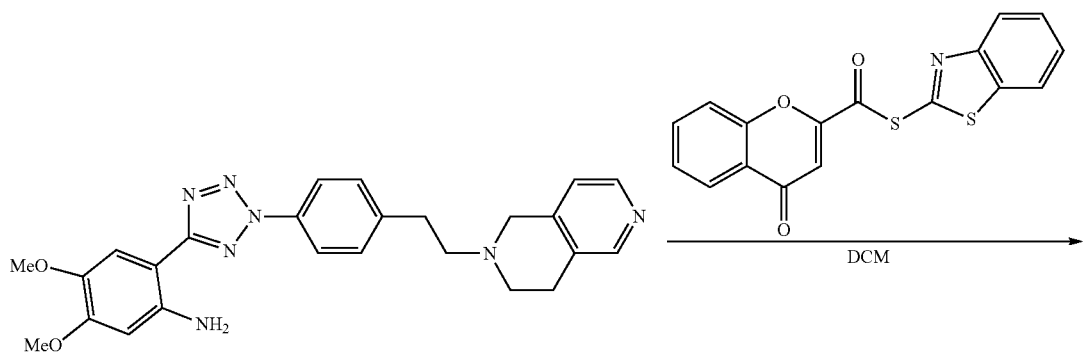

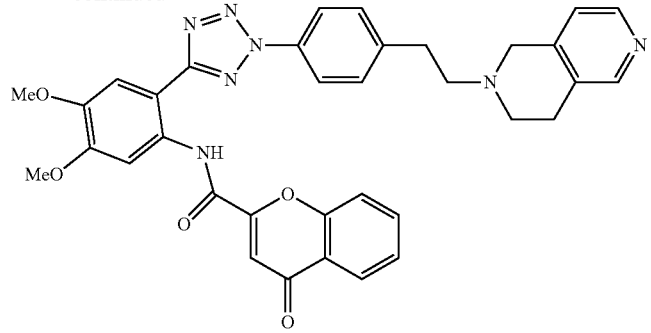

137 mg of Intermediate IE2 and 136 mg of Intermediate IF1 were used to synthesize 79 mg of the title compound (42% yield) according to the General Procedure GG. $^1$H NMR (400 MHz, DMSO-d$_6$): δ 2.76-2.83 (m, 6H), 2.91-2.95 (m, 2H), 3.69 (s, 6H), 3.71 (s, 3H), 6.71 (s, 1H), 7.13 (d, J=4 Hz, 1H), 7.36-7.43 (m, 5H), 7.68 (t, J=12 Hz, 1H), 7.82 (d, J=8 Hz, 2H), 7.91 (d, J=8 Hz, 1H), 8.01 (s, 1H), 8.27-8.31 (m, 2H), 11.70 (s, 1H). LC/MS (ESI, m/z): 630.20 [M+H]$^+$.

Example 4: Synthesis of N-(2-(2-(4-(2-(3,4-Dihydro-2,6-naphthyridin-2(1H)-yl)ethyl)phenyl)-2H-tetrazol-5-yl)-4,5-dimethoxyphenyl)quinoline-3-carboxamide (Scheme 1, Compound No. 2)

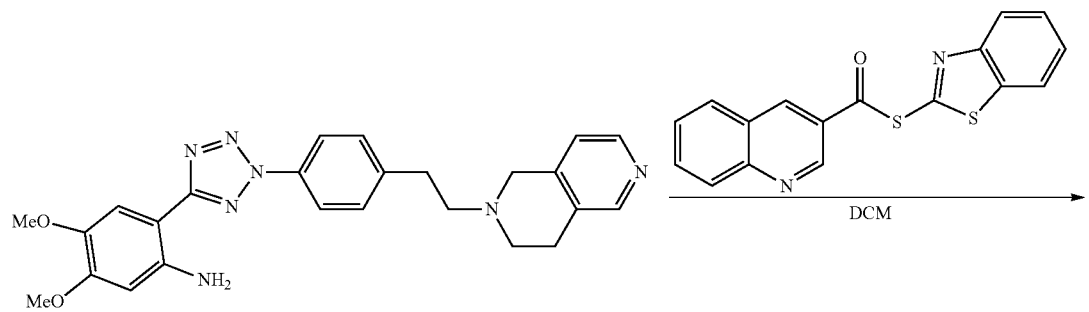

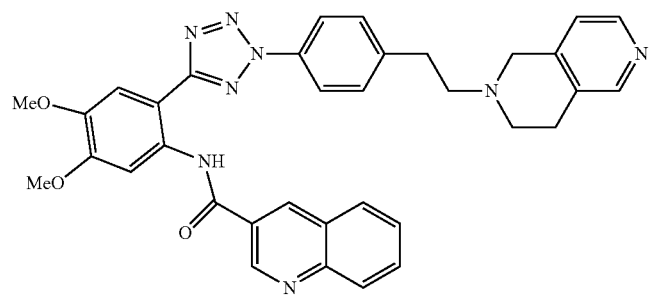

137 mg of Intermediate IE2 and 129 mg of Intermediate IF2 were used to synthesize 92 mg of the title compound (50% yield) according to the General Procedure GG. $^1$H NMR (400 MHz, DMSO-d$_6$): δ 2.49-2.51 (m, 6H), 2.75-2.79 (m, 2H), 3.65 (s, 2H), 3.87 (s, 6H), 7.10 (d, J=4.0 Hz, 1H), 7.40 (d, J=8.0 Hz, 2H), 7.67-7.69 (m, 2H), 7.87-7.89 (m, 3H), 7.91-7.99 (m, 2H), 8.10 (d, J=8.0 Hz, 1H), 8.26-8.29 (m, 2H), 8.94 (s, 1H), 9.41 (s, 1H), 10.87 (s, 1H). LC/MS (ESI, m/z): 613.20 [M+H]$^+$.

Example 5: Synthesis of N-(2-(2-(4-(2-(3,4-Dihydro-2,6-naphthyridin-2(1H)-yl)ethyl)phenyl)-2H-tetrazol-5-yl)-4,5-dimethoxyphenyl)quinoxaline-2-carboxamide (Scheme 1, Compound No. 9)

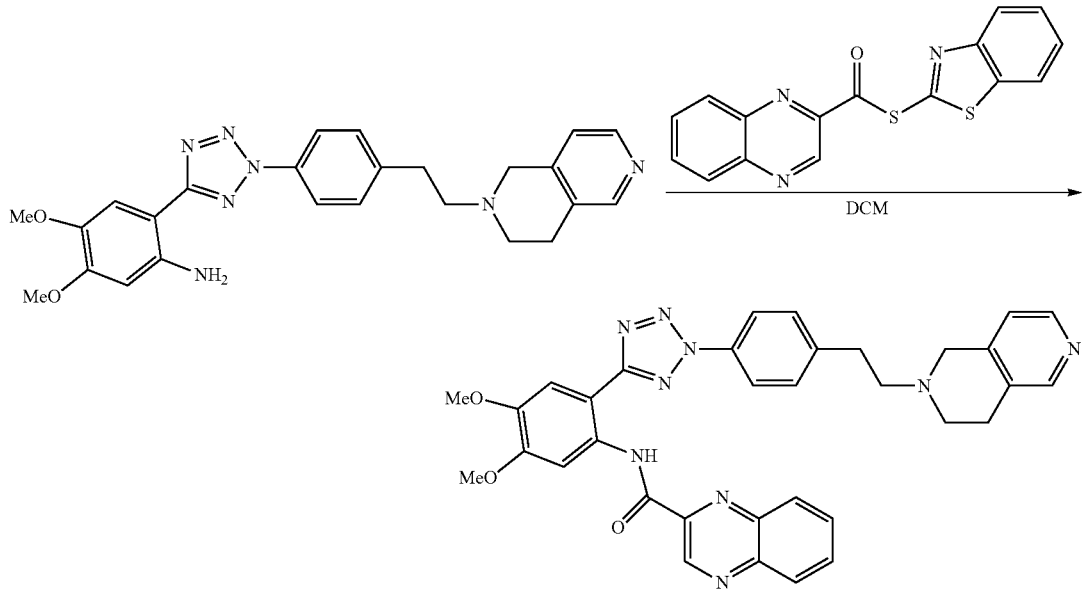

137 mg of Intermediate IE2 and 129 mg of Intermediate IF3 were used to synthesize 83 mg of the title compound (45% yield) according to the General Procedure GG. $^1$H NMR (400 MHz, DMSO-$d_6$): δ 2.78-2.82 (m, 6H), 2.93-2.97 (m, 2H), 3.69 (s, 2H), 3.84 (s, 6H), 7.12 (d, J=4.0 Hz, 1H), 7.44 (d, J=4.0 Hz, 2H), 7.63 (s, 1H), 7.82-7.99 (m, 5H), 8.12 (d, J=8.0 Hz, 1H), 8.27 (d, J=8.0 Hz, 1H), 8.32 (s, 1H), 8.41 (s, 1H), 9.46 (s, 1H), 12.02 (s, 1H). LC/MS (ESI, m/z): 614.20 [M+H]$^+$.

Example 6: Synthesis of N-(2-(2-(4-(2-(3,4-Dihydro-2,6-naphthyridin-2(1H)-yl)ethyl)phenyl)-2H-tetrazol-5-yl)-4,5-dimethoxyphenyl)-9-oxo-9H-xanthene-4-carboxamide (Scheme 1, Compound No. 11)

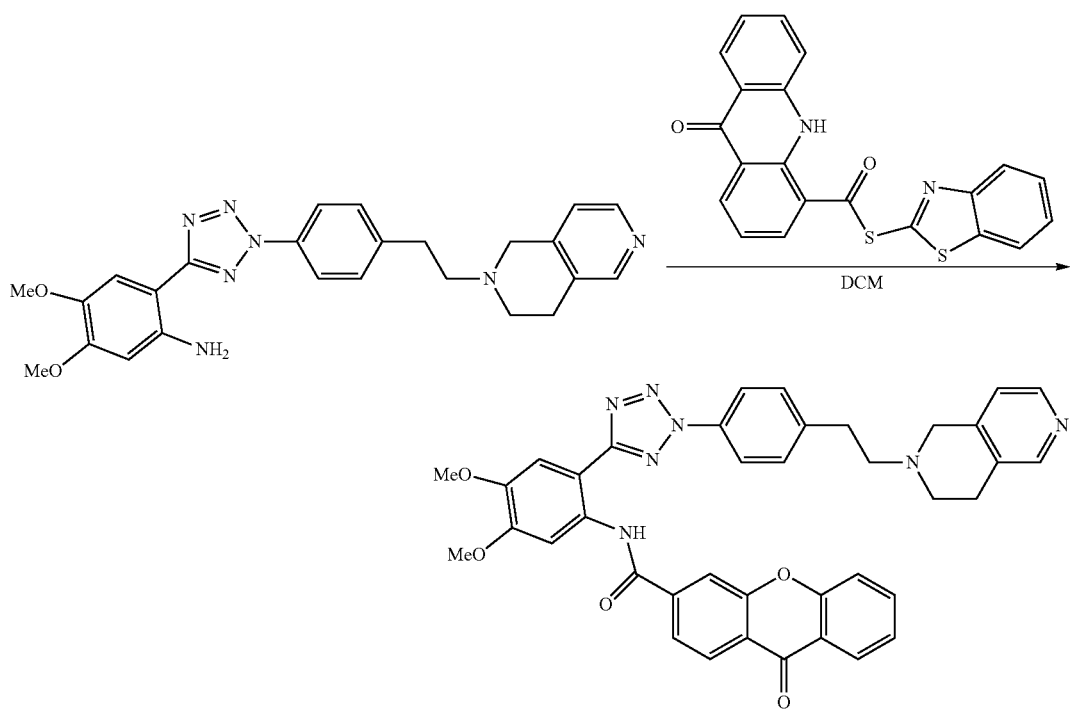

137 mg of Intermediate IE2 and 155 mg of Intermediate IF4 were used to synthesize 88 mg of the title compound (43% yield) according to the General Procedure GG. LC/MS (ESI, m/z): 679.31 [M+H]$^+$.

Example 7: Synthesis of N-(4-(Benzyloxy)-2-(2-(4-(2-(3,4-dihydro-2,6-naphthyridin-2(1H)-yl)ethyl)phenyl)-2H-tetrazol-5-yl)-5-methoxyphenyl)-4-oxo-4H-chromene-2-carboxamide (Scheme 1, Compound No. 12)

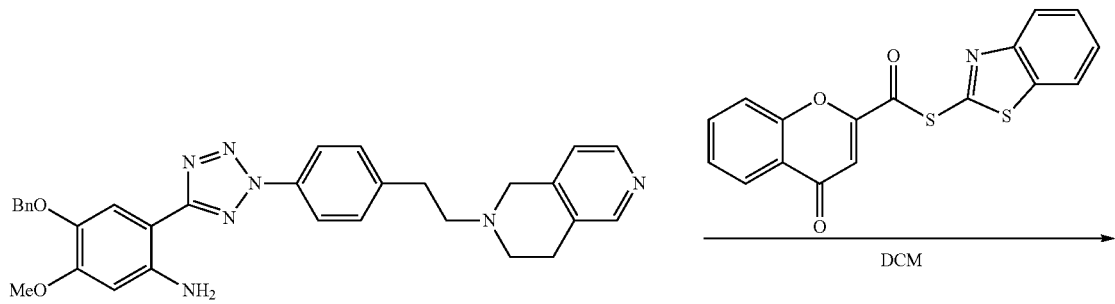

65 mg of Intermediate 58 and 46 mg of Intermediate IF1 were used to synthesize 32 mg of the title compound (38% yield) according to the General Procedure GG. $^1$H NMR (400 MHz, DMSO-d$_6$): δ 2.78 (m, 6H), 2.95 (t, J=7.4 Hz, 2H), 3.68 (s, 2H), 3.82 (s, 3H), 5.14 (s, 2H), 6.89 (s, 1H), 7.10 (d, J=4.8 Hz, 1H), 7.35-7.52 (m, 8H), 7.56 (d, J=8.4 Hz, 1H), 7.72 (s, 1H), 7.81 (m, 1H), 7.97 (d, J=8.4 Hz, 2H), 8.04 (dd, J=8.0, 1.6 Hz, 1H), 8.28 (s, 1H), 8.28 (d, J=4.8 Hz, 1H), 8.34 (s, 1H). LC/MS (ESI, m/z): 706.31 [M+H]$^+$.

Example 8: Synthesis of N-(4-(Benzyloxy)-2-(2-(4-(2-(3,4-dihydro-2,6-naphthyridin-2(1H)-yl)ethyl)phenyl)-2H-tetrazol-5-yl)-5-methoxyphenyl)quinoline-3-carboxamide (Scheme 1, Compound No. 13)

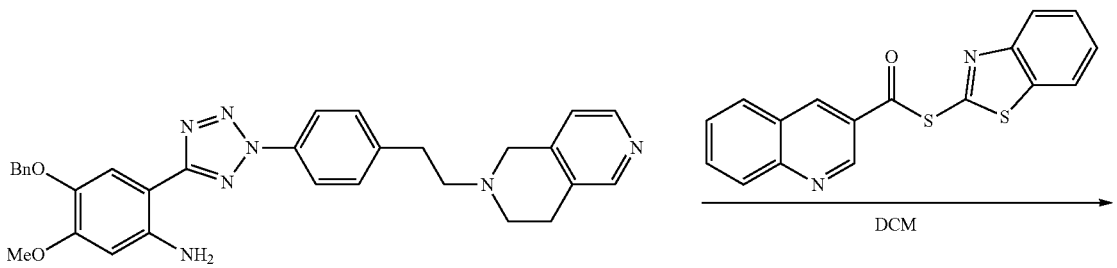

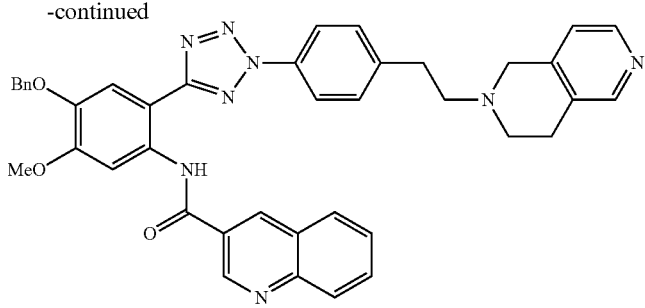

65 mg of Intermediate 58 and 42 mg of Intermediate IF2 were used to synthesize 33 mg of the title compound (40% yield) according to the General Procedure GG except the reaction was stirred at 40° C. for 72 h. $^1$H NMR (400 MHz, DMSO-$d_6$): δ 2.80-3.00 (m, 8H), 3.78 (bs, 2H), 3.92 (s, 3H), 5.23 (s, 2H), 7.10 (d, J=4.8 Hz, 1H), 7.38 (m, 1H), 7.45 (m, 4H), 7.53 (m, 2H), 7.73 (m, 1H), 7.85 (s, 1H), 7.94 (m, 4H), 8.05 (dd, J=8.4, 0.8 Hz, 1H), 8.13 (d, J=8.4 Hz, 1H), 8.30 (d, J=5.2 Hz, 1H), 8.36 (s, 1H), 9.02 (d, J=1.6 Hz, 1H), 9.45 (d, J=2.4 Hz, 1H), 10.91 (s, 1H). LC/MS (ESI, m/z): 689.31 [M+H]$^+$.

Example 9: Synthesis of N-(2-(2-(4-(2-(3,4-Dihydro-2,7-naphthyridin-2(1H)-yl)ethyl)phenyl)-2H-tetrazol-5-yl)-4,5-dimethoxyphenyl)-4-oxo-4H-chromene-2-carboxamide (Scheme 1, Compound No. 6)

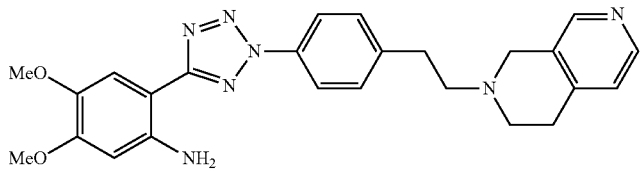
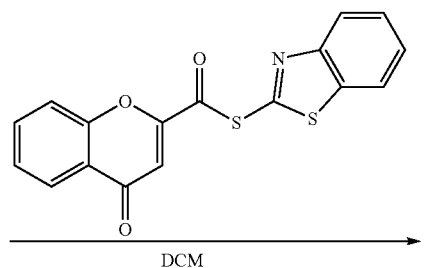

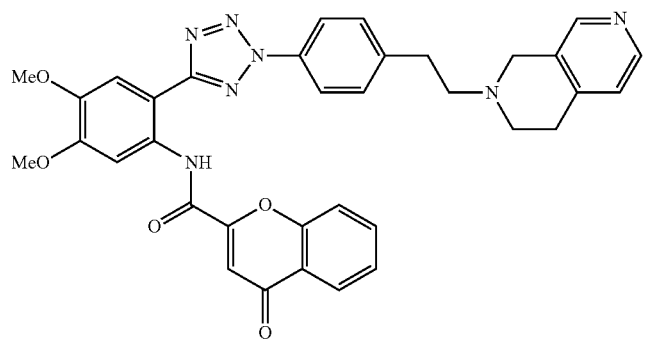

137 mg of Intermediate IE2 and 136 mg of Intermediate IF1 were used to synthesize 78 mg of the title compound (41% yield) according to the General Procedure GG. $^1$H NMR (400 MHz, DMSO-$d_6$): δ 2.51 (s, 2H), 3.22-3.26 (m, 4H), 3.54-3.58 (m, 2H), 3.77 (s, 3H), 3.82 (s, 3H), 4.69 (br s, 2H), 6.80 (s, 1H), 7.49-7.56 (m, 6H), 7.80 (t, J=12 Hz, 1H), 8.00-8.05 (m, 4H), 8.57 (d, J=4 Hz, 1H), 8.66 (s, 1H), 11.74 (s, 1H). LC/MS (ESI, m/z): 630.20 [M+H]$^+$.

Example 10: Synthesis of N-(2-(2-(4-(2-(6-(1H-Imidazol-1-yl)-3,4-dihydroisoquinolin-2(1H)-yl)ethyl)phenyl)-2H-tetrazol-5-yl)-4,5-dimethoxyphenyl)-4-oxo-4H-chromene-2-carboxamide (Scheme 2, Compound No. 8)

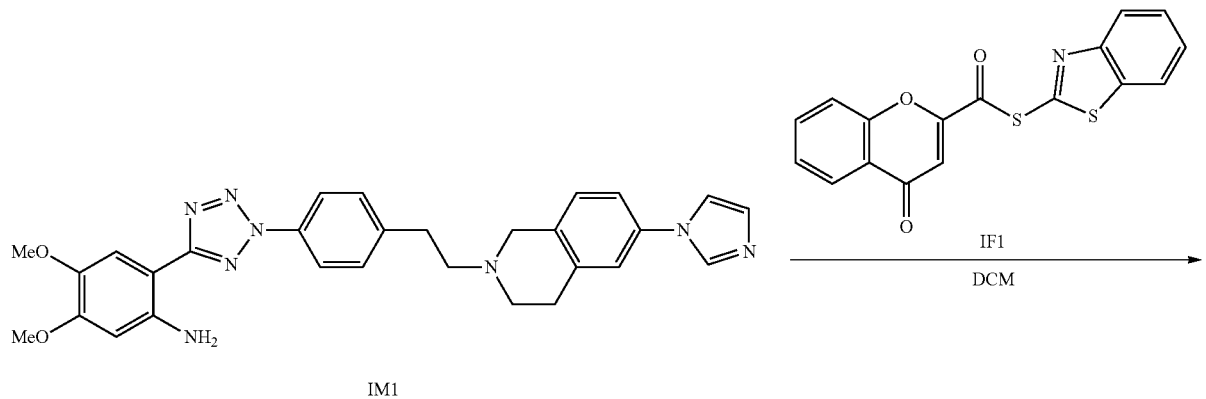

78 mg of Intermediate IM1 and 68 mg of Intermediate IF1 were used to synthesize 69 mg of the title compound (66% yield) according to the General Procedure NN. $^1$H NMR (400 MHz, DMSO-$d_6$): δ 2.76-2.79 (m, 4H), 2.86-2.89 (m, 2H), 2.94-2.97 (m, 2H), 3.68 (s, 2H), 3.82 (s, 3H), 3.84 (s, 3H), 6.90 (s, 1H), 7.07 (s, 1H), 7.19 (d, J=8.0 Hz, 1H), 7.36 (s, 1H), 7.39 (s, 1H), 7.47-7.66 (m, 6H), 7.79-7.83 (m, 1H), 7.97 (d, J=8.0 Hz, 2H), 8.03 (d, J=8.0 Hz, 1H), 8.09 (s, 1H), 8.17 (s, 1H), 11.69 (s, 1H). LC/MS (ESI, m/z): 695.41 [M+H]$^+$.

Example 11: Synthesis of N-(2-(2-(4-(2-(7-(1H-Imidazol-1-yl)-3,4-dihydroisoquinolin-2(1H)-yl)ethyl)phenyl)-2H-tetrazol-5-yl)-4,5-dimethoxyphenyl)-4-oxo-4H-chromene-2-carboxamide (Scheme 2, Compound No. 10)

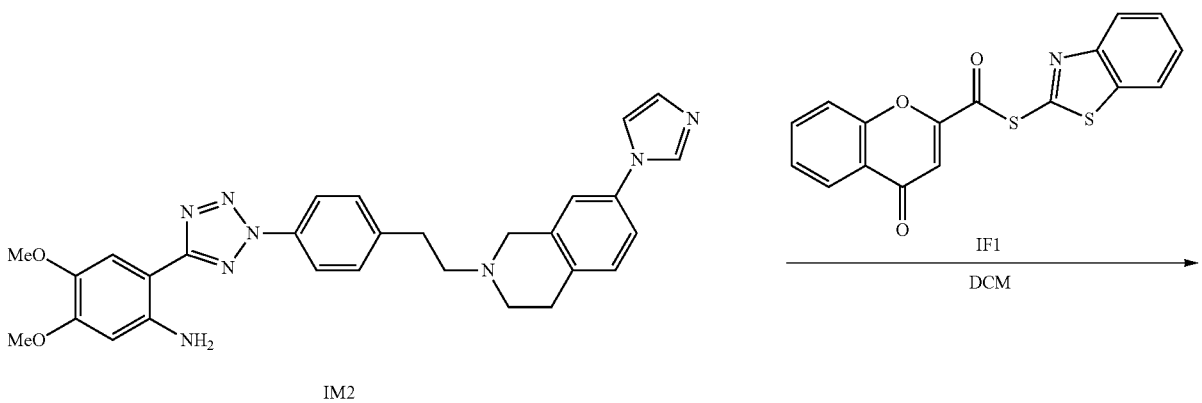

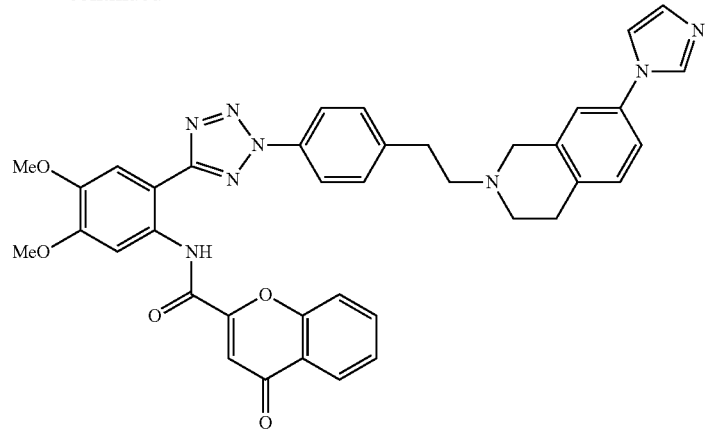

78 mg of Intermediate IM2 and 68 mg of Intermediate IF1 were used to synthesize 61 mg of the title compound (59% yield) according to the General Procedure NN. $^1$H NMR (400 MHz, DMSO-$d_6$): δ 2.76-2.79 (m, 4H), 2.86-2.97 (m, 4H), 3.68 (s, 2H), 3.83 (s, 3H), 3.85 (s, 3H), 6.91 (s, 1H), 7.07 (s, 1H), 7.19 (d, J=8.0 Hz, 1H), 7.36-7.38 (m, 2H), 7.47-7.65 (m, 6H), 7.80-7.84 (m, 1H), 7.98 (d, J=8.0 Hz, 2H), 8.03 (d, J=8.0 Hz, 1H), 8.10 (s, 1H), 8.16 (s, 1H), 11.68 (s, 1H). LC/MS (ESI, m/z): 695.31 [M+H]$^+$.

Example 12: Synthesis of N-(2-(2-(4-(2-(7-(2-(1H-Imidazol-1-yl)ethoxy)-6-methoxy-3,4-dihydroisoquinolin-2(1H)-yl)ethyl)phenyl)-2H-tetrazol-5-yl)-4,5-dimethoxyphenyl)-4-oxo-4H-chromene-2-carboxamide (Scheme 3, Compound No. 14)

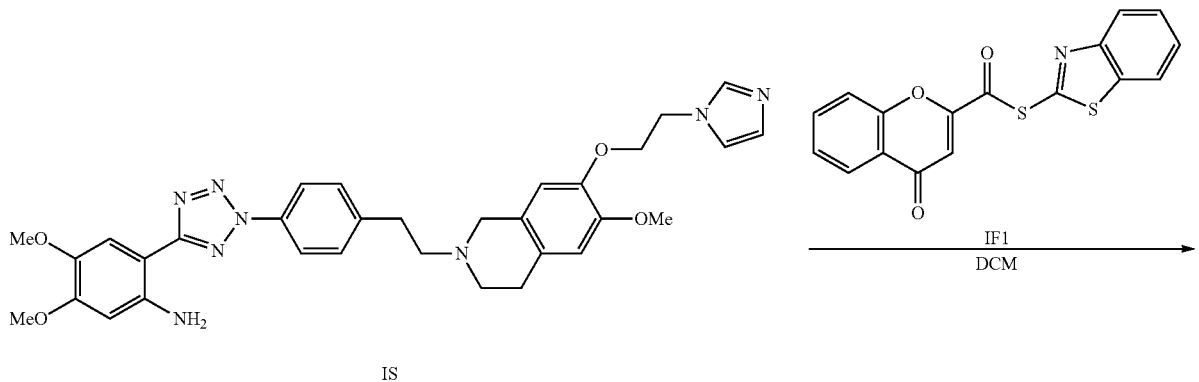

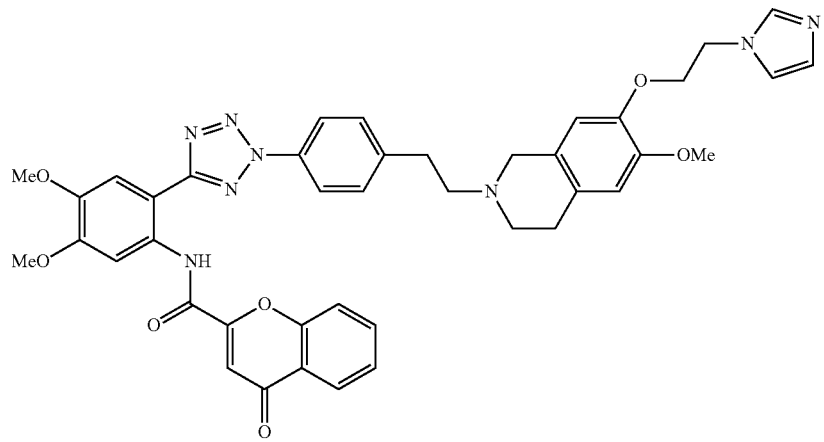

A clean, dry 40 mL vial was charged with Intermediate IS (90 mg, 0.15 mmol, 1.0 eq.), Intermediate IF1 (68 mg, 0.2 mmol, 1.33 eq.), and DCM (8.0 mL). The reaction mixture was stirred at room temperature for 3 h, and upon reaction completion, the mixture was concentrated under vacuum and purified by reverse-phase HPLC (0.1% TFA in water/MeCN). The product was then dissolved in 10% MeOH/DCM, followed by extraction with 1.0 M NaOH, drying over anhydrous sodium sulfate, filtration, and removal of the solvent under vacuum to give 32 mg of the title compound (28% yield) as a free base. LC/MS (ESI, m/z): 769.20 [M+H]$^+$.

Example 13: Synthesis of N-(2-(2-(4-(2-((3-(1H-Imidazol-1-yl)benzyl)((1-methyl-1H-indazol-5-yl)methyl)amino)ethyl)phenyl)-2H-tetrazol-5-yl)-4,5-dimethoxyphenyl)-4-oxo-4H-chromene-2-carboxamide (Scheme 4, Compound No. 3)

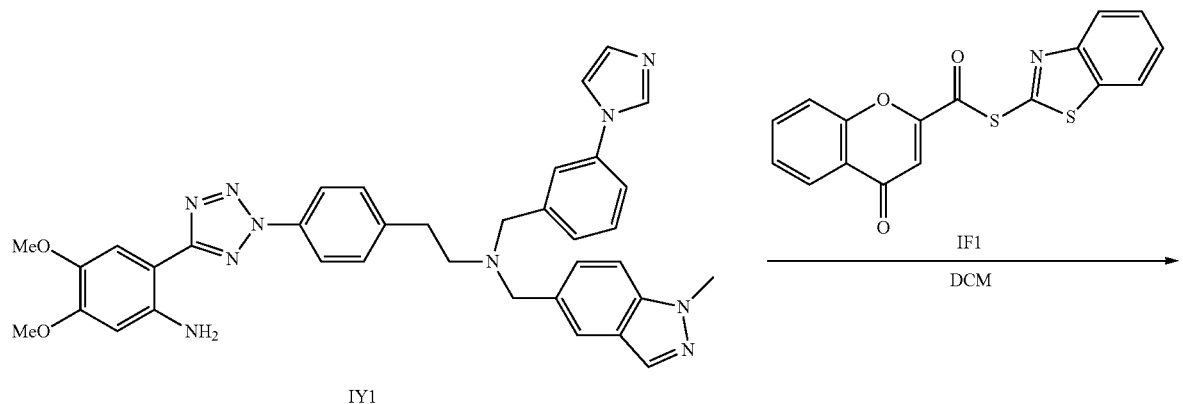

96 mg of Intermediate IY1 and 68 mg of Intermediate IF1 were used to synthesize 42 mg of the title compound (34% yield) according to the General Procedure RR. $^1$H NMR (400 MHz, DMSO-d$_6$), 2.72 (t, J=6.8 Hz, 2H), 2.91 (t, J=6.8 Hz, 2H), 3.72 (s, 2H), 3.76 (s, 2H), 3.78 (s, 3H), 3.82 (s, 3H), 3.99 (s, 3H), 6.85 (s, 1H), 7.03 (s, 1H), 7.25-7.35 (m, 4H), 7.40-7.62 (m, 9H), 7.72 (m, 1H), 7.85, 7.87 (2s, 2H), 7.95 (d, J=0.8 Hz, 1H), 7.96 (dd, J=8.0, 1.6 Hz, 1H), 8.10 (s, 1H), 8.16 (s, 1H), 11.78 (s, 1H). LC/MS (ESI, m/z): 813.5 [M+H]$^+$.

Example 14: Synthesis of N-(2-(2-(4-(2-((3-(1H-Imidazol-1-yl)benzyl)((1-methyl-1H-indazol-5-yl)methyl)amino)ethyl)phenyl)-2H-tetrazol-5-yl)-4,5-dimethoxyphenyl)quinoline-3-carboxamide (Scheme 4, Compound No. 4)

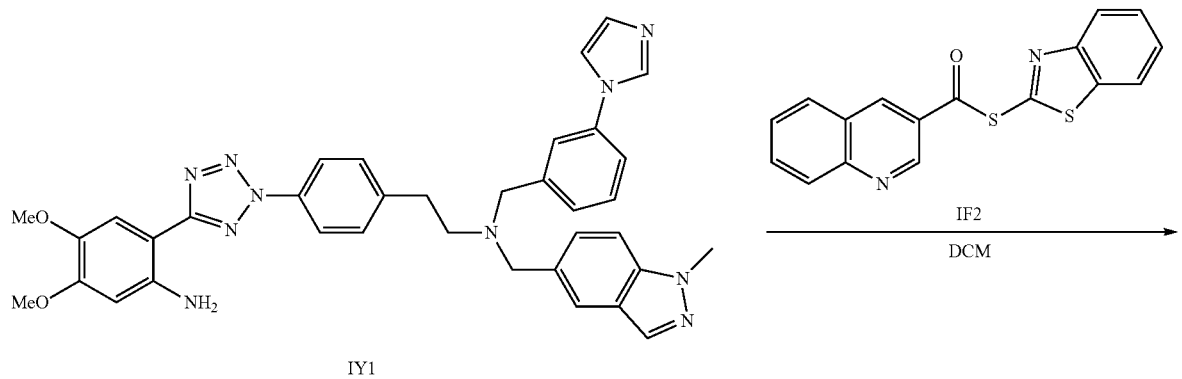

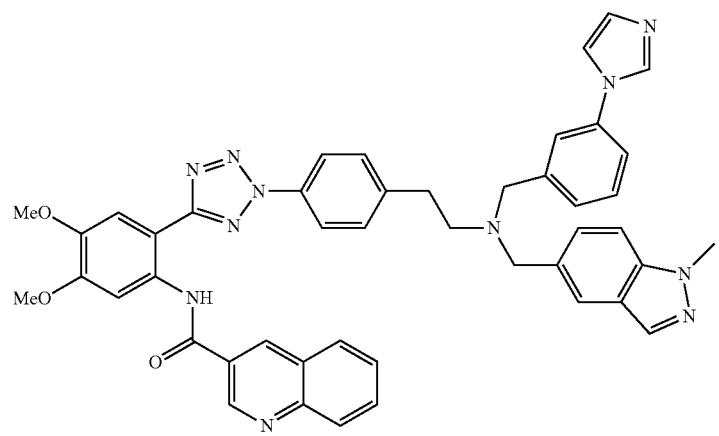

96 mg of Intermediate IY1 and 64 mg of Intermediate IF2 were used to synthesize 33 mg of the title compound (28% yield) according to the General Procedure RR. $^1$H NMR (400 MHz, DMSO-d$_6$), 2.70 (t, J=7.2 Hz, 2H), 2.91 (t, J=6.8 Hz, 2H), 3.70 (s, 2H), 3.76 (s, 2H), 3.91 (s, 3H), 3.92 (s, 3H), 3.99 (s, 3H), 7.01 (t, J=1.0 Hz, 1H), 7.27 (m, 3H), 7.33 (dd, J=4.3, 1.4 Hz, 1H), 7.39 (m, 1H), 7.45 (m, 2H), 7.52 (d, J=8.8 Hz, 1H), 7.56-7.61 (m, 3H), 7.76 (s, 1H), 7.84 (m, 1H), 7.88, 7.90 (2s, 2H), 7.93 (d, J=0.8 Hz, 1H), 7.95-7.98 (m, 2H), 8.07 (d, J=12.4 Hz, 1H), 8.13 (t, J=1.0 Hz, 1H), 8.99 (d, J=2.0 Hz, 1H), 9.45 (d, J=2.4 Hz, 1H), 10.92 (s, 1H). LC/MS (ESI, m/z): 796.3 [M+H]$^+$.

Example 15: Synthesis of N-(2-(2-(4-(2-(((3-(1H-Imidazol-1-yl)benzyl)((1-methyl-1H-indazol-5-yl)methyl)amino)ethyl)phenyl)-2H-tetrazol-5-yl)-4,5-dimethoxyphenyl)-7-methyl-4-oxo-4H-chromene-2-carboxamide (Scheme 4, Compound No. 5)

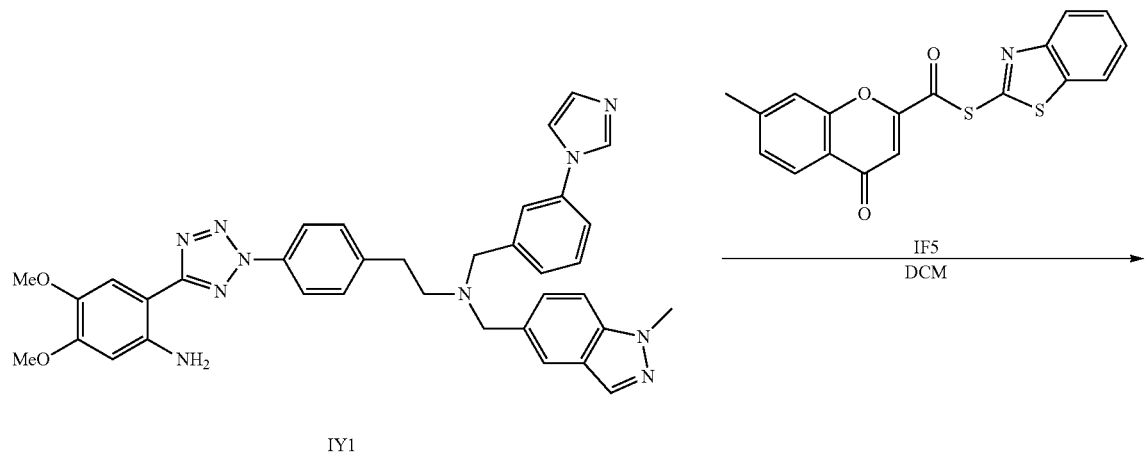

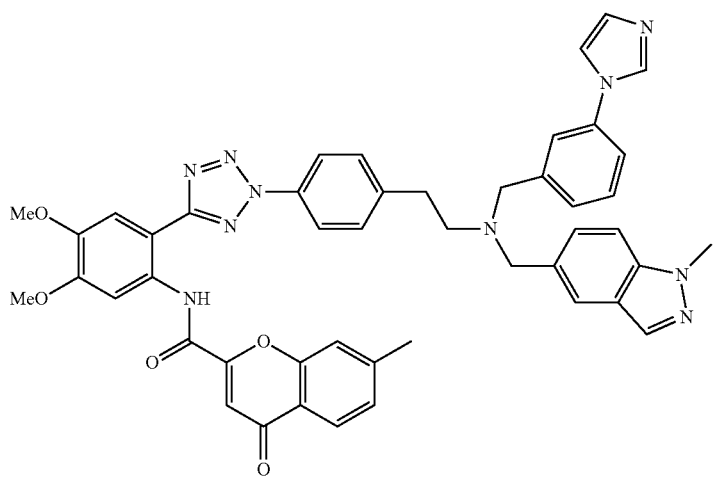

96 mg of Intermediate IY1 and 71 mg of Intermediate IF5 were used to synthesize 37 mg of the title compound (30% yield) according to the General Procedure RR. $^1$H NMR (400 MHz, DMSO-d$_6$), 2.18 (s, 3H), 2.70 (t, J=7.4 Hz, 2H), 2.88 (t, J=6.8 Hz, 2H), 3.70, 3.72, 3.75 (3s, 10H), 3.99 (s, 3H), 6.67 (s, 1H), 7.04 (s, 1H), 7.09, 7.12 (2s, 2H), 7.20, 7.22 (2s, 2H), 7.30-7.39 (m, 3H), 7.43 (t, J=8.0 Hz, 1H), 7.48, 7.50 (2s, 2H), 7.54 (d, J=8.8 Hz, 1H), 7.60 (s, 1H), 7.63 (s, 1H), 7.73, 7.75, 7.77 (3s, 3H), 7.95 (d, J=0.8 Hz, 1H), 8.02 (s, 1H), 8.17 (s, 1H), 11.68 (s, 1H). LC/MS (ESI, m/z): 827.6 [M+H]$^+$.

Example 16: Synthesis of Methyl 4-(2-(4-(2-(methyl((1-methyl-1H-indazol-5-yl)methyl)amino)ethyl)phenyl)-2H-tetrazol-5-yl)-3-(4-oxo-4H-chromene-2-carboxamido)benzoate (Compound No. 15)

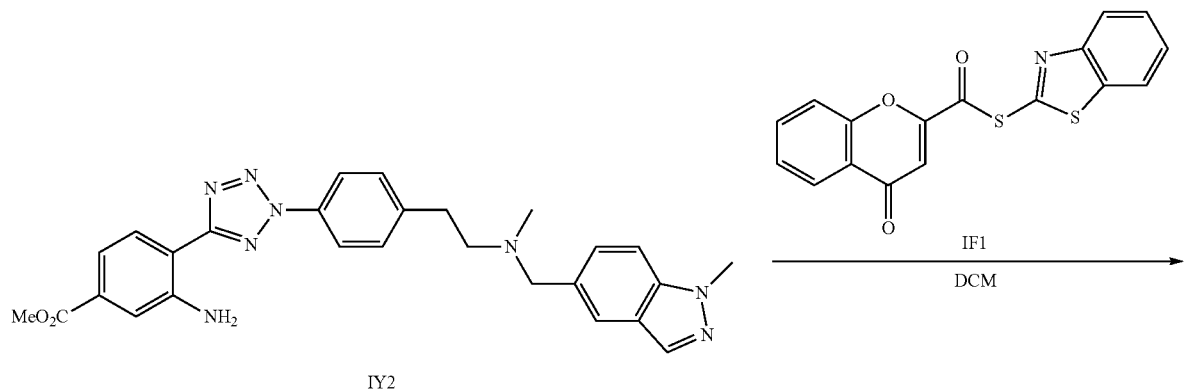

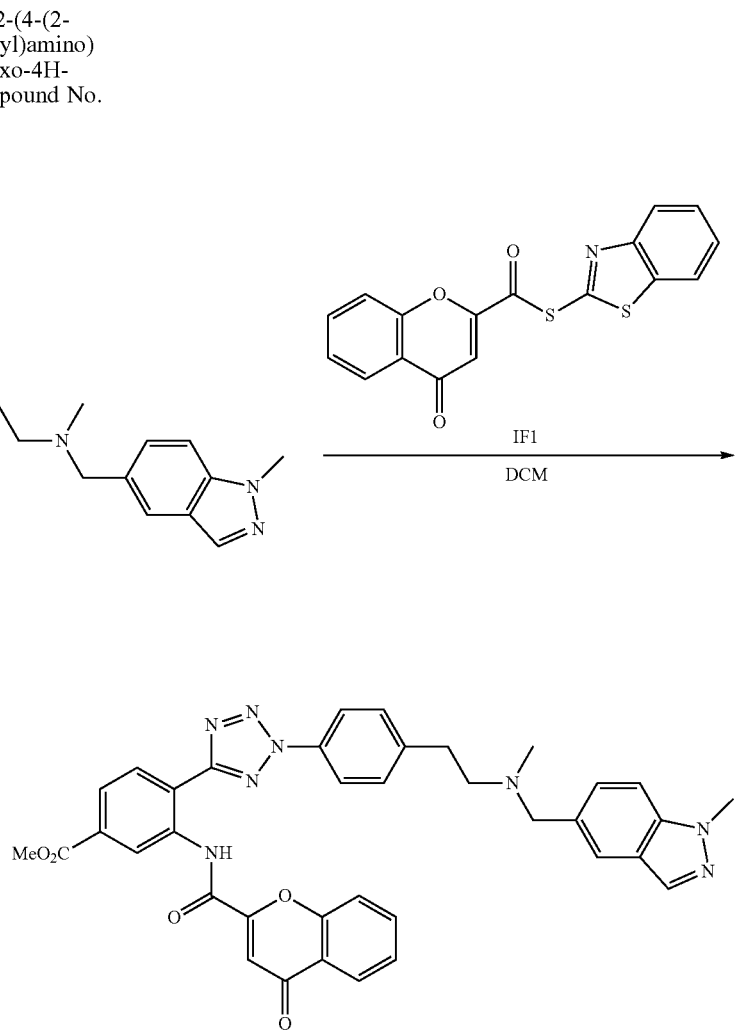

149 mg of Intermediate IY2 and 136 mg of Intermediate IF1 were used to synthesize 140 mg of the title compound (70% yield) according to the General Procedure RR. $^1$H NMR (400 MHz, DMSO-$d_6$) 2.20 (s, 3H), 2.57 (t, J=7.2 Hz, 2H), 2.71 (t, J=7.2 Hz, 2H), 3.59 (s, 5H), 3.99 (s, 3H), 6.48 (s, 1H), 7.09 (d, J=8.0 Hz, 1H), 7.15-7.34 (m, 5H), 7.50-7.61 (m, 5H), 7.70-7.75 (m, 2H), 7.93 (s, 1H), 8.69 (s, 1H), 11.66 (s, 1H). LC/MS (ESI, m/z): 669.20 [M+H]$^+$.

Example 17: Synthesis of N-(2-(2-(4-(2-(6,7-Dimethoxy-3,4-dihydroisoquinolin-2(1H)-yl)ethyl)phenyl)-2H-tetrazol-5-yl)-4,5-dimethoxyphenyl)-4-oxo-6-(pyridin-4-yl)-4H-chromene-2-carboxamide (Compound No. 19)

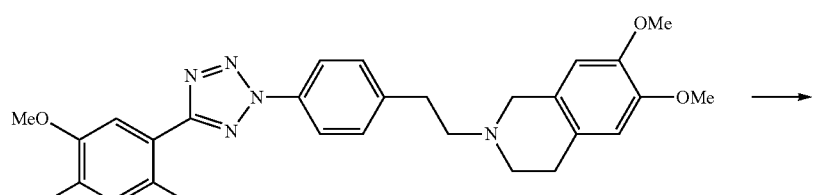

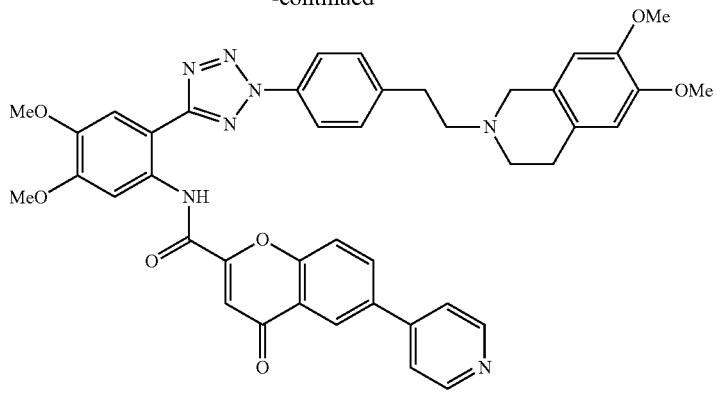

100 mg of Intermediate 1AZ and 108 mg of Intermediate IF6 were used to synthesize 52 mg of the title compound (36% yield) according to the General Procedure NN. $^1$H NMR (400 MHz, DMSO-$d_6$): δ 2.65-2.69 (m, 6H), 2.83 (t, J=8.0 Hz, 2H), 3.51 (s, 2H), 3.69 (s, 3H), 3.71 (s, 9H), 6.61 (s, 1H), 6.65 (s, 1H), 6.72 (s, 1H), 7.34-7.48 (m, 5H), 7.83 (s, 2H), 7.98-8.01 (m, 4H), 8.59 (d, J=4.0 Hz, 1H), 8.85 (s, 1H), 11.73 (s, 1H). LC/MS (ESI, m/z): 766.12 [M+H]$^+$.

Example 18: Synthesis of N-(2-(2-(4-(2-(6,7-Dimethoxy-3,4-dihydroisoquinolin-2(1H)-yl)ethyl)phenyl)-2H-tetrazol-5-yl)-4,5-dimethoxyphenyl)-6-(1H-imidazol-1-yl)-4-oxo-4H-chromene-2-carboxamide (Compound No. 20)

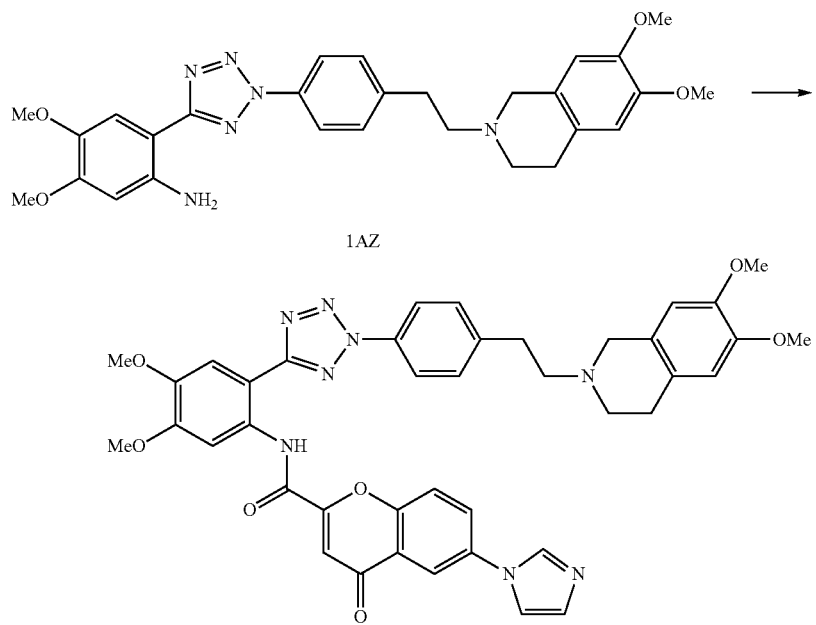

100 mg of Intermediate 1AZ and 105 mg of Intermediate IF7 were used to synthesize 48 mg of the title compound (33% yield) according to the General Procedure NN. $^1$H NMR (400 MHz, DMSO-$d_6$): δ 2.69 (s, 4H), 2.85-2.92 (m, 2H), 3.54 (s, 2H), 3.74 (s, 9H), 3.76 (s, 3H), 3.80-3.81 (m, 2H), 6.63 (d, J=8.0 Hz, 2H), 6.78 (s, 1H), 7.14 (s, 1H), 7.40-7.42 (m, 3H), 7.51-7.53 (m, 1H), 7.82-7.86 (m, 2H), 7.96-8.08 (m, 4H), 8.34 (s, 1H), 11.78 (s, 1H). LC/MS (ESI, m/z): 755.32 [M+H]$^+$.

Example 19: Synthesis of N-(2-(2-(4-(2-(6,7-Dimethoxy-3,4-dihydroisoquinolin-2(1H)-yl)ethyl)phenyl)-2H-tetrazol-5-yl)-4,5-dimethoxyphenyl)-4-(pyridin-4-yl)benzamide (Compound No. 21)

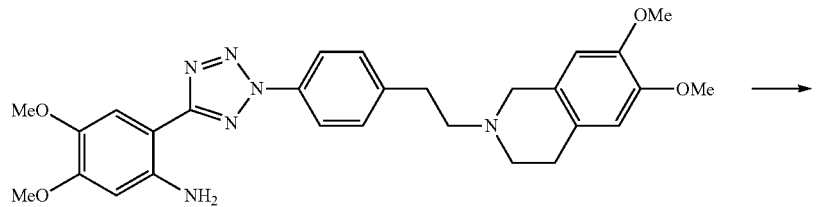

1AZ

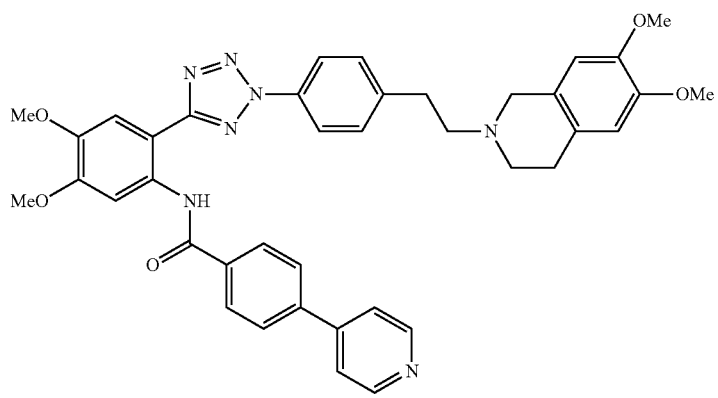

100 mg of Intermediate 1AZ and 89 mg of Intermediate IF8 were used to synthesize 49 mg of the title compound (37% yield) according to the General Procedure NN. $^1$H NMR (400 MHz, DMSO-d$_6$): δ 2.70-2.72 (m, 6H), 2.90 (t, J=16.0 Hz, 2H), 3.52 (s, 2H), 3.69 (s, 3H), 3.70 (s, 3H), 3.88 (s, 6H), 6.61 (d, J=8.0 Hz, 2H), 7.50 (d, J=12.0 Hz, 2H), 7.71 (s, 1H), 7.81 (d, J=4.0 Hz, 2H), 7.95-8.02 (m, 5H), 8.17 (d, J=8.0 Hz, 2H), 8.70 (d, J=4.0 Hz, 2H), 10.85 (s, 1H). LC/MS (ESI, m/z): 698.41 [M+H]$^+$.

Example 20: Synthesis of N-(2-(2-(4-(2-(6,7-Dimethoxy-3,4-dihydroisoquinolin-2(1H)-yl)ethyl)phenyl)-2H-tetrazol-5-yl)-4,5-dimethoxyphenyl)-4-(pyridin-3-yl)benzamide

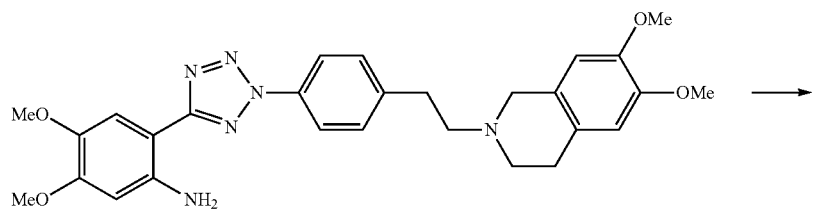

1AZ

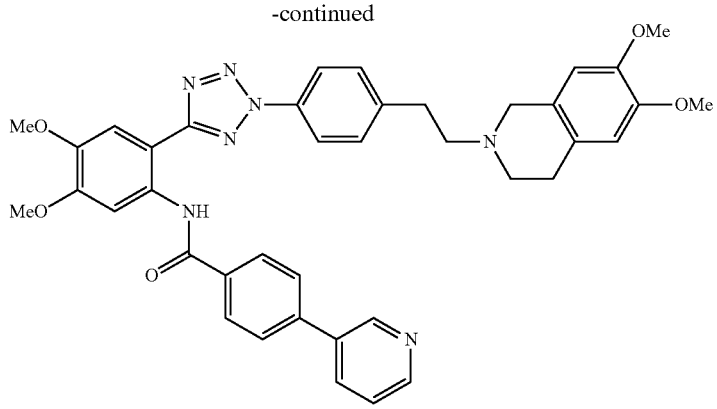

100 mg of Intermediate 1AZ and 89 mg of Intermediate IF9 were used to synthesize 35 mg of the title compound (26% yield) according to the General Procedure NN. $^1$H NMR (400 MHz, DMSO-d$_6$): δ 2.70-2.73 (m, 6H), 2.91 (t, j=16.0 Hz, 2H), 3.53 (s, 2H), 3.69 (s, 3H), 3.70 (s, 3H), 3.89 (s, 6H), 6.61 (d, J=12.0 Hz, 2H), 7.53-7.57 (m, 3H), 7.73 (s, 1H), 7.83-8.04 (m, 5H), 8.17 (d, j=12.0 Hz, 3H), 8.64-8.66 (m, 1H), 9.02 (s, 1H), 10.85 (s, 1H). LC/MS (ESI, m/z): 698.31 [M+H]$^+$.

Example 21: Synthesis of N-(2-(2-(4-(2-(6,7-Dimethoxy-3,4-dihydroisoquinolin-2(1H)-yl)ethyl)phenyl)-2H-tetrazol-5-yl)-4,5-dimethoxyphenyl)-4-(1H-imidazol-1-yl)benzamide (Compound No. 23)

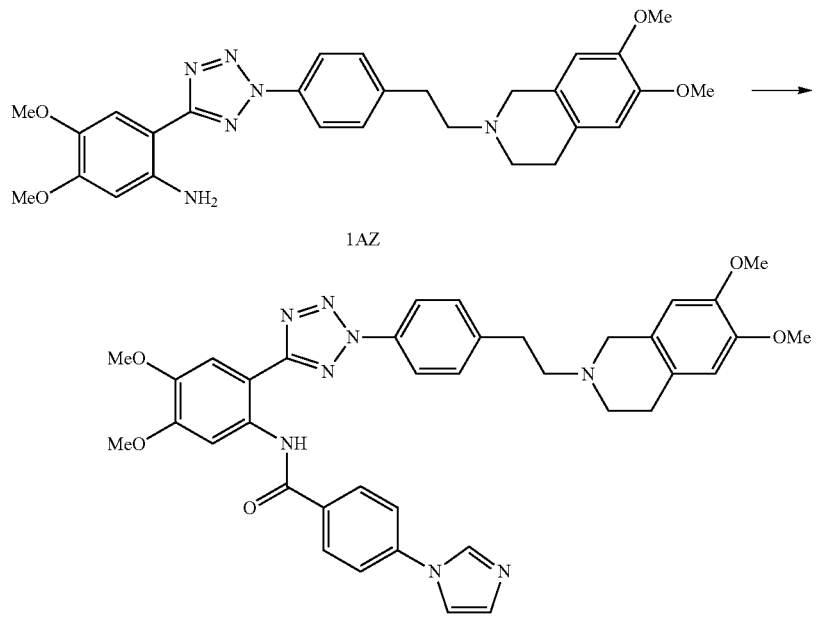

100 mg of Intermediate 1AZ and 87 mg of Intermediate IF10 were used to synthesize 45 mg of the title compound (34% yield) according to the General Procedure NN. $^1$H NMR (400 MHz, DMSO-d$_6$): δ 2.70-2.75 (m, 6H), 2.92 (t, J=12.0 Hz, 2H), 3.54 (s, 2H), 3.70 (s, 6H), 3.89 (s, 6H), 6.62 (d, J=8.0 Hz, 2H), 7.18 (s, 1H), 7.53 (d, 7=8.0 Hz, 2H), 7.73 (s, 1H), 7.87-8.01 (m, 6H), 8.18 (d, J=8.0 Hz, 2H), 8.43 (s, 1H), 10.80 (s, 1H). LC/MS (ESI, m/z): 687.21 [M+H]$^+$.

Example 22: Synthesis of N-(2-(2-(4-(2-(6,7-Dimethoxy-3,4-dihydroisoquinolin-2(1H)-yl)ethyl)phenyl)-2H-tetrazol-5-yl)-4-(pyridin-3-yloxy)phenyl)-4-oxo-4H-chromene-2-carboxamide (Compound No. 24)

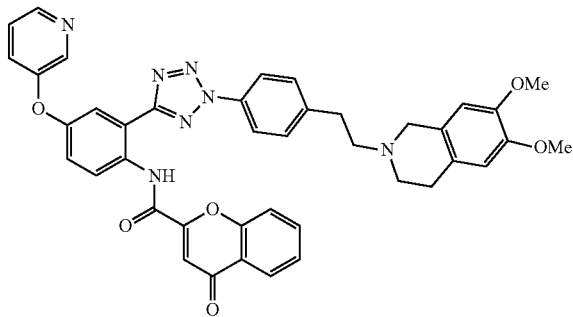 [SMILES: COc1cc2c(cc1OC)CN(CCc1ccc(-n3nnc(-c4cc(Oc5cccnc5)ccc4NC(=O)c4cc(=O)c5ccccc5o4)n3)cc1)CC2]

100 mg of Intermediate IE9 and 82 mg of Intermediate IF1 were used to synthesize 40 mg of the title compound (31% yield) according to the General Procedure RR. $^1$H NMR (400 MHz, DMSO-d$_6$): δ 2.67-2.73 (m, 6H), 2.90 (t, J=16.0 Hz, 2H), 3.55 (s, 2H), 3.70 (s, 6H), 6.63 (s, 1H), 6.65 (s, 1H), 6.96 (s, 1H), 7.37-7.40 (m, 1H), 7.45-7.63 (m, 6H), 7.82-7.87 (m, 2H), 7.98 (d, J=8.0 Hz, 2H), 8.06 (d, J=8.0 Hz, 1H), 8.40 (d, J=8.0 Hz, 1H), 8.44 (d, J=4.0 Hz, 1H), 8.50 (d, J=4.0 Hz, 1H), 11.61 (s, 1H). LC/MS (ESI, m/z): 722.21 [M+H]$^+$.

Example 23: Synthesis of N-(2-(2-(4-(2-(6,7-Dimethoxy-3,4-dihydroisoquinolin-2(1H)-yl)ethyl)phenyl)-2H-tetrazol-5-yl)-4-(pyridin-4-yloxy)phenyl)-4-oxo-4H-chromene-2-carboxamide (Compound No. 25)

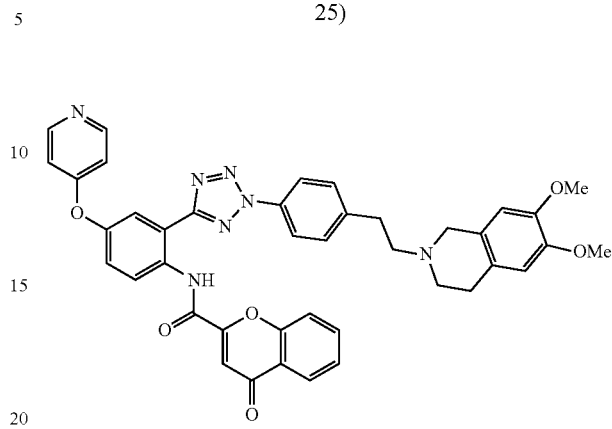

98 mg of Intermediate IE10 and 68 mg of Intermediate IF1 were used to synthesize 40 mg of the title compound (31% yield) according to the General Procedure RR. $^1$H NMR (400 MHz, DMSO-d$_6$): δ 2.72-2.76 (m, 6H), 2.95 (t, J=7.4 Hz, 2H), 3.56 (s, 2H), 3.71 (2s, 6H), 6.29 (d, J=8.0 Hz, 2H), 6.65 (d, J=9.6 Hz, 2H), 7.04 (s, 1H), 7.51-7.56 (m, 3H), 7.65 (d, J=8.4 Hz, 1H), 7.80 (dd, J=8.8, 2.8 Hz, 1H), 7.86 (dt, J=7.8, 0.8 Hz, 1H), 8.08-8.11 (m, 5H), 8.27 (d, J=2.8 Hz, 1H), 8.53 (d, J=8.8 Hz, 1H), 11.80 (bs, 1H). LC/MS (ESI, m/z): 722.31 [M+H]$^+$.

Example 24: Synthesis of N-(2-(2-(4-(2-(6,7-Dimethoxy-3,4-dihydroisoquinolin-2(1H)-yl)ethyl)phenyl)-2H-tetrazol-5-yl)-4-(pyridin-4-ylmethoxy)phenyl)-4-oxo-4H-chromene-2-carboxamide (Compound No. 26)

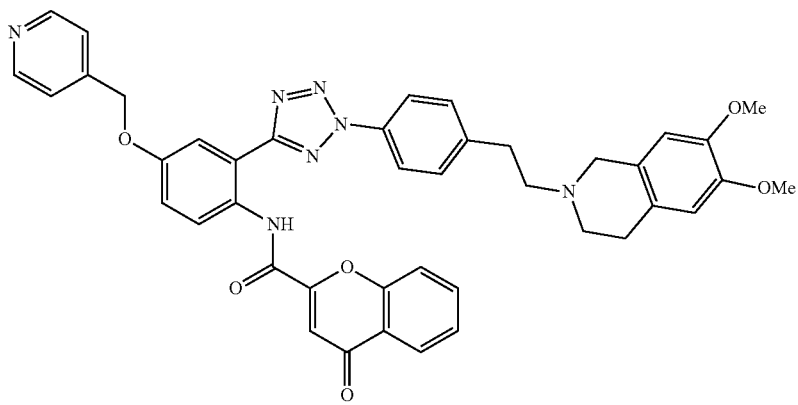 [SMILES: COc1cc2c(cc1OC)CN(CCc1ccc(-n3nnc(-c4cc(OCc5ccncc5)ccc4NC(=O)c4cc(=O)c5ccccc5o4)n3)cc1)CC2]

100 mg of Intermediate IE12 and 80 mg of Intermediate IF1 were used to synthesize 38 mg of the title compound (30% yield) according to the General Procedure RR. $^1$H NMR (400 MHz, DMSO-d$_6$): δ 2.70 (s, 6H), 2.90 (t, J=12.0 Hz, 2H), 3.55 (s, 2H), 3.70 (s, 6H), 5.27 (s, 2H), 6.63 (s, 1H), 6.66 (s, 1H), 6.91 (s, 1H), 7.27-7.30 (m, 1H), 7.44-7.60 (m, 6H), 7.80-7.83 (m, 2H), 7.98 (d, J=8.0 Hz, 2H), 8.04 (d, J=8.0 Hz, 1H), 8.25 (d, J=12.0 Hz, 1H), 8.61 (d, J=4.0 Hz, 2H), 11.47 (s, 1H). LC/MS (ESI, m/z): 736.22 [M+H]$^+$.

Example 25: Synthesis of N-(2-(2-(4-(2-(6,7-Dimethoxy-3,4-dihydroisoquinolin-2(1H)-yl)ethyl)phenyl)-2H-tetrazol-5-yl)-4-(pyridin-3-ylmethoxy)phenyl)-4-oxo-4H-chromene-2-carboxamide (Compound No. 27)

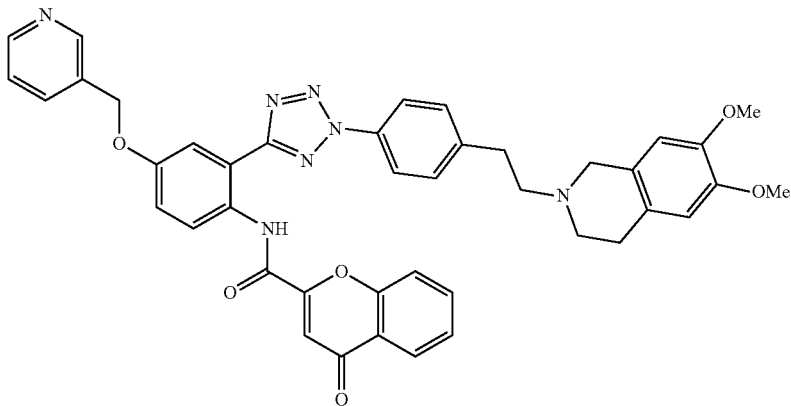 [SMILES: COc1cc2c(cc1OC)CN(CCc1ccc(-n3nnc(-c4cc(OCc5cccnc5)ccc4NC(=O)c4cc(=O)c5ccccc5o4)n3)cc1)CC2]

90 mg of Intermediate IE8 and 70 mg of Intermediate IF1 were used to synthesize 49 mg of the title compound (41% yield) according to the General Procedure RR. $^1$H NMR (400 MHz, DMSO-$d_6$): δ 2.67-2.73 (m, 6H), 2.89 (t, J=8.0 Hz, 2H), 3.54 (s, 2H), 3.70 (s, 6H), 5.22 (s, 2H), 6.63 (d, J=8.0 Hz, 2H), 6.89 (s, 1H), 7.25-7.29 (m, 1H), 7.43-7.58 (m, 5H), 7.78-7.83 (m, 2H), 7.91 (d, J=4.0 Hz, 1H), 7.94 (d, J=8.0 Hz, 2H), 8.03 (d, J=8.0 Hz, 1H), 8.26 (d, J=12.0 Hz, 1H), 8.57 (d, J=8.0 Hz, 1H), 8.73 (s, 1H), 11.49 (s, 1H). LC/MS (ESI, m/z): 736.32 [M+H]$^+$.

Example 26: Synthesis of N-(2-(2-(4-(2-(6,7-Dimethoxy-3,4-dihydroisoquinolin-2(1H)-yl)ethyl)phenyl)-2H-tetrazol-5-yl)-4-(2-(pyridin-3-yl)ethoxy)phenyl)-4-oxo-4H-chromene-2-carboxamide (Compound No. 28)

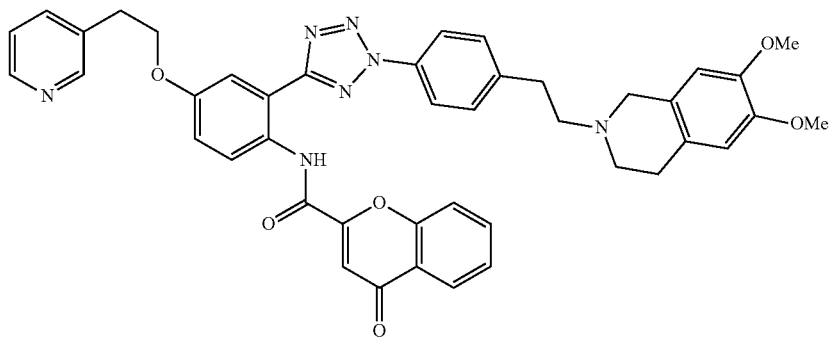 [SMILES: COc1cc2c(cc1OC)CN(CCc1ccc(-n3nnc(-c4cc(OCCc5cccnc5)ccc4NC(=O)c4cc(=O)c5ccccc5o4)n3)cc1)CC2]

49 mg of Intermediate IE11 and 34 mg of Intermediate IF1 were used to synthesize 23 mg of the title compound (36% yield) according to the General Procedure RR. $^1$H NMR (400 MHz, DMSO-$d_6$): δ 2.71 (m, 6H), 2.92 (t, j=7.4 Hz, 2H), 3.11 (t, j=6.4 Hz, 2H), 3.55 (s, 2H), 3.70 (s, 3H), 3.71 (s, 3H), 4.30 (t, j=6.6 Hz, 2H), 6.63 (s, 1H), 6.66 (s, 1H), 6.91 (s, 1H), 7.19 (dd, j=5.8, 2.8 Hz, 1H), 7.37 (dd, j=7.4, 4.6 Hz, 1H), 7.44, 7.46 (2s, 2H), 7.52 (t, j=7.4 Hz, 1H), 7.59 (d, j=8.0 Hz, 1H), 7.67 (d, j=2.8 Hz, 1H), 7.79-7.86 (m, 2H), 7.97, 8.00 (2s, 2H), 8.06 (dd, j=4.6, 1.4 Hz, 1H), 8.24 (d, j=8.8 Hz, 1H), 8.47 (dd, j=3.2, 1.6 Hz, 1H), 8.06 (d, J=1.6 Hz, 1H), 11.47 (s, 1H); LC/MS (ESI, m/z): 750.2 [M+H]$^+$.

Example 27: Synthesis of N-(4-(Benzyloxy)-2-(2-(4-(2-(6,7-dimethoxy-3,4-dihydroisoquinolin-2(1H)-yl)ethyl)phenyl)-2H-tetrazol-5-yl)-5-methoxyphenyl)-4-oxo-4H-chromene-2-carboxamide (Compound No. 29)

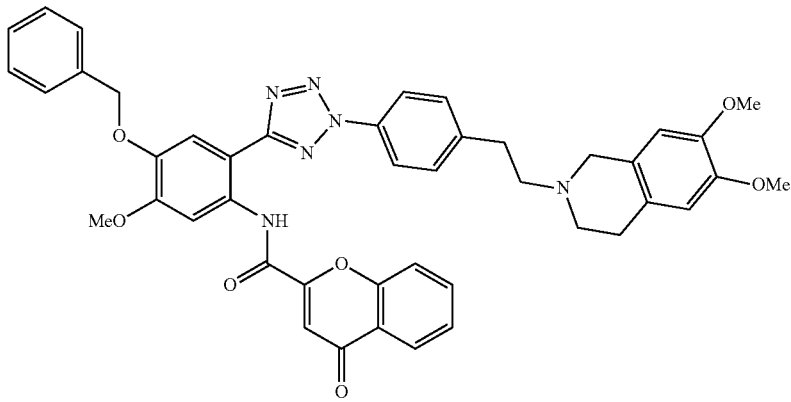 [SMILES: COc1cc2c(cc1OC)CN(CCc1ccc(-n3nnc(-c4cc(OCc5ccccc5)c(OC)cc4NC(=O)c4cc(=O)c5ccccc5o4)n3)cc1)CC2]

100 mg of Intermediate IE6 and 76 mg of Intermediate IF1 were used to synthesize 45 mg of the title compound (36% yield) according to the General Procedure RR. $^1$H NMR (400 MHz, DMSO-$d_6$): δ 2.72 (s, 6H), 2.89 (t, J=12.0 Hz, 2H), 3.58 (s, 2H), 3.70 (s, 6H), 3.72 (s, 3H), 5.02 (s, 2H), 6.64 (d, J=8.0 Hz, 2H), 6.75 (s, 1H), 7.37-7.48 (m, 9H), 7.55 (s, 1H), 7.68-7.73 (m, 1H), 7.85 (d, 7=8.0 Hz, 2H), 7.93-7.95 (m, 1H), 8.07 (s, 1H), 11.73 (s, 1H). LC/MS (ESI, m/z): 765.18 $[M+H]^+$.

Example 28: Synthesis of N-(4-(Benzyloxy)-2-(2-(4-(2-(3,4-dihydro-2,6-naphthyridin-2(1H)-yl)ethyl)phenyl)-2H-tetrazol-5-yl)-5-methoxyphenyl)-4-oxo-4H-chromene-2-carboxamide (Compound No. 16)

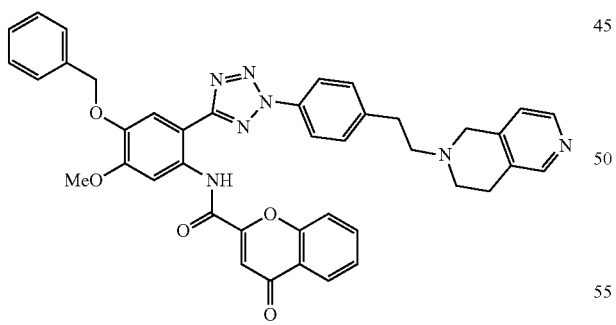

65 mg of Intermediate IE3 and 46 mg of Intermediate IF1 were used to synthesize 32 mg of the title compound (38% yield) according to the General Procedure RR. $^1$H NMR (400 MHz, DMSO-$d_6$): δ 2.78 (m, 6H), 2.95 (t, j=7.4 Hz, 2H), 3.68 (s, 2H), 3.82 (s, 3H), 5.14 (s, 2H), 6.89 (s, 1H), 7.10 (d, j=4.8 Hz, 1H), 7.35-7.52 (m, 8H), 7.56 (d, j=8.4 Hz, 1H), 7.72 (s, 1H), 7.81 (m, 1H), 7.97 (d, j=8.4 Hz, 2H), 8.04 (dd, j=8.0, 1.6 Hz, 1H), 8.28 (s, 1H), 8.28 (d, j=4.8 Hz, 1H), 8.34 (s, 1H). LC/MS (ESI, m/z): 706.31 $[M+H]^+$.

Example 29: Synthesis of N-(4-(Benzyloxy)-2-(2-(4-(2-(3,4-dihydro-2,6-naphthyridin-2(1H)-yl)ethyl)phenyl)-2H-tetrazol-5-yl)-5-methoxyphenyl)quinoline-3-carboxamide (Compound No. 17)

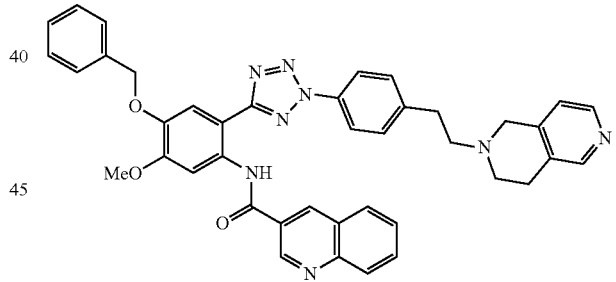

65 mg of Intermediate IE3 and 42 mg of Intermediate IF2 were used to synthesize 33 mg of the title compound (40% yield) according to the General Procedure RR. $^1$H NMR (400 MHz, DMSO-$d_6$): δ 2.80-3.00 (m, 8H), 3.78 (bs, 2H), 3.92 (s, 3H), 5.23 (s, 2H), 7.10 (d, 7=4.8 Hz, 1H), 7.38 (m, 1H), 7.45 (m, 4H), 7.53 (m, 2H), 7.73 (m, 1H), 7.85 (s, 1H), 7.94 (m, 4H), 8.05 (dd, J=8.4, 0.8 Hz, 1H), 8.13 (d, J=8.4 Hz, 1H), 8.30 (d, J=5.2 Hz, 1H), 8.36 (s, 1H), 9.02 (d, J=1.6 Hz, 1H), 9.45 (d, J=2.4 Hz, 1H), 10.91 (s, 1H). LC/MS (ESI, m/z): 689.31 $[M+H]^+$.

Example 30: Synthesis of N-(4-(Benzyloxy)-2-(2-(4-(2-(5,6-dihydroimidazo[1,5-a]pyrazin-7(8H)-yl)ethyl)phenyl)-2H-tetrazol-5-yl)-5-methoxyphenyl)-4-oxo-4H-chromene-2-carboxamide (Compound No. 18)

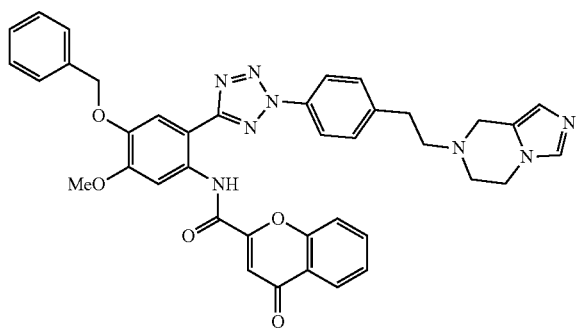 [SMILES: COc1cc(NC(=O)c2cc(=O)c3ccccc3o2)c(-c2nnn(-c3ccc(CCN4CCn5cncc5C4)cc3)n2)cc1OCc1ccccc1]

65 mg of Intermediate IE5 and 37 mg of Intermediate IF1 were used to synthesize 27 mg of the title compound (26% yield) according to the General Procedure RR. $^1$H NMR (400 MHz, DMSO-$d_6$): δ 2.77-2.94 (m, 6H), 3.68 (s, 2H), 3.79 (s, 2H), 4.0 (t, J=8.0 Hz, 2H), 5.10 (s, 2H), 6.66 (s, 1H), 6.85 (s, 1H), 7.41-7.53 (m, 10H), 7.68 (s, 1H), 7.75-7.80 (m, 1H), 7.93 (d, J=8.0 Hz, 2H), 7.99 (d, 7=12.0 Hz, 1H), 8.11 (s, 1H), 11.73 (s, 1H). LC/MS (ESI, m/z): 695.21 [M+H]$^+$.

Example 31: Synthesis of N-(2-(2-(4-(2-(6,7-Dimethoxy-3,4-dihydroisoquinolin-2(1H)-yl)ethyl)phenyl)-2H-tetrazol-5-yl)-5-methoxy-4-(pyridin-3-ylmethoxy)phenyl)-4-oxo-4H-chromene-2-carboxamide (Compound No. 30)

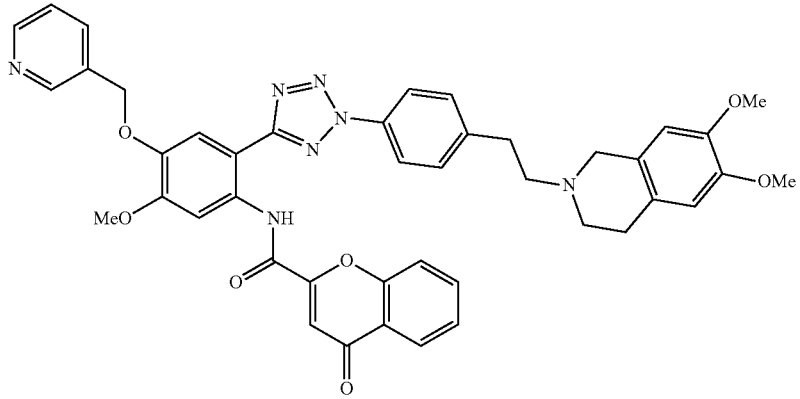 [SMILES: COc1cc2c(cc1OC)CN(CCc1ccc(-n3nnc(-c4cc(OCc5cccnc5)c(OC)cc4NC(=O)c4cc(=O)c5ccccc5o4)n3)cc1)CC2]

100 mg of Intermediate IE7 and 76 mg of Intermediate IF1 were used to synthesize 51 mg of the title compound (39% yield) according to the General Procedure RR. $^1$H NMR (400 MHz, DMSO-$d_6$): δ 2.70 (s, 6H), 2.86 (t, J=12.0 Hz, 2H), 3.55 (s, 2H), 3.67 (s, 3H), 3.69 (s, 6H), 5.00 (s, 2H), 6.62 (s, 1H), 6.65 (s, 1H), 6.69 (s, 1H), 7.35-7.44 (m, 5H), 7.49 (s, 1H), 7.65 (t, J=12.0 Hz, 1H), 7.80-7.90 (m, 4H), 8.05 (s, 1H), 7.56 (d, j=4.0 Hz, 1H), 8.66 (s, 1H), 11.72 (s, 1H). LC/MS (ESI, m/z): 766.32 [M+H]$^+$.

Example 32: Determination of P-Glycoprotein Inhibitory Activity

A P-glycoprotein overexpressing cell line derived from the human uterine sarcoma cell line MES-SA (i.e., MES-SA/DX5 cells (ATCC)) was seeded by stepwise exposures to increasing concentrations of doxorubicin, in a 96-well plate at 6,500 cells/100 μL media (McCoy's 5A+10% FBS) in each well. The cells were incubated overnight at 37° C. 5% $CO_2$. Compounds were diluted in a separate 96-well plate to yield 11× of final concentration (final Compound concentrations were 0, 5, 20, 80, 320, and 1280 nM and the final docetaxel concentration was 100 nM or the final paclitaxel concentration was 200 nM). DMSO was used as a negative control and known P-glycoprotein inhibitor, encequidar methane sulfonic acid monohydrate (HM30181A), was used as a positive control. 10 μL of the 11× dilutions was added to the appropriate well, P-glycoprotein inhibition wells comprised Compound+docetaxel (or Compound+paclitaxel). The compound toxicity wells comprised 1280 nM Compound+10 μL of culture media. Treated the cells were incubated for 3 days at 37° C. 5% $CO_2$.

To value (reflecting the starting number of cells upon Compound treatment) of 3 wells of cells was determined by performing the following steps 1-4 as described below.

1. 10 μL MTT (5 mg/mL in PBS) was added to each well and incubated for 1.5 hours at 37° C. 5% $CO_2$.
2. Culture media was removed and 100 μL of DMSO was added to each well.
3. The plate was gently shook until all purple MTT formazan crystals were dissolved. $OD_{540}$ was then measured using microplate reader.
4. Cell growth percentage was calculated with the following equation:

$$\text{Cell growth percentage} = (T-T_0)/(C-T_0) \times 100\%,$$

wherein T is OD of the test well exposure to Compound; C is OD of the control well without Compound treatment; and $T_0$ is OD at time zero. Cell growth inhibition curve and EC so (measure of P-glycoprotein inhibition) were obtained by fitting the data to nonlinear regression model using GraphPad Prism software (v6.0).

Example 33. Determination of CYP3A4 Inhibitory Activity

Test compounds, DMSO (negative control), and ketoconazole (positive control) were diluted to 4× final concentrations in water. The standard final Compound concentrations were 37, 111, 333, 1000, and 3000 nM. 12.5 µL of the Compound dilutions were transferred to a white 96-well plate. 1450 µL (enough for a whole plate) of 4× assay buffer (400 mM potassium phosphate buffer (10 mL 1M potassium phosphate buffer: 8.02 mL 1M $K_2HPO_4$+1.98 mL 1M $KH_2PO_4$ (1.4 g $K_2HPO_4$+0.27 g $KH_2PO_4$ in 10 mL $H_2O$), 32 µM Luciferin-IPA (Promega V9002)) 580 µl of 1 M $K_3PO_4$ buffer, 870 µL $H_2O$, 14 µL of 3 mM Luciferin-IPA, and 18 µL of human liver microsome (Sigma M0317-1VL) was made. 12.5 µL of 4× assay buffer was added to each well. For the well of blank control, 12.5 µL of 4× assay buffer without liver microsome was added. The plate was incubated at room temperature for 15 minutes. 2.75 mL NADPH buffer was made as follows: 2.42 mL $H_2O$, 275 µL solution A and 55 µL solution B (NADPH regeneration system, Promega V9510). 25 µL of the buffer was added to each well. The plates were incubated at 37° C. for 11 minutes. 50 µL of luciferin detection reagent (Promega V9002) was added and the plates were incubated at room temperature for 5 minutes. The plate was read with a luminometer.

The dose-response curve and $IC_{50}$ were obtained by fitting data to nonlinear regression model using GraphPad Prism software (v6.0).

For $EC_{50}$ or $IC_{50}$ values shown in Table A, "A" means $EC_{50}$ or $IC_{50}$<100 nM; "B" means $EC_{50}$ or $IC_{50}$ ranging between 100 nM and 250 nM; "C" means $EC_{50}$ or $IC_{50}$ ranging between 250 nM and 500 nM; "D" means $EC_{50}$ or $IC_{50}$ ranging between 500 nM and 1000 nM; "E" means $EC_{50}$ or $IC_{50}$>1000 nM; "Nd" means Not determined.

TABLE A

| Compound No. | P-gp $EC_{50}$ (nM) | CYP3A4 $IC_{50}$ (nM) |
|---|---|---|
| 1 | E | E |
| 2 | B | B |
| 3 | E | D |
| 4 | D | D |
| 5 | E | E |
| 6 | B | E |
| 7 | B | D |
| 8 | E | B |
| 9 | E | D |
| 10 | E | C |
| 11 | D | C |
| 12 | A | E |
| 13 | A | D |
| 14 | E | Nd |
| 15 | A | E |
| 16 | A | E |
| 17 | A | D |
| 18 | A | E |
| 19 | E | E |
| 20 | E | E |
| 21 | A | E |
| 22 | B | E |
| 23 | C | D |
| 24 | A | E |
| 25 | D | E |
| 26 | A | E |
| 27 | A | E |
| 28 | B | D |
| 29 | A | E |
| 30 | A | E |
| Elacridar | A | E |
| Tariquidar | A | E |
| Encequidar methanesulfonate monohydrate | A | E |
| Ketoconazole | E | B |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (IA) or (I):

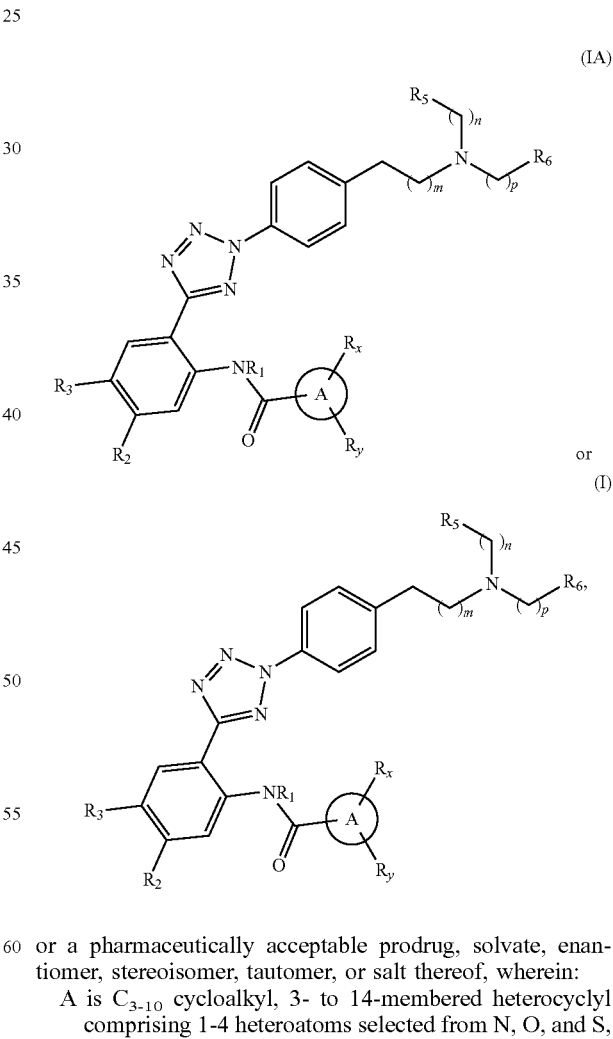

or a pharmaceutically acceptable prodrug, solvate, enantiomer, stereoisomer, tautomer, or salt thereof, wherein:

A is $C_{3-10}$ cycloalkyl, 3- to 14-membered heterocyclyl comprising 1-4 heteroatoms selected from N, O, and S, $C_{6-10}$ aryl, or 5- to 14-membered heteroaryl comprising 1-4 heteroatoms selected from N, O, and S, wherein the cycloalkyl or heterocyclyl is optionally substituted with oxo;

each $R_x$ and $R_y$ is independently H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)R$_{11}$, —C(O)OR$_{11}$, —C(O)N(R$_{11}$)$_2$, —C(O)NR$_{11}$—S(O)$_2$R$_{11}$, —C(O)NR$_{11}$—S(O)$_2$—OR$_{11}$, —C(O)NR$_{11}$—S(O)$_2$—N(R$_{11}$)$_2$, or —O-(5- to 10-membered heteroaryl comprising 1-4 heteroatoms selected from N, O, and S), wherein at least one of $R_2$ and $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)R$_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently oxo, halogen, —NH$_2$, —CN, —C(O)R$_{10}$, —C(O)OR$_{10}$, —C(O)N(R$_{10}$)$_2$, $C_{1-3}$ alkyl, $C_{2-6}$ alkenyl, $C_{2-6}$ alkynyl, $C_{1-6}$ alkoxy, —NH(C$_{1-6}$ alkyl), —N(C$_{1-6}$ alkyl)$_2$, —O—(CH$_2$)$_t$—R$_8$, —NH—(CH$_2$)$_t$—R$_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$;

$R_8$ is —OH, $C_{1-6}$ alkoxy, $C_{1-6}$ alkoxy-OH, —NH$_2$, —NH(C$_{1-6}$ alkyl), —N(C$_{1-6}$ alkyl)$_2$, —SH, —S(C$_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl, or heteroaryl is optionally substituted by one or more $R_9$;

each $R_9$ is independently —(CH$_2$)$_u$-(5- to 10-membered heteroaryl comprising 1-4 heteroatoms selected from N, O, and S) or —(CH$_2$)$_u$—(C$_{6-10}$ aryl), wherein the heteroaryl or aryl is optionally substituted with one or more halogen, —CN, —OH, or —NH$_2$;

each $R_{10}$ is independently halogen, —OH, —NH$_2$, —CN, $C_{1-6}$ alkyl, $C_{2-6}$ alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$;

each n, m, and p is independently 0 or 1;

t is 1, 2, or 3; and u is 0, 1, 2, or 3, wherein for the compound of Formula (IA), when $R_5$ and $R_6$ together with the atoms to which they are attached form a heterocyclyl or heteroaryl substituted with two $R_7$ and both $R_7$ are —O-methyl, then either (a) one of $R_2$ and $R_3$ is not —O-methyl; or (b) $R_x$ or $R_y$ is 5- to 10-membered heteroaryl comprising 1-4 heteroatoms selected from N, O, and S, and wherein for the compound of Formula (I), when $R_5$ and $R_6$ together with the atoms to which they are attached form a heterocyclyl or heteroaryl substituted with two $R_7$, then one $R_7$ is not —O-methyl.

2. A compound of Formula (I'):

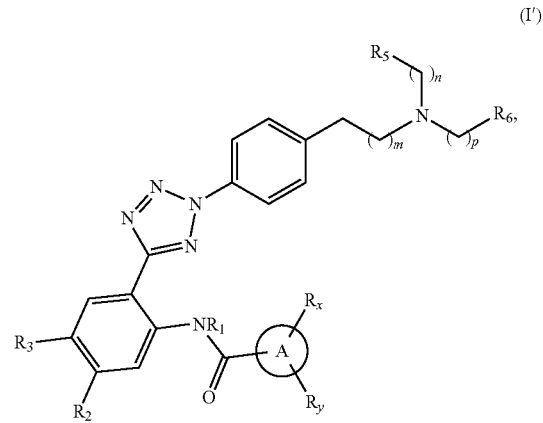

(I')

or a pharmaceutically acceptable prodrug, solvate, enantiomer, stereoisomer, tautomer, or salt thereof, wherein:

A is

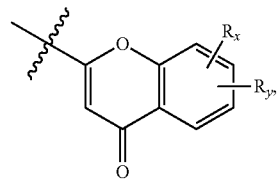

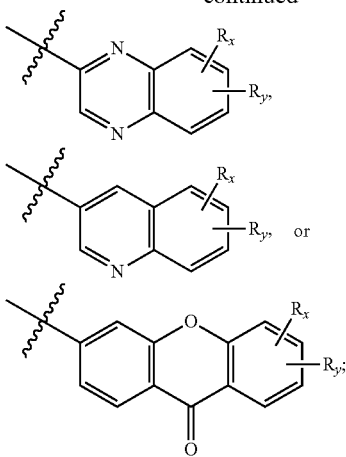

each $R_x$ and $R_y$ is independently H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)$R_{11}$, —C(O)O$R_{11}$, —C(O)N($R_{11}$)$_2$, —C(O)N$R_{11}$—S(O)$_2$$R_{11}$, —C(O)N$R_{11}$—S(O)$_2$—O$R_{11}$, —C(O)N$R_{11}$—S(O)$_2$—N($R_{11}$)$_2$, or —O-(5- to 10-membered heteroaryl comprising 1-4 heteroatoms selected from N, O, and S), wherein at least one of $R_2$ and $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently oxo, halogen, —NH$_2$, —CN, —C(O)$R_{10}$, —C(O)O$R_{10}$, —C(O)N($R_{10}$)$_2$, $C_{1-3}$ alkyl, $C_{2-6}$ alkenyl, $C_{2-6}$ alkynyl, $C_{1-6}$ alkoxy, —NH($C_{1-6}$ alkyl), —N($C_{1-6}$ alkyl)$_2$, —O—(CH$_2$)$_t$—$R_8$, —NH—(CH$_2$)$_t$—$R_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$;

$R_8$ is —OH, $C_{1-6}$ alkoxy, $C_{1-6}$ alkoxy-OH, —NH$_2$, —NH($C_{1-6}$ alkyl), —N($C_{1-6}$ alkyl)$_2$, —SH, —S($C_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl or heteroaryl is optionally substituted by one or more $R_9$;

each $R_9$ is independently —(CH$_2$)$_u$-(5- to 10-membered heteroaryl comprising 1-4 heteroatoms selected from N, O, and S) or —(CH$_2$)$_u$—($C_{6-10}$ aryl), wherein the heteroaryl or aryl is optionally substituted with one or more halogen, —CN, —OH, or —NH$_2$;

each $R_{10}$ is independently halogen, —OH, —NH$_2$, —CN, $C_{1-6}$ alkyl, $C_{2-6}$ alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$;

each n, m, and p is independently 0 or 1;

t is 1, 2, or 3; and u is 0, 1, 2, or 3, wherein when $R_5$ and $R_6$ together with the atoms to which they are attached form a heterocyclyl or heteroaryl substituted with two $R_7$, then one $R_7$ is not —O-methyl.

3. A compound of Formula (II):

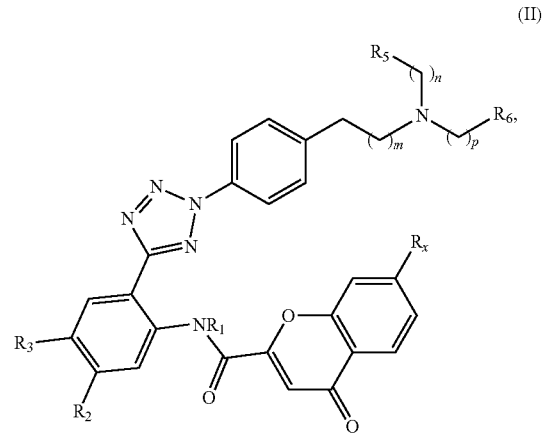

or a pharmaceutically acceptable prodrug, solvate, enantiomer, stereoisomer, tautomer, or salt thereof, wherein:

$R_x$ is H, $C_{1-6}$ alkyl, $C_{2-6}$ alkenyl, $C_{2-6}$ alkynyl, $C_{1-6}$ alkoxy, halogen, —CN, —OH, —NH$_2$, 3- to 10-membered heterocyclyl comprising 1-4 heteroatoms selected from N, O, and S, or 5- to 10-membered heteroaryl comprising 1-4 heteroatoms selected from N, O, and S;

$R_1$ is H, $C_{1-6}$ alkyl, $C_{2-6}$ alkenyl, or $C_{2-6}$ alkynyl;

each $R_2$ and $R_3$ is independently H, $C_{2-6}$ alkenyl, $C_{2-6}$ alkynyl, —O—$C_{1-6}$ alkyl, —O—$C_{2-6}$ alkenyl, —O—$C_{2-6}$ alkynyl, —C(O)R$_{11}$, —C(O)OR$_{11}$, —C(O)N(R$_{11}$)$_2$, —C(O)NR$_{11}$—S(O)$_2$R$_{11}$, —C(O)NR$_{11}$—S(O)$_2$—OR$_{11}$, —C(O)NR$_{11}$—S(O)$_2$—N(R$_{11}$)$_2$, or —O-(5- to 10-membered heteroaryl comprising 1-4 heteroatoms selected from N, O, and S), wherein at least one of $R_2$ and $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

each $R_5$ and $R_6$ is independently H, $C_{1-6}$ alkyl, $C_{2-6}$ alkenyl, $C_{2-6}$ alkynyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)R$_7$, wherein the alkyl, alkenyl, alkynyl, cycloalkyl, heterocyclyl, aryl, or heteroaryl is optionally substituted with one or more $R_7$, or $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$;

each $R_7$ is independently oxo, halogen, —NH$_2$, —CN, —C(O)R$_{10}$, —C(O)OR$_{10}$, —C(O)N(R$_{10}$)$_2$, $C_{1-3}$ alkyl, $C_{2-6}$ alkenyl, $C_{2-6}$ alkynyl, $C_{1-6}$ alkoxy, —NH($C_{1-6}$ alkyl), —N($C_{1-6}$ alkyl)$_2$, —O—(CH$_2$)$_t$—R$_8$, —NH—(CH$_2$)$_t$—R$_8$, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkyl, alkenyl, alkynyl, alkoxy, cycloalkyl, heterocyclyl, aryl, or heteroaryl is optionally substituted with one or more $R_{10}$;

$R_8$ is —OH, $C_{1-6}$ alkoxy, $C_{1-6}$ alkoxy-OH, —NH$_2$, —NH($C_{1-6}$ alkyl), —N($C_{1-6}$ alkyl)$_2$, —SH, —S($C_{1-6}$ alkyl), $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the alkoxy, alkyl, cycloalkyl, heterocyclyl, aryl or heteroaryl is optionally substituted by one or more $R_9$;

each $R_9$ is independently —(CH$_2$)$_u$-(5- to 10-membered heteroaryl comprising 1-4 heteroatoms selected from N, O, and S) or —(CH$_2$)$_u$—(C$_{6-10}$ aryl), wherein the heteroaryl or aryl is optionally substituted with one or more halogen, —CN, —OH, or —NH$_2$;

each $R_{10}$ is independently halogen, —OH, —NH$_2$, —CN, $C_{1-6}$ alkyl, $C_{2-6}$ alkenyl, $C_{2-6}$ alkynyl, $C_{1-6}$ haloalkyl, $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S;

each $R_{11}$ is independently H, $C_{1-6}$ alkyl, $C_{2-6}$ alkenyl, or $C_{2-6}$ alkynyl, wherein the alkyl, alkenyl, or alkynyl is optionally substituted with one or more $C_{3-10}$ cycloalkyl, 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the cycloalkyl, heterocyclyl, aryl, or heteroaryl is optionally substituted with one or more $C_{3-10}$ cycloalkyl, 3- to 10-membered heterocyclyl comprising 1-4 heteroatoms selected from N, O, and S, $C_{6-10}$ aryl, 5- to 10-membered heteroaryl comprising 1-4 heteroatoms selected from N, O, and S, $C_{1-6}$ alkyl, $C_{2-6}$ alkenyl, $C_{2-6}$ alkynyl, oxo, halogen, —CN, —OH, or —NH$_2$, or two $R_{11}$ together with the atom to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $C_{1-6}$ alkyl, $C_{2-6}$ alkenyl, $C_{2-6}$ alkynyl, halogen, —CN, —OH, or —NH$_2$;

each n, m, and p is independently 0 or 1;

t is 1, 2, or 3; and u is 0, 1, 2, or 3, wherein when $R_5$ and $R_6$ together with the atoms to which they are attached form a heterocyclyl or heteroaryl substituted with two $R_7$, then one $R_7$ is not —O-methyl.

4. The compound of claim 1, wherein the compound is of Formula (IA'):

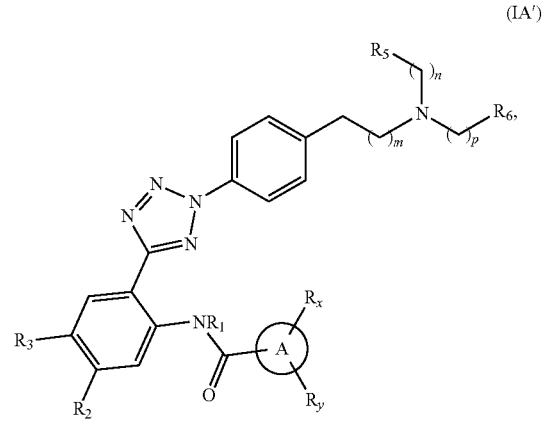

(IA')

or a pharmaceutically acceptable prodrug, solvate, enantiomer, stereoisomer, tautomer, or salt thereof, wherein:

each $R_x$ and $R_y$ is independently H or 5- to 10-membered heteroaryl comprising 1-4 heteroatoms selected from N, O, and S;

each $R_2$ and $R_3$ is independently H, —O—$C_{1-6}$ alkyl, —O—$C_{2-6}$ alkenyl, —O—$C_{2-6}$ alkynyl, or —O-(5- to 10-membered heteroaryl comprising 1-4 heteroatoms selected from N, O, and S), wherein at least one of $R_2$ and $R_3$ is not H, wherein the —O—$C_{1-6}$ alkyl, —O—$C_{2-6}$ alkenyl, or —O—$C_{2-6}$ alkynyl is optionally substituted with $C_{6-10}$ aryl or 5- to 13-membered heteroaryl comprising 1-4 heteroatoms selected from N, O, and S;

$R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is optionally substituted with one or more $R_7$; and each $R_7$ is independently $C_{1-6}$ alkoxy, wherein (a) one of $R_2$ and $R_3$ is not —O-methyl; or (b) $R_x$ or $R_y$ is 5- to 10-membered heteroaryl comprising 1-4 heteroatoms selected from N, O, and S.

5. The compound of claim 1, wherein each $R_x$ and $R_y$ is independently H, $C_{1-6}$ alkyl, or —OH.

6. The compound of claim 1, wherein $R_1$ is H or $C_{1-6}$ alkyl.

7. The compound of claim 1, wherein each $R_2$ and $R_3$ is independently —O—$C_{1-6}$ alkyl, —C(O)$R_{11}$, —C(O)O$R_{11}$, —C(O)N($R_{11}$)$_2$, or —C(O)N$R_{11}$—S(O)$_2R_{11}$.

8. The compound of claim 1, wherein each $R_5$ and $R_6$ is independently H, $C_{1-6}$ alkyl, $C_{3-10}$ cycloalkyl, 3- to 13-membered heterocyclyl comprising 1-4 heteroatoms selected from N, O, and S, $C_{6-10}$ aryl, 5- to 13-membered heteroaryl comprising 1-4 heteroatoms selected from N, O, and S, or —C(O)$R_7$, wherein the alkyl, cycloalkyl, heterocyclyl, aryl, or heteroaryl is optionally substituted with one or more $R_7$.

9. The compound of claim 1, wherein $R_5$ and $R_6$ together with the atoms to which they are attached form a 4- to 10-membered heterocyclyl comprising 1-4 heteroatoms selected from N, O, and S, or 5- to 10-membered heteroaryl comprising 1-4 heteroatoms selected from N, O, and S, wherein the heterocyclyl or heteroaryl is substituted with one or more $R_7$.

10. The compound of claim 1, wherein each $R_7$ is independently oxo, halogen, —NH$_2$, —CN, —C(O)$R_{10}$, $C_{1-3}$ alkyl, $C_{2-6}$ alkynyl, —O—(CH$_2$)$_t$—$R_8$, $C_{6-10}$ aryl, or 5- to 10-membered heteroaryl comprising 1-4 heteroatoms selected from N, O, and S, wherein the alkyl, alkynyl, alkoxy, aryl, or heteroaryl is optionally substituted with one or more $R_{10}$.

11. The compound of claim 1, wherein $R_8$ is —OH, $C_{1-6}$ alkoxy, $C_{1-6}$ alkoxy-OH, —NH$_2$, —N($C_{1-6}$ alkyl)$_2$, —S($C_{1-6}$ alkyl), 3- to 10-membered heterocyclyl comprising 1-4 heteroatoms selected from N, O, and S, or 5- to 10-membered heteroaryl comprising 1-4 heteroatoms selected from N, O, and S, wherein the alkoxy, alkyl, heterocyclyl, or heteroaryl is optionally substituted by one or more $R_9$.

12. The compound of claim 1, wherein each $R_9$ is independently —(CH$_2$)$_u$-(5- to 10-membered heteroaryl comprising 1-4 heteroatoms selected from N, O, and S) or —(CH$_2$)$_u$—($C_{6-10}$ aryl), wherein the heteroaryl or aryl is optionally substituted with one or more halogen or —OH.

13. The compound of claim 1, wherein each $R_{10}$ is independently $C_{1-6}$ alkyl, $C_{1-6}$ haloalkyl, or 5- to 10-membered heteroaryl comprising 1-4 heteroatoms selected from N, O, and S.

14. The compound of claim 1, wherein each Ru is independently H, $C_{1-6}$ alkyl optionally substituted with one or more 3- to 10-membered heterocyclyl comprising 1-4 heteroatoms selected from N, O, and S, $C_{6-10}$ aryl, or 5- to 10-membered heteroaryl comprising 1-4 heteroatoms selected from N, O, and S, wherein the heterocyclyl, aryl, or heteroaryl is optionally substituted with one or more 5- to 10-membered heteroaryl comprising 1-4 heteroatoms selected from N, O, and S, $C_{1-6}$ alkyl, or oxo.

15. The compound claim 1, wherein two Ru together with the atom to which they are attached form a 4- to 10-membered heterocyclyl comprising 1-4 heteroatoms selected from N, O, and S, optionally substituted with one or more $C_{1-6}$ alkyl, $C_{2-6}$ alkenyl, $C_{2-6}$ alkynyl, halogen, —CN, —OH, or —NH$_2$.

16. The compound of claim 1, wherein at least one of $R_2$ and $R_3$ is not H.

17. The compound claim 1, wherein when $R_5$ and $R_6$ together with the atoms to which they are attached form a heterocyclyl or heteroaryl substituted with two $R_7$, then one $R_7$ is not —O-methyl.

18. The compound of claim 1, wherein the compound is of Formula (I-a), (I-b), (I-c), (I-d), (I-e), (I-a'), (I-b'), (II-a), or (II-a'):

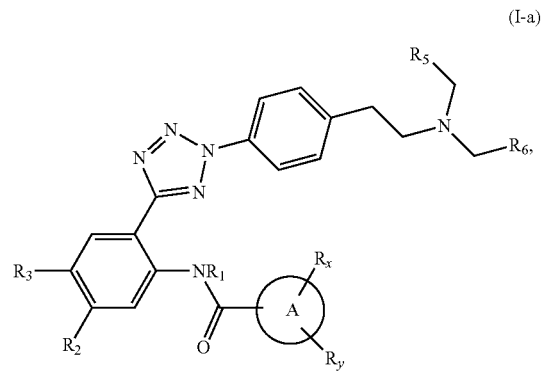

(I-a)

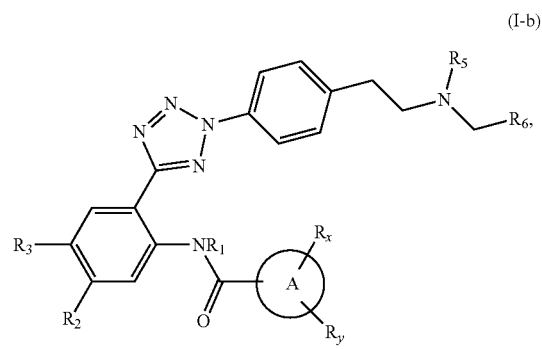

(I-b)

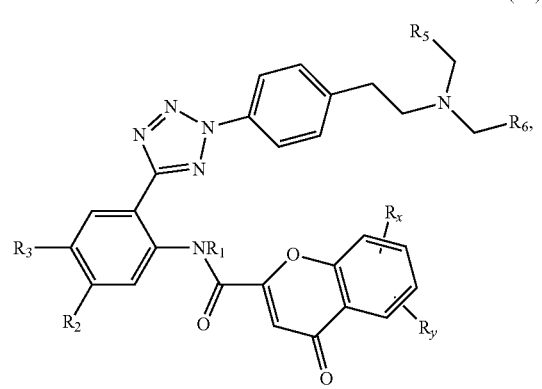

(I-c)

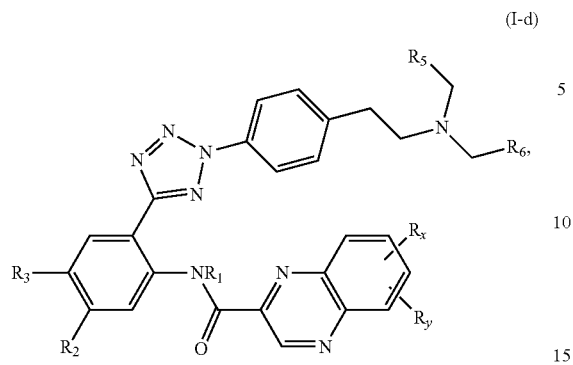
(I-d)
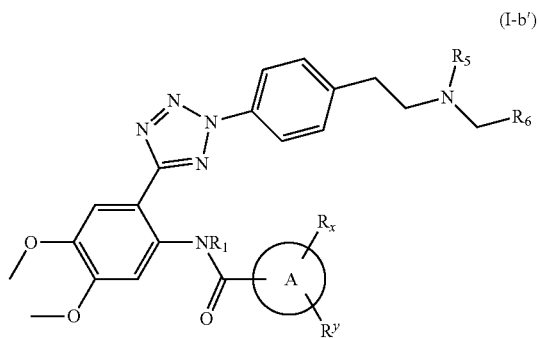
(I-b′)
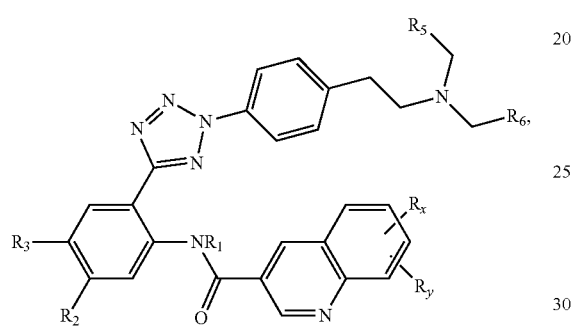
(I-e)
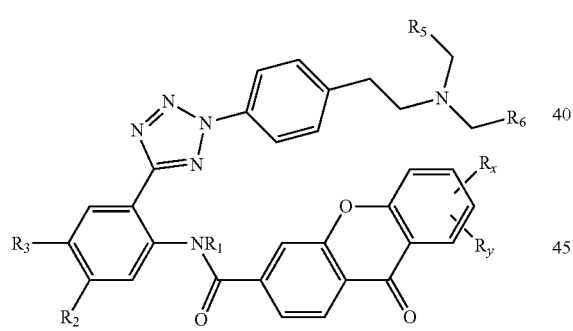
(I-f)
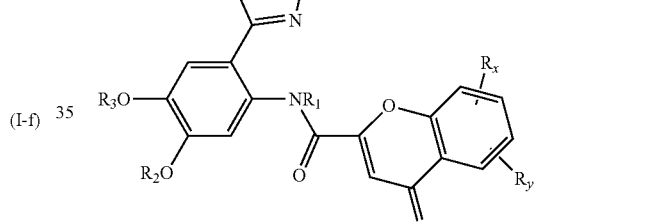
(II-a)
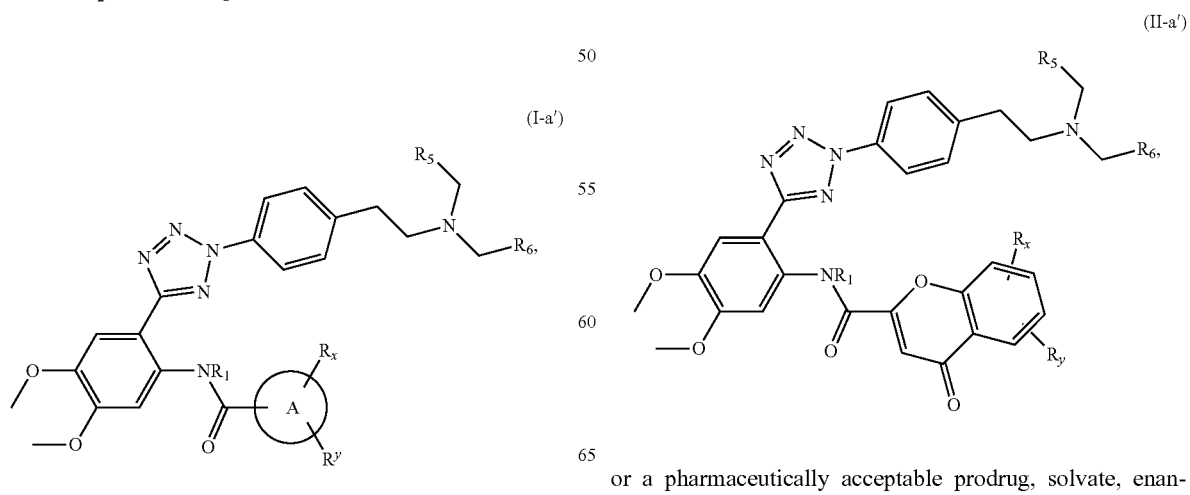
(I-a′)
(II-a′)
or a pharmaceutically acceptable prodrug, solvate, enantiomer, stereoisomer, tautomer, or salt thereof.

19. The compound of claim 1, wherein the compound is selected from
| Compound No. | Structure |
| --- | --- |
| 1 | 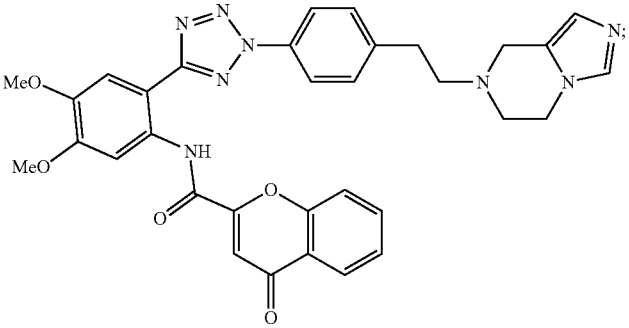 [SMILES: COc1cc(NC(=O)c2cc(=O)c3ccccc3o2)c(-c2nnn(-c3ccc(CCN4CCn5cncc5C4)cc3)n2)cc1OC] |
| 2 | 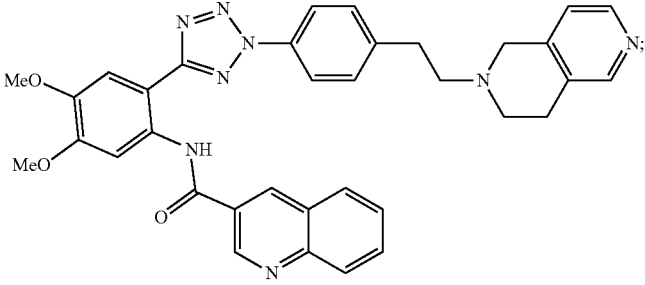 |
| 3 | 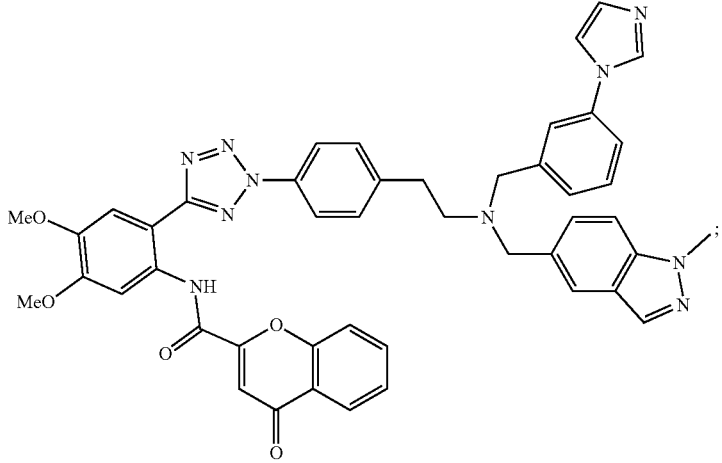 [SMILES: COc1cc(NC(=O)c2cc(=O)c3ccccc3o2)c(-c2nnn(-c3ccc(CCN(Cc4cccc(-n5ccnc5)c4)Cc4ccc5c(cnn5C)c4)cc3)n2)cc1OC] |
| 4 | 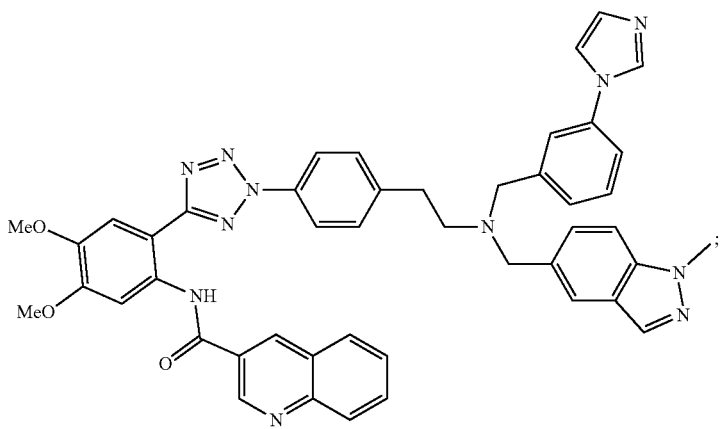 [SMILES: COc1cc(NC(=O)c2cnc3ccccc3c2)c(-c2nnn(-c3ccc(CCN(Cc4cccc(-n5ccnc5)c4)Cc4ccc5c(cnn5C)c4)cc3)n2)cc1OC] |

| Compound No. | Structure |
|---|---|
| 5 | 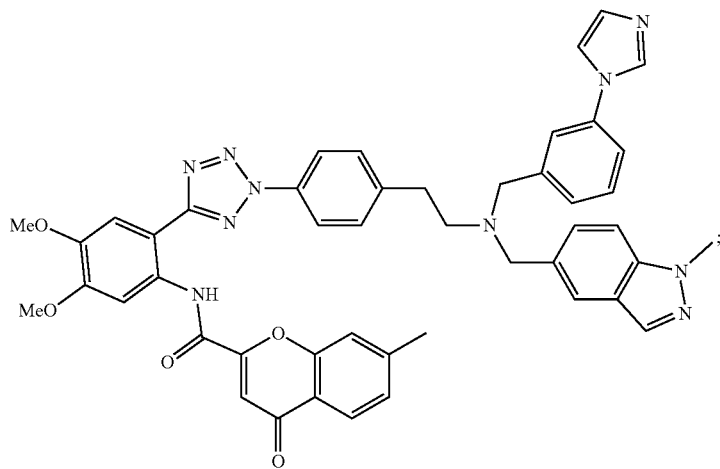 [SMILES: COc1cc(NC(=O)c2cc(=O)c3ccc(C)cc3o2)c(-c2nnn(-c3ccc(CCN(Cc4cccc(-n5ccnc5)c4)Cc4ccc5c(cnn5C)c4)cc3)n2)cc1OC] |
| 6 | 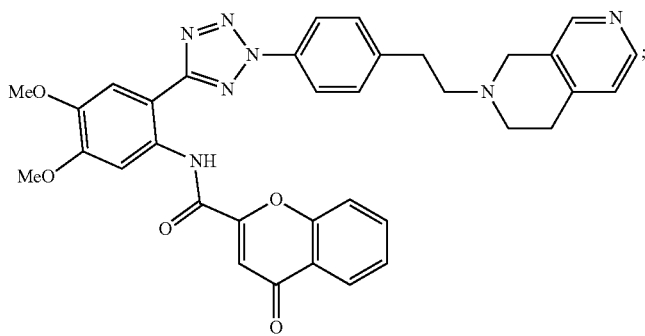 [SMILES: COc1cc(NC(=O)c2cc(=O)c3ccccc3o2)c(-c2nnn(-c3ccc(CCN4CCc5ccncc5C4)cc3)n2)cc1OC] |
| 7 | 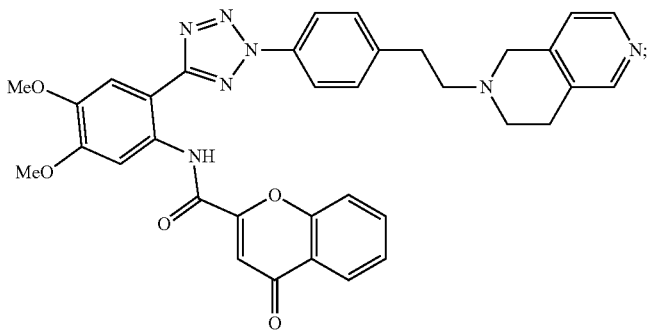 |
| 8 | 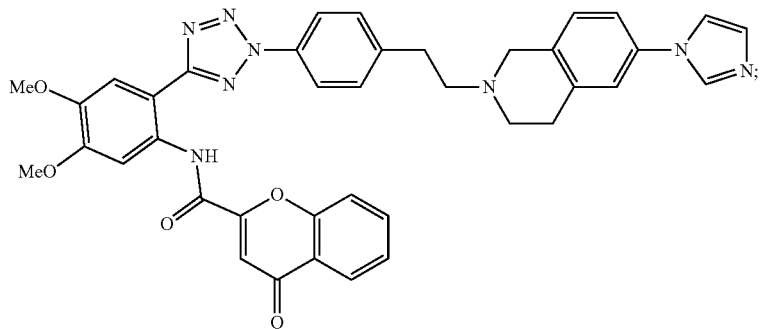 [SMILES: COc1cc(NC(=O)c2cc(=O)c3ccccc3o2)c(-c2nnn(-c3ccc(CCN4CCc5cc(-n6ccnc6)ccc5C4)cc3)n2)cc1OC] |

-continued

| Compound No. | Structure |
|---|---|
| 9 | (structure) |
| 10 | (structure) |
| 11 | (structure) |
| 12 | (structure) |

| Compound No. | Structure |
|---|---|
| 13 | 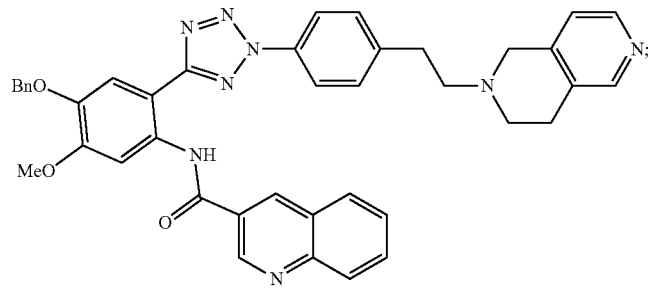 [SMILES: COc1cc(NC(=O)c2cnc3ccccc3c2)c(-c2nnn(-c3ccc(CCN4CCc5cnccc5C4)cc3)n2)cc1OCc1ccccc1] |
| 14 | 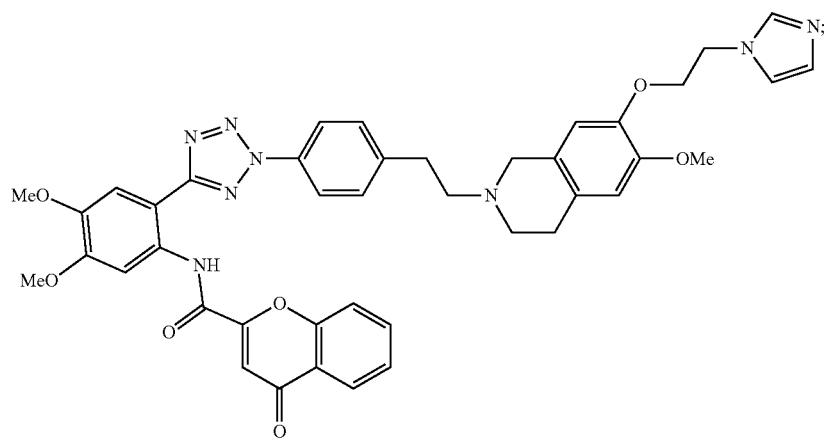 [SMILES: COc1cc(NC(=O)c2cc(=O)c3ccccc3o2)c(-c2nnn(-c3ccc(CCN4CCc5cc(OC)c(OCCn6ccnc6)cc5C4)cc3)n2)cc1OC] |
| 15 | 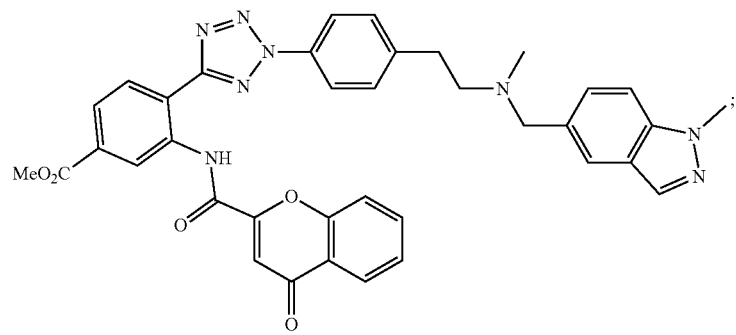 [SMILES: COC(=O)c1ccc(-c2nnn(-c3ccc(CCN(C)Cc4ccc5c(cnn5C)c4)cc3)n2)c(NC(=O)c2cc(=O)c3ccccc3o2)c1] |
| 16 | 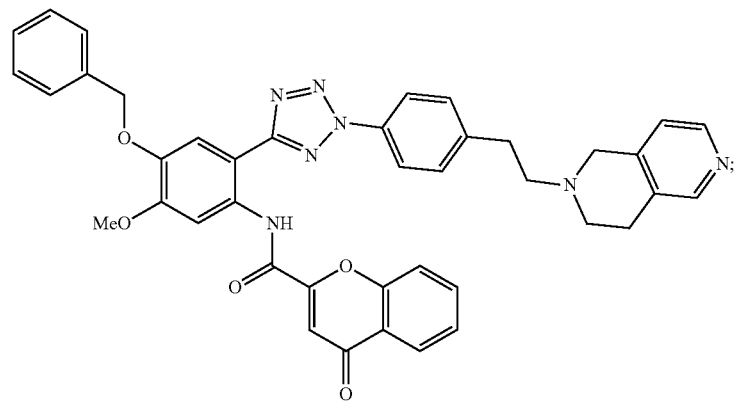 [SMILES: COc1cc(NC(=O)c2cc(=O)c3ccccc3o2)c(-c2nnn(-c3ccc(CCN4CCc5cnccc5C4)cc3)n2)cc1OCc1ccccc1] |

-continued
| Compound No. | Structure |
|---|---|
| 17 | 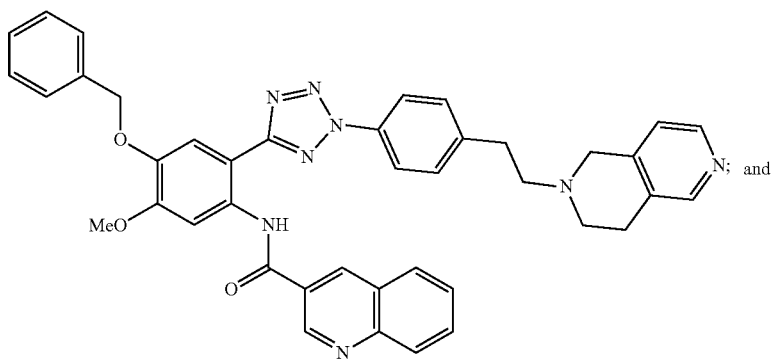 [SMILES: COc1cc(NC(=O)c2cnc3ccccc3c2)c(-c2nnn(-c3ccc(CCN4CCc5cnccc5C4)cc3)n2)cc1OCc1ccccc1] and |
| 18 | 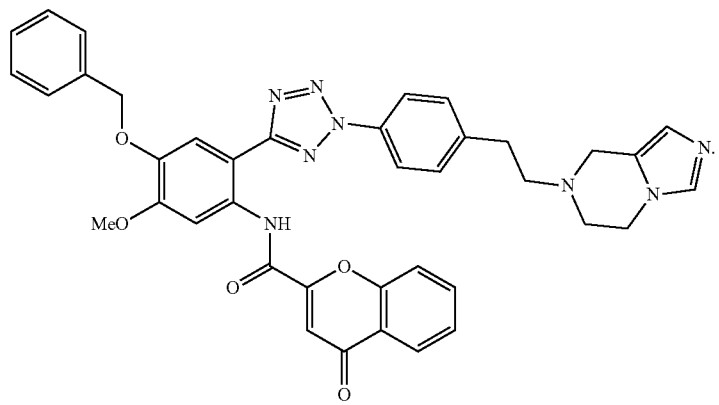 [SMILES: COc1cc(NC(=O)c2cc(=O)c3ccccc3o2)c(-c2nnn(-c3ccc(CCN4CCn5cncc5C4)cc3)n2)cc1OCc1ccccc1] |
20. The compound of claim 1, wherein the compound is selected
| Compound No. | Structure |
|---|---|
| 19 | 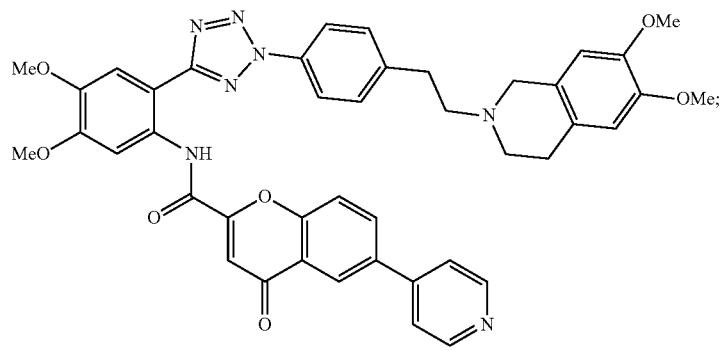 [SMILES: COc1cc2c(cc1OC)CN(CCc1ccc(-n3nnc(-c4cc(OC)c(OC)cc4NC(=O)c4cc(=O)c5cc(-c6ccncc6)ccc5o4)n3)cc1)CC2] |

-continued
| Compound No. | Structure |
|---|---|
| 20 | 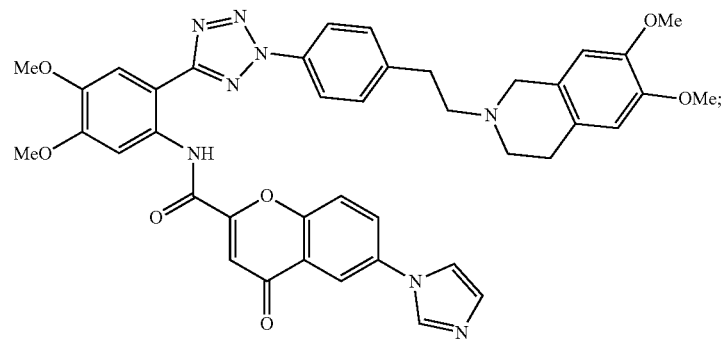 [SMILES: COc1cc2c(cc1OC)CN(CCc1ccc(-n3nnc(-c4cc(OC)c(OC)cc4NC(=O)c4cc(=O)c5cc(-n6ccnc6)ccc5o4)n3)cc1)CC2] |
| 21 | 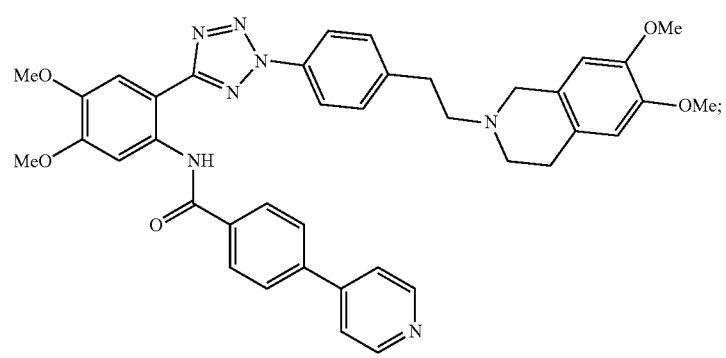 [SMILES: COc1cc2c(cc1OC)CN(CCc1ccc(-n3nnc(-c4cc(OC)c(OC)cc4NC(=O)c4ccc(-c5ccncc5)cc4)n3)cc1)CC2] |
| 22 | 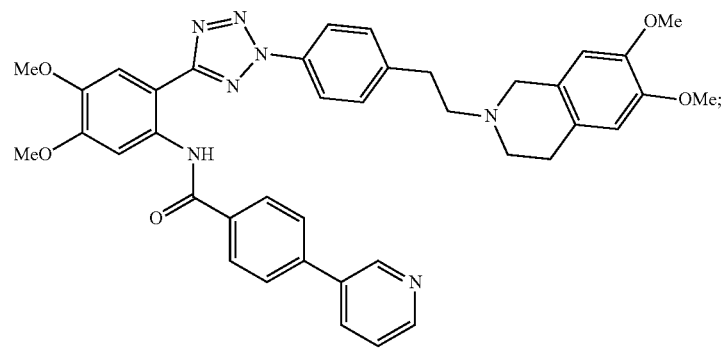 [SMILES: COc1cc2c(cc1OC)CN(CCc1ccc(-n3nnc(-c4cc(OC)c(OC)cc4NC(=O)c4ccc(-c5cccnc5)cc4)n3)cc1)CC2] |
| 23 | 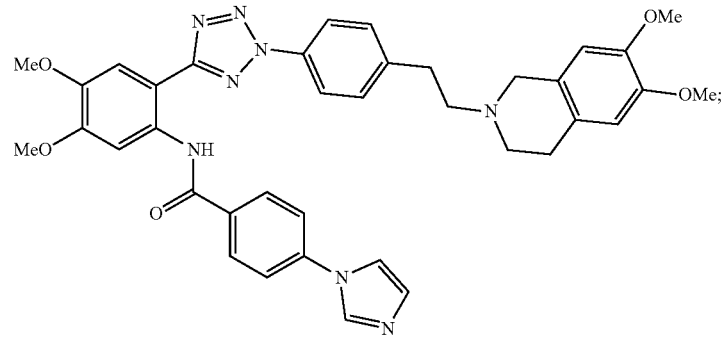 [SMILES: COc1cc2c(cc1OC)CN(CCc1ccc(-n3nnc(-c4cc(OC)c(OC)cc4NC(=O)c4ccc(-n5ccnc5)cc4)n3)cc1)CC2] |

| Compound No. | Structure |
|---|---|
| 24 | 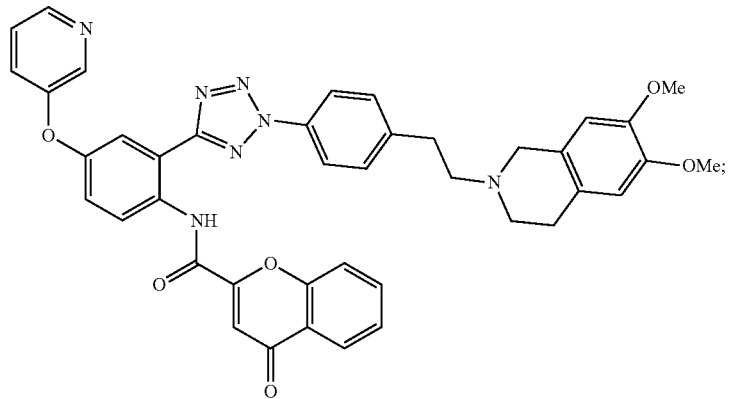 [SMILES: COc1cc2c(cc1OC)CN(CCc1ccc(-n3nnc(-c4cc(Oc5cccnc5)ccc4NC(=O)c4cc(=O)c5ccccc5o4)n3)cc1)CC2] |
| 25 | 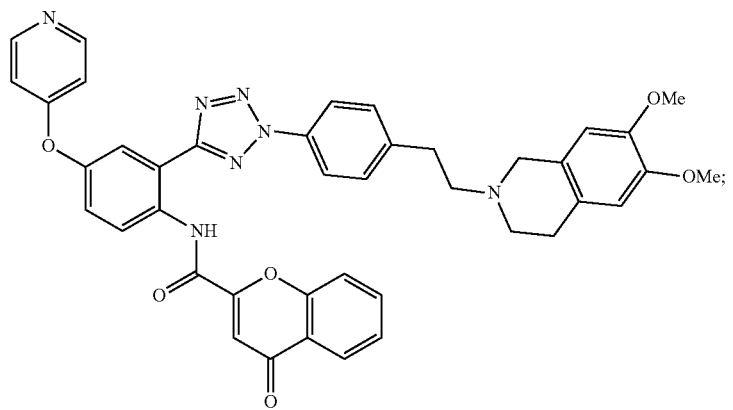 [SMILES: COc1cc2c(cc1OC)CN(CCc1ccc(-n3nnc(-c4cc(Oc5ccncc5)ccc4NC(=O)c4cc(=O)c5ccccc5o4)n3)cc1)CC2] |
| 26 | 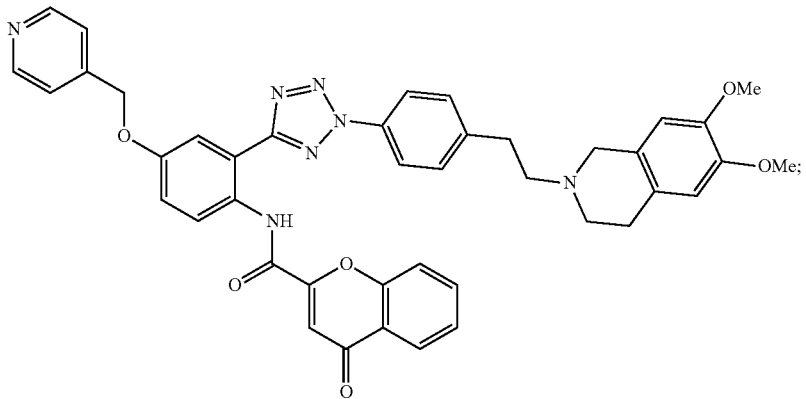 [SMILES: COc1cc2c(cc1OC)CN(CCc1ccc(-n3nnc(-c4cc(OCc5ccncc5)ccc4NC(=O)c4cc(=O)c5ccccc5o4)n3)cc1)CC2] |

-continued
| Compound No. | Structure |
|---|---|
| 27 | 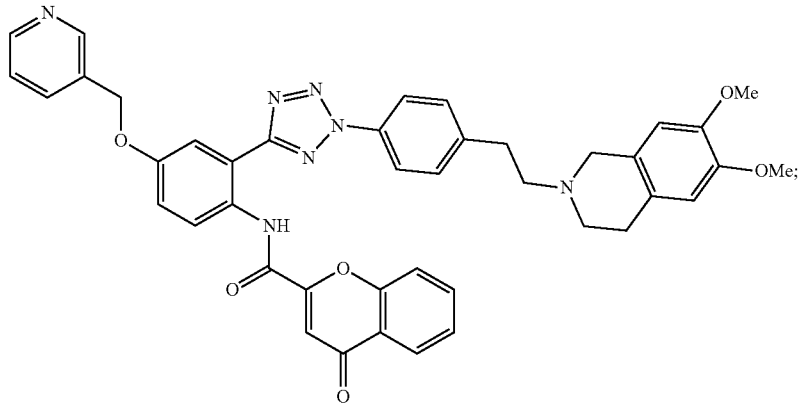 [SMILES: COc1cc2c(cc1OC)CN(CCc1ccc(-n3nnc(-c4cc(OCc5cccnc5)ccc4NC(=O)c4cc(=O)c5ccccc5o4)n3)cc1)CC2] |
| 28 | 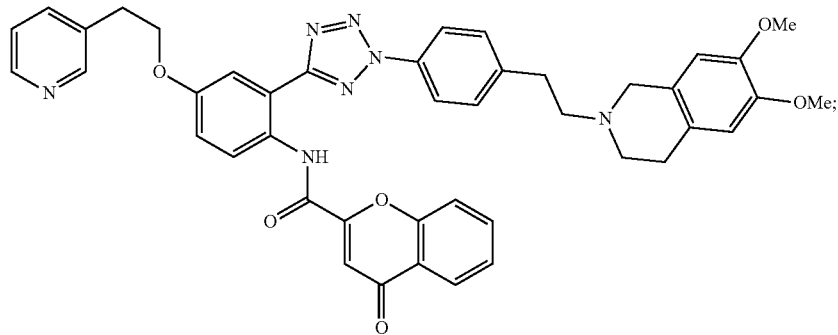 [SMILES: COc1cc2c(cc1OC)CN(CCc1ccc(-n3nnc(-c4cc(OCCc5cccnc5)ccc4NC(=O)c4cc(=O)c5ccccc5o4)n3)cc1)CC2] |
| 29 | 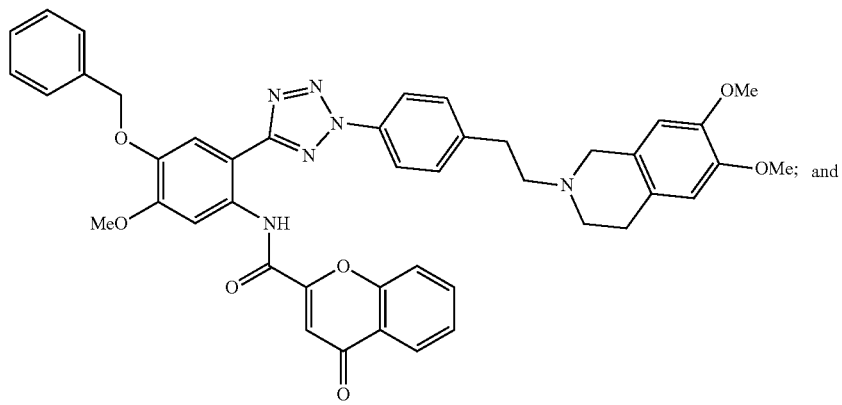 [SMILES: COc1cc2c(cc1OC)CN(CCc1ccc(-n3nnc(-c4cc(OCc5ccccc5)c(OC)cc4NC(=O)c4cc(=O)c5ccccc5o4)n3)cc1)CC2] and |
| 30 | 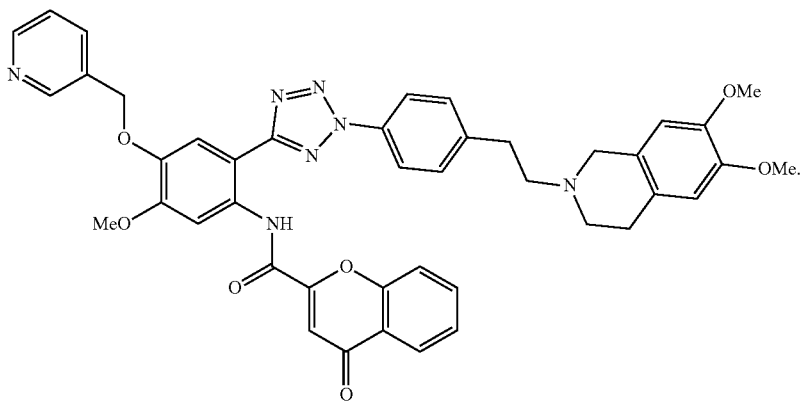 [SMILES: COc1cc2c(cc1OC)CN(CCc1ccc(-n3nnc(-c4cc(OCc5cccnc5)c(OC)cc4NC(=O)c4cc(=O)c5ccccc5o4)n3)cc1)CC2] |

21. A pharmaceutical composition comprising a compound of claim 1, or a pharmaceutically acceptable prodrug, solvate, enantiomer, stereoisomer, tautomer, or salt thereof, and a pharmaceutically acceptable diluent or carrier.

22. A method of modulating P-glycoprotein and/or cytochrome P450 activity, comprising contacting a cell with an effective amount of a compound of claim 1.

23. A method of treating a cancer in a subject in need thereof, comprising administering to the subject a therapeutically effective amount of a compound of claim 1.

* * * * *